(12) United States Patent
Xu et al.

(10) Patent No.: US 11,377,497 B2
(45) Date of Patent: Jul. 5, 2022

(54) PD-L1 BINDING POLYPEPTIDE OR COMPOSITE

(71) Applicant: SUZHOU ALPHAMAB CO., LTD., Jiangsu (CN)

(72) Inventors: Ting Xu, Suzhou (CN); Aiwu Zhou, Shanghai (CN); Yuhao Jin, Suzhou (CN); Ling Wang, Suzhou (CN); Jie Wu, Suzhou (CN); Hongqin Hu, Suzhou (CN); Xiaoxiao Wang, Suzhou (CN)

(73) Assignee: SUZHOU ALPHAMAB CO., LTD., Jiangsu (CN)

( * ) Notice: Subject to any disclaimer, the term of this patent is extended or adjusted under 35 U.S.C. 154(b) by 358 days.

(21) Appl. No.: 16/479,858

(22) PCT Filed: Jan. 23, 2018

(86) PCT No.: PCT/CN2018/073759
§ 371 (c)(1),
(2) Date: Jul. 22, 2019

(87) PCT Pub. No.: WO2018/133873
PCT Pub. Date: Jul. 26, 2018

(65) Prior Publication Data
US 2019/0352404 A1  Nov. 21, 2019

(30) Foreign Application Priority Data
Jan. 23, 2017 (CN) .......................... 201710058712.2

(51) Int. Cl.
| | |
|---|---|
| *C07K 16/28* | (2006.01) |
| *C12N 15/85* | (2006.01) |
| *A61K 39/395* | (2006.01) |
| *G01N 33/577* | (2006.01) |
| *G01N 33/68* | (2006.01) |

(52) U.S. Cl.
CPC ........ *C07K 16/2827* (2013.01); *A61K 39/395* (2013.01); *C12N 15/85* (2013.01); *G01N 33/577* (2013.01); *G01N 33/6854* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 2018/0291103 A1* | 10/2018 | Xu ..................... | A61K 39/3955 |
| 2018/0327494 A1* | 11/2018 | Xu .......................... | A61P 35/00 |
| 2019/0077867 A1 | 3/2019 | Zhu et al. | |
| 2020/0010528 A1* | 1/2020 | Seidel, III .............. | C07K 14/79 |
| 2021/0095031 A1* | 4/2021 | Xu .......................... | A61P 35/00 |
| 2021/0162061 A1* | 6/2021 | Xu ....................... | A61K 31/704 |
| 2021/0246210 A1* | 8/2021 | Xu ..................... | C07K 16/2827 |

FOREIGN PATENT DOCUMENTS

| | | |
|---|---|---|
| CN | 105777906 A | 7/2016 |
| CN | 105968200 A | 9/2016 |
| CN | 106397592 A | 2/2017 |

OTHER PUBLICATIONS

AdisInsight: Trials (Jul. 19, 2016), 3 pages.*
Business Wire (Nov. 30, 2016), 2 pages.*
Zhang, F. et al. Structural Basis of a Novel PD-L1 Nanobody for Immune Checkpoint Blockade. Cell Discovery, vol. 3, Mar. 3, 2017 (Mar. 7, 2017), ISSN: 2056-5968, pp. 1-12.
Liu, K. F. et al. Structural Basis of Anti-PD-L1 monoclonal antibody Avelumab for Tumor Therapy. Cell Research. Aug. 30, 2016 (Aug. 30, 2016), 27(1), ISSN:1748-7838, pp. 151-153.
Lee, Y. L. et al. Structural Basis of Checkpoint Blockade by Monoclonal Antibodies in Cancer Immunotherapy. Nature Communications. Aug. 30, 2016 (Aug. 30, 2016), ISSN: 2041-1723, pp. 1-10.

* cited by examiner

*Primary Examiner* — Ilia I Ouspenski
(74) *Attorney, Agent, or Firm* — Troutman Pepper Hamilton Sanders LLP

(57) ABSTRACT

The present invention relates to the field of medical biology, and discloses a high-resolution crystal structure of a complex of PD-L1-blocking heavy-chain single-domain antibody KN035 binding with PD-L1, and the use of the crystal structure. The invention also relates to novel PD-L1 binding polypeptides or compounds developed based on the crystal structure and uses thereof.

Figure 1:
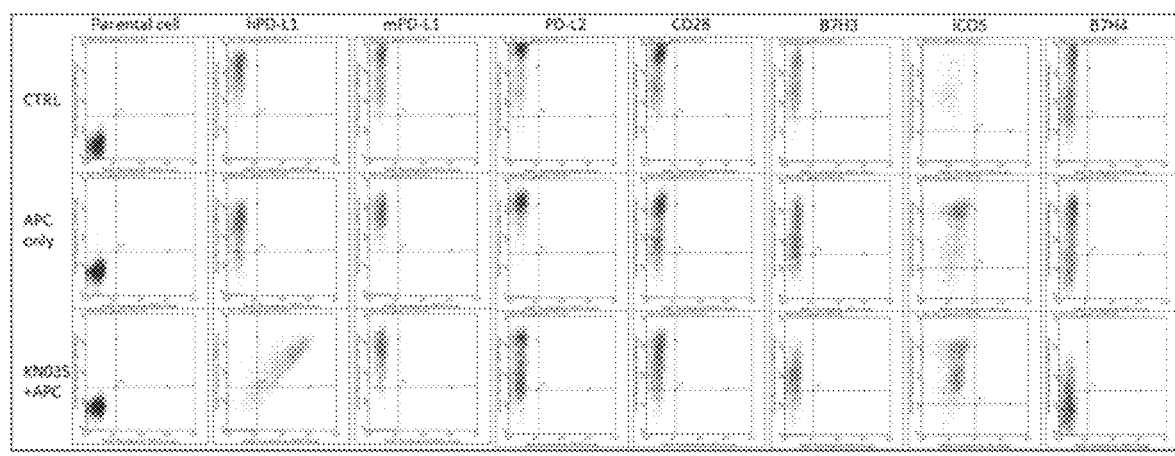

11 Claims, 8 Drawing Sheets
Specification includes a Sequence Listing.

m7 m8:

SEQUENCE LISTING

<160> NUMBER OF SEQ ID NOS: 25

<210> SEQ ID NO 1
<211> LENGTH: 128
<212> TYPE: PRT
<213> ORGANISM: Artificial Sequence
<220> FEATURE:
<223> OTHER INFORMATION: Antibody Strain 56

<400> SEQUENCE: 1

Gln Val Gln Leu Gln Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
        35                  40                  45

Ala Lys Leu Leu Thr Thr Ser Gly Ser Thr Tyr Leu Ala Asp Ser Val
    50                  55                  60

Lys Gly Arg Phe Thr Ile Ser Gln Asn Asn Ala Lys Ser Thr Val Tyr
65                  70                  75                  80

Leu Gln Met Asn Ser Leu Lys Pro Glu Asp Thr Ala Met Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Gln Val Thr Val Ser Ser
        115                 120                 125

<210> SEQ ID NO 2
<211> LENGTH: 7
<212> TYPE: PRT

<210> SEQ ID NO 2
<211> LENGTH: 6
<212> TYPE: PRT
<213> ORGANISM: Artificial Sequence
<220> FEATURE:
<223> OTHER INFORMATION: CDR1

<400> SEQUENCE: 2

Gly Lys Met Ser Ser Arg Arg
1               5

<210> SEQ ID NO 3
<211> LENGTH: 3
<212> TYPE: PRT
<213> ORGANISM: Artificial Sequence
<220> FEATURE:
<223> OTHER INFORMATION: CDR2

<400> SEQUENCE: 3

Thr Thr Ser
1

<210> SEQ ID NO 4
<211> LENGTH: 18
<212> TYPE: PRT
<213> ORGANISM: Artificial Sequence
<220> FEATURE:
<223> OTHER INFORMATION: CDR3

<400> SEQUENCE: 4

Asp Ser Phe Glu Asp Pro Thr Cys Thr Leu Val Thr Ser Ser Gly Ala
1               5                   10                  15

Phe Gln

<210> SEQ ID NO 5
<211> LENGTH: 113
<212> TYPE: PRT
<213> ORGANISM: Artificial Sequence
<220> FEATURE:
<223> OTHER INFORMATION: Human PDL1-V

<400> SEQUENCE: 5

Thr Val Thr Val Pro Lys Asp Leu Tyr Val Val Glu Tyr Gly Ser Asn
1               5                   10                  15

Met Thr Ile Glu Cys Lys Phe Pro Val Glu Lys Gln Leu Asp Leu Ala
            20                  25                  30

Ala Leu Ile Val Tyr Trp Glu Met Glu Asp Lys Asn Ile Ile Gln Phe
        35                  40                  45

Val His Gly Glu Glu Asp Leu Lys Val Gln His Ser Ser Tyr Arg Gln
    50                  55                  60

Arg Ala Arg Leu Leu Lys Asp Gln Leu Ser Leu Gly Asn Ala Ala Leu
65                  70                  75                  80

Gln Ile Thr Asp Val Lys Leu Gln Asp Ala Gly Val Tyr Arg Cys Met
                85                  90                  95

Ile Ser Tyr Gly Gly Ala Asp Tyr Lys Arg Ile Thr Val Lys Val Asn
            100                 105                 110

Ala

<210> SEQ ID NO 6
<211> LENGTH: 234
<212> TYPE: PRT
<213> ORGANISM: Artificial Sequence
<220> FEATURE:
<223> OTHER INFORMATION: Human PDL1-His

<400> SEQUENCE: 6

```
Thr Val Thr Val Pro Lys Asp Leu Tyr Val Val Glu Tyr Gly Ser Asn
1               5                   10                  15

Met Thr Ile Glu Cys Lys Phe Pro Val Glu Lys Gln Leu Asp Leu Ala
            20                  25                  30

Ala Leu Ile Val Tyr Trp Glu Met Glu Asp Lys Asn Ile Ile Gln Phe
        35                  40                  45

Val His Gly Glu Glu Asp Leu Lys Val Gln His Ser Ser Tyr Arg Gln
    50                  55                  60

Arg Ala Arg Leu Leu Lys Asp Gln Leu Ser Leu Gly Asn Ala Ala Leu
65                  70                  75                  80

Gln Ile Thr Asp Val Lys Leu Gln Asp Ala Gly Val Tyr Arg Cys Met
                85                  90                  95

Ile Ser Tyr Gly Gly Ala Asp Tyr Lys Arg Ile Thr Val Lys Val Asn
            100                 105                 110

Ala Pro Tyr Asn Lys Ile Asn Gln Arg Ile Leu Val Val Asp Pro Val
        115                 120                 125

Thr Ser Glu His Glu Leu Thr Cys Gln Ala Glu Gly Tyr Pro Lys Ala
    130                 135                 140

Glu Val Ile Trp Thr Ser Ser Asp His Gln Val Leu Ser Gly Lys Thr
145                 150                 155                 160

Thr Thr Thr Asn Ser Lys Arg Glu Glu Lys Leu Phe Asn Val Thr Ser
                165                 170                 175

Thr Leu Arg Ile Asn Thr Thr Thr Asn Glu Ile Phe Tyr Cys Thr Phe
            180                 185                 190

Arg Arg Leu Asp Pro Glu Glu Asn His Thr Ala Glu Leu Val Ile Pro
        195                 200                 205

Glu Leu Pro Leu Ala His Pro Pro Asn Glu Arg Thr Asp Lys Leu Ala
    210                 215                 220

Ala Ala Leu Glu His His His His His His
225                 230

<210> SEQ ID NO 7
<211> LENGTH: 221
<212> TYPE: PRT
<213> ORGANISM: Artificial Sequence
<220> FEATURE:
<223> OTHER INFORMATION: Human PDL1

<400> SEQUENCE: 7

Thr Val Thr Val Pro Lys Asp Leu Tyr Val Val Glu Tyr Gly Ser Asn
1               5                   10                  15

Met Thr Ile Glu Cys Lys Phe Pro Val Glu Lys Gln Leu Asp Leu Ala
            20                  25                  30

Ala Leu Ile Val Tyr Trp Glu Met Glu Asp Lys Asn Ile Ile Gln Phe
        35                  40                  45

Val His Gly Glu Glu Asp Leu Lys Val Gln His Ser Ser Tyr Arg Gln
    50                  55                  60

Arg Ala Arg Leu Leu Lys Asp Gln Leu Ser Leu Gly Asn Ala Ala Leu
65                  70                  75                  80

Gln Ile Thr Asp Val Lys Leu Gln Asp Ala Gly Val Tyr Arg Cys Met
                85                  90                  95

Ile Ser Tyr Gly Gly Ala Asp Tyr Lys Arg Ile Thr Val Lys Val Asn
            100                 105                 110

Ala Pro Tyr Asn Lys Ile Asn Gln Arg Ile Leu Val Val Asp Pro Val
        115                 120                 125
```

Thr Ser Glu His Glu Leu Thr Cys Gln Ala Glu Gly Tyr Pro Lys Ala
              130                 135                 140

Glu Val Ile Trp Thr Ser Ser Asp His Gln Val Leu Ser Gly Lys Thr
145                 150                 155                 160

Thr Thr Thr Asn Ser Lys Arg Glu Glu Asn Leu Phe Asn Val Thr Ser
                165                 170                 175

Thr Leu Arg Ile Asn Thr Thr Thr Asn Glu Ile Phe Tyr Cys Thr Phe
                180                 185                 190

Arg Arg Leu Asp Pro Glu Glu Asn His Thr Ala Glu Leu Val Ile Pro
                195                 200                 205

Glu Leu Pro Leu Ala His Pro Pro Asn Glu Arg Thr Asp
            210                 215                 220

<210> SEQ ID NO 8
<211> LENGTH: 8
<212> TYPE: PRT
<213> ORGANISM: Artificial Sequence
<220> FEATURE:
<223> OTHER INFORMATION: CDR1

<400> SEQUENCE: 8

Gly Lys Met Ser Ser Arg Arg Cys
1               5

<210> SEQ ID NO 9
<211> LENGTH: 124
<212> TYPE: PRT
<213> ORGANISM: Artificial Sequence
<220> FEATURE:
<223> OTHER INFORMATION: Antibody strain 10

<400> SEQUENCE: 9

Gln Val Gln Leu Gln Glu Ser Gly Gly Gly Ser Val Gln Ala Gly Gly
1               5                   10                  15

Ser Leu Arg Leu Ser Cys Ala Ala Ser Gly Asn Ile Val Ser Ser Tyr
                20                  25                  30

Cys Met Gly Trp Phe Arg Gln Ala Pro Gly Lys Glu Arg Val Gly Val
            35                  40                  45

Ala Ala Ile Asp Ser Asp Gly Thr Thr Lys Tyr Ala Asp Ser Met Lys
    50                  55                  60

Gly Arg Phe Thr Ile Ser Lys Asp Asn Ala Lys Asn Thr Leu Asp Leu
65                  70                  75                  80

Gln Met Asn Ser Leu Lys Pro Glu Asp Thr Ala Met Tyr Tyr Cys Val
                85                  90                  95

Ala Arg Leu Asn Cys Pro Gly Pro Val Asp Trp Val Pro Met Phe Pro
            100                 105                 110

Tyr Arg Gly Gln Gly Thr Gln Val Thr Val Ser Ser
        115                 120

<210> SEQ ID NO 10
<211> LENGTH: 127
<212> TYPE: PRT
<213> ORGANISM: Artificial Sequence
<220> FEATURE:
<223> OTHER INFORMATION: m1

<400> SEQUENCE: 10

Gln Val Gln Leu Gln Glu Ser Gly Gly Gly Ser Val Gln Ala Gly Gly
1               5                   10                  15

-continued

Ser Leu Arg Leu Ser Cys Ala Ala Ser Gly Lys Met Ser Arg Arg
            20                  25                  30

Cys Met Gly Trp Phe Arg Gln Ala Pro Gly Lys Glu Arg Val Gly Val
        35                  40                  45

Ala Ala Ile Asp Ser Asp Gly Thr Thr Lys Tyr Ala Asp Ser Met Lys
50                  55                  60

Gly Arg Phe Thr Ile Ser Lys Asp Asn Ala Lys Asn Thr Leu Asp Leu
65                  70                  75                  80

Gln Met Asn Ser Leu Lys Pro Glu Asp Thr Ala Met Tyr Tyr Cys Val
                85                  90                  95

Ala Asp Ser Phe Glu Asp Pro Thr Cys Thr Leu Val Thr Ser Ser Gly
            100                 105                 110

Ala Phe Gln Tyr Arg Gly Gln Gly Thr Gln Val Thr Val Ser Ser
        115                 120                 125

<210> SEQ ID NO 11
<211> LENGTH: 124
<212> TYPE: PRT
<213> ORGANISM: Artificial Sequence
<220> FEATURE:
<223> OTHER INFORMATION: Antibody strain 94

<400> SEQUENCE: 11

Gln Val Gln Leu Gln Glu Ser Gly Gly Gly Ser Val Gln Ala Gly Gly
1               5                   10                  15

Ser Leu Arg Leu Ser Cys Ala Ala Ser Leu Asn Ile Phe Ser Ser Tyr
            20                  25                  30

Cys Met Gly Trp Phe Arg Gln Ala Pro Gly Lys Gln Arg Val Gly Val
        35                  40                  45

Ala Thr Ile Asp Ser Asp Gly Thr Thr Arg Tyr Val Asp Ser Val Lys
50                  55                  60

Gly Arg Phe Thr Ile Ser Lys Asp Asn Ala Lys Asn Thr Leu Asp Leu
65                  70                  75                  80

Gln Met Asn Ser Leu Lys Pro Glu Asp Thr Ala Met Tyr Tyr Cys Ala
                85                  90                  95

Ala Arg Leu Asn Cys Pro Gly Pro Val Asp Trp Val Pro Met Phe Pro
            100                 105                 110

Tyr Arg Gly Gln Gly Thr Gln Val Thr Val Ser Ser
        115                 120

<210> SEQ ID NO 12
<211> LENGTH: 127
<212> TYPE: PRT
<213> ORGANISM: Artificial Sequence
<220> FEATURE:
<223> OTHER INFORMATION: m2

<400> SEQUENCE: 12

Gln Val Gln Leu Gln Glu Ser Gly Gly Gly Ser Val Gln Ala Gly Gly
1               5                   10                  15

Ser Leu Arg Leu Ser Cys Ala Ala Ser Gly Lys Met Ser Ser Arg Arg
            20                  25                  30

Cys Met Gly Trp Phe Arg Gln Ala Pro Gly Lys Gln Arg Val Gly Val
        35                  40                  45

Ala Thr Ile Asp Ser Asp Gly Thr Thr Arg Tyr Val Asp Ser Val Lys
50                  55                  60

Gly Arg Phe Thr Ile Ser Lys Asp Asn Ala Lys Asn Thr Leu Asp Leu
65                  70                  75                  80

Gln Met Asn Ser Leu Lys Pro Glu Asp Thr Ala Met Tyr Tyr Cys Ala
                85                  90                  95

Ala Asp Ser Phe Glu Asp Pro Thr Cys Thr Leu Val Thr Ser Ser Gly
            100                 105                 110

Ala Phe Gln Tyr Arg Gly Gln Gly Thr Gln Val Thr Val Ser Ser
        115                 120                 125

<210> SEQ ID NO 13
<211> LENGTH: 17
<212> TYPE: PRT
<213> ORGANISM: Artificial Sequence
<220> FEATURE:
<223> OTHER INFORMATION: CDR2

<400> SEQUENCE: 13

Lys Leu Leu Thr Thr Ser Gly Ser Thr Tyr Leu Ala Asp Ser Val Lys
1               5                   10                  15

Gly

<210> SEQ ID NO 14
<211> LENGTH: 17
<212> TYPE: PRT
<213> ORGANISM: Artificial Sequence
<220> FEATURE:
<223> OTHER INFORMATION: CDR2-KABAT of the heavy chain of Pertuzumab
      antibody

<400> SEQUENCE: 14

Asp Val Asn Pro Asn Ser Gly Gly Ser Ile Tyr Asn Gln Arg Phe Lys
1               5                   10                  15

Gly

<210> SEQ ID NO 15
<211> LENGTH: 128
<212> TYPE: PRT
<213> ORGANISM: Artificial Sequence
<220> FEATURE:
<223> OTHER INFORMATION: m3

<400> SEQUENCE: 15

Gln Val Gln Leu Gln Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
        35                  40                  45

Ala Asp Val Asn Pro Asn Ser Gly Gly Ser Ile Tyr Asn Gln Arg Phe
    50                  55                  60

Lys Gly Arg Phe Thr Ile Ser Gln Asn Asn Ala Lys Ser Thr Val Tyr
65                  70                  75                  80

Leu Gln Met Asn Ser Leu Lys Pro Glu Asp Thr Ala Met Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Gln Val Thr Val Ser Ser
        115                 120                 125

<210> SEQ ID NO 16
<211> LENGTH: 128
<212> TYPE: PRT

<213> ORGANISM: Artificial Sequence
<220> FEATURE:
<223> OTHER INFORMATION: m4

<400> SEQUENCE: 16

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
        35                  40                  45

Ala Lys Leu Leu Ala Thr Ser Gly Ser Thr Tyr Leu Ala Asp Ser Val
    50                  55                  60

Lys Gly Arg Phe Thr Ile Ser Gln Asn Asn Ala Lys Ser Thr Val Tyr
65                  70                  75                  80

Leu Gln Met Asn Ser Leu Lys Pro Glu Asp Thr Ala Met Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Gln Val Thr Val Ser Ser
        115                 120                 125
```

<210> SEQ ID NO 17
<211> LENGTH: 128
<212> TYPE: PRT
<213> ORGANISM: Artificial Sequence
<220> FEATURE:
<223> OTHER INFORMATION: m5

<400> SEQUENCE: 17

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
        35                  40                  45

Ala Lys Leu Leu Thr Ala Ser Gly Ser Thr Tyr Leu Ala Asp Ser Val
    50                  55                  60

Lys Gly Arg Phe Thr Ile Ser Gln Asn Asn Ala Lys Ser Thr Val Tyr
65                  70                  75                  80

Leu Gln Met Asn Ser Leu Lys Pro Glu Asp Thr Ala Met Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Gln Val Thr Val Ser Ser
        115                 120                 125
```

<210> SEQ ID NO 18
<211> LENGTH: 128
<212> TYPE: PRT
<213> ORGANISM: Artificial Sequence
<220> FEATURE:
<223> OTHER INFORMATION: m6

<400> SEQUENCE: 18

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30
```

```
Cys Met Ala Trp Phe Arg Gln Ala Pro Gly Lys Glu Arg Glu Arg Val
            35                  40                  45

Ala Lys Leu Leu Thr Thr Ala Gly Ser Thr Tyr Leu Ala Asp Ser Val
 50                  55                  60

Lys Gly Arg Phe Thr Ile Ser Gln Asn Asn Ala Lys Ser Thr Val Tyr
 65                  70                  75                  80

Leu Gln Met Asn Ser Leu Lys Pro Glu Asp Thr Ala Met Tyr Tyr Cys
                 85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Gln Val Thr Val Ser Ser
            115                 120                 125
```

<210> SEQ ID NO 19
<211> LENGTH: 129
<212> TYPE: PRT
<213> ORGANISM: Artificial Sequence
<220> FEATURE:
<223> OTHER INFORMATION: Antibody C38

<400> SEQUENCE: 19

```
Gln Val Gln Leu Gln Glu Ser Gly Gly Gly Ser Val Gln Ala Gly Gly
 1               5                  10                  15

Ser Leu Arg Leu Ser Cys Ala Ala Ser Arg Tyr Thr Ala Ser Ser Asn
             20                  25                  30

Cys Met Ala Trp Phe Arg Gln Ala Pro Gly Lys Glu Arg Glu Gly Val
             35                  40                  45

Ala Thr Ile Tyr Asn Gly Gly Gly Ser Thr Ala Tyr Ala Asp Ser Val
 50                  55                  60

Lys Gly Arg Phe Thr Ile Ser Gln Asp Asn Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Gly Ala Gly Ser Pro Arg Phe Cys Ala Ser Ala Thr Met Thr Gly Gly
            100                 105                 110

His His Leu Phe Gly Tyr Trp Gly Gln Gly Thr Gln Val Thr Val Ser
            115                 120                 125

Ser
```

<210> SEQ ID NO 20
<211> LENGTH: 136
<212> TYPE: PRT
<213> ORGANISM: Artificial Sequence
<220> FEATURE:
<223> OTHER INFORMATION: m7

<400> SEQUENCE: 20

```
Gln Val Gln Leu Gln Glu Ser Gly Gly Gly Ser Val Gln Ala Gly Gly
 1               5                  10                  15

Ser Leu Arg Leu Ser Cys Ala Ala Ser Arg Tyr Thr Ala Ser Ser Asn
             20                  25                  30

Cys Met Ala Trp Phe Arg Gln Ala Pro Gly Lys Glu Arg Glu Gly Val
             35                  40                  45

Ala Thr Ile Tyr Asn Gly Gly Gly Ser Thr Ala Tyr Ala Asp Ser Val
 50                  55                  60

Lys Gly Arg Phe Thr Ile Ser Gln Asp Asn Ala Lys Asn Thr Val Tyr
 65                  70                  75                  80
```

```
Leu Gln Met Asn Ser Leu Lys Pro Glu Asp Thr Ala Met Tyr Tyr Cys
                85                  90                  95

Gly Ala Gly Ser Pro Arg Phe Cys Ala Ser Asp Ser Phe Glu Asp Pro
            100                 105                 110

Thr Cys Thr Leu Val Thr Ser Ser Gly Ala Phe Gln Tyr Trp Gly Gln
        115                 120                 125

Gly Thr Gln Val Thr Val Ser Ser
        130                 135

<210> SEQ ID NO 21
<211> LENGTH: 8
<212> TYPE: PRT
<213> ORGANISM: Artificial Sequence
<220> FEATURE:
<223> OTHER INFORMATION: C38 CDR1 plus Cys

<400> SEQUENCE: 21

Arg Tyr Thr Ala Ser Ser Asn Cys
1               5

<210> SEQ ID NO 22
<211> LENGTH: 17
<212> TYPE: PRT
<213> ORGANISM: Artificial Sequence
<220> FEATURE:
<223> OTHER INFORMATION: C38 CDR2-KABAT

<400> SEQUENCE: 22

Thr Ile Tyr Asn Gly Gly Gly Ser Thr Ala Tyr Ala Asp Ser Val Lys
1               5                   10                  15

Gly

<210> SEQ ID NO 23
<211> LENGTH: 128
<212> TYPE: PRT
<213> ORGANISM: Artificial Sequence
<220> FEATURE:
<223> OTHER INFORMATION: m8

<400> SEQUENCE: 23

Gln Val Gln Leu Gln Glu Ser Gly Gly Gly Leu Val Gln Pro Gly Gly
1               5                   10                  15

Ser Leu Arg Leu Ser Cys Ala Ala Ser Arg Tyr Thr Ala Ser Ser Asn
            20                  25                  30

Cys Met Ala Trp Phe Arg Gln Ala Pro Gly Lys Glu Arg Glu Arg Val
        35                  40                  45

Ala Thr Ile Tyr Asn Gly Gly Gly Ser Thr Ala Tyr Ala Asp Ser Val
    50                  55                  60

Lys Gly Arg Phe Thr Ile Ser Gln Asn Asn Ala Lys Ser Thr Val Tyr
65                  70                  75                  80

Leu Gln Met Asn Ser Leu Lys Pro Glu Asp Thr Ala Met Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Gln Val Thr Val Ser Ser
        115                 120                 125

<210> SEQ ID NO 24
<211> LENGTH: 10
<212> TYPE: PRT
```

```
<213> ORGANISM: Artificial Sequence
<220> FEATURE:
<223> OTHER INFORMATION: CDR1

<400> SEQUENCE: 24

Gly Lys Met Ser Ser Arg Arg Cys Met Ala
1               5                   10

<210> SEQ ID NO 25
<211> LENGTH: 6
<212> TYPE: PRT
<213> ORGANISM: Artificial Sequence
<220> FEATURE:
<223> OTHER INFORMATION: CDR2

<400> SEQUENCE: 25

Leu Thr Thr Ser Gly Ser
1               5
```

PD-L1 BINDING POLYPEPTIDE OR COMPOSITE

CROSS-REFERENCE TO RELATED APPLICATIONS

This application is a United States national stage entry of an International Application serial no. PCT/CN2018/073759 filed Jan. 23, 2018 which claims priority to Chinese Patent Application serial no. 201710058712.2 filed Jan. 23, 2017. The contents of these applications are incorporated herein by reference in their entirety.

SEQUENCE LISTING

This application contains a Sequence Listing which has been submitted in ASCII format via EFS-Web and is hereby incorporated by reference in its entirety. Said ASCII copy, created on Jul. 22, 2019, is named NP2019TC505_seq.txt, and is 24,576 bytes in size.

TECHNICAL FIELD

The present invention relates to the field of medical biology, and discloses a high-resolution crystal structure of a complex of PD-L1-blocking heavy-chain single-domain antibody KN035 binding with PD-L1, and the use of the crystal structure. The invention also relates to novel PD-L1 binding polypeptides or compounds developed based on the crystal structure and uses thereof.

BACKGROUND TECHNIQUE

Programmed death-1 (PD-1) is a member of the CD28 receptor family, which includes CD28, CTLA-4, ICOS, PD-1, and BTLA. The original members of this family, CD28 and ICOS, were discovered through enhancement of T cell proliferation by the addition of monoclonal antibodies (Hutloff et al. (1999), Nature 397: 263-266; Hansen et al. (1980), Immunogenics 10: 247-260). Two cell surface glycoprotein ligands, PD-L1 and PD-L2, have been identified and have been shown to down-regulate T cell activation and cytokine secretion upon binding to PD-1 (Freeman et al. (2000), J Exp Med 192:1027-34; Latchman et al (2001), Nat Immunol 2:261-8; Cater et al (2002), Eur J Immunol 32:634-43; Ohigashi et al (2005), Clin Cancer Res 11:2947-53). Both PD-L1 (B7-H1) and PD-L2 (B7-DC) are B7 homologs that bind to PD-1 but do not bind to other CD28 family members (Blank et al. 2004). It has also been shown that PD-L1 expression on the cell surface is upregulated by IFN-γ stimulation.

Expression of PD-L1 has been found in several murine and human cancers, including human lung cancer, ovarian cancer, colon cancer, melanoma, and various myeloma (Iwai et al. (2002), PNAS 99: 12293-7; Ohigashi et al (2005), Clin Cancer Res 11: 2947-53). Currently available results have shown that PD-L1, which is highly expressed in tumor cells, plays an important role in the immune escape of tumors by increasing the apoptosis of T cells. The researchers found that the P815 tumor cell line transfected with the PD-L1 gene can resist the lyses by specific CTL in vitro, and it is more tumorigenic and invasive after being inoculated into mice. These biological properties can be reversed by blocking PD-L1. In mice with PD-1 gene knocked out, the PD-L1/PD-1 pathway is blocked, and tumors could not formed after the inoculation of tumor cells (Dong et al. (2002), Nat Med 8: 793-800). It has also been suggested that PD-L1 may be involved in inflammation of the intestinal mucosa, and inhibition of PD-L1 prevents atrophy associated with colitis (Kanai et al. (2003), J Immunol 171: 4156-63).

Recently immunotherapy using antibodies blocking PD1/PD-L1 pathway have shown impressive clinical outcome with durable tumor regression and improved patient survival. At least two PD1 antibodies (Optivo and Kytruda) have been approved, and several PD-L1 antibodies have entered late stage clinical development. Nevertheless there is limited structural information on how these antibodies bind and block the interaction between PD1 and PD-L1, which has hindered the further development of the treatment.

SUMMARY OF THE INVENTION

The present invention provides an isolated polypeptide comprising an amino acid sequence set forth in SEQ ID NO: 4, said polypeptide is capable of specifically binding to PD-L1 and blocking the interaction of PD-L1 and PD1. In some embodiments, the polypeptide does not comprise the amino acid sequence of CDR1 and/or CDR2 of the antibody of SEQ ID NO: 1. The amino acid sequence of CDR1 of the antibody of SEQ ID NO: 1 may be selected from SEQ ID NO: 2, 8, or 24, depending on various methods for CDR definition. The amino acid sequence of CDR2 of the antibody of SEQ ID NO: 1 may be selected from SEQ ID NO: 3, 13 or 25, depending on various methods for CDR definition.

In some embodiments, the polypeptide consists of the amino acid sequence set forth in SEQ ID NO: 4 (CDR3 of the antibody of SEQ ID NO: 1).

As used herein, "PD-L1" or "hPD-L1" refers to human PD-L1. In some embodiments, it has the sequence of SEQ ID NO:7.

The invention provides a method of producing a PD-L1 binding polypeptide, comprising replacing the CDR1 and/or the CDR2 of an antibody of SEQ ID NO: 1 with a CDR of an antibody recognizing an additional target and/or with a polypeptide binding to an additional target, thereby producing a polypeptide that binds to PD-L1 and the additional target. The amino acid sequence of said CDR1 is set forth in SEQ ID NO: 2, 8 or 24, and the amino acid sequence of said CDR2 is set forth in SEQ ID NO: 3, 13 or 25.

As used herein, the term "additional target" refers to a target other than PD-L1, including but not limited to tumor antigens such as VEGFR, ERBB family proteins, CMET, or immunological checkpoint-associated antigens such as CTLA4.

The present invention also provides a PD-L1 binding polypeptide which is a variant of the antibody of SEQ ID NO: 1, in which the amino acid sequence corresponding to CDR1 and/or CDR2 of the antibody of SEQ ID NO: 1 is replaced by the CDR(s) of an antibody recognizing an additional target and/or by a polypeptide binding to an additional target, thereby the PD-L1 binding polypeptide is capable of binding to PD-L1 and the additional target. The amino acid sequence of said CDR1 is set forth in SEQ ID NO: 2, 8 or 24, and the amino acid sequence of said CDR2 is set forth in SEQ ID NO: 3, 13 or 25. The amino acid sequence of CDR3 of the antibody of SEQ ID NO: 1 is set forth in SEQ ID NO: 4.

The invention also provides a method of producing a PD-L1 binding polypeptide, comprising grafting CDR3 of the antibody of SEQ ID NO: 1 onto an antibody recognizing an additional target, thereby producing a polypeptide binding to PD-L1 and the additional target. The amino acid sequence of the CDR3 is shown in SEQ ID NO:4. A number of antibodies are known in the art that recognize additional targets, such as VEGFR, CMET or CTLA4.

The present invention also provides a method of producing a PD-L1 binding polypeptide, comprising grafting CDR3 of the antibody of SEQ ID NO: 1 onto a non-immunoglobulin having a CDR loop-like structure, thereby the non-immunoglobulin is capable of binding to PD-L1. The amino acid sequence of the CDR3 is shown in SEQ ID NO:4. The "non-immunoglobulin" is, for example, a CTLA4 protein having three loop structures, a fibronectin type III domain, and the like. In some embodiments, the CDR loop-like structure of the "non-immunoglobulin" is replaced by the CDR3 of the antibody of SEQ ID NO:1.

The present invention also provides a method for producing a PD-L1 binding polypeptide, which comprises chemically modifying a polypeptide consisting of the amino acid sequence shown by SEQ ID NO: 4 (corresponding to CDR3 of the antibody of SEQ ID NO: 1), so that it forms a stable helical structure. For example, the polypeptide can be chemically modified to form a stable helical structure similar to that exhibited by the CDR3 of the antibody of SEQ ID NO: 1 when it binds to PDL1 in the Examples. For example, the polypeptide can be chemically coupled to TBMB to form a helical structure.

The invention also provides a PD-L1 binding polypeptide produced by the above method of the invention. In some embodiments, the PD-L1 binding polypeptide of the invention comprises the amino acid sequence of any one of SEQ ID NOs: 10, 12, 15-18, 20, 23.

The present invention also provides a PD-L1 binding polypeptide which interacts (binds) with one or more of amino acid residues I54, Y56, E58, Q66 and R113 of PD-L1. In some embodiments, the binding polypeptide further interacts (binds) with one or more of amino acid residues D61, N63, V68, M115, S117, Y123, and R125 of PD-L1. In one embodiment, the PD-L1 binding polypeptide does not comprise SEQ ID NO: 2, 8 or 24, and/or SEQ ID NO: 3, 13 or 25, and/or SEQ ID NO: 4. In one embodiment, the PD-L1 binding polypeptide does not comprise SEQ ID NO: 1.

The present invention also provides a crystal complex comprising an anti-PD-L1 single domain antibody and an N-terminal immunoglobulin variable (IgV) domain of PD-L1, the amino acid sequence of said anti-PD-L1 single domain antibody is shown in SEQ ID NO: 1, the amino acid sequence of the N-terminal immunoglobulin variable (IgV) domain of the PD-L1 is shown in SEQ ID NO: 5. In some embodiments, the crystal complex belongs to space group P61, and the cell dimensions are a=b=83.13 Å, c=73.23 Å, and α=β=90°, γ=120°.

The present invention also provides a crystal of PD-L1 which belongs to the space group C2221, and has cell dimensions of a=72.24 Å, b=91.51 Å, c=143.83 Å, and α=β=γ=90°.

The present invention also provides an atomic coordinate set or a subset thereof of the crystal structure of the above crystal complex of the present invention. In some embodiments, it is the atomic coordinates set provided in Appendix I or a subset thereof.

The present invention also provides a computer readable medium having recorded thereon data representing atomic coordinates or a subset thereof of a crystal structure of the above crystal complex of the present invention; or atomic coordinates provided in Appendix I or a subset thereof; and/or a model generated using the atomic coordinates.

The present invention provides a computer-assisted method for identifying a compound that binds to PD-L1, comprising the steps of:
i) docking the structure of the candidate compound with the structure defined by the atomic coordinates of the crystal structure of the invention or a subset thereof, or the atomic coordinates provided in Appendix I, or a subset thereof, and
ii) identify candidate compounds that can bind to PD-L1.

In some embodiments, the subset of atomic coordinates is the atomic coordinates corresponding to an N-terminal immunoglobulin variable (IgV) domain of PD-L1.

In some embodiments, the method further comprises synthesizing or obtaining the identified candidate compound and determining whether the compound binds to PD-L1. Preferably, the compound blocks the binding of PD-L1 to PD1.

The present invention provides a method of producing a compound that binds to PD-L1, comprising designing a compound molecule that binds to at least a portion of an interface defined by amino acid residues I54, Y56, E58, Q66, and R113 of PD-L1, synthesizing the compound molecule, and determining whether the compound binds to PD-L1. In some embodiments, the method comprises designing a compound molecule that binds to at least a portion of an interface defined by amino acid residues I54, Y56, E58, Q66, R113, D61, N63, V68, M115, S117, Y123, and R125 of PD-L1, synthesizing the compound molecule, and determining whether the compound binds to PD-L1. Preferably, the compound blocks the binding of PD-L1 to PD1.

The present invention provides an anti-PD-L1 antibody that binds to a conformational epitope on PD-L1 defined by amino acid residues I54, Y56, E58, Q66 and R113. In some embodiments, the anti-PD-L1 antibody binds to a conformational epitope on PD-L1 defined by amino acid residues I54, Y56, E58, Q66, R113, D61, N63, V68, M115, S117, Y123, and R125.

Nucleic Acid, Vector, Host Cell

In another aspect, the invention involves a nucleic acid molecule encoding a PD-L1 binding polypeptide of the invention. The nucleic acid of the invention may be RNA, DNA or cDNA. According to one embodiment of the invention, the nucleic acid of the invention is a substantially isolated nucleic acid.

The nucleic acids of the invention may also be in the form of a vector, which may be present in the vector and/or may be part of a vector such as a plasmid, a cosmid or YAC. The vector may especially be an expression vector, i.e., a vector that provides expression of the PD-L1 binding polypeptide in vitro and/or in vivo (i.e., in a suitable host cell, host organism, and/or expression system). The expression vector typically comprises at least one nucleic acid of the invention operably linked to one or more suitable expression control elements (e.g., promoters, enhancers, terminators, etc.). Selection of the elements and their sequences for expression in a particular host is common knowledge to those skilled in the art. Specific examples of regulatory elements and other elements useful or essential for the expression of the PD-L1 binding polypeptides of the invention, such as promoters, enhancers, terminators, integration factors, selection markers, leader sequences, reporter genes.

The nucleic acids of the invention may be prepared or obtained in a known manner (for example by automated DNA synthesis and/or recombinant DNA techniques) based on information about the amino acid sequence of the polypeptides of the invention presented herein, and/or may be separated from a suitable natural sources.

In another aspect, the invention involves a host cell that expresses or is capable of expressing one or more of the PD-L1 binding polypeptides of the invention and/or comprises a nucleic acid or vector of the invention. Preferred host cell of the invention are bacterial cell, fungal cell or mammalian cell.

Suitable bacterial cell includes cell of Gram-negative bacterial strains (e.g., *Escherichia coli* strains, *Proteus* strains, and *Pseudomonas* strains) and Gram-positive bacterial strains (eg, *Bacillus* strains, *Streptomyces* strains, *Staphylococcus* strains, and *Lactococcus* strains.

Suitable fungal cell includes cell of the species of *Trichoderma, Neurospora*, and *Aspergillus*; or includes cell of the species of *Saccharomyces* (e.g., *Saccharomyces cerevisiae*), *Schizosaccharomyces* (e.g. *Schizosaccharomyces pombe*), *Pichia* (e.g. *Pichia pastoris* and *Pichia methanolica*) and *Hansenula*.

Suitable mammalian cell includes, for example, HEK293 cell, CHO cell, BHK cell, HeLa cell, COS cell, and the like.

However, amphibian cell, insect cell, plant cell, and any other cell in the art for expressing a heterologous protein can also be used in the present invention.

The invention also provides a method of preparing a PD-L1 binding polypeptide of the invention, generally comprising the steps of:

cultivating the host cell of the present invention under conditions enabling the expression of the PD-L1 binding polypeptide of the present invention; and recovering the PD-L1 binding polypeptide expressed by the host cell from the culture; and optionally further purifying and/or modifying the PD-L1 binding polypeptide of the invention.

In a preferred embodiment, the PD-L1 binding polypeptides of the invention are produced using mammalian cells.

The PD-L1 binding polypeptide of the invention may be produced in an intracellular manner (e.g., in the cytoplasm, in the periplasm, or in inclusion bodies) in a cell as described above, followed by isolation from the host cell and optionally further purification; or it may be produced in an extracellular manner (for example in a medium in which the host cells are cultured), followed by isolation from the medium and optionally further purification.

Methods and reagents for recombinant production of polypeptides, such as specific suitable expression vectors, transformation or transfection methods, selection markers, methods for inducing protein expression, culture conditions, and the like, are known in the art. Similarly, protein separation and purification techniques suitable for the methods of making the PD-L1 binding polypeptides of the invention are well known to those skilled in the art.

However, the PD-L1 binding polypeptide of the invention can also be obtained by other methods of protein production known in the art, such as chemical synthesis, including solid phase or liquid phase synthesis.

Immunoconjugate

In another aspect, the invention involves a PD-L1 binding polypeptide conjugated to a therapeutic moiety, such as a cytotoxin, a radioisotope, or a biologically active protein. These conjugates are referred to herein as "immunoconjugates." An immunoconjugate comprising one or more cytotoxins is referred to as an "immunotoxin". Cytotoxins include any agent that is detrimental to cells (e.g., killing cells). Examples include: paclitaxel, cytochalasin B, gramicidin D, ethidium bromide, ipecaine, mitomycin, etoposide, teniposide, vincristine, vinblastine, colchicine, doxorubicin, daunorubicin, dihydroxy anthrax dione, mitoxantrone, phosfomycin, actinomycin D, 1-dehydrotestosterone, glucocorticoid, Pru Cain, tetracaine, lidocaine, propranolol and puromycin and their analogs or homologs.

Therapeutic agents useful for conjugation also include, for example, antimetabolites (e.g., methotrexate, 6-mercaptopurine, 6-thioguanine, cytarabine, 5-fluorouracil, aminomethamine), alkylating agents (e.g., nitrogen mustard, chlorambucil, phenylalanine mustard, carmustine (BSNU) and lomustine (CCNU), cyclophosphamide, busulfan, dibromomannitol, streptozotocin, mitomycin C and cis-dichlorodiamine platinum (II) (DDP) cisplatin), anthracyclines (e.g., daunorubicin (formerly known as daunorubicin) and antibiotics (e.g., actinomycin D (formerly known as actinomycin), bleomycin, phosfomycin, and acitretin (AMC)), and antimitotic agents (e.g., vincristine and vinblastine).

Other preferred examples of therapeutic cytotoxins which can be conjugated to the PD-L1 binding polypeptide of the present invention include doxorubicin, calicheamicin, maytansin, auristatin, and derivatives thereof.

Cytotoxin can be conjugated to a PD-L1 binding polypeptide of the invention using linker techniques in the art. Examples of linker that have been used to conjugate cytotoxins to PD-L1 binding polypeptides include, but are not limited to, guanidine, thioether, ester, disulfide, and peptide-containing linkers. Alternatively, for example, a linker that is susceptible to cleavage by low pH or cleavage by a protease in a lysosomal compartment, such as a protease preferentially expressed in tumor tissues, such as cathepsins (e.g., cathepsins B, C, D), may be selected.

For further discussion of types of cytotoxins, linkers and methods for conjugating therapeutic agents to antibodies, see Saito, G. et al. (2003) Adv. Drug Deliv. Rev. 55:199-215; Trail, P A et al. (2003).) Cancer. Immunol. Immunother. 52:328-337; Payne, G. (2003) Cancer Cell 3: 207-212; Allen, T M (2002) Nat. Rev. Cancer 2: 750-763; Pastan, I. and Kreitman, R J (2002) Curr. Opin. Investig. Drugs 3: 1089-1091; Senter, P D and Springer, C J (2001) Adv. Drug Deliv. Rev. 53: 247-264.

The PD-L1 binding polypeptides of the invention may also be conjugated to a radioisotope to produce a cytotoxic radiopharmaceutical, also known as a radioimmunoconjugate. Examples of radioisotope that can be conjugated to diagnostic or therapeutically used antibodies include, but are not limited to, iodine$^{131}$, indium$^{111}$, hydrazine$^{90}$, and hydrazine$^{177}$. Methods of preparing radioimmunoconjugates have been established in the art. Examples of radioimmunoconjugate are commercially available, including Zevalin™ (IDEC Pharmaceuticals) and Bexxar™ (Corixa Pharmaceuticals), and radioimmunoconjugates can be prepared using similar methods using the PD-L1 binding polypeptides of the invention.

The PD-L1 binding polypeptides of the invention can also be conjugated to proteins having the desired biological activity and can be used to modify specific biological responses. Such biologically active proteins include, for example, enzymatically active toxins or active fragments thereof, such as abrin, ricin A, *Pseudomonas* exotoxin or diphtheria toxin; proteins such as tumor necrosis factor or interferon-γ; or biological response modifiers such as lymphokine, interleukin-1 ("IL-1"), interleukin-2 ("IL-2"), interleukin-6 ("IL-6"), interleukin-10 ("IL-10"), granulocyte macrophage colony-stimulating factor ("GM-CSF"), granulocyte colony-stimulating factor ("G-CSF") or other immune factors such as IFN.

Techniques for conjugating such therapeutic moieties to antibody molecules are well known, see, for example, Arnon et al, "Monoclonal Antibodies For Immunotargeting Of Drugs In Cancer Therapy", Monoclonal Antibodies And Cancer Therapy, Reisfeld et al (ed.), pp 0.243-56 (Alan R. Liss, Inc. 1985); Hellstrom et al, "Antibodies For Drug Delivery", Controlled Drug Delivery (2nd Ed.), Robinson et al. (ed.), pp. 623-53 (Marcel Dekker, Inc. 1987); Thorpe, "Antibody Carriers Of Cytotoxic Agents In Cancer Therapy: A Review", Monoclonal Antibodies '84: Biological And Clinical Applications, Pinchera et al. (ed.), pp. 475-506 (1985); "Analysis, Results, And Future Prospective Of The Therapeutic Use Of Radiolabeled Antibody In Cancer Therapy", Monoclonal Antibodies For Cancer Detection And Therapy, Baldwin et al (ed.), pp. 303-16 (Academic Press 1985), and Thorpe et al, "The Preparation And Cytotoxic Properties Of Antibody-Toxin Conjugates," Immunol. Rev., 62: 119-58 (1982).

Pharmaceutical Compositions

In another aspect, the present invention provides a composition, e.g., a pharmaceutical composition, containing one or a combination of the PD-L1 binding polypeptide and/or the compound that binds to PD-L1 and/or anti-PD-L1 antibody of the present invention, formulated together with a pharmaceutically acceptable carrier. Such composition may include one or a combination of (e.g., two or more different) PD-L1 binding polypeptide or immunoconjugate of the invention. For example, a pharmaceutical composition of the invention can comprise a combination of antibody molecules that bind to different epitopes on the target antigen.

Pharmaceutical compositions of the invention also can be administered in combination therapy, i.e., combined with other agents. For example, the combination therapy can include a PD-L1 binding polypeptide or compound of the present invention combined with at least one other anti-tumor agent. For example, PD-L1 binding polypeptide or compound or antibody of the invention may be administered in combination with antibody targeting other tumor-specific antigen. Said antibody targeting other tumor-specific antigen includes, but is not limited to anti-EGFR antibody, anti-EGFR variant antibody, anti-VEGFa antibody, anti-HER2 antibody, or anti-CMET antibody. Preferably, said antibody is monoclonal.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, or immunoconjugate, may be coated in a material to protect the compound from the action of acid and other natural conditions that may inactivate the compound.

The pharmaceutical compound of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

These compositions may also contain adjuvants such as preservatives, wetting agents, emulsifying agents and dispersing agents.

Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carrier includes sterile aqueous solution or dispersion and sterile powder for the extemporaneous preparation of sterile injectable solution or dispersion. The use of such media and agents for pharmaceutically active substances is known in the art. Except those is incompatible with the active compound, any conventional media or agent can be used in the pharmaceutical compositions of the invention. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high concentration of drug. The carrier can be a solvent or dispersion medium containing, for example, water, ethanol, polyol (for example, glycerol, propylene glycol, and liquid polyethylene glycol, and the like), and the suitable mixtures thereof. The proper fluidity can be maintained, for example, by the use of a coating such as lecithin, by the maintenance of the required particle size in the case of dispersion and by the use of surfactants.

Sterile injectable solutions can be prepared by incorporating the active compound in the required amount in an appropriate solvent with one or a combination of ingredients listed above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01% to about 99% of active ingredient, preferably from about 0.1% to about 70%, most preferably from about 1% to about 30% of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are limited by and directly dependent on (a) the unique characteristics of the active compound and the particular therapeutic effect to be achieved, and (b) the limitations inherent in the art of compounding such an active compound for the treatment of sensitivity in individuals.

For administration of the PD-L1 binding polypeptide or compound or antibody of the present invention, the dosage ranges from about 0.0001 to 100 mg/kg, and more usually 0.01 to 20 mg/kg, of the subject body weight. For example dosages can be 0.3 mg/kg body weight, 1 mg/kg body weight, 3 mg/kg body weight, 5 mg/kg body weight, 10 mg/kg body weight or 20 mg/kg body weight or within the range of 1-20 mg/kg. An exemplary treatment regime entails administration once per week, once every two weeks, once every three weeks, once every four weeks, once a month, once every 3 months or once every three to 6 months, or with a short administration interval at the beginning (such as once per week to once every three weeks), and then an extended interval later (such as once a month to once every three to 6 months).

Alternatively, the PD-L1 binding polypeptide or compound or antibody of the present invention can be administered as a sustained release formulation, in which case less frequent administration is required. Dosage and frequency vary depending on the half-life of the molecule in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective amount" of the PD-L1 binding polypeptide or compound or antibody of the present invention preferably results in a decrease in severity of disease symptoms, an increase in frequency and duration of disease symptom-free periods, or a prevention of impairment or disability due to the disease affliction. For example, for the treatment of PD-L1 relating tumors, a "therapeutically effective amount" preferably inhibits cell growth or tumor growth by at least about 10%, preferably at least about 20%, more preferably by at least about 30%, more preferably by at least about 40%, more preferably by at least about 50%, even more preferably by at least about 60%, more preferably by at least about 70%, and still more preferably by at least about 80% relative to untreated subjects. The ability to inhibit tumor growth can be evaluated in an animal model system predictive of efficacy in human tumors. Alternatively, this property of a composition can be evaluated by examining the ability of the compound to inhibit cell growth; such inhibition can be determined in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for the PD-L1 binding polypeptide or compound or antibody of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, the PD-L1 binding polypeptide or compound or antibody of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable microinfusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the PD-L1 binding polypeptide or compound or antibody of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al); mannosides (Umezawa et al., (1988) Biochem. Biophys. Res. Commun. 153:1038): antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J. Physiol. 1233: 134); p 120 (Schreier et al. (1994) J Biol. Chem. 269:9090): see also K. Keinanen; M. L. Laukkanen (1994) FEBS Lett. 346:123; J J. Killion; L J. Fidler (1994) Immunomethods 4:273.

Preventing and Treating of Diseases

In another aspect, the present invention provides the use of the PD-L1 binding polypeptide or compound or antibody, nucleic acid, host cell, immunoconjugate and pharmaceutical composition of the invention for preventing and/or treating PD-L1 relating diseases, as well as the corresponding methods. PD-L1 relating diseases that can be prevented and/or treated with the PD-L1 binding polypeptide or compound or antibody of the invention are described in detailed as follows.

Cancer

Blockade of PD-L1 by a PD-L1 binding polypeptide or compound or antibody of the invention can enhance an immune response to cancer cells in a patient. PD-L1 is enriched in a variety of human cancers (Dong et al. (2002) Nat Med. 8:78 7-9). The interaction of PD-1 with PD-L1 leads to a decrease in lymphocytes infiltrating tumors, a decrease in T cell receptor-mediated proliferation, and an immune escape of cancer cells (Dong et al. (2003) J Mol Med 81:281-7; Blank Et al. (2004) Cancer Immunol Immunother [epub]; Konishi et al (2004) Clin Cancer Res 10: 5094-5100). Inhibition of local interactions between PD-L1 and PD-1 reverses immunosuppression, and when PD-L2 interacts with PD-1 is also blocked, the effects are synergistic (Iwai et al. (2002) PNAS 99:12293-7 Brown et al. (2003) J Immunol 170:1 257-66). The PD-L1 binding polypeptide or compound or antibody of the invention may be used alone to inhibit the growth of cancerous tumors. Or as described below, the PD-L1 binding polypeptide or compound or antibody of the invention may be used in conjunction with other anti-tumor therapies, for example, in combination with other immunogenic agents, standard cancer treatments, or other antibodies molecule.

Accordingly, in one embodiment, the invention provides a method of preventing and/or treating cancer in a subject, comprising administering to the subject a therapeutically effective amount of the PD-L1 binding polypeptide or compound or antibody of the invention so as to inhibit growth of tumor cells in the subject.

Preferred cancers which may be prevented and/or treated using the PD-L1 binding polypeptide or compound or antibody of the invention include cancers typically responsive to immunotherapy. Non-limiting examples of preferred cancers for treatment include lung cancer, ovarian cancer, colon cancer, rectal cancer, melanoma (e.g., metastatic malignant melanoma), renal cancer, bladder cancer, breast cancer, liver cancer, lymphoma, hematological malignancy, head and neck cancer, glioma, gastric cancer, nasopharyngeal cancer, laryngeal cancer, cervical cancer, corpus carcinoma, osteosarcoma. Examples of other cancers that may be treated using the methods of the invention include bone cancer, pancreatic cancer, prostatic cancer, skin cancer, cancer of the head or neck, cutaneous or intraocular malignant melanoma, uterine cancer, cancer of the anal region, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stein glioma, pituitary adenoma, Kaposi's sarcoma, epidermoid cancer, squamous cell cancer, T-cell lymphoma, environmentally induced cancers including those induced by asbestos, and combinations of said cancers. The invention is also useful for the treatment of metastatic cancer, particularly metastatic carcinoma expressing PD-L1 (Iwai et al. (2005) Int Immunol 17: 133-144).

Optionally, the PD-L1 binding polypeptide or compound or antibody of the invention can be combined with an immunogenic agent, such as cancerous cells, purified tumor antigens (including recombinant proteins, peptides, and carbohydrate molecules), cells, and cells transfected with genes encoding immune stimulating cytokines (He et al. (2004) J. Immunol. 173:4919-28). Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

In humans, some tumors have been shown to be immunogenic such as melanomas. It is anticipated that by raising the threshold of T cell activation by blocking PD-L1 with PD-L1 binding polypeptide of the invention, it is possible to activate tumor responses in the host. PD-L1 blocking agent (such as PD-L1 antibody, e.g., the PD-L1 binding polypeptide of the invention) is likely to be most effective when combined with a vaccination protocol. Many experimental strategies for vaccination against tumors have been devised (see Rosenberg, S., 2000, Development of Cancer Vaccines, ASCO Educational Book Spring: 60-62; Logothetis, C, 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, Cancer: Principles and Practice of Oncology. Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) Proc. Natl. Acad. Sd U.S.A. 90: 3539-43).

The study of gene expression and large-scale gene expression patterns in various tumors has led to the definition of so-called tumor specific antigens (Rosenberg, S A (1999) Immunity 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. The PD-L1 binding polypeptide or compound or antibody of the invention may be used in combination with recombinant produced tumor-specific proteins and/or peptides in order to generate an immune response to these proteins. These proteins are normally regarded by the immune system as autoantigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et al. (1994) Science 266: 2011-2013). Tumor antigen may also be "neo-antigens" expressed in cancer cells because of somatic mutations that alter protein sequence or create fusion proteins between two unrelated sequences (i.e. bcr-abl in the Philadelphia chromosome).

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in combination with PD-L1 blocking agent (such as PD-L1 antibody, e.g., the PD-L1 binding polypeptide or compound or antibody of the invention) is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) Science 269:1585-1588; Tamura, Y. et al. (1997) Science 278:117-120).

Dendritic cells (DCs) are potent antigen presenting cells that can be used to prime antigen-specific responses. DCs can be produced ex vivo and loaded with various protein and peptide antigens as well as tumor cell extracts (Nestle, F. et al. (1998) Nature Medicine 4: 328-332). DCs may also be transduced by genetic means to express these tumor antigens as well. DCs have also been fused directly to tumor cells for the purposes of immunization (Kugler, A. et al. (2000) Nature Medicine 6:332-336). As a method of vaccination, DC immunization may be effectively combined with PD-L1 blocking agent (such as PD-L1 antibody, e.g., the PD-L1 binding polypeptide or compound or antibody of the invention) to activate more potent anti-tumor responses.

CAR-T (Chimeric Antigen Receptor T-Cell Immunotherapy) is another cell therapy for treating tumors. Chimeric Antigen Receptor T-Cell (CAR-T cells) are T cells from a patient that have been genetically infected with a chimeric protein of an antigen-binding moiety of an antibody against certain tumor antigen coupled with CD3-ζchain or intracellular portion of FcεRIγ for expressing a chimeric antigen receptor (CAR). Also, co-stimulate signaling sequence may be introduced for increasing cytotoxic activity, proliferation and survival of T cells, and promoting the release of cytokines. After reprogramming, T cells from the patient expanded in vitro to produce a large number tumor-specific CAR-T cells which are then transfused back into the patient for treating tumor. PD-L1 blocking agent (such as PD-L1 antibody, e.g., the PD-L1 binding polypeptide or compound or antibody of the invention) may be used in combination with CAR-T cell therapy for activate stronger anti-tumor response.

The PD-L1 binding polypeptide or compound or antibody of the invention may also be combined with standard cancer treatments. The PD-L1 binding polypeptide or compound or antibody of the invention may be effectively combined with chemotherapeutic regimes. In these examples, it can reduce the dose of chemotherapeutic agent administered (Mokyr, M. et al. (1998) Cancer Research 58: 5301-5304). An example of such combination is the treatment of melanoma with a PD-L1 binding polypeptide or compound or antibody in combination with amylamidine. Another example of such combination is the treatment of melanoma with a PD-L1 binding polypeptide or compound or antibody in combination with interleukin-2 (IL-2). The scientific rationale behind the combined use of the PD-L1 binding polypeptide or compound or antibody of the invention and chemotherapy is that cell death, that is a consequence of the cytotoxic action of most chemotherapeutic compounds, should result in increased levels of tumor antigen in the antigen presentation pathway. Other combination therapies that can synergize with PD-L1 by cell death have radiotherapy, surgery, and hormone deprivation. Each of these protocols creates a source of tumor antigen in the host. Angiogenesis inhibitors may also be combined with the PD-L1 binding polypeptide or compound or antibody of the invention. Inhibition of angiogenesis leads to tumor cell death which may feed tumor antigen into host antigen presentation pathways.

The PD-L1 binding polypeptide or compound or antibody of the invention can also be used in combination with antibody against other tumor-specific antigen. Said antibody against other tumor-specific antigen includes but not limited to anti-EGFR antibody, anti-EGFR variant antibody, anti-VEGFa antibody, anti-HER2 antibody, or anti-CMET antibody. Preferably, said antibody is an monoclonal antibody.

The PD-L1 binding polypeptide or compound or antibody of the invention can also be used in combination with bispecific antibodies that target Fc alpha or Fc gamma receptor-expressing effectors cells to tumor cells (see, e.g., U.S. Pat. Nos. 5,922,845 and 5,837,243). Bispecific antibodies can be used to target two separate antigens. For example anti-Fc receptor/anti-tumor antigen (e.g., Her-2/neu) bispecific antibodies have been used to target macrophages to sites of tumor. This targeting may more effectively activate tumor specific responses. The T cell aspect of these responses would be augmented by the use of PD-L1 blocking agent. Alternatively, antigen may be delivered directly to DCs by the use of bispecific antibodies which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al. (1986) J. Exp. Med. 163: 1037-1050), IL-10 (Howard, M. & O'Garra, A. (1992) Immunology Today 13: 198-200), and Fas ligand (Hahne, M. et al. (1996) Science 274: 1363-1365). Antibodies to each of these entities may be used in combination with the PD-L1 binding polypeptide or compound or antibody of the invention to counteract the effects of the immunosuppressive agent and favor tumor immune responses by the host.

Other antibodies which may be used to activate host immune responsiveness can be used in combination with the PD-L1 binding polypeptide or compound or antibody of the present invention. Anti-CD40 antibodies are able to substitute effectively for T cell helper activity (Ridge, J. et al. (1998) Nature 393: 474-478) and can be used in conjunction with PD-L1 binding polypeptide of the invention (Ito, N. et. al (2000) Immunobiology 201(5)527-40). Activating antibodies to T cell costimulatory molecules such as OX-40 (Weinberg, A. et al. (2000) Immunol 164: 2160-2169), 4-1BB (Melero, I. et al. (1997) Nature Medicine 3: 682-685 (1997), and ICOS (Hutloff, A. et al. (1999) Nature 397: 262-266) as well as antibodies which block the activity of negative costimulatory molecules such as CTLA-4 (e.g., U.S. Pat. No. 5,811,097) or BTLA (Watanabe, N. et al. (2003) Nat Immunol 4:670-9), B7-H4 (Sica, G L et al. (2003) Immunity 18:849-61) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. PD-L1 blocking agent can be used to increase the effectiveness of the donor engrafted tumor specific T cells. There are also several experimental treatment protocols that involve ex vivo activation and expansion of antigen specific T cells and adoptive transfer of these cells into recipients in order to antigen-specific T cells against tumor (Greenberg, R. & Riddell, S. (1999) Science 285: 546-51). These methods may also be used to activate T cell responses to infectious agents such as CMV. Ex vivo activation in the presence of the PD-L1 binding polypeptide or compound or antibody of the invention may be expected to increase the frequency and activity of the adoptively transferred T cells. Accordingly, the present invention also provides a method of activating an immune cell (such as PBMC or T cell) ex vivo, comprising contacting the immune cell with a PD-L1 binding polypeptide or compound or antibody of the present invention.

Infectious Diseases

Other methods of the invention are used to treat patients that have been exposed to particular toxins or pathogens. Accordingly, another aspect of the invention provides a method of preventing or treating an infectious disease in a subject, comprising administering the PD-L1 binding polypeptide or compound or antibody of the invention to the subject.

Similar to its application to tumors as discussed above, PD-L1 blocking agent can be used alone, or as an adjuvant, in combination with vaccines, to stimulate the immune response to pathogens, toxins, and autoantigens. Examples of pathogens for which this therapeutic approach may be particularly useful, include pathogens for which there is currently no effective vaccine, or pathogens for which conventional vaccines are less than completely effective. These include, but are not limited to HTV, Hepatitis (A, B, & C), Influenza, Herpes, *Giardia*, Malaria, *Leishmania, Staphylococcus aureus, Pseudomonas Aeruginosa*. PD-L1 blocking agent is particularly useful against established infections by agents such as HIV that present altered antigens over the course of the infections. These novel epitopes are recognized as foreign at the time of administration of anti-human PD-L1 antibody, thus provoking a strong T cell response that is not dampened by negative signals of PD-L1.

Some examples of pathogenic viruses causing infections treatable by methods of the invention include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the invention include *chlamydia*, rickettsial bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, and Lyme's disease bacteria.

Some examples of pathogenic fungi causing infections treatable by methods of the invention include *Candida* (*albicans, krusei, glabrata, tropicalis*, etc.), *Cryptococcus neoformans, Aspergillus* (*fumigatus, niger*, etc.), Genus *Mucorales* (*mucor, absidia*, rhizophus), *Sporothrix schenkii, Blastomyces dermatitidis, Paracoccidioides brasiliensis, Coccidioides immitis* and *Histoplasma capsulatum*.

Some examples of pathogenic parasites causing infections treatable by methods of the invention include *Entamoeba histolytica, Balantidium coli*, Naegleriafowleri, *Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi, Nippostrongylus brasiliensis*.

In all of the above methods, PD-L1 blocking agent can be combined with other forms of immunotherapy such as cytokine treatment (e.g., interferons, GM-CSF, G-CSF, IL-2), or bispecific antibody therapy, which provides for enhanced presentation of tumor antigens (see, e.g., Holliger (1993) Proc. Natl. Acad. Sci USA 90:6444-6448; Poljak (1994) Structure 2:1121-1123).

Autoimmune Response

Anti-PD-L1 antibodies can stimulate and amplify autoimmune responses. Therefore, it is contemplated to utilize the PD-L1 binding polypeptide or compound or antibody of the invention in combination with a variety of autoproteins to design a vaccination regimen to effectively produce an immune response against these autoproteins for use in disease treatment.

For example, Alzheimer involves the improper accumulation of $A\beta$ peptides in amyloid deposits in the brain; an antibody response to amyloid can clear these amyloid deposits (Schenk et al. (1999) Nature 400: 173-177). Other autoproteins can also be used as targets, such as IgE, which is involved in the treatment of allergies and asthma, and TNFα, which is involved in rheumatoid arthritis. Finally, the PD-L1 binding polypeptide or compound or antibody can be utilized to induce an antibody response to various hormones. The response of neutralizing antibody to reproductive hormone can be used for contraception. The response of neutralizing antibody to hormone and other soluble factor required for specific tumor growth can also be considered as a possible vaccination target.

As described above, a similar method using a PD-L1 binding polypeptide or compound or antibody can be used to induce a therapeutic autoimmune response to treat patients with inappropriate accumulation of autoantigen, such as amyloid deposit including Aβ in the Alzheimer, cytokine such as TNFα and IgE.

Chronic Inflammatory Disease

The PD-L1 binding polypeptide or compound or antibody of the present invention can also be used for the treatment of diseases such as chronic inflammatory diseases such as lichen planus, T cell-mediated chronic inflammatory skin mucosal disease (Youngnak-Piboonratanakit et al (2004) Immunol Letters 94; 215-22). Accordingly, in one aspect, the invention provides a method of eliminating chronic inflammatory disease with T cells, comprising administering the PD-L1 binding polypeptide or compound or antibody of the invention to a subject.

Vaccine Adjuvant

One aspect of the invention provides the use of a PD-L1 binding polypeptide or compound or antibody of the invention as a vaccine adjuvant. By co-administering a PD-L1 binding polypeptide or compound or antibody and a target antigen (e.g., a vaccine), a PD-L1 binding polypeptide can be utilized to increase a specific immune response against the antigen.

Accordingly, one aspect of the invention provides a method of enhancing an immune response to an antigen in a subject, comprising administering to the subject: (i) an antigen; and (ii) a PD-L1 binding polypeptide or compound or antibody of the invention, such that rhe immune response to the antigen in the subject is enhanced. The antigen may be, for example, a tumor antigen, a viral antigen, a bacterial antigen, or an antigen derived from a pathogen. Non-limiting examples of such antigens include those described in the above sections, such as the tumor antigen (or tumor vaccine) described above, or antigen from the above viruses, bacteria or other pathogens.

Detection

In another aspect, the present invention provides a method of detecting the presence of PD-L1 or the expression level of PD-L1 in a biological sample, comprising under the condition of capable of forming a complex of the PD-L1 binding polypeptide or compound or antibody of the present invention and PD-L1, contacting the biological sample and the control sample with the PD-L1 binding polypeptide or compound or antibody of the present invention. The formation of the complex is then detected, wherein the difference in complex formation between the biological sample and the control sample is indicative of the presence of PD-L1 or the expression level of PD-L1 in the sample.

It has been found that PD-L1 is highly expressed in many tumors, or tumors or pathogens cause high expression of PD-L1 by immune cells in the vicinity of the tumor or pathogen infection site. Therefore, the PD-L1 binding polypeptide or compound or antibody of the present invention can be used for diagnosing a disease associated with PD-L1, such as a tumor or an infectious disease (such as a viral infection) associated with high expression of PD-L1.

In some embodiments, the PD-L1 binding polypeptide or compound or antibody of the invention is further conjugated to a fluorescent dye, chemical, polypeptide, enzyme, isotope, tag, or the like that can be used to detect or be detectable by other agents.

Kit

Also included within the scope of the invention is a kit comprising the PD-L1 binding polypeptide or compound or antibody, immunoconjugate or pharmaceutical composition of the invention, and an instruction for use. The kit may further comprise at least one additional agent or one or more additional PD-L1 binding polypeptides or compounds or antibodies of the invention (e.g., binding polypeptides that bind to different epitopes of PD-L1). Kit typically includes a label indicating the intended use of the contents of the kit. The term label includes any written or recorded material provided on or with the kit or otherwise provided with the kit.

FIGURE DESCRIPTION

FIG. 1. shows binding specificity of KN035 towards various members of B7/CD28 superfamily. HEK293T cells were transfected with PD-L1-EGFP, PD-L2-EGFP, mPD-L1-EGFP, B7H3-EGFP, ICOS-EGFP and B7H4-EGFP, respectively and then incubated with APC anti-human IgG Fc antibody or KN035-Fc+APC anti-human IgG Fc antibody with the signal detected by flow cytometer. KN035 only shows high binding affinity towards hPD-L1.

Figure 2:
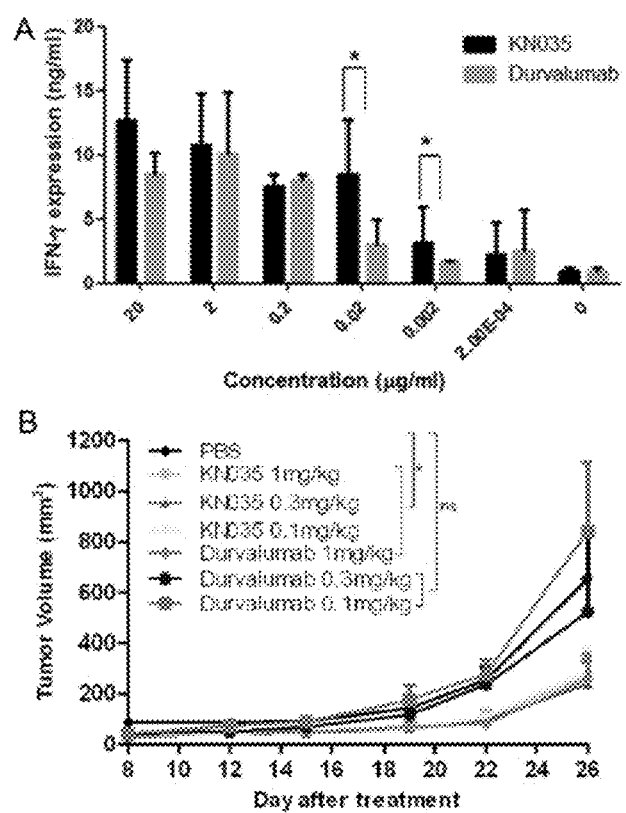

FIG. 2. shows activity assay of KN035. (A) The levels of IFN-γ secreted by CD4+ T cells following the treatment of KN035 and Durvalumab at different concentrations. (B) Tumor suppressive activity of KN035 was assessed in a xenograft tumor model, in which mixture of A375-hPD-L1 cells and PBMC at 4:1 ratio were inoculated into mice with tumor growth continuous measured. KN035 shows strong antitumor effect at all three doses, while Durvalumab only shows strong anti-tumor activity at high concentration (1 mg/kg). *$p<0.05$; ns, not significant. KN035 here represents fusion protein fused with Fc domain.

Figure 3:
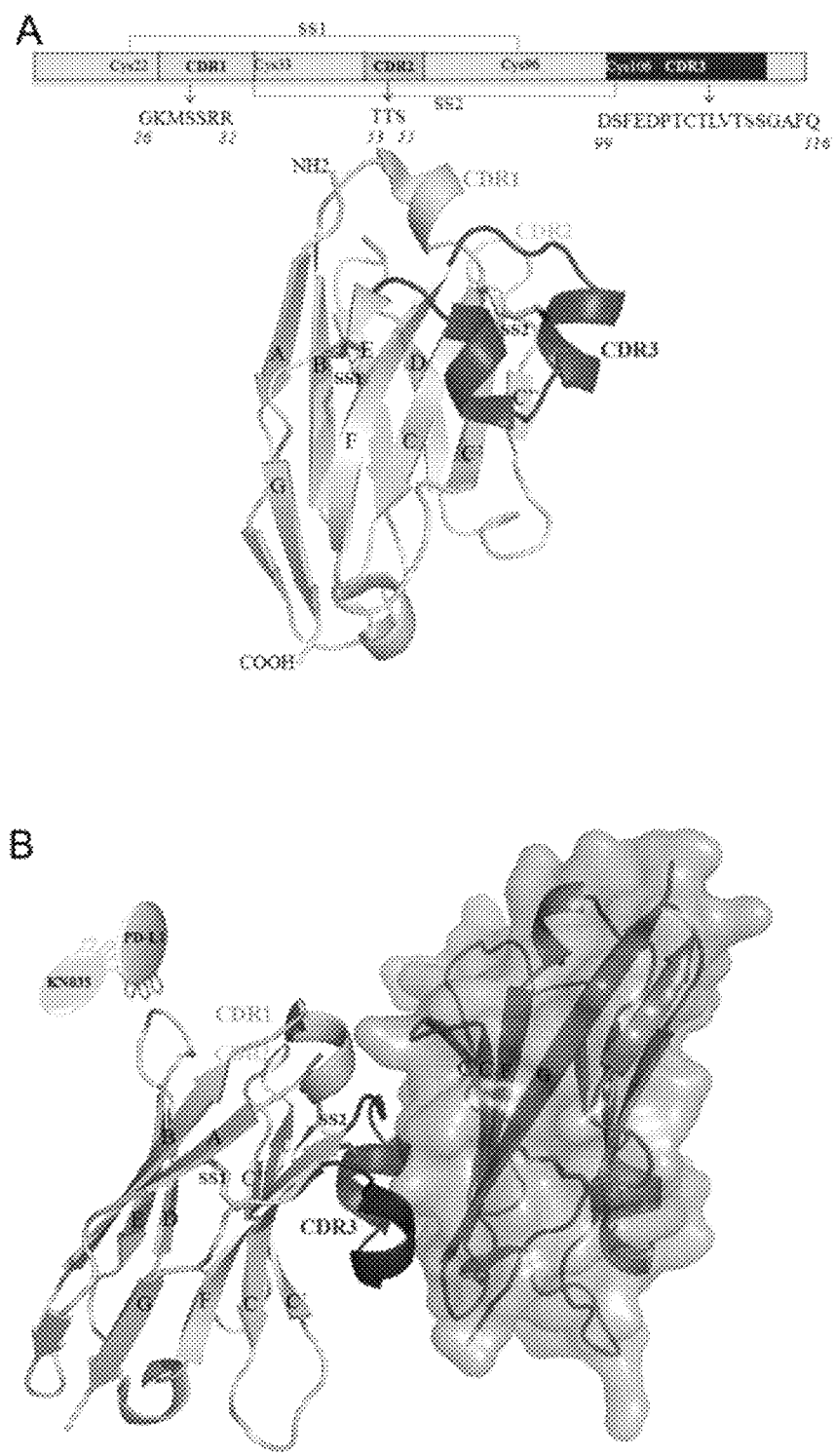

FIG. 3. shows overall structure of KN035/hPD-L1. (A) Sequence and structure of KN035. The locations of the CDR1, CDR2 and CDR3 are indicated as well as the positions of disulphide bridges (SS1 and SS2). (B) Structure of the KN035/PD-L1 complex. PD-L1 is shown as slate semi-transparent surface. The secondary structures of PD-L1 and KN035 are numbered as previously described.

Figure 4:
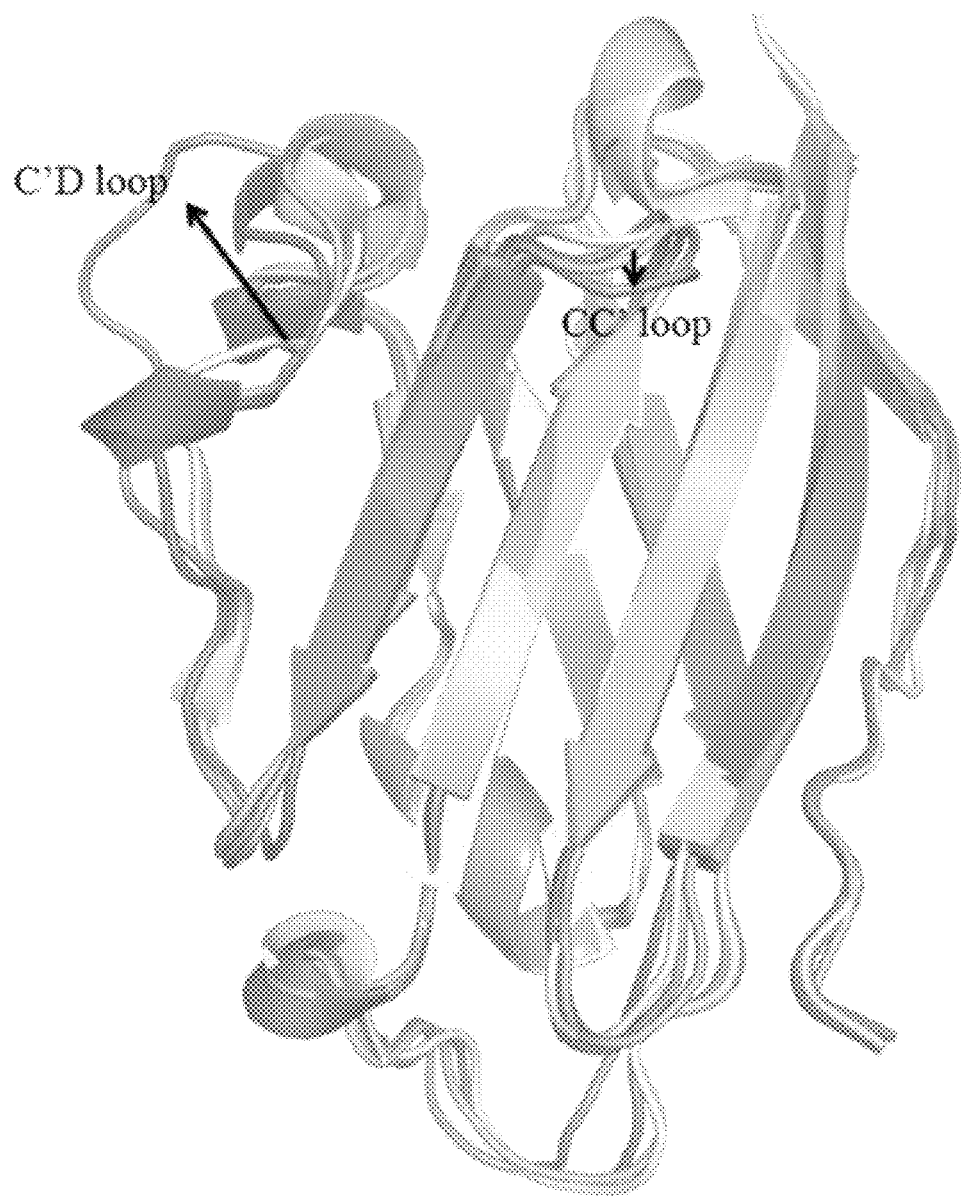

FIG. 4. shows overlaid structures of the IgV domains of PD-L1. The Ig V domains of PD-L1 from PD-1/PD-L1 complex (PDB: 4ZQK, magenta) and KN035/PD-L1, free PD-L1 structure solved herein and previous reported PD-L1 (PDB: 5C3T) structures are superposed.

Figure 5:
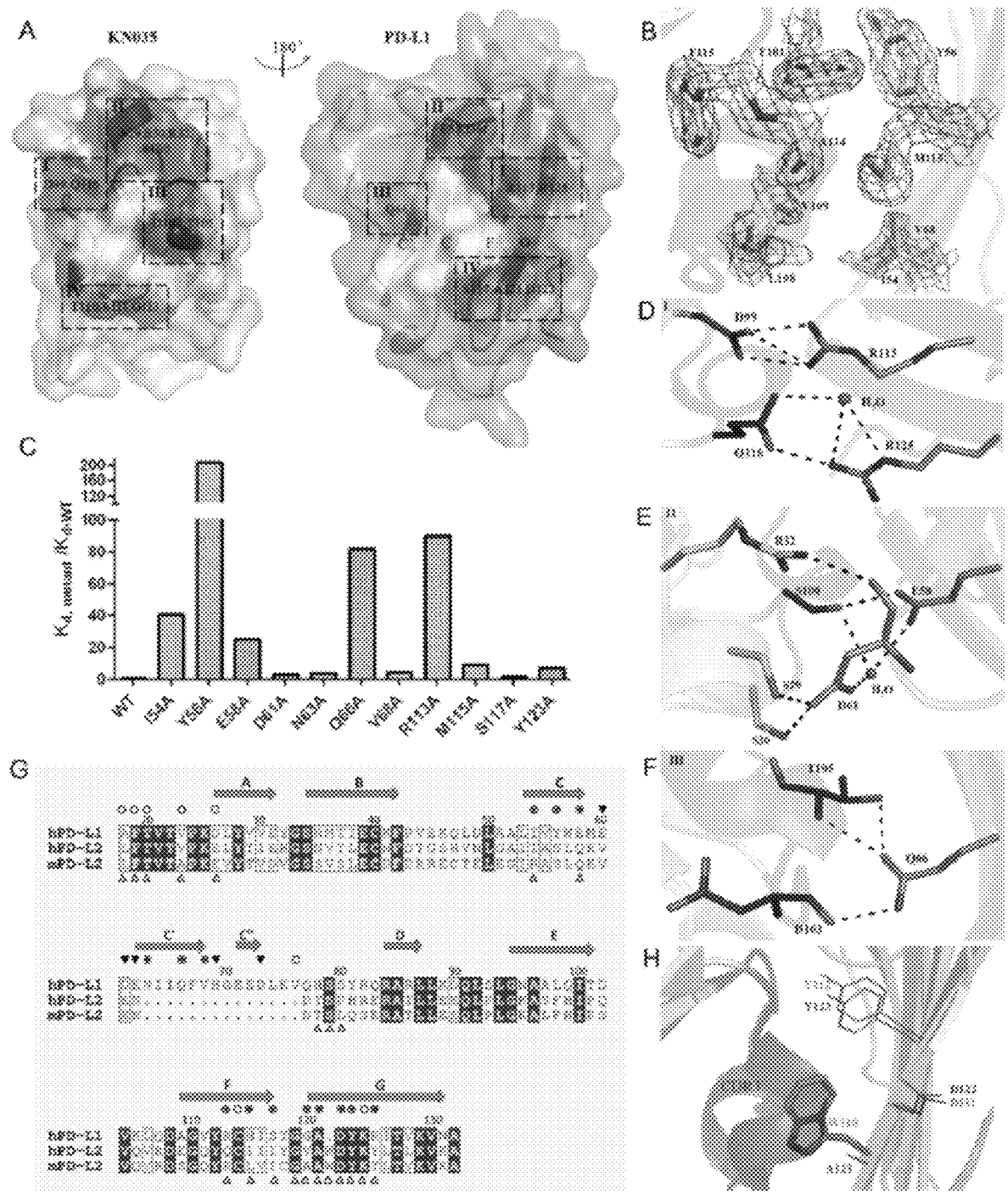

FIG. 5. shows the binding interface of KN035/PD-L1 complex (A) Open-up view of the binding surfaces of KN035 (left) and PD-L1 (right). (B) The electron density map shows the phenol ring of F101 in KN035 is stacked with the aromatic ring of Y56 and F115 in PD-L1, which forms stable interaction with neighboring hydrophobic residues. C, Changes in affinity of PD-L1 mutant binding to KN035. Detailed interactions of KN035/PD-L1 are shown in D, E and F. G, Comparison of PD-L1 and PD-L2 sequences based on three-dimensional crystal structure shows the similarities and differences of PD1 and KN035 binding to P-L1 surface residues. The residues bound to PD1 are indicated by open circles, the residues bound to KN035 are indicated by solid inverted triangles, the common residues are indicated by triangular circles, and the residues of PD-L2 binding to PD1 are indicated by open positive triangles. H, the stacked PD-L1/KN035 and PDL2 structures show that W110 of PD-L2 would block the binding of KN035 to PD-L2.

Figure 6:
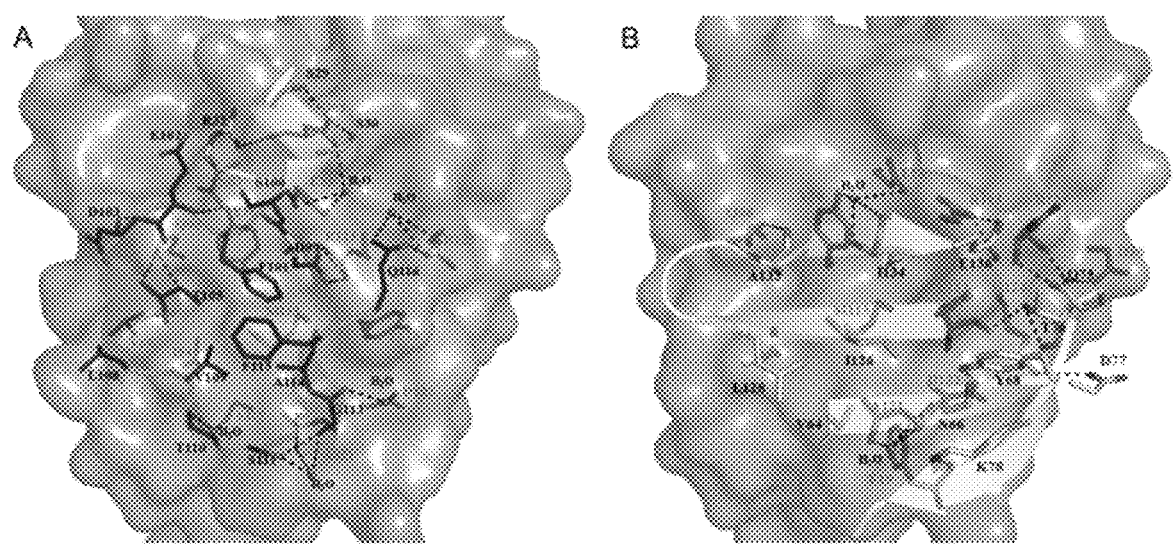

FIG. 6. shows the detailed binding interactions of the interfaces of KN035/PD-L1 and PD-1/PD-L1.

Figure 7:
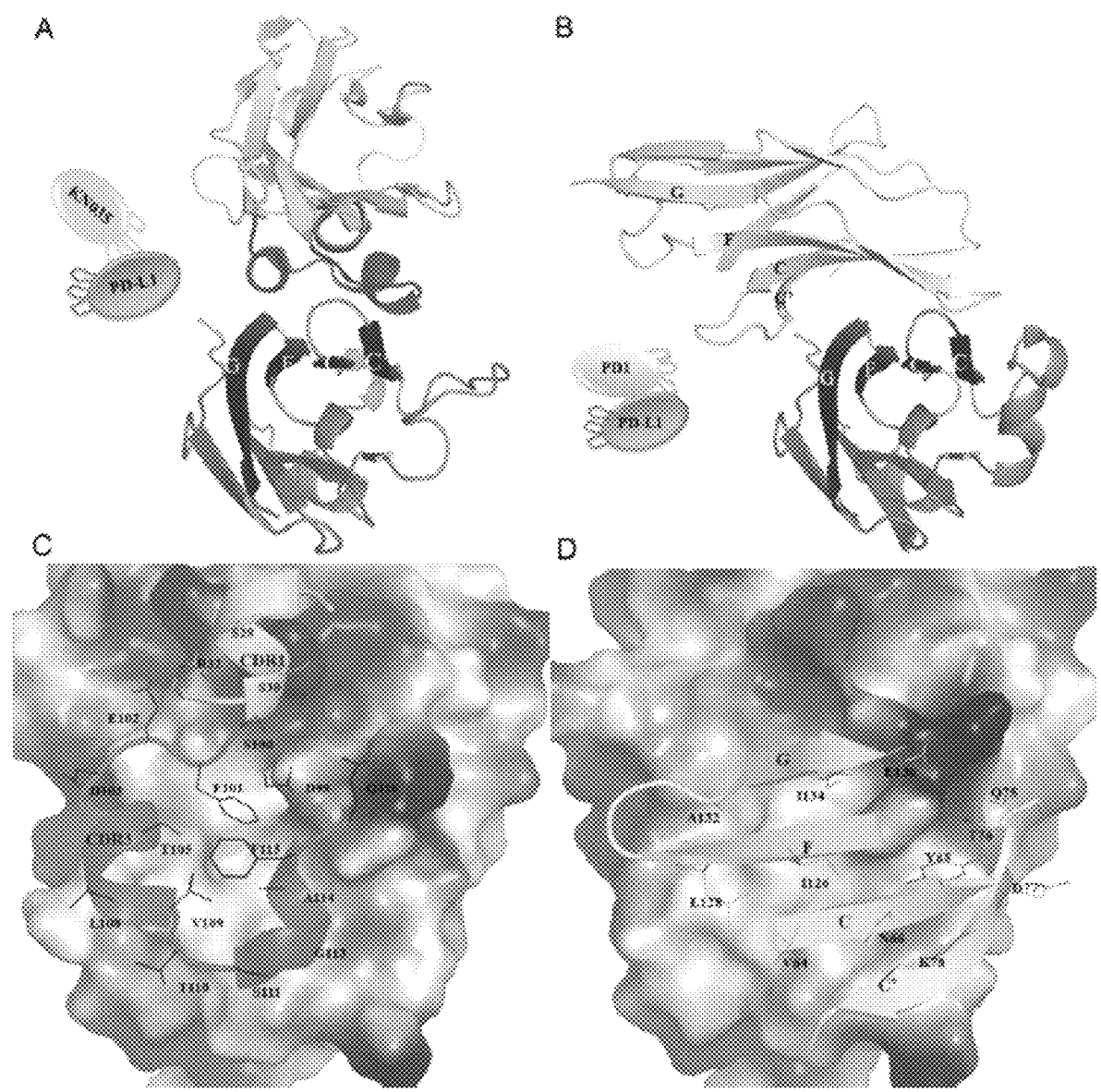

FIG. 7. shows a comparison of binding interfaces of PD-L1 with KN035 (A, C) and PD-L1 with PD1 (B, D).

Figure 8:
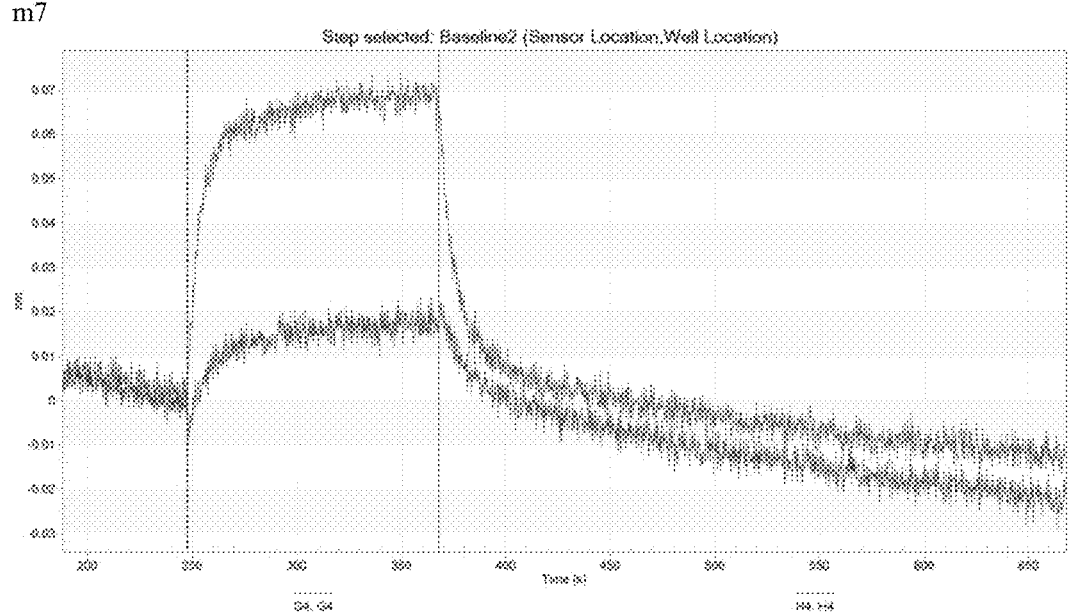
Figure 8:
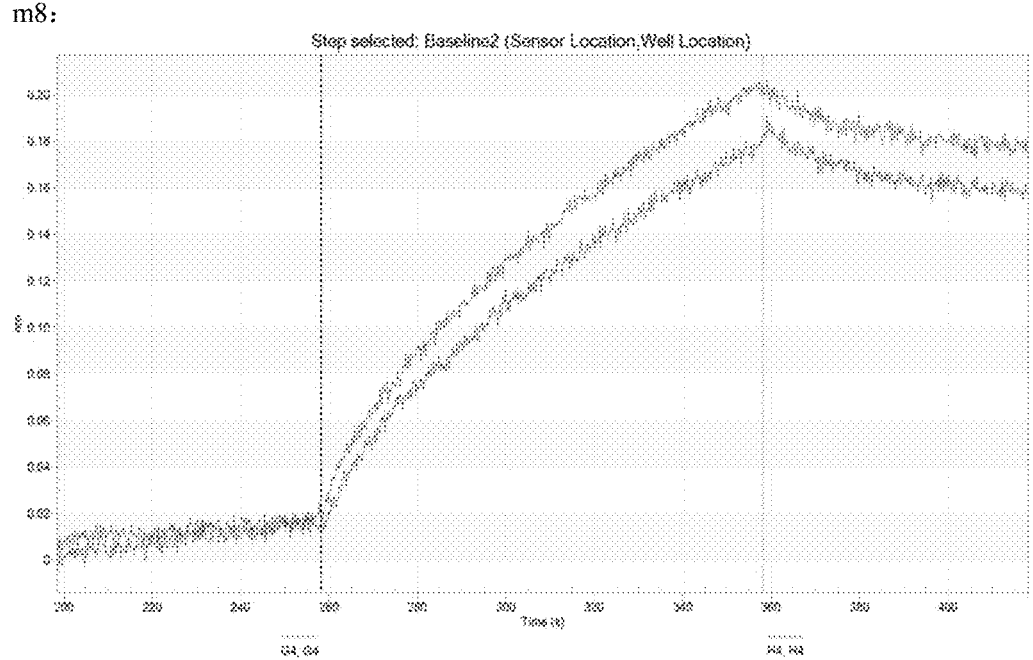

FIG. 8. shows that chimeric antibodies m7 and m8 bind to human PDL1 protein.

EXAMPLE

Example 1. Identification and Structural Analysis of Single Domain Antibody of PDL1

Experiment Material and Method

Generation of Camelids sdAbs Against hPD-L1

The PDL1-Fc fusion protein for immunization was expressed by CHO cells (pCDNA4, Invitrogen, Cat V86220) and purified by Protein A affinity chromatography. A *Camelus bactrianus* was selected for immunization. 100 ml peripheral blood lymphocytes were isolated after 4 immunization sessions and were extracted for total RNA, then the extracted RNA was reverse transcribed into cDNA using the Super-Script III FIRST STRANDSUPERMIX kit according to the instructions. Then, the nucleic acid fragment encoding the variable domain of the heavy-chain antibody were amplified by nested PCR, and then the product is used to create a heavy-chain single domain (sdAb) phage display library against the PD-L1 which has a size of $1.33 \times 10^8$ and 100% insertion ratio.

Enrichment screening against hPD-L1 Fc was processed with 96 well plates coated with 10 ug protein per well. High affinity bacteriophages were obtained after 4-round screenings. Single colonies were picked up randomly and amplified by culture. Positive colonies verified by ELISA were sequenced and clones sharing the same CDR1, CDR2 and CDR3 are defined as one antibody strain, while clones sharing different CDR sequences are defined as different antibody strains. The single domain antibody (sdAb) coding genes were cloned into PET-32b (Novagen) and expressed and purified in *E. coli*. PD-L1 sdAbs were investigated for effect in blocking interaction between PD-1 and PD-L1 by competitive ELISA.

Preparation of hPD-L1 or its Complex with KN035

Genes encoding human PD-L1 amino acids 19-239 were cloned into pET-28a. Protein with C-terminal His-tag (SEQ ID NO:6) were expressed in *E. coli* BL21(DE3) as inclusion bodies. Cells were cultured at 37° C. in LB and induced with 1 mM IPTG at OD600 of 1.0. After a further 16 hours incubation at 37° C., cells were collected by centrifugation, resuspended in lysis buffer containing 20 mM Tris-HCl pH7.4, 1% Triton X-100, 20 mM EDTA and lysed by sonication. Inclusion bodies were recovered by centrifuging at 15000 g for 10 minutes, washed 3 times with lysis buffer and followed by washing with buffer free of Triton X-100. The inclusion bodies were dissolved in 20 mM Tris pH7.4 containing 6M GuHCl, 500 mM EDTA and 10 mM DTT. Solubilized fraction was clarified by centrifugation and dialyzed against 10 mm HCl solution. After dialysis, the sample was re-dissolved in 6M GuHCl and added drop-wise into refolding buffer (1M Arg hydrochloride, 0.1M Tris pH8.0, 2 mM Na-EDTA, 0.25 mM oxidized glutathione and 0.25 mM reduced glutathione). After incubation at 4° C. overnight, the complex was dialyzed against 10 mM Tris pH8.0 and purified to homogeneity by HisTrap Ni-Sepharose column, HiTrap SP ion-exchange column and Superdex 75 (GE Healthcare). Other hPD-L1 variants such as (I54A, Y56A, E58A, D61A, N63A, Q66A, V68A, R113A, M115A, S117A, Y123A, R125A) were prepared following same procedure.

For preparation of PD-L1/KN035 complex, the N-terminal IgV domain of hPD-L1 was similarly cloned into pET28a and expressed in *E. coli* as protein with C-terminal His-tag (SEQ ID NO:5). Its refolding was performed in refolding buffer containing 0.1 mg/ml of KN035. The PD-L1 IgV domain/KN035 complexes (termed PD-L1/KN035 complex hereafter) were subsequently purified by ion exchange and gel filtration columns (GE Healthcare).

Crystallization of hPD-L1 and its Complexes with KN035

Both purified PD-L1 and its complex with KN035 were concentrated to ~15 mg/ml and screened for crystallization conditions using commercially available buffer (Hampton Research, HR2-110) through sitting-drop vapor diffusion where 0.2 μl of protein complex solution was mixed with 0.2 μl of reservoir solution. Diffraction-quality crystals of PD-L1/KN035 were obtained at room temperature from 1.4M (NH4)SO4, 2M Nacl after optimization. The crystals of PD-L1 were grown with precipitation solution of 0.2 mM ammonium acetate and 20% PEG3350.

Structure Determination and Refinement

Crystals were cryo-protected in 20% glycerol in the mother liquor and flash-cooled in liquid nitrogen. X-ray diffraction is performed and diffraction data were collected, and used for analyzing the structure.

Dissociation Rate Constant

A fortéBio Octet K2 instrument was used to measure binding kinetics of hPD-L1 variants to KN035-Fc with protein A sensor. All sensors were activated in PBS with 0.1% w/v bovine serum albumin (BSA) by agitating 96-well microtiter plates at 1000 rpm to minimize nonspecific interactions. The final volume for all solutions was 200 μl per well. Probes saturated with 10 μg/ml KN035 for 40 s before equilibrated 60 s in PBS+1% BSA. hPD-L1 variants were prepared as a 2-fold serial dilution (31.25, 62.5, 125, 250 and 500 nM) in 0.1% BSA and separately incubated with the KN035 bound on the tips for 120 s. Then hPD-L1 variants were allowed to dissociate for 320 s depending on the observed dissociation rate. All measurements were corrected for baseline drift by subtracting a control sensor exposed to running buffer only. Data analysis and curve fitting were carried out using Octet software. As the affinity between hPD1 and hPD-L1 is very low (~8 uM), the affinity of PD-L1 variants towards PD1 could not be accurately measured.

Competitive and Sandwich ELISA

ELISA plates were coated with hPD-L1-Fc at 2 μg/ml dissolved in 50 mM Na2CO3/NaHCO3, pH 9.6. After the plates were washed three times with PBST containing 0.05% Tween-20 and blocked with 3% BSA in PBS for 1 h, serially diluted sdAb were applied to the ELISA plate containing hPD-1-hIgG-biotin (10 m/ml) and incubated for 2 h at 37° C. Binding was detected with the horseradish peroxidase (HRP)-conjugated goat anti-human IgG, which was developed using tetramethylbenzidine (TMB) substrate and stopped by $H_2SO_4$. The concentration was determined byabsorbance at 450 nm.

Analysis of IFN-γ Production

PBMCs were obtained by Ficoll-Hypaque density gradient centrifuge from heparinized peripheral blood samples of the healthy donors. After induced by TNF-α, mature dendritic cells were harvested and confirmed to be HLA-DR positive and PD-L1 positive by flow cytometry. The purified CD4 T cells were added to the 96 U bottom hole containing DC at 10-20:1 ratio in the presence of KN035 or Durvalumab. The cells were incubated for five days. The supernatant was collected, and the levels of IFN-γ were evaluated by ELISA kit according to the manufacturer instructions.

In Vivo Studies

To evaluate the antitumor effect of KN035 in vivo, a xenograft mouse model was prepared by inoculating A375 hPD-L1/human PBMC cells subcutaneously into NOD-SCID mice (6-12 weeks old, 6 per group). Four hours after tumor inoculation, KN035 antibody or Durvalumab was administered intraperitoneally, followed by weekly administration for 4 weeks. Tumor volumes were measured along three orthogonal axes (a, b, and c) and calculated as tumor volume=(abc)/2. Mice with a tumor volume greater than 2000 mm$^3$ were killed by treatment with carbon dioxide.

Flow Cytometry Analysis

Binding property of KN035-Fc with other B7/CD28 superfamily proteins were evaluated by flow cytometry analysis. HEK293T cells were seeded in T75 flasks in complete DMEM supplemented medium and transfected with B7/CD28 superfamily plasmids (PD-L1-EGFP, PD-L2-EGFP, mPD-L1-EGFP, B7H3-EGFP, ICOS-EGFP and B7H4-EGFP) respectively. After 48 hours, cells were harvested and divided into groups. APC anti-human IgG Fc antibody was used to detect KN035-Fc. Data were acquired by a BD FACS Calibur flow cytometer running BD Cell quest software. Data analysis was conducted using FlowJo software.

Experiment Result

Screening and Identification of hPD-L1 Single Domain Antibody KN035

One single domain antibody is identified, named KN035, of which the sequence is set forth in SEQ ID NO:1. This antibody binds PD-L1 specifically with a Kd value of 5.9 nM and has no binding towards PDL2 (FIG. 1). KN035 blocks the interaction between hPD-L1 and hPD1 when assessed by competitive ELISA with EC50 of 420 ng/ml. When fused with Fc fragment, KN035 is effective in enhance T cell responses and cytokine production in the mixed lymphocyte reaction comparing with Durvalumab (FIG. 2A). In an immune co-grafting tumor model, KN035 demonstrated strong anti-tumor activity and inhibited tumor growth more effectively than Durvalumab at lower concentrations (FIG. 2B). These results show that KN035 is a potent inhibitor for blocking PD-1/PD-L1 interaction and has strong anti-tumor activity.

Overall Structure of KN035/PD-L1 Complex

To further investigate the molecular mechanism underlying PD-L1/KN035 interaction, we solved crystal structures of N-terminal immunoglobulin variable domain (IgV) complex of KN035/PD-L1 at 1.7 Å resolution and free PD-L1 at 2.7 Å resolution. The models were built and refined to good geometry, while the result is shown in Table 1. The crystal structure of KN035/PD-L1 complex contained a single assembly of KN035 and the N-terminal immunoglobulin-variable (IgV) domain of PD-L1 with ratio of 1:1 in the asymmetric unit. Similar to other sdAb structures, KN035 shares the typical IgV scaffold containing four framework regions (FRs) that form the core structure of the immunoglobulin domain and three hypervariable CDR1 (SEQ ID NO:2), CDR2 (SEQ ID NO:3) and CDR3 (SEQ ID NO:4) loops consist of 7, 3 and 18 amino acid residues respectively (FIG. 3A). The overall structure of KN035 superimposes well with previous published sdAb structures (PDB: lmel, lhcv) with root-mean-square deviations (RMSD) ranging between 0.72 and 0.92 Å for the $C^\alpha$ atoms of all residues excluding those of CDR loops. Like most other sdAbs from camelids, KN035 has a conserved disulfide bond connecting strand B and E (SS1: Cys22-Cys96). The CDR1 loop of KN035 forms a short a-helix while the CDR3 loop adopts one short a-helix and a short $3_{10}$ helix which is unique amongst sdABs. The short alpha-helix of CDR3 loop is held to the strand C of KN035 by an additional disulfide bond (SS2: Cys33-Cys113) (FIG. 3), while the CDR3 loop is further stabilized by its hydrophobic interaction with the body of KN035.

KN035 binds to the IgV domain of PD-L1 with its CDR1 and CDR3 packing against the surface formed by the CC' FG strands of PD-L1 with a burial of total surface area 1,245 Å$^2$ (FIG. 4). The binding of KN035 induces minor conformational changes in PD-L1 when comparing PD-L1 structure solved here with previously reported structures of PD-L1. The connecting loop linking strand C and C' of PD-L1 bends about 2 Å to form interactions with KN035 in the KN035/PDL complex. Also the connecting loop linking strands C' and D of PD-L1 shifted about 7.5 Å which is likely caused by the crystal packing (FIG. 4). These results indicate that the binding surface of PD-L1 is relatively rigid.

TABLE 1

Crystallographic data collection and refinement statistics

|  | PD-L1 | PD-L1/KN035 complex |
|---|---|---|
| Data collection: | | |
| beamline | SSRF 17U | SSRF 19U |
| space group | C2 2 21 | P61 |
| Cell dimensions | | |
| a, b, c (Å) | 72.24, 91.51, 141.83 | 83.13, 83.13, 73,23 |
| α, β, γ (°) | 90, 90, 90 | 90, 90, 120 |
| Wavelength (Å) | 0.9792 | 0.9785 |
| Resolution (Å) | 56.70-2.70 (2.83-2.70) | 51.34-1.70 (1.73-1.70) |
| Total NO. of observation | 89216 (12036) | 219698 (6935) |
| Total NO. unique | 13282 (1731) | 31640 (1657) |
| $R_{merge}$ (%) | 0.128 (0.745) | 0.104 (0.883) |
| I/σI | 10.8 (2.5) | 9.6 (1.5) |
| Completeness (%) | 99.9 (100.0) | 99.9 (99.1) |
| Multiplicity | 6.7 (7.0) | 6.9 (4.2) |
| Refinement: | | |
| Resolution (Å) | 70.92-2.70 (2.77-2.70) | 41.6-1.70 (1.74-1.70) |
| No. of reflections | 12575 (934) | 29996 (2193) |
| No. of residues | 418 | 248 |
| No. of atoms | | |
| Protein | 3373 | 1888 |
| H$_2$O | 7 | 159 |
| Ligand | 0 | 10 |
| $R_{work}/R_{free}$ | 0.2275/0.2756 | 0.1784/0.2044 |
| B-factors (Å$^2$) | 51 | 25 |
| RMSD | | |
| Bond lengths (Å) | 0.007 | 0.011 |
| Bond angles (°) | 1.188 | 1.455 |
| Ramachaudran plot | 95.66%/0 | 97.93%/0 |

KN035/PD-L1 Interaction Surface

The CDR1 and CDR3 loops of KN035 form a binding surface with a hydrophobic patch surrounded by hydrophilic surfaces, which is complementary that of PD-L1 (FIG. 5, FIG. 6). A pronounced π-π stacking interaction was observed where the aromatic ring of Phe101 of KN035 is perpendicular stacked with that of Tyr56 of PD-L1 (FIG. 5B) which is further stabilized by other hydrophobic residues of Val109, Leu108, Ala114 and Phe115 in KN035 CDR3 of KN035 and Ile54, Val68 and Met115 of PD-L1.

Mutagenesis study and subsequent affinity measurements experiments (FIG. 5C) show that replacement of Tyr56 by Ala in PD-L1 reduce its binding affinity towards KN035 by more than 200-fold and mutation of Ile54 to Ala in PD-L1 reduced the binding affinity by 40-fold (FIG. 5C, Table 2). Also KN035 forms about seven hydrogen bonds and two ionic bonds with PD-L1 involving nine KN035 residues and six PD-L1 residues (Table 3). These polar interactions include strong salt bridges between Asp99 of KN035 and Arg113 of PD-L1 with side chains of both residues fully extended and stabilized by surrounding residues (FIG. 5D). Replacement of Arg 113 with an Ala reduces the binding affinity between KN035 and PD-L1 by nearly 90-fold. The salt bridge of Arg113 is important for KN035 because the binding affinity of KN035 to mouse PD-L1 with Cys at position 113 is almost negligible. Glu58 of PD-L1 forms two hydrogen bonds with Ser100 of KN035 (FIG. 5E) and Gln66 in the C' strand of PD-L1 forms three hydrogen bonds with the main chain or side chain of Thr105 and Asp103 of KN035 (FIG. 5F). Similar replacement of Glu58 and Gln66 of PD-L1 decreases the KN035 binding affinity by 25 and 82-fold respectively. Thus, these five residues (FIG. 5C) are likely to represent hotspot residues at the PD1/PD-L1 binding interface. Other residues of PD-L1 involved in forming hydrophobic or polar interactions also play an important role in stabilizing KN035/PD-L1 complex with mutation of all the residues in PD-L1 resulting about 2-10 folds decrease in binding affinity respectively (Table 2). Interestingly, although residue Asp61 in the connecting loop between strand C and C' of PD-L1 moves about 2 Å towards KN035 forming hydrogen bonds with residue Ser29 and Ser30 in the helix of CDR1 loop, substitution of this residue with an Ala reduced the binding affinity by merely 3.4-fold. This indicates that the high binding affinity of KN035 towards PD-L1 predominantly attributes to the interactions formed by the CDR3 loop with minor contribution from its CDR1 loop.

Our initial screening has revealed that KN035 binds hPD-L1 with nanomolar affinity, but it does not bind hPDL2. Based on the structures of hPD1/hPD-L1, mPD1/mPDL2 complexes and the structure of KN035/PD-L1 complex shown here, the sequences of hPD-L1, hPDL2 and mPDL2 are aligned with the residues involved in binding highlighted (FIG. 5G). PDL2 has a shorter connecting loop between strand C and D in Ig V domain and this connecting loop forming strand C and C' in PD-L1 is part of the binding surface for KN035. Lacking of this loop is expected to decrease the binding of PDL2 towards KN035. More importantly when the structure of PDL2 is superposed with that of PD-L1/KN035 complex, it becomes apparent that Trp101 (an important residue in the binding interface of PD-1/PD-L2, in the position of A121 of PD-L1), would clash with the CDR3 loop of KN035 and prevent PDL2 from binding due to its bulky sidechain (FIG. 5H). These results indicate that KN035 is a highly specific antibody against PD-L1 and will have less off-target effects in vivo.

TABLE 2

PD-L1 mutants and binding affinities

| hPD-L1mutation | $K_d(M)$ | $K_{d,\ mutant}/K_{d,\ WT}$ | mPD-L1 mutation Wang, et al.[35] | Binding to mPD-1 by ELISA, % |
|---|---|---|---|---|
| WT | 5.92E−09 | 1 | WT | 100 |
| I54A | 2.42E−07 | 40.9 | — | — |
| Y56A | 1.24E−06 | 209.5 | Y56S | 100 |
| E58A | 1.49E−07 | 25.2 | E58S | 300 |
| D61A | 1.99E−08 | 3.4 | — | — |
| N63A | 2.30E−08 | 3.9 | — | — |
| Q66A | 4.88E−07 | 82.4 | — | — |
| V68A | 2.76E−08 | 4.7 | — | — |
| R113A | 5.34E−07 | 90.2 | C113Y | 300 |
| M115A | 5.51E−08 | 9.3 | I115A | 3 |
| S117A | 1.26E−08 | 2.1 | S117Y | 100 |
| Y123A | 4.24E−08 | 7.2 | — | — |
| R125A | 2.97E−08 | 5.0 | — | — |

Comparison with PD-1/PD-L1 Structures

It has been shown by previous structures that PD-1 having a Ig V-type topology binds PD-L1 through its residues from GFCC' strands (KN035 through CDR loops) (FIGS. 7A and B), with a total buried surface area of 1500 Å$^2$, however PD1 binds PD-L1 relatively weakly with a Kd of ~5 uM, more than 800 times weaker than that of KN035. the hotspot residues of PD-L1 forms similar interactions with PD1 and with KN035 and its binding interface largely covers that of KN035 (FIGS. 7C and D). Arg113 in hPD-L1 forms a salt bridge with Glu136 of hPD-1 which is reminiscent of its salt bridge with Asp99 of KN035 (FIG. 5 and FIG. 7B). However this salt bridge in hPD1/hPD-L1 complex is relatively weak with the side chains of Arg113 and Glu136 poorly aligned (FIG. 6B). According to previously mutagenesis study derived from mouse PD1 and mouse PD-L1, the ionic interaction from this residue is dispensable in the mPD1/mPD-L1 interface with corresponding mutant (Cys133Tyr) binds PD1 about 3-fold higher. Similarly Glu58 which contributes about 25-fold in binding affinity on hPD-L1 towards KN035, is redundant or negative for mPD1 binding where Glu58Ser mPD-L1 mutant binds mPD1 about 3-fold tighter. Also the hydrophobic interactions between mPD1 and mPD-L1 appear to be centered on residue 115 (Met115 in human and Ile 115 in mouse) rather than Tyr56 of PD-L1 where Ile115Ala mutant binds mPD1 ~33-fold weaker than wild type PD-L1 and Tyr56Ser mutant binds mPD1 with the same binding affinity as wild type. In contrast, the key hydrophobic interaction of KN035/hPD-L1 interface is from Tyr56 where similar hPD-L1 variants Met115Ala and Tyr56Ala bind KN035 with affinity decreased by 9-fold and 200-fold respectively. Furthermore it has been shown that the hydrophobic interactions between mPD1 and mPD-L1 could be enhanced by A132L substitution in PD1 resulting increase binding affinity towards both mPD-L1 and mPDL2. Altogether, these results suggest that the binding surface of PD1 is less optimal for PD-L1 than that of KN035.

DISCUSSION

It is now clear that tumor cells often co-opt immune-checkpoint pathways as a major mechanism of immune resistance, particularly against T cells that are specific for tumor antigen. Because the ligand-receptor interactions of these checkpoints could be blocked by antibodies or recombinant ligands or receptors, several antibodies against CTLA4 and PD1 of these pathways have been approved by FDA for cancer immunotherapy and many other antibodies are in clinical trials. However there is limited structural information on how these antibodies block these immune checkpoints, it is the first time to report herein the co-crystal structure of such anti-tumor antibody, KN035, in complex with human PD-L1 which paves the way for further antibody optimization for higher binding affinity and specificity.

It was noted from previous structural studies of PD1 with its ligands that the receptor/ligand binding interface is relatively flat (FIG. 6B). We found that KN035, a single domain antibody, binds the flat surface of PD-L1 mainly through its CDR3 loop which forms one turn of alpha-helix and a unique short $3_{10}$ helix. The nanomolar binding affinity of KN035 towards PD-L1 is mainly achieved through harnessing both hydrophobic interactions and ionic interactions on its binding surface and by making full use of all the residues from the binding interface. For example residues Phe101 and Asp99 of KN035 are optimally aligned to interact with corresponding residues Tyr56 and Arg113 from the complimentary binding surface of PD-L1, in contrast, the contribution of these two residues of PD-L1 for PD1 binding appears minimal (FIG. 6B and Table 3). Another contributing factor to the hudge difference in the binding affinities of KN035 and PD1 towards PD-L1 likely arises from the flexibility of CDR loop which can adapt to interact with residues around the interface, whereas the binding face of PD1 is mainly formed through beta-strands of limited freedom. This may imply the interface between PD1 and PD-L1 is not purposely optimized for maximal binding affinity in vivo and the modest binding affinity of PD1 towards its ligands at micro molar range is selected for optimal immune activation and suppression.

Furthermore the structure of KN035 and PD-L1 complex readily explains that KN035 could not bind PDL2 due to the shorter loop of PDL2 between strand C and D and the steric hindrance of Tyr101 in PDL2. Therefore this specific PD-L1 sdAb could be used for further study dissecting the roles of PD-L1 and PDL2 in tumors which would be crucial to guide the clinical usage of different checkpoint blocker.

Although various crystal structures of PD1 complexed with its ligands have been published, rational design towards PD1/PD-L1 surface have achieved limited success largely due to the difficulty in targeting a flat surface of protein. The identification of KN035 binding surface here may provide useful information for selecting peptides or chemical mimetic based on the configuration of CDR3 loop. Most importantly the semi-independent folding of KN035 CDR3 loop would allow generating bi-specific antibodies or multi-specific antibodies for combinational immunotherapy.

TABLE 3

Polar interactions between KN035 and PD-L1 (distance ≤ 3.5Å)

| KN035 contact residue | KN035 residue location | PD-L1 contact residue | PD-L1 residue location |
|---|---|---|---|
| hydrogen bonds and salt bridges | | | |
| S29 | CDR1 | D61 | CC' loop |
| S30 | CDR1 | D61 | CC' loop |
| K32 | CDR1 | D61 | CC' loop |
| D99 | CDR3 | R113 | F strand |
| S100 | CDR3 | E58 | C strand |
| E102 | CDR3 | Y56 | C strand |
| D103 | CDR3 | Q66 | C' strand |
| T105 | CDR3 | Q66 | C' strand |
| Q116 | CDR3 | P125 | G strand |
| water-mediated hydrogen bonds | | | |
| S100 | CDR3 | D61 | CC' loop |
| T110 | CDR3 | S117 | F strand |

TABLE 3-continued

Polar interactions between KN035 and PD-L1 (distance ≤ 3.5Å)

| KN035 contact residue | KN035 residue location | PD-L1 contact residue | PD-L1 residue location |
|---|---|---|---|
| S111 | CDR3 | A121 | G strand |
| G113 | CDR3 | A121, D122 | G strand |

Example 2. Construction of Variants of PDL1 sdAb Based on Structural Analysis

Experimental Materials and Methods

Preparation of PDL1 sdAb Mutant

According to the crystal structure, using the amino acid sequence of the sdAb No. 10 (low affinity to human PDL1) (SEQ ID NO: 9) of the patent application CN 106397592 A as the template, the sequence of CDR1 together with the following cysteine residue (SEQ ID NO: 8) and CDR3 (SEQ ID No: 4) of the KN035 sdAb were replaced thereon to obtain mutant 1 (SEQ ID NO: 10). Using the amino acid sequence of the sdAb No. 94 (which does not block the interaction between human PD1 and PDL1) (SEQ ID NO: 11) of the patent application CN 106397592 A as the template, the CDR1 sequence (SEQ ID NO: 8) and CDR3 (SEQ ID No: 4) of the KN035 sdAb were replaced thereon to obtain mutant 2 (SEQ ID NO: 12). The gene encoding these KN035 sdAb mutants was ligated with a His-tagged coding sequence at the C-terminus and cloned into the pCDNA4 mammalian expression vector. The obtained recombinant vector was transiently transfected into suspension cultured human HEK293 cells by PEI. After 6 to 7 days of culture, the culture supernatant was taken and purified by IMAC affinity chromatography in one step to obtain a KN035 single domain antibody mutant protein.

Using the sequence of the KN035 sdAb (SEQ ID NO: 1) as the template, the CDR2-KABAT sequence (SEQ ID NO: 13) predicted according to KABAT method was replaced with the CDR2-KABAT (SEQ ID NO: 14) of the heavy chain of the Pertuzumab antibody (U.S. Pat. No. 7,879,325) which is also a VH3 subtype, to obtain a new KN035 single domain antibody mutant sequence m3 (SEQ ID NO: 15). The m3 mutant protein was further obtained by the above method.

Using the sequence of the KN035 sdAb (SEQ ID NO: 1) as the template, and the amino acid residues in the CDR2 (SEQ ID No: 3) were substituted with Ala one by one to obtain a series of mutant KN035 sdAb sequences m4, m5, m6 (SEQ ID NO: 16-18). These mutant proteins were further obtained by the above methods.

Preparation of PDL1 sdAb CDR3 Chimeric Antibody

The CDR3 sequence of the KN035 sdAb (SEQ ID No: 4) was replaced into the single domain antibody C38 (CN201610332590.7) framework (SEQ ID NO: 19) which does not recognize PDL1, resulting in a new chimeric sdAb m7 (SEQ ID NO: 20) with chimeric KN035 CDR3 sequence. Alternatively, the CDR1+Cys (SEQ ID NO:8) and CDR2-KABAT (SEQ ID NO: 13) sequences in the KN035 sdAb are replaced with CDR1+Cys (SEQ ID NO: 21) and CDR2-KABAT (SEQ ID NO: 22) in the C38 sequence, to obtain chimeric sdAb m8 (SEQ ID NO: 23). The chimeric sdAb protein was further obtained by the above method.

Affinity Between PD-L1 Variant and PD1

A fortéBio Octet K2 instrument was used to measure binding of hPD-L1-Fc protein to KN035 variants with Bio-Layer Interferometry (BLI). The AHC sensor was used in this experiment to immobilize the PDL1-Fc protein. The basic steps are as described above, in which AHC immobilization Threshold 1 nm, and the control program is set to bind for 60 s and dissociate for 100 s. The dilution was 0.02 PBST 20% (pH 7.4), the regenerating solution was glycine-HCl (pH 1.7), and loading volume of the sample and regenerating solution was 200 μL. The results obtained were analyzed using Data analysis 9.0 software. According to different properties, KN035 variants were prepared into either 2-fold serial dilutions (31.25, 62.5, 125, 250 and 500 nM) or directly diluted to 100 nM and 1 μM.

Investigating the Blocking Effect of KN035 Variant on PD1-PDL1 Interaction by Competitive ELISA ELISA plates were coated with hPD-L1-Fc at 2 μg/ml dissolved in 50 mM Na$_2$CO$_3$/NaHCO$_3$, pH 9.6. After the plates were washed three times with PBST containing 0.05% Tween-20 and blocked with 3% BSA in PBS for 1 h, serially diluted KN035 varients were applied to the ELISA plate containing hPD-1-hIgG-biotin (10 μg/ml) and incubated for 2 h at 37° C. Binding was detected with the horseradish peroxidase (HRP)-conjugated goat anti-human IgG, which was developed using tetramethylbenzidine (TMB) substrate and stopped by H$_2$SO$_4$. The concentration was determined by absorbance at 450 nm.

Experimental Result

Preparation of KN035 sdAb CDR2 Mutants, as Well as Investigation of Affinity and Blocking Function.

A series of CDR2 region-altered KN035 sdAb mutants were obtained by transient expression of human HEK293 cells. The expression levels of these mutants are close to those of the wild-type KN035 sdAb. The protein obtained by one-step purification of IMAC was analyzed by SDS-PAGE non-reduction electrophoresis, and the purity thereof was more than 85%. The binding of these mutants to human PDL1 protein was then investigated by fortibio, and the KD values obtained were compared with wild-type KN035, and the values were all within one order of magnitude. The activity of these CDR2 mutants to block the human PDL1-PD1 interaction was examined by ELISA, and it was found that these proteins all have a clear blocking function, and the blocking activity relative to the wild-type KN035 sdAb were between 70% and 130%.

| Mutant | KD/KD wt | Relative blocking activity (EC50 wt/EC50 m × 100%) |
| --- | --- | --- |
| m1 | 1.21 | 80% |
| m2 | 1.73 | 71% |
| m3 | 2.01 | 91% |
| m4 | 0.85 | 90% |
| m5 | 1.2 | 103% |
| m6 | 0.98 | 113% |

Preparation of KN035 CDR3 Chimeric sdAb, and the Binding to PDL1

Two KN035 sdAb CDR3 chimeras m7 and m8 were obtained by transient expression of human HEK293 cells. Its binding to human PDL1 protein was analyzed by Fortibio, and it was clear that binding and dissociation curves were observed at high and low concentrations, indicating that both chimeras bind well to human PDL1 protein (Figure. 8).

DISCUSSION

Co-crystallization result of the KN035 sdAb to its target protein PDL1 showed that the CDR3 sequence plays a major role in the binding of PDL1 in the KN035 sdAb, while the CDR2, including its surrounding amino acid residues (a longer CDR2 region obtained according to the KABAT numbering, SEQ ID NO: 13), does not substantially participate in the binding of the target.

The inventors examined a series of KN035 mutants and found that the sequence of the CDR2 region under the KABAT encoding (SEQ ID NO: 13) was replaced with another sdAb, the CDR2 sequence of the antibody heavy chain, or directly replaced with other non-functional amino acids, having essentially no effect on the binding of sdAbs to PDL1 or on the blocking of PDL1-PD1. Similarly, the CDR1 sequence of the KN035 sdAb (including the C-terminal Cys residue, SEQ ID NO: 8) and the CDR3 sequence (SEQ ID NO: 4) were replaced with the backbone of other antibodies or similar antibodies, which also substantially maintains their original activity. Although the dissociation constant KD value and the blocking EC50 are slightly fluctuating, it is speculated that it is mainly due to fluctuations in the purity of the mutant protein.

Given that CDR3 is the major functional sequence of the KN035 single domain antibody, the inventors constructed CDR3 chimeric single domain antibodies and further investigated their binding to the PDL1 target protein. Both chimeric antibodies are effective in binding to the PDL1 protein.

Sequence Listing
56

SEQ ID NO: 1
QVQLQESGGGLVQPGGSLRLSCAASGKMSSRRCMAWFRQAPGKERERVAK

LLTTSGSTYLADSVKGRFTISQNNAKSTVYLQMNSLKPEDTAMYYCAADS

FEDPTCTLVTSSGAFQYWGQGTQVTVSS

SEQ ID NO: 2
GKMSSRR

SEQ ID NO: 3
TTS

SEQ ID NO: 4
DSFEDPTCTLVTSSGAFQ

Human PDL1-V
SEQ ID NO: 5
TVTVPKDLYVVEYGSNMTIECKFPVEKQLDLAALIVYWEMEDKNIIQFVH

GEEDLKVQHSSYRQRARLLKDQLSLGNAALQITDVKLQDAGVYRCMISYG

GADYKRITVKVNA

Human PDL1-His
SEQ ID NO: 6
TVTVPKDLYVVEYGSNMTIECKFPVEKQLDLAALIVYWEMEDKNIIQFVH

GEEDLKVQHSSYRQRARLLKDQLSLGNAALQITDVKLQDAGVYRCMISYG

GADYKRITVKVNAPYNKINQRILVVDPVTSEHELTCQAEGYPKAEVIWTS

SDHQVLSGKTTTTNSKREEKLFNVTSTLRINTTTNEIFYCTFRRLDPEEN

HTAELVIPELPLAHPPNERTDKLAAALEHHHHHH

Human PDL1
SEQ ID NO: 7
TVTVPKDLYVVEYGSNMTIECKFPVEKQLDLAALIVYWEMEDKNIIQFVH

GEEDLKVQHSSYRQRARLLKDQLSLGNAALQITDVKLQDAGVYRCMISYG

-continued

GADYKRITVKVNAPYNKINQRILVVDPVTSEHELTCQAEGYPKAEVIWTS
SDHQVLSGKTTTTNSKREENLFNVTSTLRINTTTNEIFYCTFRRLDPEEN
HTAELVIPELPLAHPPNERTD

SEQ ID NO: 8
GKMSSRRC

SEQ ID NO: 9
QVQLQESGGGSVQAGGSLRLSCAASGNIVSSYCMGWFRQAPGKERVGVAA
IDSDGTTKYADSMKGRFTISKDNAKNTLDLQMNSLKPEDTAMYYCVARLN
CPGPVDWVPMFPYRGQGTQVTVSS m1
SEQ ID NO: 10
QVQLQESGGGSVQAGGSLRLSCAASGKMSSRRCMGWFRQAPGKERVGVAA
IDSDGTTKYADSMKGRFTISKDNAKNTLDLQMNSLKPEDTAMYYCVADSF
EDPTCTLVTSSGAFQYRGQGTQVTVSS

94
SEQ ID NO: 11
QVQLQESGGGSVQAGGSLRLSCAASLNIFSSYCMGWFRQAPGKQRVGVAT
IDSDGTTRYVDSVKGRFTISKDNAKNTLDLQMNSLKPEDTAMYYCAARLN
CPGPVDWVPMFPYRGQGTQVTVSS m2
SEQ ID NO: 12
QVQLQESGGGSVQAGGSLRLSCAASGKMSSRRCMGWFRQAPGKQRVGVAT
IDSDGTTRYVDSVKGRFTISKDNAKNTLDLQMNSLKPEDTAMYYCAADSF
EDPTCTLVTSSGAFQYRGQGTQVTVSS

SEQ ID NO: 13
KLLTTSGSTYLADSVKG

SEQ ID NO: 14
DVNPNSGGSIYNQRFKG m3
SEQ ID NO: 15
QVQLQESGGGLVQPGGSLRLSCAASGKMSSRRCMAWFRQAPGKERERVAD
VNPNSGGSIYNQRFKGRFTISQNNAKSTVYLQMNSLKPEDTAMYYCAADS
FEDPTCTLVTSSGAFQYWGQGTQVTVSS m4
SEQ ID NO: 16
QVQLQESGGGLVQPGGSLRLSCAASGKMSSRRCMAWFRQAPGKERERVAK
LLATSGSTYLADSVKGRFTISQNNAKSTVYLQMNSLKPEDTAMYYCAADS
FEDPTCTLVTSSGAFQYWGQGTQVTVSS m5
SEQ ID NO: 17
QVQLQESGGGLVQPGGSLRLSCAASGKMSSRRCMAWFRQAPGKERERVAK
LLTASGSTYLADSVKGRFTISQNNAKSTVYLQMNSLKPEDTAMYYCAADS
FEDPTCTLVTSSGAFQYWGQGTQVTVSS m6
SEQ ID NO: 18
QVQLQESGGGLVQPGGSLRLSCAASGKMSSRRCMAWFRQAPGKERERVAK
LLTTAGSTYLADSVKGRFTISQNNAKSTVYLQMNSLKPEDTAMYYCAADS
FEDPTCTLVTSSGAFQYWGQGTQVTVSS

SEQ ID NO: 19
QVQLQESGGGSVQAGGSLRLSCAASRYTASSNCMAWFRQAPGKEREGVAT
IYNGGGSTAYADSVKGRFTISQDNAKNTVYLQMNSLKPEDTAMYYCGAGS
PRFCASATMTGGHHLFGYWGQGTQVTVSS m7
SEQ ID NO: 20
QVQLQESGGGSVQAGGSLRLSCAASRYTASSNCMAWFRQAPGKEREGVAT
IYNGGGSTAYADSVKGRFTISQDNAKNTVYLQMNSLKPEDTAMYYCGAGS
PRFCASDSFEDPTCTLVTSSGAFQYWGQGTQVTVSS

SEQ ID NO: 21
RYTASSNC

SEQ ID NO: 21
TIYNGGGSTAYADSVKG m8
SEQ ID NO: 23
QVQLQESGGGLVQPGGSLRLSCAASRYTASSNCMAWFRQAPGKERERVAT
IYNGGGSTAYADSVKGRFTISQNNAKSTVYLQMNSLKPEDTAMYYCAADS
FEDPTCTLVTSSGAFQYWGQGTQVTVSS

SEQ ID NO: 24
GKMSSRRCMA

SEQ ID NO: 25
LTTSGS

APPENDIX I

```
 1  HEADER ----
 2
 3  REMARK 3
 4  REMARK 3 REFINEMENT.
 5  REMARK 3 PROGRAM: REFMAC 5.7.0032
 6  REMARK 3 AUTHORS: MURSHUDOV, SKUBAK, LEBEDEV, PANNU,
 7  REMARK 3          STEINER, NICHOLLS, WINN, LONG, VAGIN
 8  REMARK 3
 9  REMARK 3 REFINEMENT TARGET: MAXIMUM LIKELIHOOD
10  REMARK 3
11  REMARK 3 DATA USED IN REFINEMENT.
12  REMARK 3 RESOLUTION RANGE HIGH (ANGSTROMS): 1.70
13  REMARK 3 RESOLUTION RANGE LOW  (ANGSTROMS): 41.60
14  REMARK 3 DATA CUTOFF (SIGMA(F)): NONE
15  REMARK 3 COMPLETENESS FOR RANGE (%): 99.83
16  REMARK 3 NUMBER OF REFLECTIONS: 29996
17  REMARK 3
18  REMARK 3 FIT TO DATA USED IN REFINEMENT.
19  REMARK 3 CROSS-VALIDATION METHOD: THROUGHOUT
```

APPENDIX I-continued

```
20  REMARK 3   FREE R VALUE TEST SET SELECTION: RANDOM
21  REMARK 3   R VALUE (WORKING + TEST SET): 0.17969
22  REMARK 3   R VALUE (WORKING SET): 0.17839
23  REMARK 3   FREE R VALUE: 0.20439
24  REMARK 3   FREE R VALUE TEST SET SIZE (%): 5.1
25  REMARK 3   FREE R VALUE TEST SET COUNT: 1611
26  REMARK 3
27  REMARK 3  FIT IN THE HIGHEST RESOLUTION BIN.
28  REMARK 3   TOTAL NUMBER OF BINS USED: 20
29  REMARK 3   BIN RESOLUTION RANGE HIGH: 1.700
30  REMARK 3   BIN RESOLUTION RANGE LOW: 1.744
31  REMARK 3   REFLECTION IN BIN (WORKING SET): 2193
32  REMARK 3   BIN COMPLETENESS (WORKING + TEST) (%): 99.26
33  REMARK 3   BIN R VALUE (WORKING SET): 0.309
34  REMARK 3   BIN FREE R VALUE SET COUNT: 98
35  REMARK 3   BIN FREE R VALUE: 0.300
36  REMARK 3
37  REMARK 3  NUMBER OF NON-HYDROGEN ATOMS USED IN REFINEMENT.
38  REMARK 3   ALL ATOMS: 2057
39  REMARK 3
40  REMARK 3  B VALUES.
41  REMARK 3   FROM WILSON PLOT (A**2): NULL
42  REMARK 3   MEAN B VALUE (OVERALL, A**2): 18.529
43  REMARK 3   OVERALL ANISOTROPIC B VALUE.
44  REMARK 3    B11 (A**2): 0.05
45  REMARK 3    B22 (A**2): 0.05
46  REMARK 3    B33 (A**2): -0.17
47  REMARK 3    B12 (A**2): 0.05
48  REMARK 3    B13 (A**2): -0.00
49  REMARK 3    B23 (A**2): -0.00
50  REMARK 3
51  REMARK 3  ESTIMATED OVERALL COORDINATE ERROR.
52  REMARK 3   ESU BASED ON R VALUE (A): 0.095
53  REMARK 3   ESU BASED ON FREE R VALUE (A): 0.093
54  REMARK 3   ESU BASED ON MAXIMUM LIKELIHOOD (A): 0.061
55  REMARK 3   ESU FOR B VALUES BASED ON MAXIMUM LIKELIHOOD (A**2): 3.657
56  REMARK 3
57  REMARK 3  CORRELATION COEFFICIENTS.
58  REMARK 3   CORRELATION COEFFICIENT FO-FC: 0.963
59  REMARK 3   CORRELATION COEFFICIENT FO-FC FREE: 0.952
60  REMARK 3
61  REMARK 3  RMS DEVIATIONS FROM IDEAL VALUES        COUNT    RMS    WEIGHT
62  REMARK 3   BOND LENGTHS REFINED ATOMS        (A): 1930; 0.011; 0.020
63  REMARK 3   BOND LENGTHS OTHERS               (A): 1836; 0.001; 0.020
64  REMARK 3   BOND ANGLES REFINED ATOMS   (DEGREES): 2617; 1.455; 1.958
65  REMARK 3   BOND ANGLES OTHERS          (DEGREES): 4218; 0.718; 3.003
66  REMARK 3   TORSION ANGLES, PERIOD 1    (DEGREES): 246; 6.740; 5.000
67  REMARK 3   TORSION ANGLES, PERIOD 2    (DEGREES): 84; 33.408; 24.286
68  REMARK 3   TORSION ANGLES, PERIOD 3    (DEGREES): 342; 13.237; 15.000
69  REMARK 3   TORSION ANGLES, PERIOD 4    (DEGREES): 12; 17.879; 15.000
70  REMARK 3   CHIRAL-CENTER RESTRAINTS       (A**3): 293; 0.084; 0.200
71  REMARK 3   GENERAL PLANES REFINED ATOMS      (A): 2194; 0.006; 0.020
72  REMARK 3   GENERAL PLANES OTHERS             (A): 442; 0.001; 0.020
73  REMARK 3
74  REMARK 3  ISOTROPIC THERMAL FACTOR RESTRAINTS.   COUNT   RMS    WEIGHT
75  REMARK 3   MAIN-CHAIN BOND REFINED ATOMS  (A**2): 972; 1.210; 1.667
76  REMARK 3   MAIN-CHAIN BOND OTHER ATOMS    (A**2): 971; 1.210; 1.665
77  REMARK 3   MAIN-CHAIN ANGLE REFINED ATOMS (A**2): 1213; 2.024; 2.491
78  REMARK 3   MAIN-CHAIN ANGLE OTHER ATOMS   (A**2): 1214; 2.023; 2.492
79  REMARK 3   SIDE-CHAIN BOND REFINED ATOMS  (A**2): 958; 1.680; 1.904
80  REMARK 3   SIDE-CHAIN BOND OTHER ATOMS    (A**2): 955; 1.668; 1.896
81  REMARK 3   SIDE-CHAIN ANGLE OTHER ATOMS   (A**2): 1392; 2.679; 2.753
82  REMARK 3   LONG RANGE B REFINED ATOMS     (A**2): 2116; 5.439; 13.938
83  REMARK 3   LONG RANGE B OTHER ATOMS       (A**2): 2075; 5.325; 13.647
84  REMARK 3
85  REMARK 3 NCS RESTRAINTS STATISTICS
86  REMARK 3  NUMBER OF NCS GROUPS: NULL
87  REMARK 3
88  REMARK 3 TWIN DETAILS
89  REMARK 3  NUMBER OF TWIN DOMAINS: NULL
90  REMARK 3
91  REMARK 3
92  REMARK 3 TLS DETAILS
93  REMARK 3  NUMBER OF TLS GROUPS: 2
94  REMARK 3  ATOM RECORD CONTAINS RESIDUAL B FACTORS ONLY
95  REMARK 3
96  REMARK 3  TLS GROUP: 1
97  REMARK 3   NUMBER OF COMPONENTS GROUP: 1
98  REMARK 3   COMPONENTS        C SSSEQI   TO  C SSSEQI
99  REMARK 3   RESIDUE RANGE:    B   -10        B   9999
```

APPENDIX I-continued

```
100  REMARK 3  ORIGIN FOR THE GROUP (A): 13.1969 -47.0791 -12.5326
101  REMARK 3  T TENSOR
102  REMARK 3  T11: 0.0526  T22: 0.0451
103  REMARK 3  T33: 0.0288  T12: 0.0000
104  REMARK 3  T13: 0.0001  T23: -0.0124
105  REMARK 3  L TENSOR
106  REMARK 3  L11: 0.8752  L22: 1.6173
107  REMARK 3  L33: 1.8728  L12: -0.3223
108  REMARK 3  L13: -0.4066  L23: 1.4231
109  REMARK 3  S TENSOR
110  REMARK 3  S11: -0.0554  S12: -0.1457  S13: 0.0822
111  REMARK 3  S21: 0.1195   S22: 0.0468   S23: 0.0171
112  REMARK 3  S31: 0.0853   S32: -0.0291  S33: 0.0087
113  REMARK 3
114  REMARK 3  TLS GROUP: 2
115  REMARK 3  NUMBER OF COMPONENTS GROUP: 1
116  REMARK 3  COMPONENTS C SSSEQI TO C SSSEQI
117  REMARK 3  RESIDUE RANGE: A -10 A 9999
118  REMARK 3  ORIGIN FOR THE GROUP (A): 23.6916 -52.5211 -37.5199
119  REMARK 3  T TENSOR
120  REMARK 3  T11: 0.0440  T22: 0.0566
121  REMARK 3  T33: 0.0462  T12: -0.0267
122  REMARK 3  T13: -0.0072 T23: 0.0220
123  REMARK 3  L TENSOR
124  REMARK 3  L11: 1.2046  L22: 1.4572
125  REMARK 3  L33: 0.8358  L12: -0.0872
126  REMARK 3  L13: -0.3271 L23: -0.2923
127  REMARK 3  S TENSOR
128  REMARK 3  S11: -0.0316 S12: 0.1741   S13: -0.0646
129  REMARK 3  S21: -0.1522 S22: -0.0260  S23: -0.0371
130  REMARK 3  S31: 0.0541  S32: -0.0288  S33: 0.0577
131  REMARK 3
132  REMARK 3
133  REMARK 3  BULK SOLVENT MODELLING.
134  REMARK 3  METHOD USED: MASK
135  REMARK 3  PARAMETERS FOR MASK CALCULATION
136  REMARK 3  VDW PROBE RADIUS: 1.20
137  REMARK 3  ION PROBE RADIUS: 0.80
138  REMARK 3  SHRINKAGE RADIUS: 0.80
139  REMARK 3
140  REMARK 3  OTHER REFINEMENT REMARKS:
141  REMARK 3  HYDROGENS HAVE BEEN ADDED IN THE RIDING POSITIONS
142  REMARK 3  U VALUES: RESIDUAL ONLY
143  REMARK 3
144  SSBOND  1 CYS A 114    CYS A 40
145  SSBOND  2 CYS B 106    CYS B 33
146  LINKR   SG ACYS B 96   SG CYS B 22   SS
147  LINKR   SG BCYS B 96   SG CYS B 22   SS
148  LINKR   ASP B 99       THR B 107     gap
149  LINKR   HIS A 78       ARG A 82      gap
150  LINKR   GLN A 77       ARG A 82      gap
151  CISPEP  1 ASP B 103    PRO B 104  0.00
152  CRYST1   83.130  83.130  73.230  90.00  90.00 120.00 P 61
153  SCALE1   0.012029  0.006945  0.000000    0.00000
154  SCALE2  -0.000000  0.013890  0.000000    0.00000
155  SCALE3   0.000000 -0.000000  0.013656    0.00000
156  ATOM     1   N    GLN  B   1     5.933  -39.375  -29.839  1.00  40.55 N
157  ATOM     2   CA   GLN  B   1     6.510  -40.668  -29.385  1.00  38.68 C
158  ATOM     3   CB   GLN  B   1     7.971  -40.803  -29.864  1.00  39.29 C
159  ATOM     4   CG   GLN  B   1     8.863  -39.597  -29.547  1.00  41.02 C
160  ATOM     5   CD   GLN  B   1    10.067  -39.479  -30.473  1.00  41.29 C
161  ATOM     6   OE1  GLN  B   1    10.294  -40.329  -31.331  1.00  47.70 O
162  ATOM     7   NE2  GLN  B   1    10.841  -38.421  -30.302  1.00  43.04 N
163  ATOM     8   C    GLN  B   1     6.351  -40.742  -27.867  1.00  33.25 C
164  ATOM     9   O    GLN  B   1     5.306  -40.328  -27.327  1.00  37.15 O
165  ATOM    10   N    VAL  B   2     7.381  -41.180  -27.163  1.00  25.58 N
166  ATOM    11   CA   VAL  B   2     7.214  -41.576  -25.773  1.00  22.10 C
167  ATOM    12   CB   VAL  B   2     8.224  -42.684  -25.421  1.00  20.25 C
168  ATOM    13   CG1  VAL  B   2     8.155  -43.054  -23.958  1.00  19.44 C
169  ATOM    14   CG2  VAL  B   2     7.962  -43.903  -26.309  1.00  20.37 C
170  ATOM    15   C    VAL  B   2     7.350  -40.398  -24.812  1.00  21.03 C
171  ATOM    16   O    VAL  B   2     8.240  -39.552  -24.970  1.00  20.09 O
172  ATOM    17   N    GLN  B   3     6.451  -40.350  -23.833  1.00  19.80 N
173  ATOM    18   CA   GLN  B   3     6.553  -39.412  -22.734  1.00  21.06 C
174  ATOM    19   CB   GLN  B   3     5.426  -38.372  -22.769  1.00  24.26 C
175  ATOM    20   CG   GLN  B   3     5.498  -37.414  -23.941  1.00  27.41 C
176  ATOM    21   CD   GLN  B   3     4.929  -36.049  -23.601  1.00  33.93 C
177  ATOM    22   OE1  GLN  B   3     3.853  -35.941  -23.008  1.00  37.07 O
178  ATOM    23   NE2  GLN  B   3     5.661  -34.991  -23.955  1.00  37.57 N
179  ATOM    24   C    GLN  B   3     6.508  -40.181  -21.422  1.00  18.94 C
```

APPENDIX I-continued

| 180 | ATOM | 25 | O | GLN | B | 3 | 5.810 | −41.193 | −21.309 | 1.00 | 18.28 | O |
|---|---|---|---|---|---|---|---|---|---|---|---|---|
| 181 | ATOM | 26 | N | LEU | B | 4 | 7.264 | −39.688 | −20.447 | 1.00 | 18.64 | N |
| 182 | ATOM | 27 | CA | LEU | B | 4 | 7.384 | −40.299 | −19.116 | 1.00 | 17.38 | C |
| 183 | ATOM | 28 | CB | LEU | B | 4 | 8.728 | −41.006 | −18.951 | 1.00 | 16.80 | C |
| 184 | ATOM | 29 | CG | LEU | B | 4 | 9.135 | −42.039 | −20.009 | 1.00 | 16.40 | C |
| 185 | ATOM | 30 | CD1 | LEU | B | 4 | 10.551 | −42.509 | −19.727 | 1.00 | 16.42 | C |
| 186 | ATOM | 31 | CD2 | LEU | B | 4 | 8.210 | −43.241 | −20.031 | 1.00 | 15.93 | C |
| 187 | ATOM | 32 | C | LEU | B | 4 | 7.258 | −39.231 | −18.027 | 1.00 | 19.77 | C |
| 188 | ATOM | 33 | O | LEU | B | 4 | 7.906 | −38.197 | −18.094 | 1.00 | 19.04 | O |
| 189 | ATOM | 34 | N | GLN | B | 5 | 6.420 | −39.487 | −17.033 | 1.00 | 23.03 | N |
| 190 | ATOM | 35 | CA | GLN | B | 5 | 6.254 | −38.547 | −15.917 | 1.00 | 25.89 | C |
| 191 | ATOM | 36 | CB | GLN | B | 5 | 5.039 | −37.657 | −16.121 | 1.00 | 28.97 | C |
| 192 | ATOM | 37 | CG | GLN | B | 5 | 5.039 | −36.475 | −15.170 | 1.00 | 32.42 | C |
| 193 | ATOM | 38 | CD | GLN | B | 5 | 3.693 | −35.797 | −15.071 | 1.00 | 38.12 | C |
| 194 | ATOM | 39 | OE1 | GLN | B | 5 | 3.049 | −35.492 | −16.081 | 1.00 | 41.34 | O |
| 195 | ATOM | 40 | NE2 | GLN | B | 5 | 3.257 | −35.550 | −13.843 | 1.00 | 41.50 | N |
| 196 | ATOM | 41 | C | GLN | B | 5 | 6.173 | −39.265 | −14.583 | 1.00 | 23.44 | C |
| 197 | ATOM | 42 | O | GLN | B | 5 | 5.279 | −40.094 | −14.361 | 1.00 | 23.42 | O |
| 198 | ATOM | 43 | N | GLU | B | 6 | 7.136 | −38.942 | −13.727 | 1.00 | 23.12 | N |
| 199 | ATOM | 44 | CA | GLU | B | 6 | 7.275 | −39.546 | −12.413 | 1.00 | 23.41 | C |
| 200 | ATOM | 45 | CB | GLU | B | 6 | 8.680 | −39.425 | −11.829 | 1.00 | 23.54 | C |
| 201 | ATOM | 46 | CG | GLU | B | 6 | 9.812 | −40.185 | −12.481 | 1.00 | 24.03 | C |
| 202 | ATOM | 47 | CD | GLU | B | 6 | 10.611 | −39.354 | −13.435 | 1.00 | 22.89 | C |
| 203 | ATOM | 48 | OE1 | GLU | B | 6 | 10.220 | −38.214 | −13.783 | 1.00 | 26.07 | O |
| 204 | ATOM | 49 | OE2 | GLU | B | 6 | 11.625 | −39.835 | −13.874 | 1.00 | 21.38 | O |
| 205 | ATOM | 50 | C | GLU | B | 6 | 6.379 | −38.845 | −11.421 | 1.00 | 25.20 | C |
| 206 | ATOM | 51 | O | GLU | B | 6 | 6.085 | −37.630 | −11.541 | 1.00 | 25.08 | O |
| 207 | ATOM | 52 | N | SER | B | 7 | 6.010 | −39.602 | −10.401 | 1.00 | 24.05 | N |
| 208 | ATOM | 53 | CA | SER | B | 7 | 5.441 | −39.032 | −9.192 | 1.00 | 23.39 | C |
| 209 | ATOM | 54 | CB | SER | B | 7 | 3.924 | −38.943 | −9.335 | 1.00 | 26.23 | C |
| 210 | ATOM | 55 | OG | SER | B | 7 | 3.351 | −40.219 | −9.607 | 1.00 | 29.13 | O |
| 211 | ATOM | 56 | C | SER | B | 7 | 5.857 | −39.947 | −8.049 | 1.00 | 19.97 | C |
| 212 | ATOM | 57 | O | SER | B | 7 | 6.393 | −41.021 | −8.312 | 1.00 | 18.17 | O |
| 213 | ATOM | 58 | N | GLY | B | 8 | 5.680 | −39.509 | −6.804 | 1.00 | 17.41 | N |
| 214 | ATOM | 59 | CA | GLY | B | 8 | 5.856 | −40.388 | −5.617 | 1.00 | 16.32 | C |
| 215 | ATOM | 60 | C | GLY | B | 8 | 6.988 | −40.115 | −4.617 | 1.00 | 16.73 | C |
| 216 | ATOM | 61 | O | GLY | B | 8 | 7.082 | −40.786 | −3.554 | 1.00 | 16.08 | O |
| 217 | ATOM | 62 | N | GLY | B | 9 | 7.836 | −39.149 | −4.951 | 1.00 | 14.31 | N |
| 218 | ATOM | 63 | CA | GLY | B | 9 | 8.974 | −38.773 | −4.112 | 1.00 | 12.96 | C |
| 219 | ATOM | 64 | C | GLY | B | 9 | 8.615 | −38.190 | −2.771 | 1.00 | 11.91 | C |
| 220 | ATOM | 65 | O | GLY | B | 9 | 7.487 | −37.843 | −2.539 | 1.00 | 12.33 | O |
| 221 | ATOM | 66 | N | GLY | B | 10 | 9.594 | −38.070 | −1.879 | 1.00 | 11.19 | N |
| 222 | ATOM | 67 | CA | GLY | B | 10 | 9.318 | −37.549 | −0.559 | 1.00 | 10.60 | C |
| 223 | ATOM | 68 | C | GLY | B | 10 | 10.492 | −37.737 | 0.361 | 1.00 | 10.89 | C |
| 224 | ATOM | 69 | O | GLY | B | 10 | 11.616 | −38.008 | −0.086 | 1.00 | 10.90 | O |
| 225 | ATOM | 70 | N | LEU | B | 11 | 10.220 | −37.596 | 1.645 | 1.00 | 10.69 | N |
| 226 | ATOM | 71 | CA | LEU | B | 11 | 11.241 | −37.709 | 2.661 | 1.00 | 11.76 | C |
| 227 | ATOM | 72 | CB | LEU | B | 11 | 11.457 | −36.371 | 3.366 | 1.00 | 12.57 | C |
| 228 | ATOM | 73 | CG | LEU | B | 11 | 12.608 | −36.362 | 4.393 | 1.00 | 13.68 | C |
| 229 | ATOM | 74 | CD1 | LEU | B | 11 | 13.339 | −35.022 | 4.344 | 1.00 | 14.24 | C |
| 230 | ATOM | 75 | CD2 | LEU | B | 11 | 12.087 | −36.665 | 5.789 | 1.00 | 13.78 | C |
| 231 | ATOM | 76 | C | LEU | B | 11 | 10.788 | −38.733 | 3.659 | 1.00 | 11.95 | C |
| 232 | ATOM | 77 | O | LEU | B | 11 | 9.681 | −38.621 | 4.183 | 1.00 | 11.35 | O |
| 233 | ATOM | 78 | N | VAL | B | 12 | 11.671 | −39.688 | 3.955 | 1.00 | 12.33 | N |
| 234 | ATOM | 79 | CA | VAL | B | 12 | 11.428 | −40.662 | 5.013 | 1.00 | 13.69 | C |
| 235 | ATOM | 80 | CB | VAL | B | 12 | 11.118 | −42.046 | 4.443 | 1.00 | 13.53 | C |
| 236 | ATOM | 81 | CG1 | VAL | B | 12 | 9.804 | −42.010 | 3.681 | 1.00 | 14.80 | C |
| 237 | ATOM | 82 | CG2 | VAL | B | 12 | 12.252 | −42.536 | 3.550 | 1.00 | 13.26 | C |
| 238 | ATOM | 83 | C | VAL | B | 12 | 12.599 | −40.795 | 5.970 | 1.00 | 14.83 | C |
| 239 | ATOM | 84 | O | VAL | B | 12 | 13.736 | −40.428 | 5.647 | 1.00 | 14.14 | O |
| 240 | ATOM | 85 | N | GLN | B | 13 | 12.291 | −41.300 | 7.161 | 1.00 | 16.26 | N |
| 241 | ATOM | 86 | CA | GLN | B | 13 | 13.304 | −41.768 | 8.089 | 1.00 | 17.81 | C |
| 242 | ATOM | 87 | CB | GLN | B | 13 | 12.747 | −41.893 | 9.510 | 1.00 | 20.09 | C |
| 243 | ATOM | 88 | CG | GLN | B | 13 | 12.547 | −40.564 | 10.232 | 1.00 | 23.18 | C |
| 244 | ATOM | 89 | CD | GLN | B | 13 | 12.744 | −40.686 | 11.735 | 1.00 | 27.70 | C |
| 245 | ATOM | 90 | OE1 | GLN | B | 13 | 13.703 | −41.319 | 12.203 | 1.00 | 31.68 | O |
| 246 | ATOM | 91 | NE2 | GLN | B | 13 | 11.853 | −40.067 | 12.505 | 1.00 | 30.38 | N |
| 247 | ATOM | 92 | C | GLN | B | 13 | 13.794 | −43.145 | 7.621 | 1.00 | 17.11 | C |
| 248 | ATOM | 93 | O | GLN | B | 13 | 13.091 | −43.841 | 6.900 | 1.00 | 17.49 | O |
| 249 | ATOM | 94 | N | PRO | B | 14 | 15.001 | −43.541 | 8.041 | 1.00 | 16.47 | N |
| 250 | ATOM | 95 | CA | PRO | B | 14 | 15.472 | −44.871 | 7.693 | 1.00 | 16.65 | C |
| 251 | ATOM | 96 | CB | PRO | B | 14 | 16.788 | −44.977 | 8.458 | 1.00 | 16.73 | C |
| 252 | ATOM | 97 | CG | PRO | B | 14 | 17.279 | −43.569 | 8.553 | 1.00 | 16.62 | C |
| 253 | ATOM | 98 | CD | PRO | B | 14 | 16.029 | −42.764 | 8.763 | 1.00 | 16.66 | C |
| 254 | ATOM | 99 | C | PRO | B | 14 | 14.508 | −45.956 | 8.114 | 1.00 | 16.29 | C |
| 255 | ATOM | 100 | O | PRO | B | 14 | 13.869 | −45.843 | 9.149 | 1.00 | 16.08 | O |
| 256 | ATOM | 101 | N | GLY | B | 15 | 14.419 | −46.997 | 7.294 | 1.00 | 16.96 | N |
| 257 | ATOM | 102 | CA | GLY | B | 15 | 13.408 | −48.024 | 7.444 | 1.00 | 17.75 | C |
| 258 | ATOM | 103 | C | GLY | B | 15 | 12.097 | −47.666 | 6.754 | 1.00 | 18.03 | C |
| 259 | ATOM | 104 | O | GLY | B | 15 | 11.241 | −48.522 | 6.594 | 1.00 | 19.25 | O |

APPENDIX I-continued

| 260 | ATOM | 105 | N | GLY | B | 16 | 11.926 | −46.404 | 6.336 | 1.00 | 18.10 | N |
|---|---|---|---|---|---|---|---|---|---|---|---|---|
| 261 | ATOM | 106 | CA | GLY | B | 16 | 10.649 | −45.947 | 5.769 | 1.00 | 17.61 | C |
| 262 | ATOM | 107 | C | GLY | B | 16 | 10.431 | −46.460 | 4.344 | 1.00 | 16.65 | C |
| 263 | ATOM | 108 | O | GLY | B | 16 | 11.284 | −47.165 | 3.813 | 1.00 | 16.67 | O |
| 264 | ATOM | 109 | N | SER | B | 17 | 9.292 | −46.109 | 3.736 | 1.00 | 16.43 | N |
| 265 | ATOM | 110 | CA | ASER | B | 17 | 8.969 | −46.563 | 2.374 | 0.50 | 16.53 | C |
| 266 | ATOM | 111 | CA | BSER | B | 17 | 8.954 | −46.565 | 2.379 | 0.50 | 15.76 | C |
| 267 | ATOM | 112 | CB | ASER | B | 17 | 7.981 | −47.740 | 2.387 | 0.50 | 17.32 | C |
| 268 | ATOM | 113 | CB | BSER | B | 17 | 7.942 | −47.721 | 2.413 | 0.50 | 15.69 | C |
| 269 | ATOM | 114 | OG | ASER | B | 17 | 8.539 | −48.904 | 2.975 | 0.50 | 18.06 | O |
| 270 | ATOM | 115 | OG | BSER | B | 17 | 6.635 | −47.272 | 2.758 | 0.50 | 14.35 | O |
| 271 | ATOM | 116 | C | SER | B | 17 | 8.373 | −45.443 | 1.538 | 1.00 | 16.33 | C |
| 272 | ATOM | 117 | O | SER | B | 17 | 7.747 | −44.529 | 2.065 | 1.00 | 14.83 | O |
| 273 | ATOM | 118 | N | LEU | B | 18 | 8.612 | −45.533 | 0.226 | 1.00 | 15.51 | N |
| 274 | ATOM | 119 | CA | LEU | B | 18 | 8.002 | −44.658 | −0.756 | 1.00 | 16.08 | C |
| 275 | ATOM | 120 | CB | LEU | B | 18 | 8.962 | −43.527 | −1.186 | 1.00 | 16.66 | C |
| 276 | ATOM | 121 | CG | LEU | B | 18 | 9.251 | −42.456 | −0.141 | 1.00 | 17.49 | C |
| 277 | ATOM | 122 | CD1 | LEU | B | 18 | 10.475 | −41.624 | −0.494 | 1.00 | 18.47 | C |
| 278 | ATOM | 123 | CD2 | LEU | B | 18 | 8.048 | −41.552 | 0.053 | 1.00 | 17.76 | C |
| 279 | ATOM | 124 | C | LEU | B | 18 | 7.626 | −45.540 | −1.955 | 1.00 | 15.83 | C |
| 280 | ATOM | 125 | O | LEU | B | 18 | 8.207 | −46.625 | −2.162 | 1.00 | 15.64 | O |
| 281 | ATOM | 126 | N | ARG | B | 19 | 6.684 | −45.051 | −2.755 | 1.00 | 15.32 | N |
| 282 | ATOM | 127 | CA | ARG | B | 19 | 6.285 | −45.724 | −3.982 | 1.00 | 14.81 | C |
| 283 | ATOM | 128 | CB | ARG | B | 19 | 4.890 | −46.278 | −3.865 | 1.00 | 16.62 | C |
| 284 | ATOM | 129 | CG | ARG | B | 19 | 4.469 | −47.153 | −5.032 | 1.00 | 17.21 | C |
| 285 | ATOM | 130 | CD | ARG | B | 19 | 3.057 | −47.598 | −4.760 | 1.00 | 18.53 | C |
| 286 | ATOM | 131 | NE | ARG | B | 19 | 2.496 | −48.418 | −5.811 | 1.00 | 19.83 | N |
| 287 | ATOM | 132 | CZ | ARG | B | 19 | 2.791 | −49.696 | −6.021 | 1.00 | 19.86 | C |
| 288 | ATOM | 133 | NH1 | ARG | B | 19 | 3.678 | −50.320 | −5.279 | 1.00 | 20.43 | N |
| 289 | ATOM | 134 | NH2 | ARG | B | 19 | 2.177 | −50.362 | −6.995 | 1.00 | 20.67 | N |
| 290 | ATOM | 135 | C | ARG | B | 19 | 6.335 | −44.726 | −5.106 | 1.00 | 14.78 | C |
| 291 | ATOM | 136 | O | ARG | B | 19 | 5.610 | −43.723 | −5.096 | 1.00 | 14.49 | O |
| 292 | ATOM | 137 | N | LEU | B | 20 | 7.240 | −44.965 | −6.042 | 1.00 | 13.08 | N |
| 293 | ATOM | 138 | CA | LEU | B | 20 | 7.339 | −44.106 | −7.217 | 1.00 | 13.90 | C |
| 294 | ATOM | 139 | CB | LEU | B | 20 | 8.797 | −43.986 | −7.672 | 1.00 | 13.42 | C |
| 295 | ATOM | 140 | CG | LEU | B | 20 | 9.818 | −43.631 | −6.593 | 1.00 | 13.99 | C |
| 296 | ATOM | 141 | CD1 | LEU | B | 20 | 11.168 | −43.346 | −7.256 | 1.00 | 13.53 | C |
| 297 | ATOM | 142 | CD2 | LEU | B | 20 | 9.385 | −42.450 | −5.733 | 1.00 | 14.13 | C |
| 298 | ATOM | 143 | C | LEU | B | 20 | 6.483 | −44.683 | −8.343 | 1.00 | 14.22 | C |
| 299 | ATOM | 144 | O | LEU | B | 20 | 6.340 | −45.896 | −8.429 | 1.00 | 13.80 | O |
| 300 | ATOM | 145 | N | SER | B | 21 | 5.956 | −43.800 | −9.192 | 1.00 | 16.55 | N |
| 301 | ATOM | 146 | CA | SER | B | 21 | 5.198 | −44.169 | −10.398 | 1.00 | 17.42 | C |
| 302 | ATOM | 147 | CB | SER | B | 21 | 3.705 | −43.751 | −10.298 | 1.00 | 19.40 | C |
| 303 | ATOM | 148 | OG | SER | B | 21 | 3.087 | −44.441 | −9.263 | 1.00 | 24.54 | O |
| 304 | ATOM | 149 | C | SER | B | 21 | 5.762 | −43.444 | −11.571 | 1.00 | 17.03 | C |
| 305 | ATOM | 150 | O | SER | B | 21 | 6.194 | −42.288 | −11.475 | 1.00 | 17.32 | O |
| 306 | ATOM | 151 | N | CYS | B | 22 | 5.725 | −44.105 | −12.713 | 1.00 | 17.88 | N |
| 307 | ATOM | 152 | CA | CYS | B | 22 | 6.134 | −43.504 | −13.932 | 1.00 | 17.93 | C |
| 308 | ATOM | 153 | CB | CYS | B | 22 | 7.393 | −44.222 | −14.433 | 1.00 | 17.55 | C |
| 309 | ATOM | 154 | SG | CYS | B | 22 | 7.913 | −43.628 | −16.054 | 1.00 | 18.78 | S |
| 310 | ATOM | 155 | C | CYS | B | 22 | 4.990 | −43.688 | −14.909 | 1.00 | 20.09 | C |
| 311 | ATOM | 156 | O | CYS | B | 22 | 4.689 | −44.803 | −15.271 | 1.00 | 19.27 | O |
| 312 | ATOM | 157 | N | ALA | B | 23 | 4.330 | −42.593 | −15.279 | 1.00 | 21.16 | N |
| 313 | ATOM | 158 | CA | ALA | B | 23 | 3.254 | −42.610 | −16.233 | 1.00 | 20.47 | C |
| 314 | ATOM | 159 | CB | ALA | B | 23 | 2.350 | −41.397 | −16.035 | 1.00 | 22.94 | C |
| 315 | ATOM | 160 | C | ALA | B | 23 | 3.871 | −42.585 | −17.617 | 1.00 | 20.51 | C |
| 316 | ATOM | 161 | O | ALA | B | 23 | 4.533 | −41.613 | −17.978 | 1.00 | 20.56 | O |
| 317 | ATOM | 162 | N | ALA | B | 24 | 3.650 | −43.661 | −18.361 | 1.00 | 19.47 | N |
| 318 | ATOM | 163 | CA | ALA | B | 24 | 4.277 | −43.869 | −19.667 | 1.00 | 19.84 | C |
| 319 | ATOM | 164 | CB | ALA | B | 24 | 5.050 | −45.184 | −19.657 | 1.00 | 19.01 | C |
| 320 | ATOM | 165 | C | ALA | B | 24 | 3.243 | −43.874 | −20.789 | 1.00 | 19.90 | C |
| 321 | ATOM | 166 | O | ALA | B | 24 | 2.185 | −44.525 | −20.691 | 1.00 | 21.10 | O |
| 322 | ATOM | 167 | N | SER | B | 25 | 3.567 | −43.177 | −21.876 | 1.00 | 19.58 | N |
| 323 | ATOM | 168 | CA | SER | B | 25 | 2.701 | −43.074 | −23.033 | 1.00 | 21.46 | C |
| 324 | ATOM | 169 | CB | SER | B | 25 | 1.898 | −41.766 | −23.007 | 1.00 | 21.56 | C |
| 325 | ATOM | 170 | OG | SER | B | 25 | 2.741 | −40.632 | −22.865 | 1.00 | 22.70 | O |
| 326 | ATOM | 171 | C | SER | B | 25 | 3.530 | −43.117 | −24.304 | 1.00 | 20.71 | C |
| 327 | ATOM | 172 | O | SER | B | 25 | 4.744 | −42.936 | −24.264 | 1.00 | 20.44 | O |
| 328 | ATOM | 173 | N | GLY | B | 26 | 2.858 | −43.332 | −25.424 | 1.00 | 19.84 | N |
| 329 | ATOM | 174 | CA | GLY | B | 26 | 3.536 | −43.472 | −26.720 | 1.00 | 20.21 | C |
| 330 | ATOM | 175 | C | GLY | B | 26 | 3.521 | −44.923 | −27.144 | 1.00 | 18.80 | C |
| 331 | ATOM | 176 | O | GLY | B | 26 | 3.127 | −45.809 | −26.381 | 1.00 | 18.91 | O |
| 332 | ATOM | 177 | N | LYS | B | 27 | 4.014 | −45.176 | −28.346 | 1.00 | 19.37 | N |
| 333 | ATOM | 178 | CA | LYS | B | 27 | 3.984 | −46.503 | −28.929 | 1.00 | 19.96 | C |
| 334 | ATOM | 179 | CB | LYS | B | 27 | 4.756 | −46.458 | −30.246 | 1.00 | 23.07 | C |
| 335 | ATOM | 180 | CG | LYS | B | 27 | 4.485 | −47.635 | −31.129 | 1.00 | 25.57 | C |
| 336 | ATOM | 181 | CD | LYS | B | 27 | 4.764 | −47.304 | −32.591 | 1.00 | 27.04 | C |
| 337 | ATOM | 182 | CE | LYS | B | 27 | 6.237 | −47.046 | −32.838 | 1.00 | 27.74 | C |
| 338 | ATOM | 183 | NZ | LYS | B | 27 | 6.588 | −47.430 | −34.247 | 1.00 | 30.37 | N |
| 339 | ATOM | 184 | C | LYS | B | 27 | 4.615 | −47.539 | −28.015 | 1.00 | 19.61 | C |

APPENDIX I-continued

| | | | | | | | | | | | |
|---|---|---|---|---|---|---|---|---|---|---|---|
| 340 | ATOM | 185 | O | LYS | B | 27 | 5.710 | −47.319 | −27.565 | 1.00 | 18.21 O |
| 341 | ATOM | 186 | N | MET | B | 28 | 3.926 | −48.636 | −27.708 | 1.00 | 19.93 N |
| 342 | ATOM | 187 | CA | MET | B | 28 | 4.413 | −49.554 | −26.680 | 1.00 | 20.93 C |
| 343 | ATOM | 188 | CB | MET | B | 28 | 3.362 | −50.631 | −26.363 | 1.00 | 24.70 C |
| 344 | ATOM | 189 | CG | MET | B | 28 | 2.327 | −50.185 | −25.314 | 1.00 | 27.81 C |
| 345 | ATOM | 190 | SD | MET | B | 28 | 0.585 | −50.566 | −25.646 | 1.00 | 30.14 S |
| 346 | ATOM | 191 | CE | MET | B | 28 | 0.273 | −49.201 | −26.789 | 1.00 | 33.21 C |
| 347 | ATOM | 192 | C | MET | B | 28 | 5.779 | −50.163 | −27.043 | 1.00 | 18.42 C |
| 348 | ATOM | 193 | O | MET | B | 28 | 6.647 | −50.301 | −26.183 | 1.00 | 16.12 O |
| 349 | ATOM | 194 | N | SER | B | 29 | 5.968 | −50.497 | −28.318 | 1.00 | 16.17 N |
| 350 | ATOM | 195 | CA | SER | B | 29 | 7.251 | −51.000 | −28.810 | 1.00 | 14.25 C |
| 351 | ATOM | 196 | CB | SER | B | 29 | 7.226 | −51.367 | −30.298 | 1.00 | 14.64 C |
| 352 | ATOM | 197 | OG | SER | B | 29 | 6.877 | −50.259 | −31.142 | 1.00 | 14.48 O |
| 353 | ATOM | 198 | C | SER | B | 29 | 8.425 | −50.050 | −28.539 | 1.00 | 13.04 C |
| 354 | ATOM | 199 | O | SER | B | 29 | 9.556 | −50.504 | −28.462 | 1.00 | 12.86 O |
| 355 | ATOM | 200 | N | SER | B | 30 | 8.160 | −48.753 | −28.457 | 1.00 | 12.69 N |
| 356 | ATOM | 201 | CA | SER | B | 30 | 9.225 | −47.764 | −28.249 | 1.00 | 12.49 C |
| 357 | ATOM | 202 | CB | SER | B | 30 | 8.788 | −46.397 | −28.757 | 1.00 | 12.47 C |
| 358 | ATOM | 203 | OG | SER | B | 30 | 8.718 | −46.387 | −30.178 | 1.00 | 13.72 O |
| 359 | ATOM | 204 | C | SER | B | 30 | 9.620 | −47.629 | −26.800 | 1.00 | 12.85 C |
| 360 | ATOM | 205 | O | SER | B | 30 | 10.620 | −46.991 | −26.504 | 1.00 | 11.90 O |
| 361 | ATOM | 206 | N | ARG | B | 31 | 8.824 | −48.226 | −25.906 | 1.00 | 13.46 N |
| 362 | ATOM | 207 | CA | ARG | B | 31 | 9.057 | −48.162 | −24.464 | 1.00 | 13.52 C |
| 363 | ATOM | 208 | CB | ARG | B | 31 | 8.089 | −47.167 | −23.803 | 1.00 | 14.88 C |
| 364 | ATOM | 209 | CG | ARG | B | 31 | 6.620 | −47.397 | −24.147 | 1.00 | 15.62 C |
| 365 | ATOM | 210 | CD | ARG | B | 31 | 5.777 | −46.313 | −23.480 | 1.00 | 16.92 C |
| 366 | ATOM | 211 | NE | ARG | B | 31 | 4.381 | −46.402 | −23.874 | 1.00 | 17.76 N |
| 367 | ATOM | 212 | CZ | ARG | B | 31 | 3.411 | −47.037 | −23.215 | 1.00 | 20.00 C |
| 368 | ATOM | 213 | NH1 | ARG | B | 31 | 3.627 | −47.695 | −22.078 | 1.00 | 20.67 N |
| 369 | ATOM | 214 | NH2 | ARG | B | 31 | 2.176 | −46.995 | −23.707 | 1.00 | 21.62 N |
| 370 | ATOM | 215 | C | ARG | B | 31 | 8.969 | −49.529 | −23.790 | 1.00 | 13.86 C |
| 371 | ATOM | 216 | O | ARG | B | 31 | 8.717 | −49.602 | −22.583 | 1.00 | 13.83 O |
| 372 | ATOM | 217 | N | ARG | B | 32 | 9.269 | −50.612 | −24.523 | 1.00 | 13.26 N |
| 373 | ATOM | 218 | CA | ARG | B | 32 | 9.205 | −51.966 | −23.935 | 1.00 | 12.26 C |
| 374 | ATOM | 219 | CB | ARG | B | 32 | 9.260 | −53.051 | −25.003 | 1.00 | 12.10 C |
| 375 | ATOM | 220 | CG | ARG | B | 32 | 10.554 | −53.126 | −25.785 | 1.00 | 12.07 C |
| 376 | ATOM | 221 | CD | ARG | B | 32 | 10.603 | −54.347 | −26.699 | 1.00 | 11.69 C |
| 377 | ATOM | 222 | NE | ARG | B | 32 | 9.653 | −54.381 | −27.798 | 1.00 | 12.60 N |
| 378 | ATOM | 223 | CZ | ARG | B | 32 | 9.928 | −54.017 | −29.064 | 1.00 | 12.75 C |
| 379 | ATOM | 224 | NH1 | ARG | B | 32 | 11.113 | −53.505 | −29.401 | 1.00 | 13.13 N |
| 380 | ATOM | 225 | NH2 | ARG | B | 32 | 9.028 | −54.172 | −30.016 | 1.00 | 13.38 N |
| 381 | ATOM | 226 | C | ARG | B | 32 | 10.277 | −52.239 | −22.866 | 1.00 | 12.40 C |
| 382 | ATOM | 227 | O | ARG | B | 32 | 10.080 | −53.087 | −21.967 | 1.00 | 13.22 O |
| 383 | ATOM | 228 | N | CYS | B | 33 | 11.394 | −51.531 | −22.963 | 1.00 | 11.52 N |
| 384 | ATOM | 229 | CA | CYS | B | 33 | 12.474 | −51.613 | −21.981 | 1.00 | 12.17 C |
| 385 | ATOM | 230 | CB | CYS | B | 33 | 13.830 | −51.586 | −22.666 | 1.00 | 12.35 C |
| 386 | ATOM | 231 | SG | CYS | B | 33 | 15.203 | −51.826 | −21.526 | 1.00 | 12.00 S |
| 387 | ATOM | 232 | C | CYS | B | 33 | 12.303 | −50.431 | −21.014 | 1.00 | 12.15 C |
| 388 | ATOM | 233 | O | CYS | B | 33 | 12.571 | −49.295 | −21.353 | 1.00 | 12.65 O |
| 389 | ATOM | 234 | N | MET | B | 34 | 11.826 | −50.724 | −19.816 | 1.00 | 12.65 N |
| 390 | ATOM | 235 | CA | MET | B | 34 | 11.625 | −49.690 | −18.791 | 1.00 | 12.15 C |
| 391 | ATOM | 236 | CB | MET | B | 34 | 10.255 | −49.859 | −18.169 | 1.00 | 12.52 C |
| 392 | ATOM | 237 | CG | MET | B | 34 | 9.071 | −49.585 | −19.103 | 1.00 | 13.18 C |
| 393 | ATOM | 238 | SD | MET | B | 34 | 9.045 | −47.921 | −19.788 | 1.00 | 15.12 S |
| 394 | ATOM | 239 | CE | MET | B | 34 | 8.978 | −46.993 | −18.263 | 1.00 | 15.05 C |
| 395 | ATOM | 240 | C | MET | B | 34 | 12.678 | −49.848 | −17.710 | 1.00 | 12.44 C |
| 396 | ATOM | 241 | O | MET | B | 34 | 13.073 | −50.952 | −17.356 | 1.00 | 12.29 O |
| 397 | ATOM | 242 | N | ALA | B | 35 | 13.128 | −48.734 | −17.156 | 1.00 | 12.12 N |
| 398 | ATOM | 243 | CA | ALA | B | 35 | 14.114 | −48.796 | −16.099 | 1.00 | 11.41 C |
| 399 | ATOM | 244 | CB | ALA | B | 35 | 15.499 | −48.717 | −16.703 | 1.00 | 11.88 C |
| 400 | ATOM | 245 | C | ALA | B | 35 | 13.909 | −47.669 | −15.105 | 1.00 | 11.10 C |
| 401 | ATOM | 246 | O | ALA | B | 35 | 13.326 | −46.638 | −15.440 | 1.00 | 11.83 O |
| 402 | ATOM | 247 | N | TRP | B | 36 | 14.397 | −47.880 | −13.884 | 1.00 | 11.25 N |
| 403 | ATOM | 248 | CA | TRP | B | 36 | 14.585 | −46.817 | −12.908 | 1.00 | 11.87 C |
| 404 | ATOM | 249 | CB | TRP | B | 36 | 13.922 | −47.126 | −11.588 | 1.00 | 12.34 C |
| 405 | ATOM | 250 | CG | TRP | B | 36 | 12.436 | −47.070 | −11.630 | 1.00 | 13.05 C |
| 406 | ATOM | 251 | CD1 | TRP | B | 36 | 11.598 | −48.095 | −11.821 | 1.00 | 13.24 C |
| 407 | ATOM | 252 | NE1 | TRP | B | 36 | 10.303 | −47.663 | −11.808 | 1.00 | 14.75 N |
| 408 | ATOM | 253 | CE2 | TRP | B | 36 | 10.294 | −46.313 | −11.572 | 1.00 | 13.99 C |
| 409 | ATOM | 254 | CD2 | TRP | B | 36 | 11.634 | −45.908 | −11.447 | 1.00 | 13.53 C |
| 410 | ATOM | 255 | CE3 | TRP | B | 36 | 11.918 | −44.564 | −11.202 | 1.00 | 14.11 C |
| 411 | ATOM | 256 | CZ3 | TRP | B | 36 | 10.854 | −43.675 | −11.088 | 1.00 | 14.47 C |
| 412 | ATOM | 257 | CH2 | TRP | B | 36 | 9.538 | −44.119 | −11.201 | 1.00 | 13.84 C |
| 413 | ATOM | 258 | CZ2 | TRP | B | 36 | 9.237 | −45.430 | −11.462 | 1.00 | 14.73 C |
| 414 | ATOM | 259 | C | TRP | B | 36 | 16.074 | −46.569 | −12.696 | 1.00 | 11.36 C |
| 415 | ATOM | 260 | O | TRP | B | 36 | 16.855 | −47.501 | −12.502 | 1.00 | 12.72 O |
| 416 | ATOM | 261 | N | PHE | B | 37 | 16.448 | −45.305 | −12.787 | 1.00 | 11.52 N |
| 417 | ATOM | 262 | CA | PHE | B | 37 | 17.806 | −44.819 | −12.506 | 1.00 | 10.95 C |
| 418 | ATOM | 263 | CB | PHE | B | 37 | 18.352 | −44.049 | −13.703 | 1.00 | 11.92 C |
| 419 | ATOM | 264 | CG | PHE | B | 37 | 18.806 | −44.912 | −14.871 | 1.00 | 11.12 C |

APPENDIX I-continued

| | | | | | | | | | | | |
|---|---|---|---|---|---|---|---|---|---|---|---|
| 420 | ATOM | 265 | CD1 | PHE | B | 37 | 20.153 | −45.195 | −15.044 | 1.00 | 11.59 C |
| 421 | ATOM | 266 | CE1 | PHE | B | 37 | 20.596 | −45.937 | −16.124 | 1.00 | 11.24 C |
| 422 | ATOM | 267 | CZ | PHE | B | 37 | 19.681 | −46.406 | −17.057 | 1.00 | 11.20 C |
| 423 | ATOM | 268 | CE2 | PHE | B | 37 | 18.338 | −46.105 | −16.921 | 1.00 | 11.37 C |
| 424 | ATOM | 269 | CD2 | PHE | B | 37 | 17.906 | −45.358 | −15.834 | 1.00 | 11.51 C |
| 425 | ATOM | 270 | C | PHE | B | 37 | 17.765 | −43.878 | −11.312 | 1.00 | 11.60 C |
| 426 | ATOM | 271 | O | PHE | B | 37 | 16.711 | −43.335 | −10.970 | 1.00 | 10.33 O |
| 427 | ATOM | 272 | N | ARG | B | 38 | 18.899 | −43.701 | −10.656 | 1.00 | 11.78 N |
| 428 | ATOM | 273 | CA | ARG | B | 38 | 18.980 | −42.709 | −9.590 | 1.00 | 12.33 C |
| 429 | ATOM | 274 | CB | ARG | B | 38 | 18.803 | −43.363 | −8.231 | 1.00 | 12.37 C |
| 430 | ATOM | 275 | CG | ARG | B | 38 | 19.939 | −44.241 | −7.798 | 1.00 | 12.60 C |
| 431 | ATOM | 276 | CD | ARG | B | 38 | 19.553 | −44.886 | −6.493 | 1.00 | 13.42 C |
| 432 | ATOM | 277 | NE | ARG | B | 38 | 20.593 | −45.782 | −5.999 | 1.00 | 13.85 N |
| 433 | ATOM | 278 | CZ | ARG | B | 38 | 20.478 | −46.498 | −4.891 | 1.00 | 15.42 C |
| 434 | ATOM | 279 | NH1 | ARG | B | 38 | 19.351 | −46.460 | −4.195 | 1.00 | 15.48 N |
| 435 | ATOM | 280 | NH2 | ARG | B | 38 | 21.475 | −47.298 | −4.499 | 1.00 | 16.37 N |
| 436 | ATOM | 281 | C | ARG | B | 38 | 20.281 | −41.930 | −9.680 | 1.00 | 13.25 C |
| 437 | ATOM | 282 | O | ARG | B | 38 | 21.293 | −42.447 | −10.151 | 1.00 | 13.91 O |
| 438 | ATOM | 283 | N | GLN | B | 39 | 20.237 | −40.667 | −9.257 | 1.00 | 14.11 N |
| 439 | ATOM | 284 | CA | GLN | B | 39 | 21.433 | −39.838 | −9.261 | 1.00 | 16.44 C |
| 440 | ATOM | 285 | CB | GLN | B | 39 | 21.363 | −38.818 | −10.378 | 1.00 | 17.66 C |
| 441 | ATOM | 286 | CG | GLN | B | 39 | 22.646 | −38.014 | −10.544 | 1.00 | 20.88 C |
| 442 | ATOM | 287 | CD | GLN | B | 39 | 22.627 | −37.138 | −11.773 | 1.00 | 23.83 C |
| 443 | ATOM | 288 | OE1 | GLN | B | 39 | 21.574 | −36.715 | −12.228 | 1.00 | 27.19 O |
| 444 | ATOM | 289 | NE2 | GLN | B | 39 | 23.800 | −36.844 | −12.308 | 1.00 | 26.58 N |
| 445 | ATOM | 290 | C | GLN | B | 39 | 21.559 | −39.115 | −7.933 | 1.00 | 16.77 C |
| 446 | ATOM | 291 | O | GLN | B | 39 | 20.712 | −38.319 | −7.587 | 1.00 | 16.07 O |
| 447 | ATOM | 292 | N | ALA | B | 40 | 22.599 | −39.420 | −7.190 | 1.00 | 18.28 N |
| 448 | ATOM | 293 | CA | ALA | B | 40 | 22.946 | −38.612 | −6.023 | 1.00 | 20.68 C |
| 449 | ATOM | 294 | CB | ALA | B | 40 | 23.690 | −39.455 | −5.015 | 1.00 | 21.02 C |
| 450 | ATOM | 295 | C | ALA | B | 40 | 23.806 | −37.428 | −6.472 | 1.00 | 23.66 C |
| 451 | ATOM | 296 | O | ALA | B | 40 | 24.571 | −37.555 | −7.420 | 1.00 | 24.03 O |
| 452 | ATOM | 297 | N | PRO | B | 41 | 23.706 | −36.263 | −5.784 | 1.00 | 26.46 C |
| 453 | ATOM | 298 | CA | PRO | B | 41 | 24.607 | −35.187 | −6.190 | 1.00 | 29.48 C |
| 454 | ATOM | 299 | CB | PRO | B | 41 | 24.235 | −34.019 | −5.253 | 1.00 | 30.79 C |
| 455 | ATOM | 300 | CG | PRO | B | 41 | 22.899 | −34.357 | −4.696 | 1.00 | 28.81 C |
| 456 | ATOM | 301 | CD | PRO | B | 41 | 22.843 | −35.861 | −4.658 | 1.00 | 28.56 C |
| 457 | ATOM | 302 | C | PRO | B | 41 | 26.074 | −35.584 | −6.002 | 1.00 | 30.38 C |
| 458 | ATOM | 303 | O | PRO | B | 41 | 26.446 | −36.229 | −4.999 | 1.00 | 31.41 O |
| 459 | ATOM | 304 | N | GLY | B | 42 | 26.890 | −35.217 | −6.982 | 1.00 | 31.00 N |
| 460 | ATOM | 305 | CA | GLY | B | 42 | 28.291 | −35.600 | −7.010 | 1.00 | 31.37 C |
| 461 | ATOM | 306 | C | GLY | B | 42 | 28.510 | −36.947 | −7.669 | 1.00 | 32.51 C |
| 462 | ATOM | 307 | O | GLY | B | 42 | 29.637 | −37.449 | −7.678 | 1.00 | 32.66 O |
| 463 | ATOM | 308 | N | LYS | B | 43 | 27.449 | −37.531 | −8.237 | 1.00 | 30.54 N |
| 464 | ATOM | 309 | CA | LYS | B | 43 | 27.538 | −38.868 | −8.842 | 1.00 | 30.85 C |
| 465 | ATOM | 310 | CB | LYS | B | 43 | 27.056 | −39.921 | −7.849 | 1.00 | 32.67 C |
| 466 | ATOM | 311 | CG | LYS | B | 43 | 27.822 | −39.875 | −6.537 | 1.00 | 35.19 C |
| 467 | ATOM | 312 | CD | LYS | B | 43 | 27.831 | −41.201 | −5.783 | 1.00 | 38.68 C |
| 468 | ATOM | 313 | CE | LYS | B | 43 | 26.988 | −41.169 | −4.515 | 1.00 | 41.43 C |
| 469 | ATOM | 314 | NZ | LYS | B | 43 | 27.632 | −41.991 | −3.449 | 1.00 | 43.27 N |
| 470 | ATOM | 315 | C | LYS | B | 43 | 26.801 | −38.995 | −10.164 | 1.00 | 30.62 C |
| 471 | ATOM | 316 | O | LYS | B | 43 | 26.009 | −38.136 | −10.532 | 1.00 | 30.06 O |
| 472 | ATOM | 317 | N | GLU | B | 44 | 27.115 | −40.060 | −10.905 | 1.00 | 30.46 N |
| 473 | ATOM | 318 | CA | GLU | B | 44 | 26.500 | −40.328 | −12.202 | 1.00 | 31.36 C |
| 474 | ATOM | 319 | CB | GLU | B | 44 | 27.402 | −41.264 | −13.006 | 1.00 | 34.42 C |
| 475 | ATOM | 320 | CG | GLU | B | 44 | 28.757 | −40.691 | −13.363 | 1.00 | 39.28 C |
| 476 | ATOM | 321 | CD | GLU | B | 44 | 29.604 | −41.644 | −14.206 | 1.00 | 43.52 C |
| 477 | ATOM | 322 | OE1 | GLU | B | 44 | 29.130 | −42.760 | −14.558 | 1.00 | 46.19 O |
| 478 | ATOM | 323 | OE2 | GLU | B | 44 | 30.751 | −41.269 | −14.528 | 1.00 | 47.43 O |
| 479 | ATOM | 324 | C | GLU | B | 44 | 25.149 | −41.019 | −12.004 | 1.00 | 28.23 C |
| 480 | ATOM | 325 | O | GLU | B | 44 | 24.937 | −41.615 | −10.953 | 1.00 | 26.17 O |
| 481 | ATOM | 326 | N | ARG | B | 45 | 24.245 | −40.950 | −12.996 | 1.00 | 25.49 N |
| 482 | ATOM | 327 | CA | ARG | B | 45 | 23.021 | −41.734 | −12.930 | 1.00 | 23.19 C |
| 483 | ATOM | 328 | CB | ARG | B | 45 | 22.031 | −41.416 | −14.057 | 1.00 | 24.25 C |
| 484 | ATOM | 329 | CG | ARG | B | 45 | 21.326 | −40.097 | −13.860 | 1.00 | 26.58 C |
| 485 | ATOM | 330 | CD | ARG | B | 45 | 20.368 | −39.766 | −14.965 | 1.00 | 26.33 C |
| 486 | ATOM | 331 | NE | ARG | B | 45 | 20.124 | −38.342 | −14.923 | 1.00 | 28.24 N |
| 487 | ATOM | 332 | CZ | ARG | B | 45 | 19.144 | −37.711 | −15.554 | 1.00 | 30.30 C |
| 488 | ATOM | 333 | NH1 | ARG | B | 45 | 18.272 | −38.379 | −16.294 | 1.00 | 29.43 N |
| 489 | ATOM | 334 | NH2 | ARG | B | 45 | 19.040 | −36.399 | −15.429 | 1.00 | 30.26 N |
| 490 | ATOM | 335 | C | ARG | B | 45 | 23.422 | −43.192 | −12.949 | 1.00 | 21.53 C |
| 491 | ATOM | 336 | O | ARG | B | 45 | 24.305 | −43.588 | −13.733 | 1.00 | 22.49 O |
| 492 | ATOM | 337 | N | GLU | B | 46 | 22.825 | −43.974 | −12.051 | 1.00 | 17.94 N |
| 493 | ATOM | 338 | CA | GLU | B | 46 | 23.057 | −45.411 | −11.969 | 1.00 | 17.36 C |
| 494 | ATOM | 339 | CB | GLU | B | 46 | 23.803 | −45.807 | −10.695 | 1.00 | 19.00 C |
| 495 | ATOM | 340 | CG | GLU | B | 46 | 23.030 | −45.566 | −9.401 | 1.00 | 23.03 C |
| 496 | ATOM | 341 | CD | GLU | B | 46 | 23.773 | −46.003 | −8.140 | 1.00 | 26.97 C |
| 497 | ATOM | 342 | OE1 | GLU | B | 46 | 25.027 | −45.835 | −8.095 | 1.00 | 31.44 O |
| 498 | ATOM | 343 | OE2 | GLU | B | 46 | 23.103 | −46.503 | −7.195 | 1.00 | 25.00 O |
| 499 | ATOM | 344 | C | GLU | B | 46 | 21.714 | −46.140 | −12.037 | 1.00 | 14.31 C |

APPENDIX I-continued

| | | | | | | | | | | | |
|---|---|---|---|---|---|---|---|---|---|---|---|
| 500 | ATOM | 345 | O | GLU | B | 46 | 20.737 | −45.748 | −11.409 | 1.00 | 12.11 O |
| 501 | ATOM | 346 | N | ARG | B | 47 | 21.687 | −47.237 | −12.769 | 1.00 | 12.66 N |
| 502 | ATOM | 347 | CA | ARG | B | 47 | 20.463 | −47.978 | −12.895 | 1.00 | 12.05 C |
| 503 | ATOM | 348 | CB | ARG | B | 47 | 20.519 | −48.913 | −14.120 | 1.00 | 11.98 C |
| 504 | ATOM | 349 | CG | ARG | B | 47 | 19.137 | −49.220 | −14.658 | 1.00 | 12.14 C |
| 505 | ATOM | 350 | CD | ARG | B | 47 | 19.231 | −50.153 | −15.852 | 1.00 | 12.33 C |
| 506 | ATOM | 351 | NE | ARG | B | 47 | 19.522 | −51.521 | −15.447 | 1.00 | 12.54 N |
| 507 | ATOM | 352 | CZ | ARG | B | 47 | 19.430 | −52.583 | −16.260 | 1.00 | 14.14 C |
| 508 | ATOM | 353 | NH1 | ARG | B | 47 | 19.591 | −53.782 | −15.751 | 1.00 | 15.47 N |
| 509 | ATOM | 354 | NH2 | ARG | B | 47 | 19.142 | −52.455 | −17.556 | 1.00 | 13.31 N |
| 510 | ATOM | 355 | C | ARG | B | 47 | 20.238 | −48.780 | −11.630 | 1.00 | 12.74 C |
| 511 | ATOM | 356 | O | ARG | B | 47 | 21.204 | −49.322 | −11.059 | 1.00 | 13.51 O |
| 512 | ATOM | 357 | N | VAL | B | 48 | 18.983 | −48.847 | −11.175 | 1.00 | 12.32 N |
| 513 | ATOM | 358 | CA | VAL | B | 48 | 18.613 | −49.755 | −10.068 | 1.00 | 12.52 C |
| 514 | ATOM | 359 | CB | VAL | B | 48 | 18.180 | −48.988 | −8.803 | 1.00 | 13.13 C |
| 515 | ATOM | 360 | CG1 | VAL | B | 48 | 16.945 | −48.147 | −9.050 | 1.00 | 13.66 C |
| 516 | ATOM | 361 | CG2 | VAL | B | 48 | 19.339 | −48.135 | −8.300 | 1.00 | 13.71 C |
| 517 | ATOM | 362 | C | VAL | B | 48 | 17.576 | −50.844 | −10.412 | 1.00 | 12.74 C |
| 518 | ATOM | 363 | O | VAL | B | 48 | 17.483 | −51.808 | −9.696 | 1.00 | 12.25 O |
| 519 | ATOM | 364 | N | ALA | B | 49 | 16.796 | −50.692 | −11.477 | 1.00 | 12.32 N |
| 520 | ATOM | 365 | CA | ALA | B | 49 | 15.753 | −51.662 | −11.791 | 1.00 | 12.25 C |
| 521 | ATOM | 366 | CB | ALA | B | 49 | 14.485 | −51.379 | −10.965 | 1.00 | 12.54 C |
| 522 | ATOM | 367 | C | ALA | B | 49 | 15.429 | −51.622 | −13.267 | 1.00 | 11.90 C |
| 523 | ATOM | 368 | O | ALA | B | 49 | 15.611 | −50.581 | −13.904 | 1.00 | 11.20 O |
| 524 | ATOM | 369 | N | LYS | B | 50 | 14.991 | −52.775 | −13.770 | 1.00 | 11.52 N |
| 525 | ATOM | 370 | CA | LYS | B | 50 | 14.631 | −52.972 | −15.168 | 1.00 | 11.74 C |
| 526 | ATOM | 371 | CB | LYS | B | 50 | 15.802 | −53.563 | −15.925 | 1.00 | 11.75 C |
| 527 | ATOM | 372 | CG | LYS | B | 50 | 15.480 | −54.194 | −17.300 | 1.00 | 11.85 C |
| 528 | ATOM | 373 | CD | LYS | B | 50 | 15.089 | −55.657 | −17.187 | 1.00 | 11.88 C |
| 529 | ATOM | 374 | CE | LYS | B | 50 | 14.705 | −56.338 | −18.504 | 1.00 | 11.56 C |
| 530 | ATOM | 375 | NZ | LYS | B | 50 | 14.294 | −57.752 | −18.281 | 1.00 | 11.78 N |
| 531 | ATOM | 376 | C | LYS | B | 50 | 13.403 | −53.869 | −15.256 | 1.00 | 11.74 C |
| 532 | ATOM | 377 | O | LYS | B | 50 | 13.265 | −54.806 | −14.471 | 1.00 | 11.22 O |
| 533 | ATOM | 378 | N | LEU | B | 51 | 12.560 | −53.566 | −16.228 | 1.00 | 12.24 N |
| 534 | ATOM | 379 | CA | LEU | B | 51 | 11.390 | −54.381 | −16.598 | 1.00 | 13.61 C |
| 535 | ATOM | 380 | CB | LEU | B | 51 | 10.120 | −53.759 | −15.991 | 1.00 | 14.51 C |
| 536 | ATOM | 381 | CG | LEU | B | 51 | 8.768 | −54.200 | −16.627 | 1.00 | 16.01 C |
| 537 | ATOM | 382 | CD1 | LEU | B | 51 | 8.462 | −55.590 | −16.139 | 1.00 | 17.03 C |
| 538 | ATOM | 383 | CD2 | LEU | B | 51 | 7.636 | −53.242 | −16.294 | 1.00 | 17.99 C |
| 539 | ATOM | 384 | C | LEU | B | 51 | 11.252 | −54.392 | −18.107 | 1.00 | 12.78 C |
| 540 | ATOM | 385 | O | LEU | B | 51 | 11.256 | −53.348 | −18.734 | 1.00 | 11.90 O |
| 541 | ATOM | 386 | N | LEU | B | 52 | 11.160 | −55.577 | −18.710 | 1.00 | 11.96 N |
| 542 | ATOM | 387 | CA | LEU | B | 52 | 10.759 | −55.684 | −20.110 | 1.00 | 12.10 C |
| 543 | ATOM | 388 | CB | LEU | B | 52 | 11.402 | −56.873 | −20.791 | 1.00 | 12.00 C |
| 544 | ATOM | 389 | CG | LEU | B | 52 | 11.145 | −56.879 | −22.313 | 1.00 | 12.51 C |
| 545 | ATOM | 390 | CD1 | LEU | B | 52 | 11.973 | −55.786 | −22.991 | 1.00 | 13.40 C |
| 546 | ATOM | 391 | CD2 | LEU | B | 52 | 11.450 | −58.242 | −22.925 | 1.00 | 13.21 C |
| 547 | ATOM | 392 | C | LEU | B | 52 | 9.235 | −55.882 | −20.085 | 1.00 | 12.12 C |
| 548 | ATOM | 393 | O | LEU | B | 52 | 8.713 | −56.845 | −19.496 | 1.00 | 12.00 O |
| 549 | ATOM | 394 | N | THR | B | 53 | 8.501 | −54.955 | −20.676 | 1.00 | 11.92 N |
| 550 | ATOM | 395 | CA | THR | B | 53 | 7.067 | −54.888 | −20.423 | 1.00 | 12.09 C |
| 551 | ATOM | 396 | CB | THR | B | 53 | 6.429 | −53.607 | −21.003 | 1.00 | 12.84 C |
| 552 | ATOM | 397 | OG1 | THR | B | 53 | 6.646 | −53.564 | −22.415 | 1.00 | 13.55 O |
| 553 | ATOM | 398 | CG2 | THR | B | 53 | 7.031 | −52.368 | −20.378 | 1.00 | 13.08 C |
| 554 | ATOM | 399 | C | THR | B | 53 | 6.317 | −56.050 | −21.050 | 1.00 | 11.80 C |
| 555 | ATOM | 400 | O | THR | B | 53 | 5.284 | −56.457 | −20.559 | 1.00 | 11.69 O |
| 556 | ATOM | 401 | N | THR | B | 54 | 6.858 | −56.594 | −22.132 | 1.00 | 12.64 N |
| 557 | ATOM | 402 | CA | THR | B | 54 | 6.152 | −57.600 | −22.922 | 1.00 | 12.90 C |
| 558 | ATOM | 403 | CB | THR | B | 54 | 6.747 | −57.683 | −24.330 | 1.00 | 13.86 C |
| 559 | ATOM | 404 | OG1 | THR | B | 54 | 8.169 | −57.800 | −24.252 | 1.00 | 13.98 O |
| 560 | ATOM | 405 | CG2 | THR | B | 54 | 6.417 | −56.441 | −25.104 | 1.00 | 14.64 C |
| 561 | ATOM | 406 | C | THR | B | 54 | 6.216 | −58.987 | −22.275 | 1.00 | 13.19 C |
| 562 | ATOM | 407 | O | THR | B | 54 | 5.235 | −59.724 | −22.291 | 1.00 | 14.12 O |
| 563 | ATOM | 408 | N | SER | B | 55 | 7.354 | −59.303 | −21.690 | 1.00 | 13.35 N |
| 564 | ATOM | 409 | CA | SER | B | 55 | 7.557 | −60.570 | −20.947 | 1.00 | 13.32 C |
| 565 | ATOM | 410 | CB | SER | B | 55 | 8.995 | −61.059 | −21.182 | 1.00 | 14.11 C |
| 566 | ATOM | 411 | OG | SER | B | 55 | 9.908 | −60.271 | −20.416 | 1.00 | 12.99 O |
| 567 | ATOM | 412 | C | SER | B | 55 | 7.325 | −60.450 | −19.456 | 1.00 | 14.12 C |
| 568 | ATOM | 413 | O | SER | B | 55 | 7.147 | −61.459 | −18.761 | 1.00 | 14.05 O |
| 569 | ATOM | 414 | N | GLY | B | 56 | 7.339 | −59.234 | −18.925 | 1.00 | 13.28 N |
| 570 | ATOM | 415 | CA | GLY | B | 56 | 7.257 | −59.053 | −17.501 | 1.00 | 14.32 C |
| 571 | ATOM | 416 | C | GLY | B | 56 | 8.532 | −59.329 | −16.723 | 1.00 | 14.49 C |
| 572 | ATOM | 417 | O | GLY | B | 56 | 8.531 | −59.239 | −15.490 | 1.00 | 15.17 O |
| 573 | ATOM | 418 | N | SER | B | 57 | 9.614 | −59.656 | −17.440 | 1.00 | 15.32 N |
| 574 | ATOM | 419 | CA | SER | B | 57 | 10.889 | −60.020 | −16.827 | 1.00 | 14.71 C |
| 575 | ATOM | 420 | CB | SER | B | 57 | 11.858 | −60.566 | −17.883 | 1.00 | 16.06 C |
| 576 | ATOM | 421 | OG | SER | B | 57 | 12.892 | −61.302 | −17.266 | 1.00 | 19.06 O |
| 577 | ATOM | 422 | C | SER | B | 57 | 11.562 | −58.828 | −16.178 | 1.00 | 13.31 C |
| 578 | ATOM | 423 | O | SER | B | 57 | 11.777 | −57.789 | −16.838 | 1.00 | 12.73 O |
| 579 | ATOM | 424 | N | THR | B | 58 | 11.911 | −58.974 | −14.906 | 1.00 | 13.07 N |

APPENDIX I-continued

| 580 | ATOM | 425 | CA | THR | B | 58 | 12.510 | −57.869 | −14.151 | 1.00 | 13.59 | C |
|---|---|---|---|---|---|---|---|---|---|---|---|---|
| 581 | ATOM | 426 | CB | THR | B | 58 | 11.684 | −57.505 | −12.909 | 1.00 | 13.72 | C |
| 582 | ATOM | 427 | OG1 | THR | B | 58 | 11.613 | −58.614 | −12.021 | 1.00 | 15.24 | O |
| 583 | ATOM | 428 | CG2 | THR | B | 58 | 10.297 | −57.081 | −13.314 | 1.00 | 14.14 | C |
| 584 | ATOM | 429 | C | THR | B | 58 | 13.932 | −58.157 | −13.704 | 1.00 | 13.33 | C |
| 585 | ATOM | 430 | O | THR | B | 58 | 14.361 | −59.318 | −13.671 | 1.00 | 14.88 | O |
| 586 | ATOM | 431 | N | TYR | B | 59 | 14.630 | −57.103 | −13.288 | 1.00 | 13.54 | N |
| 587 | ATOM | 432 | CA | TYR | B | 59 | 15.992 | −57.196 | −12.807 | 1.00 | 13.52 | C |
| 588 | ATOM | 433 | CB | TYR | B | 59 | 16.978 | −57.116 | −13.970 | 1.00 | 14.53 | C |
| 589 | ATOM | 434 | CG | TYR | B | 59 | 18.399 | −57.239 | −13.496 | 1.00 | 15.80 | C |
| 590 | ATOM | 435 | CD1 | TYR | B | 59 | 19.018 | −58.471 | −13.439 | 1.00 | 17.33 | C |
| 591 | ATOM | 436 | CE1 | TYR | B | 59 | 20.319 | −58.600 | −12.994 | 1.00 | 18.83 | C |
| 592 | ATOM | 437 | CZ | TYR | B | 59 | 21.013 | −57.485 | −12.565 | 1.00 | 18.81 | C |
| 593 | ATOM | 438 | OH | TYR | B | 59 | 22.311 | −57.643 | −12.103 | 1.00 | 19.63 | O |
| 594 | ATOM | 439 | CE2 | TYR | B | 59 | 20.421 | −56.256 | −12.596 | 1.00 | 17.86 | C |
| 595 | ATOM | 440 | CD2 | TYR | B | 59 | 19.117 | −56.127 | −13.060 | 1.00 | 17.06 | C |
| 596 | ATOM | 441 | C | TYR | B | 59 | 16.255 | −56.067 | −11.823 | 1.00 | 13.33 | C |
| 597 | ATOM | 442 | O | TYR | B | 59 | 15.834 | −54.944 | −12.071 | 1.00 | 12.36 | O |
| 598 | ATOM | 443 | N | LEU | B | 60 | 16.898 | −56.381 | −10.692 | 1.00 | 13.55 | N |
| 599 | ATOM | 444 | CA | LEU | B | 60 | 17.195 | −55.391 | −9.666 | 1.00 | 14.22 | C |
| 600 | ATOM | 445 | CB | LEU | B | 60 | 16.472 | −55.726 | −8.349 | 1.00 | 14.88 | C |
| 601 | ATOM | 446 | CG | LEU | B | 60 | 14.951 | −55.752 | −8.416 | 1.00 | 16.65 | C |
| 602 | ATOM | 447 | CD1 | LEU | B | 60 | 14.385 | −56.510 | −7.210 | 1.00 | 17.72 | C |
| 603 | ATOM | 448 | CD2 | LEU | B | 60 | 14.453 | −54.315 | −8.473 | 1.00 | 16.77 | C |
| 604 | ATOM | 449 | C | LEU | B | 60 | 18.692 | −55.355 | −9.428 | 1.00 | 14.14 | C |
| 605 | ATOM | 450 | O | LEU | B | 60 | 19.334 | −56.416 | −9.314 | 1.00 | 13.98 | O |
| 606 | ATOM | 451 | N | ALA | B | 61 | 19.250 | −54.155 | −9.344 | 1.00 | 14.26 | N |
| 607 | ATOM | 452 | CA | ALA | B | 61 | 20.677 | −53.974 | −8.995 | 1.00 | 14.68 | C |
| 608 | ATOM | 453 | CB | ALA | B | 61 | 21.019 | −52.511 | −8.987 | 1.00 | 14.92 | C |
| 609 | ATOM | 454 | C | ALA | B | 61 | 20.968 | −54.580 | −7.620 | 1.00 | 15.75 | C |
| 610 | ATOM | 455 | O | ALA | B | 61 | 20.089 | −54.616 | −6.756 | 1.00 | 14.20 | O |
| 611 | ATOM | 456 | N | ASP | B | 62 | 22.197 | −55.054 | −7.412 | 1.00 | 17.73 | N |
| 612 | ATOM | 457 | CA | ASP | B | 62 | 22.547 | −55.686 | −6.142 | 1.00 | 18.75 | C |
| 613 | ATOM | 458 | CB | ASP | B | 62 | 24.012 | −56.132 | −6.135 | 1.00 | 19.70 | C |
| 614 | ATOM | 459 | CG | ASP | B | 62 | 24.252 | −57.406 | −6.928 | 1.00 | 21.92 | C |
| 615 | ATOM | 460 | OD1 | ASP | B | 62 | 23.293 | −58.095 | −7.371 | 1.00 | 22.77 | O |
| 616 | ATOM | 461 | OD2 | ASP | B | 62 | 25.442 | −57.735 | −7.102 | 1.00 | 23.89 | O |
| 617 | ATOM | 462 | C | ASP | B | 62 | 22.297 | −54.759 | −4.955 | 1.00 | 18.38 | C |
| 618 | ATOM | 463 | O | ASP | B | 62 | 21.950 | −55.217 | −3.882 | 1.00 | 17.87 | O |
| 619 | ATOM | 464 | N | SER | B | 63 | 22.490 | −53.462 | −5.154 | 1.00 | 18.55 | N |
| 620 | ATOM | 465 | CA | SER | B | 63 | 22.323 | −52.480 | −4.079 | 1.00 | 19.34 | C |
| 621 | ATOM | 466 | CB | SER | B | 63 | 22.715 | −51.082 | −4.593 | 1.00 | 20.09 | C |
| 622 | ATOM | 467 | OG | SER | B | 63 | 22.086 | −50.791 | −5.822 | 1.00 | 22.60 | O |
| 623 | ATOM | 468 | C | SER | B | 63 | 20.904 | −52.418 | −3.516 | 1.00 | 18.50 | C |
| 624 | ATOM | 469 | O | SER | B | 63 | 20.709 | −51.950 | −2.401 | 1.00 | 16.55 | O |
| 625 | ATOM | 470 | N | VAL | B | 64 | 19.911 | −52.835 | −4.302 | 1.00 | 16.48 | N |
| 626 | ATOM | 471 | CA | VAL | B | 64 | 18.507 | −52.724 | −3.879 | 1.00 | 16.11 | C |
| 627 | ATOM | 472 | CB | VAL | B | 64 | 17.739 | −51.730 | −4.804 | 1.00 | 14.92 | C |
| 628 | ATOM | 473 | CG1 | VAL | B | 64 | 18.486 | −50.419 | −4.891 | 1.00 | 15.01 | C |
| 629 | ATOM | 474 | CG2 | VAL | B | 64 | 17.528 | −52.305 | −6.192 | 1.00 | 15.25 | C |
| 630 | ATOM | 475 | C | VAL | B | 64 | 17.718 | −54.034 | −3.869 | 1.00 | 16.80 | C |
| 631 | ATOM | 476 | O | VAL | B | 64 | 16.531 | −54.033 | −3.519 | 1.00 | 16.05 | O |
| 632 | ATOM | 477 | N | LYS | B | 65 | 18.338 | −55.130 | −4.302 | 1.00 | 19.34 | N |
| 633 | ATOM | 478 | CA | LYS | B | 65 | 17.696 | −56.450 | −4.263 | 1.00 | 21.18 | C |
| 634 | ATOM | 479 | CB | LYS | B | 65 | 18.695 | −57.554 | −4.636 | 1.00 | 23.00 | C |
| 635 | ATOM | 480 | CG | LYS | B | 65 | 18.757 | −57.911 | −6.105 | 1.00 | 25.45 | C |
| 636 | ATOM | 481 | CD | LYS | B | 65 | 19.815 | −58.984 | −6.408 | 1.00 | 26.39 | C |
| 637 | ATOM | 482 | CE | LYS | B | 65 | 19.886 | −59.380 | −7.889 | 1.00 | 28.17 | C |
| 638 | ATOM | 483 | NZ | LYS | B | 65 | 20.760 | −58.547 | −8.794 | 1.00 | 29.51 | N |
| 639 | ATOM | 484 | C | LYS | B | 65 | 17.129 | −56.724 | −2.867 | 1.00 | 21.03 | C |
| 640 | ATOM | 485 | O | LYS | B | 65 | 17.817 | −56.523 | −1.874 | 1.00 | 22.35 | O |
| 641 | ATOM | 486 | N | GLY | B | 66 | 15.862 | −57.133 | −2.799 | 1.00 | 21.08 | N |
| 642 | ATOM | 487 | CA | GLY | B | 66 | 15.203 | −57.480 | −1.532 | 1.00 | 20.62 | C |
| 643 | ATOM | 488 | C | GLY | B | 66 | 14.536 | −56.334 | −0.772 | 1.00 | 20.63 | C |
| 644 | ATOM | 489 | O | GLY | B | 66 | 13.920 | −56.557 | 0.287 | 1.00 | 22.03 | O |
| 645 | ATOM | 490 | N | ARG | B | 67 | 14.684 | −55.120 | −1.296 | 1.00 | 18.37 | N |
| 646 | ATOM | 491 | CA | ARG | B | 67 | 14.145 | −53.905 | −0.726 | 1.00 | 18.33 | C |
| 647 | ATOM | 492 | CB | ARG | B | 67 | 15.287 | −52.972 | −0.321 | 1.00 | 17.77 | C |
| 648 | ATOM | 493 | CG | ARG | B | 67 | 16.258 | −53.632 | 0.648 | 1.00 | 18.19 | C |
| 649 | ATOM | 494 | CD | ARG | B | 67 | 17.224 | −52.660 | 1.296 | 1.00 | 17.90 | C |
| 650 | ATOM | 495 | NE | ARG | B | 67 | 18.086 | −52.021 | 0.306 | 1.00 | 17.27 | N |
| 651 | ATOM | 496 | CZ | ARG | B | 67 | 18.084 | −50.721 | −0.003 | 1.00 | 16.47 | C |
| 652 | ATOM | 497 | NH1 | ARG | B | 67 | 17.303 | −49.851 | 0.642 | 1.00 | 15.98 | N |
| 653 | ATOM | 498 | NH2 | ARG | B | 67 | 18.909 | −50.281 | −0.940 | 1.00 | 15.86 | N |
| 654 | ATOM | 499 | C | ARG | B | 67 | 13.235 | −53.199 | −1.729 | 1.00 | 18.18 | C |
| 655 | ATOM | 500 | O | ARG | B | 67 | 12.174 | −52.692 | −1.363 | 1.00 | 16.73 | O |
| 656 | ATOM | 501 | N | PHE | B | 68 | 13.678 | −53.126 | −2.988 | 1.00 | 17.59 | N |
| 657 | ATOM | 502 | CA | PHE | B | 68 | 12.914 | −52.467 | −4.063 | 1.00 | 17.49 | C |
| 658 | ATOM | 503 | CB | PHE | B | 68 | 13.826 | −51.597 | −4.938 | 1.00 | 17.46 | C |
| 659 | ATOM | 504 | CG | PHE | B | 68 | 14.399 | −50.374 | −4.251 | 1.00 | 17.14 | C |

APPENDIX I-continued

| | | | | | | | | | | |
|---|---|---|---|---|---|---|---|---|---|---|
| 660 | ATOM | 505 | CD1 | PHE | B | 68 | 14.351 | −50.196 | −2.869 | 1.00 | 17.50 C |
| 661 | ATOM | 506 | CE1 | PHE | B | 68 | 14.924 | −49.077 | −2.275 | 1.00 | 17.54 C |
| 662 | ATOM | 507 | CZ | PHE | B | 68 | 15.559 | −48.139 | −3.048 | 1.00 | 17.46 C |
| 663 | ATOM | 508 | CE2 | PHE | B | 68 | 15.620 | −48.305 | −4.416 | 1.00 | 17.15 C |
| 664 | ATOM | 509 | CD2 | PHE | B | 68 | 15.057 | −49.425 | −5.001 | 1.00 | 16.86 C |
| 665 | ATOM | 510 | C | PHE | B | 68 | 12.242 | −53.480 | −4.985 | 1.00 | 17.84 C |
| 666 | ATOM | 511 | O | PHE | B | 68 | 12.755 | −54.560 | −5.195 | 1.00 | 18.62 O |
| 667 | ATOM | 512 | N | THR | B | 69 | 11.111 | −53.095 | −5.564 | 1.00 | 18.89 N |
| 668 | ATOM | 513 | CA | THR | B | 69 | 10.412 | −53.913 | −6.556 | 1.00 | 20.20 C |
| 669 | ATOM | 514 | CB | THR | B | 69 | 9.179 | −54.603 | −5.918 | 1.00 | 21.88 C |
| 670 | ATOM | 515 | OG1 | THR | B | 69 | 9.609 | −55.403 | −4.825 | 1.00 | 24.78 O |
| 671 | ATOM | 516 | CG2 | THR | B | 69 | 8.475 | −55.505 | −6.942 | 1.00 | 23.56 C |
| 672 | ATOM | 517 | C | THR | B | 69 | 9.922 | −53.079 | −7.727 | 1.00 | 19.21 C |
| 673 | ATOM | 518 | O | THR | B | 69 | 9.320 | −52.021 | −7.536 | 1.00 | 18.98 O |
| 674 | ATOM | 519 | N | ILE | B | 70 | 10.124 | −53.576 | −8.954 | 1.00 | 16.84 N |
| 675 | ATOM | 520 | CA | ILE | B | 70 | 9.609 | −52.902 | −10.146 | 1.00 | 16.20 C |
| 676 | ATOM | 521 | CB | ILE | B | 70 | 10.739 | −52.656 | −11.166 | 1.00 | 16.14 C |
| 677 | ATOM | 522 | CG1 | ILE | B | 70 | 10.272 | −51.810 | −12.348 | 1.00 | 15.75 C |
| 678 | ATOM | 523 | CD1 | ILE | B | 70 | 11.401 | −51.450 | −13.298 | 1.00 | 15.92 C |
| 679 | ATOM | 524 | CG2 | ILE | B | 70 | 11.310 | −53.979 | −11.649 | 1.00 | 16.32 C |
| 680 | ATOM | 525 | C | ILE | B | 70 | 8.428 | −53.704 | −10.747 | 1.00 | 16.21 C |
| 681 | ATOM | 526 | O | ILE | B | 70 | 8.455 | −54.941 | −10.774 | 1.00 | 17.52 O |
| 682 | ATOM | 527 | N | SER | B | 71 | 7.380 | −52.990 | −11.173 | 1.00 | 16.42 N |
| 683 | ATOM | 528 | CA | SER | B | 71 | 6.136 | −53.620 | −11.689 | 1.00 | 15.59 C |
| 684 | ATOM | 529 | CB | SER | B | 71 | 5.214 | −54.035 | −10.512 | 1.00 | 16.25 C |
| 685 | ATOM | 530 | OG | SER | B | 71 | 4.810 | −52.875 | −9.783 | 1.00 | 15.39 O |
| 686 | ATOM | 531 | C | SER | B | 71 | 5.408 | −52.644 | −12.595 | 1.00 | 15.64 C |
| 687 | ATOM | 532 | O | SER | B | 71 | 5.807 | −51.478 | −12.698 | 1.00 | 16.16 O |
| 688 | ATOM | 533 | N | GLN | B | 72 | 4.333 | −53.108 | −13.252 | 1.00 | 14.78 N |
| 689 | ATOM | 534 | CA | GLN | B | 72 | 3.487 | −52.239 | −14.081 | 1.00 | 15.53 C |
| 690 | ATOM | 535 | CB | GLN | B | 72 | 3.856 | −52.379 | −15.572 | 1.00 | 15.72 C |
| 691 | ATOM | 536 | CG | GLN | B | 72 | 3.673 | −53.794 | −16.094 | 1.00 | 15.78 C |
| 692 | ATOM | 537 | CD | GLN | B | 72 | 4.206 | −53.970 | −17.506 | 1.00 | 15.94 C |
| 693 | ATOM | 538 | OE1 | GLN | B | 72 | 4.360 | −53.002 | −18.259 | 1.00 | 16.15 O |
| 694 | ATOM | 539 | NE2 | GLN | B | 72 | 4.452 | −55.206 | −17.871 | 1.00 | 15.38 N |
| 695 | ATOM | 540 | C | GLN | B | 72 | 2.005 | −52.554 | −13.862 | 1.00 | 15.64 C |
| 696 | ATOM | 541 | O | GLN | B | 72 | 1.666 | −53.593 | −13.311 | 1.00 | 15.43 O |
| 697 | ATOM | 542 | N | ASN | B | 73 | 1.125 | −51.638 | −14.271 | 1.00 | 16.36 N |
| 698 | ATOM | 543 | CA | ASN | B | 73 | −0.304 | −51.881 | −14.181 | 1.00 | 17.73 C |
| 699 | ATOM | 544 | CB | ASN | B | 73 | −1.077 | −50.578 | −13.986 | 1.00 | 18.04 C |
| 700 | ATOM | 545 | CG | ASN | B | 73 | −0.959 | −49.609 | −15.150 | 1.00 | 18.09 C |
| 701 | ATOM | 546 | OD1 | ASN | B | 73 | −0.230 | −49.831 | −16.124 | 1.00 | 17.69 O |
| 702 | ATOM | 547 | ND2 | ASN | B | 73 | −1.706 | −48.508 | −15.052 | 1.00 | 18.75 N |
| 703 | ATOM | 548 | C | ASN | B | 73 | −0.777 | −52.677 | −15.417 | 1.00 | 18.55 C |
| 704 | ATOM | 549 | O | ASN | B | 73 | −0.004 | −52.898 | −16.348 | 1.00 | 17.00 O |
| 705 | ATOM | 550 | N | ASN | B | 74 | −2.028 | −53.125 | −15.383 | 1.00 | 20.34 N |
| 706 | ATOM | 551 | CA | ASN | B | 74 | −2.612 | −53.918 | −16.470 | 1.00 | 21.25 C |
| 707 | ATOM | 552 | CB | ASN | B | 74 | −4.070 | −54.287 | −16.157 | 1.00 | 23.53 C |
| 708 | ATOM | 553 | CG | ASN | B | 74 | −4.189 | −55.574 | −15.382 | 1.00 | 24.79 C |
| 709 | ATOM | 554 | OD1 | ASN | B | 74 | −3.260 | −56.385 | −15.350 | 1.00 | 27.23 O |
| 710 | ATOM | 555 | ND2 | ASN | B | 74 | −5.337 | −55.786 | −14.782 | 1.00 | 26.75 N |
| 711 | ATOM | 556 | C | ASN | B | 74 | −2.568 | −53.253 | −17.826 | 1.00 | 22.82 C |
| 712 | ATOM | 557 | O | ASN | B | 74 | −2.313 | −53.908 | −18.828 | 1.00 | 23.49 O |
| 713 | ATOM | 558 | N | ALA | B | 75 | −2.827 | −51.950 | −17.875 | 1.00 | 23.97 N |
| 714 | ATOM | 559 | CA | ALA | B | 75 | −2.851 | −51.240 | −19.154 | 1.00 | 23.21 C |
| 715 | ATOM | 560 | CB | ALA | B | 75 | −3.664 | −49.951 | −19.041 | 1.00 | 24.60 C |
| 716 | ATOM | 561 | C | ALA | B | 75 | −1.439 | −50.947 | −19.632 | 1.00 | 21.68 C |
| 717 | ATOM | 562 | O | ALA | B | 75 | −1.266 | −50.528 | −20.776 | 1.00 | 21.06 O |
| 718 | ATOM | 563 | N | LYS | B | 76 | −0.459 | −51.146 | −18.732 | 1.00 | 21.50 N |
| 719 | ATOM | 564 | CA | LYS | B | 76 | 0.983 | −50.840 | −18.905 | 1.00 | 21.41 C |
| 720 | ATOM | 565 | CB | LYS | B | 76 | 1.605 | −51.748 | −19.935 | 1.00 | 22.79 C |
| 721 | ATOM | 566 | CG | LYS | B | 76 | 1.313 | −53.210 | −19.626 | 1.00 | 22.57 C |
| 722 | ATOM | 567 | CD | LYS | B | 76 | 1.724 | −54.117 | −20.735 | 1.00 | 23.55 C |
| 723 | ATOM | 568 | CE | LYS | B | 76 | 1.619 | −55.560 | −20.276 | 1.00 | 22.59 C |
| 724 | ATOM | 569 | NZ | LYS | B | 76 | 1.867 | −56.510 | −21.372 | 1.00 | 23.60 N |
| 725 | ATOM | 570 | C | LYS | B | 76 | 1.254 | −49.382 | −19.209 | 1.00 | 21.42 C |
| 726 | ATOM | 571 | O | LYS | B | 76 | 2.174 | −49.049 | −19.925 | 1.00 | 22.81 O |
| 727 | ATOM | 572 | N | SER | B | 77 | 0.414 | −48.519 | −18.671 | 1.00 | 20.46 N |
| 728 | ATOM | 573 | CA | SER | B | 77 | 0.589 | −47.084 | −18.810 | 1.00 | 20.92 C |
| 729 | ATOM | 574 | CB | SER | B | 77 | −0.781 | −46.416 | −18.943 | 1.00 | 21.55 C |
| 730 | ATOM | 575 | OG | SER | B | 77 | −1.649 | −46.860 | −17.916 | 1.00 | 22.48 O |
| 731 | ATOM | 576 | C | SER | B | 77 | 1.311 | −46.528 | −17.591 | 1.00 | 19.74 C |
| 732 | ATOM | 577 | O | SER | B | 77 | 1.610 | −45.337 | −17.531 | 1.00 | 20.64 O |
| 733 | ATOM | 578 | N | THR | B | 78 | 1.533 | −47.383 | −16.600 | 1.00 | 19.09 N |
| 734 | ATOM | 579 | CA | THR | B | 78 | 2.195 | −46.963 | −15.369 | 1.00 | 18.76 C |
| 735 | ATOM | 580 | CB | THR | B | 78 | 1.189 | −46.639 | −14.254 | 1.00 | 19.47 C |
| 736 | ATOM | 581 | OG1 | THR | B | 78 | 0.177 | −45.738 | −14.748 | 1.00 | 20.06 O |
| 737 | ATOM | 582 | CG2 | THR | B | 78 | 1.916 | −45.999 | −13.048 | 1.00 | 20.31 C |
| 738 | ATOM | 583 | C | THR | B | 78 | 3.173 | −48.021 | −14.883 | 1.00 | 17.65 C |
| 739 | ATOM | 584 | O | THR | B | 78 | 2.856 | −49.193 | −14.837 | 1.00 | 17.79 O |

APPENDIX I-continued

| | | | | | | | | | | |
|---|---|---|---|---|---|---|---|---|---|---|
| 740 | ATOM | 585 | N | VAL | B | 79 | 4.399 | −47.594 | −14.575 | 1.00 | 16.96 N |
| 741 | ATOM | 586 | CA | VAL | B | 79 | 5.432 | −48.479 | −14.077 | 1.00 | 16.55 C |
| 742 | ATOM | 587 | CB | VAL | B | 79 | 6.682 | −48.460 | −14.992 | 1.00 | 18.41 C |
| 743 | ATOM | 588 | CG1 | VAL | B | 79 | 7.827 | −49.249 | −14.373 | 1.00 | 19.56 C |
| 744 | ATOM | 589 | CG2 | VAL | B | 79 | 6.342 | −49.026 | −16.359 | 1.00 | 18.74 C |
| 745 | ATOM | 590 | C | VAL | B | 79 | 5.786 | −47.981 | −12.667 | 1.00 | 16.27 C |
| 746 | ATOM | 591 | O | VAL | B | 79 | 5.891 | −46.769 | −12.438 | 1.00 | 16.51 O |
| 747 | ATOM | 592 | N | TYR | B | 80 | 5.947 | −48.904 | −11.737 | 1.00 | 15.05 N |
| 748 | ATOM | 593 | CA | TYR | B | 80 | 6.168 | −48.558 | −10.330 | 1.00 | 14.80 C |
| 749 | ATOM | 594 | CB | TYR | B | 80 | 5.137 | −49.271 | −9.432 | 1.00 | 14.90 C |
| 750 | ATOM | 595 | CG | TYR | B | 80 | 3.709 | −49.074 | −9.876 | 1.00 | 15.53 C |
| 751 | ATOM | 596 | CD1 | TYR | B | 80 | 3.005 | −47.929 | −9.530 | 1.00 | 16.14 C |
| 752 | ATOM | 597 | CE1 | TYR | B | 80 | 1.686 | −47.738 | −9.949 | 1.00 | 17.20 C |
| 753 | ATOM | 598 | CZ | TYR | B | 80 | 1.071 | −48.701 | −10.733 | 1.00 | 16.98 C |
| 754 | ATOM | 599 | OH | TYR | B | 80 | −0.225 | −48.510 | −11.154 | 1.00 | 18.69 O |
| 755 | ATOM | 600 | CE2 | TYR | B | 80 | 1.752 | −49.848 | −11.091 | 1.00 | 16.42 C |
| 756 | ATOM | 601 | CD2 | TYR | B | 80 | 3.060 | −50.033 | −10.672 | 1.00 | 15.69 C |
| 757 | ATOM | 602 | C | TYR | B | 80 | 7.540 | −48.984 | −9.853 | 1.00 | 14.94 C |
| 758 | ATOM | 603 | O | TYR | B | 80 | 8.087 | −49.983 | −10.315 | 1.00 | 16.44 O |
| 759 | ATOM | 604 | N | LEU | B | 81 | 8.074 | −48.237 | −8.883 | 1.00 | 14.27 N |
| 760 | ATOM | 605 | CA | LEU | B | 81 | 9.189 | −48.681 | −8.048 | 1.00 | 14.11 C |
| 761 | ATOM | 606 | CB | LEU | B | 81 | 10.426 | −47.799 | −8.247 | 1.00 | 14.31 C |
| 762 | ATOM | 607 | CG | LEU | B | 81 | 11.712 | −48.297 | −7.606 | 1.00 | 14.93 C |
| 763 | ATOM | 608 | CD1 | LEU | B | 81 | 12.212 | −49.566 | −8.273 | 1.00 | 14.59 C |
| 764 | ATOM | 609 | CD2 | LEU | B | 81 | 12.821 | −47.246 | −7.642 | 1.00 | 14.49 C |
| 765 | ATOM | 610 | C | LEU | B | 81 | 8.737 | −48.579 | −6.589 | 1.00 | 14.94 C |
| 766 | ATOM | 611 | O | LEU | B | 81 | 8.603 | −47.476 | −6.049 | 1.00 | 14.72 O |
| 767 | ATOM | 612 | N | GLN | B | 82 | 8.509 | −49.732 | −5.975 | 1.00 | 15.49 N |
| 768 | ATOM | 613 | CA | GLN | B | 82 | 8.174 | −49.824 | −4.542 | 1.00 | 16.51 C |
| 769 | ATOM | 614 | CB | GLN | B | 82 | 7.335 | −51.065 | −4.244 | 1.00 | 17.98 C |
| 770 | ATOM | 615 | CG | GLN | B | 82 | 6.904 | −51.205 | −2.769 | 1.00 | 18.22 C |
| 771 | ATOM | 616 | CD | GLN | B | 82 | 6.116 | −50.016 | −2.257 | 1.00 | 18.98 C |
| 772 | ATOM | 617 | OE1 | GLN | B | 82 | 5.168 | −49.566 | −2.897 | 1.00 | 20.80 O |
| 773 | ATOM | 618 | NE2 | GLN | B | 82 | 6.499 | −49.497 | −1.090 | 1.00 | 19.88 N |
| 774 | ATOM | 619 | C | GLN | B | 82 | 9.475 | −49.896 | −3.752 | 1.00 | 16.23 C |
| 775 | ATOM | 620 | O | GLN | B | 82 | 10.270 | −50.802 | −3.954 | 1.00 | 15.97 O |
| 776 | ATOM | 621 | N | MET | B | 83 | 9.710 | −48.907 | −2.895 | 1.00 | 16.19 N |
| 777 | ATOM | 622 | CA | MET | B | 83 | 10.989 | −48.772 | −2.210 | 1.00 | 16.67 C |
| 778 | ATOM | 623 | CB | MET | B | 83 | 11.574 | −47.372 | −2.450 | 1.00 | 18.60 C |
| 779 | ATOM | 624 | CG | MET | B | 83 | 11.799 | −47.031 | −3.917 | 1.00 | 21.15 C |
| 780 | ATOM | 625 | SD | MET | B | 83 | 12.238 | −45.287 | −4.142 | 1.00 | 25.44 S |
| 781 | ATOM | 626 | CE | MET | B | 83 | 13.941 | −45.398 | −3.805 | 1.00 | 24.42 C |
| 782 | ATOM | 627 | C | MET | B | 83 | 10.746 | −49.003 | −0.727 | 1.00 | 16.09 C |
| 783 | ATOM | 628 | O | MET | B | 83 | 10.226 | −48.124 | −0.040 | 1.00 | 15.79 O |
| 784 | ATOM | 629 | N | ASN | B | 84 | 11.064 | −50.197 | −0.260 | 1.00 | 15.52 N |
| 785 | ATOM | 630 | CA | ASN | B | 84 | 11.010 | −50.493 | 1.178 | 1.00 | 16.47 C |
| 786 | ATOM | 631 | CB | ASN | B | 84 | 10.338 | −51.845 | 1.407 | 1.00 | 16.63 C |
| 787 | ATOM | 632 | CG | ASN | B | 84 | 8.925 | −51.905 | 0.848 | 1.00 | 17.07 C |
| 788 | ATOM | 633 | OD1 | ASN | B | 84 | 8.223 | −50.899 | 0.731 | 1.00 | 17.82 O |
| 789 | ATOM | 634 | ND2 | ASN | B | 84 | 8.493 | −53.092 | 0.520 | 1.00 | 18.25 N |
| 790 | ATOM | 635 | C | ASN | B | 84 | 12.389 | −50.459 | 1.841 | 1.00 | 16.31 C |
| 791 | ATOM | 636 | O | ASN | B | 84 | 13.433 | −50.469 | 1.162 | 1.00 | 16.40 O |
| 792 | ATOM | 637 | N | SER | B | 85 | 12.382 | −50.416 | 3.174 | 1.00 | 16.79 N |
| 793 | ATOM | 638 | CA | SER | B | 85 | 13.604 | −50.473 | 3.993 | 1.00 | 17.66 C |
| 794 | ATOM | 639 | CB | SER | B | 85 | 14.240 | −51.874 | 3.929 | 1.00 | 18.20 C |
| 795 | ATOM | 640 | OG | SER | B | 85 | 13.361 | −52.851 | 4.465 | 1.00 | 20.17 O |
| 796 | ATOM | 641 | C | SER | B | 85 | 14.626 | −49.450 | 3.539 | 1.00 | 16.86 C |
| 797 | ATOM | 642 | O | SER | B | 85 | 15.794 | −49.773 | 3.346 | 1.00 | 17.10 O |
| 798 | ATOM | 643 | N | LEU | B | 86 | 14.173 | −48.216 | 3.352 | 1.00 | 16.76 N |
| 799 | ATOM | 644 | CA | LEU | B | 86 | 15.017 | −47.190 | 2.787 | 1.00 | 16.15 C |
| 800 | ATOM | 645 | CB | LEU | B | 86 | 14.187 | −45.950 | 2.436 | 1.00 | 16.39 C |
| 801 | ATOM | 646 | CG | LEU | B | 86 | 13.457 | −46.011 | 1.084 | 1.00 | 16.32 C |
| 802 | ATOM | 647 | CD1 | LEU | B | 86 | 12.314 | −45.010 | 1.049 | 1.00 | 16.24 C |
| 803 | ATOM | 648 | CD2 | LEU | B | 86 | 14.406 | −45.757 | −0.076 | 1.00 | 16.77 C |
| 804 | ATOM | 649 | C | LEU | B | 86 | 16.177 | −46.874 | 3.735 | 1.00 | 15.86 C |
| 805 | ATOM | 650 | O | LEU | B | 86 | 16.036 | −46.941 | 4.949 | 1.00 | 15.36 O |
| 806 | ATOM | 651 | N | LYS | B | 87 | 17.328 | −46.567 | 3.149 | 1.00 | 16.68 N |
| 807 | ATOM | 652 | CA | LYS | B | 87 | 18.550 | −46.251 | 3.878 | 1.00 | 17.81 C |
| 808 | ATOM | 653 | CB | LYS | B | 87 | 19.614 | −47.314 | 3.583 | 1.00 | 21.57 C |
| 809 | ATOM | 654 | CG | LYS | B | 87 | 19.134 | −48.732 | 3.851 | 1.00 | 23.34 C |
| 810 | ATOM | 655 | CD | LYS | B | 87 | 20.242 | −49.760 | 3.748 | 1.00 | 24.90 C |
| 811 | ATOM | 656 | CE | LYS | B | 87 | 20.825 | −49.829 | 2.356 | 1.00 | 25.71 C |
| 812 | ATOM | 657 | NZ | LYS | B | 87 | 21.875 | −50.869 | 2.259 | 1.00 | 26.62 N |
| 813 | ATOM | 658 | C | LYS | B | 87 | 19.049 | −44.882 | 3.419 | 1.00 | 16.71 C |
| 814 | ATOM | 659 | O | LYS | B | 87 | 18.719 | −44.448 | 2.329 | 1.00 | 14.96 O |
| 815 | ATOM | 660 | N | PRO | B | 88 | 19.851 | −44.188 | 4.250 | 1.00 | 16.53 N |
| 816 | ATOM | 661 | CA | PRO | B | 88 | 20.342 | −42.875 | 3.838 | 1.00 | 16.43 C |
| 817 | ATOM | 662 | CB | PRO | B | 88 | 21.310 | −42.493 | 4.969 | 1.00 | 16.67 C |
| 818 | ATOM | 663 | CG | PRO | B | 88 | 20.685 | −43.130 | 6.170 | 1.00 | 16.07 C |
| 819 | ATOM | 664 | CD | PRO | B | 88 | 20.157 | −44.455 | 5.671 | 1.00 | 16.17 C |

APPENDIX I-continued

| 820 | ATOM | 665 | C | PRO | B | 88 | 21.043 | −42.884 | 2.500 | 1.00 | 16.94 | C |
|---|---|---|---|---|---|---|---|---|---|---|---|---|
| 821 | ATOM | 666 | O | PRO | B | 88 | 20.899 | −41.930 | 1.736 | 1.00 | 17.05 | O |
| 822 | ATOM | 667 | N | GLU | B | 89 | 21.758 | −43.958 | 2.180 | 1.00 | 17.60 | N |
| 823 | ATOM | 668 | CA | GLU | B | 89 | 22.453 | −44.017 | 0.896 | 1.00 | 18.92 | C |
| 824 | ATOM | 669 | CB | GLU | B | 89 | 23.483 | −45.144 | 0.899 | 1.00 | 23.19 | C |
| 825 | ATOM | 670 | CG | GLU | B | 89 | 22.906 | −46.544 | 0.874 | 1.00 | 25.29 | C |
| 826 | ATOM | 671 | CD | GLU | B | 89 | 23.978 | −47.597 | 1.098 | 1.00 | 29.60 | C |
| 827 | ATOM | 672 | OE1 | GLU | B | 89 | 23.634 | −48.771 | 1.363 | 1.00 | 31.83 | O |
| 828 | ATOM | 673 | OE2 | GLU | B | 89 | 25.175 | −47.238 | 1.009 | 1.00 | 32.02 | O |
| 829 | ATOM | 674 | C | GLU | B | 89 | 21.522 | −44.135 | −0.328 | 1.00 | 16.89 | C |
| 830 | ATOM | 675 | O | GLU | B | 89 | 21.972 | −44.016 | −1.477 | 1.00 | 16.27 | O |
| 831 | ATOM | 676 | N | ASP | B | 90 | 20.233 | −44.369 | −0.103 | 1.00 | 15.04 | N |
| 832 | ATOM | 677 | CA | ASP | B | 90 | 19.271 | −44.339 | −1.202 | 1.00 | 13.44 | C |
| 833 | ATOM | 678 | CB | ASP | B | 90 | 18.030 | −45.144 | −0.876 | 1.00 | 13.54 | C |
| 834 | ATOM | 679 | CG | ASP | B | 90 | 18.313 | −46.607 | −0.630 | 1.00 | 14.36 | C |
| 835 | ATOM | 680 | OD1 | ASP | B | 90 | 19.045 | −47.255 | −1.425 | 1.00 | 14.44 | O |
| 836 | ATOM | 681 | OD2 | ASP | B | 90 | 17.758 | −47.121 | 0.360 | 1.00 | 15.60 | O |
| 837 | ATOM | 682 | C | ASP | B | 90 | 18.830 | −42.915 | −1.614 | 1.00 | 12.95 | C |
| 838 | ATOM | 683 | O | ASP | B | 90 | 18.080 | −42.747 | −2.591 | 1.00 | 11.97 | O |
| 839 | ATOM | 684 | N | THR | B | 91 | 19.278 | −41.905 | −0.873 | 1.00 | 12.60 | N |
| 840 | ATOM | 685 | CA | THR | B | 91 | 18.913 | −40.524 | −1.162 | 1.00 | 11.43 | C |
| 841 | ATOM | 686 | CB | THR | B | 91 | 19.483 | −39.578 | −0.073 | 1.00 | 11.18 | C |
| 842 | ATOM | 687 | OG1 | THR | B | 91 | 18.879 | −39.874 | 1.196 | 1.00 | 10.61 | O |
| 843 | ATOM | 688 | CG2 | THR | B | 91 | 19.222 | −38.124 | −0.441 | 1.00 | 10.85 | C |
| 844 | ATOM | 689 | C | THR | B | 91 | 19.430 | −40.162 | −2.554 | 1.00 | 11.77 | C |
| 845 | ATOM | 690 | O | THR | B | 91 | 20.616 | −40.363 | −2.858 | 1.00 | 11.62 | O |
| 846 | ATOM | 691 | N | ALA | B | 92 | 18.533 | −39.649 | −3.399 | 1.00 | 11.72 | N |
| 847 | ATOM | 692 | CA | ALA | B | 92 | 18.843 | −39.302 | −4.797 | 1.00 | 11.35 | C |
| 848 | ATOM | 693 | CB | ALA | B | 92 | 19.345 | −40.532 | −5.566 | 1.00 | 11.64 | C |
| 849 | ATOM | 694 | C | ALA | B | 92 | 17.629 | −38.747 | −5.503 | 1.00 | 11.41 | C |
| 850 | ATOM | 695 | O | ALA | B | 92 | 16.501 | −38.877 | −5.010 | 1.00 | 11.20 | O |
| 851 | ATOM | 696 | N | MET | B | 93 | 17.843 | −38.126 | −6.665 | 1.00 | 12.17 | N |
| 852 | ATOM | 697 | CA | MET | B | 93 | 16.772 | −37.940 | −7.657 | 1.00 | 12.70 | C |
| 853 | ATOM | 698 | CB | MET | B | 93 | 17.129 | −36.819 | −8.675 | 1.00 | 14.56 | C |
| 854 | ATOM | 699 | CG | MET | B | 93 | 17.090 | −35.393 | −8.104 | 1.00 | 17.07 | C |
| 855 | ATOM | 700 | SD | MET | B | 93 | 15.414 | −34.795 | −7.996 | 1.00 | 23.21 | S |
| 856 | ATOM | 701 | CE | MET | B | 93 | 14.931 | −34.608 | −9.723 | 1.00 | 21.77 | C |
| 857 | ATOM | 702 | C | MET | B | 93 | 16.591 | −39.254 | −8.398 | 1.00 | 12.40 | C |
| 858 | ATOM | 703 | O | MET | B | 93 | 17.580 | −39.840 | −8.850 | 1.00 | 11.81 | O |
| 859 | ATOM | 704 | N | TYR | B | 94 | 15.351 | −39.704 | −8.530 | 1.00 | 11.43 | N |
| 860 | ATOM | 705 | CA | TYR | B | 94 | 15.032 | −40.971 | −9.203 | 1.00 | 11.70 | C |
| 861 | ATOM | 706 | CB | TYR | B | 94 | 14.172 | −41.875 | −8.337 | 1.00 | 11.57 | C |
| 862 | ATOM | 707 | CG | TYR | B | 94 | 14.919 | −42.588 | −7.249 | 1.00 | 11.75 | C |
| 863 | ATOM | 708 | CD1 | TYR | B | 94 | 15.465 | −41.884 | −6.173 | 1.00 | 11.96 | C |
| 864 | ATOM | 709 | CE1 | TYR | B | 94 | 16.185 | −42.535 | −5.169 | 1.00 | 11.87 | C |
| 865 | ATOM | 710 | CZ | TYR | B | 94 | 16.361 | −43.906 | −5.230 | 1.00 | 12.15 | C |
| 866 | ATOM | 711 | OH | TYR | B | 94 | 17.070 | −44.576 | −4.231 | 1.00 | 11.69 | O |
| 867 | ATOM | 712 | CE2 | TYR | B | 94 | 15.827 | −44.610 | −6.281 | 1.00 | 11.92 | C |
| 868 | ATOM | 713 | CD2 | TYR | B | 94 | 15.123 | −43.966 | −7.285 | 1.00 | 11.98 | C |
| 869 | ATOM | 714 | C | TYR | B | 94 | 14.329 | −40.677 | −10.496 | 1.00 | 11.90 | C |
| 870 | ATOM | 715 | O | TYR | B | 94 | 13.400 | −39.829 | −10.546 | 1.00 | 11.68 | O |
| 871 | ATOM | 716 | N | TYR | B | 95 | 14.783 | −41.361 | −11.547 | 1.00 | 12.12 | N |
| 872 | ATOM | 717 | CA | TYR | B | 95 | 14.279 | −41.160 | −12.884 | 1.00 | 12.61 | C |
| 873 | ATOM | 718 | CB | TYR | B | 95 | 15.405 | −40.702 | −13.820 | 1.00 | 12.78 | C |
| 874 | ATOM | 719 | CG | TYR | B | 95 | 15.968 | −39.377 | −13.440 | 1.00 | 13.01 | C |
| 875 | ATOM | 720 | CD1 | TYR | B | 95 | 16.988 | −39.297 | −12.505 | 1.00 | 14.19 | C |
| 876 | ATOM | 721 | CE1 | TYR | B | 95 | 17.514 | −38.073 | −12.119 | 1.00 | 14.98 | C |
| 877 | ATOM | 722 | CZ | TYR | B | 95 | 17.005 | −36.926 | −12.651 | 1.00 | 15.57 | C |
| 878 | ATOM | 723 | OH | TYR | B | 95 | 17.546 | −35.709 | −12.240 | 1.00 | 15.81 | O |
| 879 | ATOM | 724 | CE2 | TYR | B | 95 | 15.974 | −36.988 | −13.583 | 1.00 | 14.91 | C |
| 880 | ATOM | 725 | CD2 | TYR | B | 95 | 15.475 | −38.217 | −13.976 | 1.00 | 14.73 | C |
| 881 | ATOM | 726 | C | TYR | B | 95 | 13.769 | −42.446 | −13.460 | 1.00 | 13.16 | C |
| 882 | ATOM | 727 | O | TYR | B | 95 | 14.412 | −43.506 | −13.336 | 1.00 | 13.63 | O |
| 883 | ATOM | 728 | N | CYS | B | 96 | 12.657 | −42.338 | −14.160 | 1.00 | 13.88 | N |
| 884 | ATOM | 729 | CA | ACYS | B | 96 | 12.282 | −43.446 | −15.031 | 0.50 | 13.60 | C |
| 885 | ATOM | 730 | CA | BCYS | B | 96 | 12.157 | −43.346 | −15.056 | 0.50 | 14.18 | C |
| 886 | ATOM | 731 | CB | ACYS | B | 96 | 10.781 | −43.793 | −15.007 | 0.50 | 14.44 | C |
| 887 | ATOM | 732 | CB | BCYS | B | 96 | 10.664 | −43.079 | −15.175 | 0.50 | 15.46 | C |
| 888 | ATOM | 733 | SG | ACYS | B | 96 | 9.647 | −42.551 | −15.650 | 0.50 | 13.87 | S |
| 889 | ATOM | 734 | SG | BCYS | B | 96 | 9.802 | −44.251 | −16.186 | 0.50 | 17.13 | S |
| 890 | ATOM | 735 | C | CYS | B | 96 | 12.803 | −43.173 | −16.433 | 1.00 | 13.71 | C |
| 891 | ATOM | 736 | O | CYS | B | 96 | 12.926 | −42.028 | −16.882 | 1.00 | 13.13 | O |
| 892 | ATOM | 737 | N | ALA | B | 97 | 13.180 | −44.268 | −17.110 | 1.00 | 13.03 | N |
| 893 | ATOM | 738 | CA | ALA | B | 97 | 13.742 | −44.218 | −18.456 | 1.00 | 12.64 | C |
| 894 | ATOM | 739 | CB | ALA | B | 97 | 15.255 | −44.388 | −18.403 | 1.00 | 13.23 | C |
| 895 | ATOM | 740 | C | ALA | B | 97 | 13.093 | −45.323 | −19.281 | 1.00 | 11.75 | C |
| 896 | ATOM | 741 | O | ALA | B | 97 | 12.683 | −46.337 | −18.718 | 1.00 | 10.82 | O |
| 897 | ATOM | 742 | N | ALA | B | 98 | 12.995 | −45.121 | −20.602 | 1.00 | 12.00 | N |
| 898 | ATOM | 743 | CA | ALA | B | 98 | 12.398 | −46.102 | −21.505 | 1.00 | 11.98 | C |
| 899 | ATOM | 744 | CB | ALA | B | 98 | 10.933 | −45.784 | −21.733 | 1.00 | 12.03 | C |

APPENDIX I-continued

| | | | | | | | | | | | |
|---|---|---|---|---|---|---|---|---|---|---|---|
| 900 | ATOM | 745 | C | ALA | B | 98 | 13.101 | −46.110 | −22.850 | 1.00 | 11.85 C |
| 901 | ATOM | 746 | O | ALA | B | 98 | 13.645 | −45.108 | −23.302 | 1.00 | 10.92 O |
| 902 | ATOM | 747 | N | ASP | B | 99 | 13.064 | −47.266 | −23.463 | 1.00 | 11.47 N |
| 903 | ATOM | 748 | CA | ASP | B | 99 | 13.529 | −47.444 | −24.845 | 1.00 | 11.55 C |
| 904 | ATOM | 749 | CB | ASP | B | 99 | 15.074 | −47.378 | −24.932 | 1.00 | 12.29 C |
| 905 | ATOM | 750 | CG | ASP | B | 99 | 15.551 | −46.626 | −26.180 | 1.00 | 13.75 C |
| 906 | ATOM | 751 | OD1 | ASP | B | 99 | 16.484 | −45.780 | −26.082 | 1.00 | 12.59 O |
| 907 | ATOM | 752 | OD2 | ASP | B | 99 | 14.964 | −46.853 | −27.273 | 1.00 | 14.32 O |
| 908 | ATOM | 753 | C | ASP | B | 99 | 12.976 | −48.742 | −25.405 | 1.00 | 11.16 C |
| 909 | ATOM | 754 | O | ASP | B | 99 | 12.173 | −49.439 | −24.768 | 1.00 | 10.74 O |
| 910 | ATOM | 755 | N | SER | B | 100 | 13.422 | −49.093 | −26.601 | 1.00 | 10.67 N |
| 911 | ATOM | 756 | CA | SER | B | 100 | 12.838 | −50.192 | −27.327 | 1.00 | 10.55 C |
| 912 | ATOM | 757 | CB | SER | B | 100 | 12.791 | −49.804 | −28.796 | 1.00 | 10.58 C |
| 913 | ATOM | 758 | OG | SER | B | 100 | 14.089 | −49.456 | −29.268 | 1.00 | 11.44 O |
| 914 | ATOM | 759 | C | SER | B | 100 | 13.563 | −51.526 | −27.187 | 1.00 | 10.80 C |
| 915 | ATOM | 760 | O | SER | B | 100 | 13.195 | −52.499 | −27.855 | 1.00 | 10.85 O |
| 916 | ATOM | 761 | N | PHE | B | 101 | 14.610 | −51.571 | −26.375 | 1.00 | 10.27 N |
| 917 | ATOM | 762 | CA | PHE | B | 101 | 15.510 | −52.736 | −26.384 | 1.00 | 10.73 C |
| 918 | ATOM | 763 | CB | PHE | B | 101 | 16.707 | −52.541 | −25.452 | 1.00 | 11.13 C |
| 919 | ATOM | 764 | CG | PHE | B | 101 | 17.423 | −51.258 | −25.675 | 1.00 | 11.28 C |
| 920 | ATOM | 765 | CD1 | PHE | B | 101 | 17.927 | −50.943 | −26.933 | 1.00 | 12.14 C |
| 921 | ATOM | 766 | CE1 | PHE | B | 101 | 18.576 | −49.741 | −27.144 | 1.00 | 12.55 C |
| 922 | ATOM | 767 | CZ | PHE | B | 101 | 18.700 | −48.834 | −26.102 | 1.00 | 12.34 C |
| 923 | ATOM | 768 | CE2 | PHE | B | 101 | 18.210 | −49.131 | −24.856 | 1.00 | 12.68 C |
| 924 | ATOM | 769 | CE2 | PHE | B | 101 | 17.579 | −50.344 | −24.639 | 1.00 | 11.87 C |
| 925 | ATOM | 770 | C | PHE | B | 101 | 14.764 | −54.002 | −25.981 | 1.00 | 10.52 C |
| 926 | ATOM | 771 | O | PHE | B | 101 | 14.155 | −54.043 | −24.922 | 1.00 | 10.81 O |
| 927 | ATOM | 772 | N | GLU | B | 102 | 14.883 | −55.046 | −26.799 | 1.00 | 10.91 N |
| 928 | ATOM | 773 | CA | GLU | B | 102 | 14.446 | −56.374 | −26.404 | 1.00 | 10.99 C |
| 929 | ATOM | 774 | CB | GLU | B | 102 | 14.421 | −57.296 | −27.627 | 1.00 | 11.68 C |
| 930 | ATOM | 775 | CG | GLU | B | 102 | 13.426 | −56.861 | −28.671 | 1.00 | 12.89 C |
| 931 | ATOM | 776 | CD | GLU | B | 102 | 12.006 | −57.208 | −28.341 | 1.00 | 14.16 C |
| 932 | ATOM | 777 | OE1 | GLU | B | 102 | 11.716 | −57.668 | −27.214 | 1.00 | 15.42 O |
| 933 | ATOM | 778 | OE2 | GLU | B | 102 | 11.165 | −57.006 | −29.249 | 1.00 | 16.47 O |
| 934 | ATOM | 779 | C | GLU | B | 102 | 15.455 | −56.929 | −25.407 | 1.00 | 10.74 C |
| 935 | ATOM | 780 | O | GLU | B | 102 | 16.562 | −56.394 | −25.230 | 1.00 | 10.59 O |
| 936 | ATOM | 781 | N | ASP | B | 103 | 15.067 | −58.002 | −24.737 | 1.00 | 10.37 N |
| 937 | ATOM | 782 | CA | ASP | B | 103 | 16.046 | −58.756 | −23.966 | 1.00 | 10.53 C |
| 938 | ATOM | 783 | CB | ASP | B | 103 | 15.367 | −59.617 | −22.870 | 1.00 | 10.75 C |
| 939 | ATOM | 784 | CG | ASP | B | 103 | 15.261 | −58.897 | −21.523 | 1.00 | 11.55 C |
| 940 | ATOM | 785 | OD1 | ASP | B | 103 | 16.184 | −58.099 | −21.199 | 1.00 | 11.03 O |
| 941 | ATOM | 786 | OD2 | ASP | B | 103 | 14.301 | −59.160 | −20.738 | 1.00 | 11.73 O |
| 942 | ATOM | 787 | C | ASP | B | 103 | 16.880 | −59.661 | −24.876 | 1.00 | 10.74 C |
| 943 | ATOM | 788 | O | ASP | B | 103 | 16.421 | −60.055 | −25.970 | 1.00 | 11.04 O |
| 944 | ATOM | 789 | N | PRO | B | 104 | 18.098 | −60.031 | −24.440 | 1.00 | 10.05 N |
| 945 | ATOM | 790 | CA | PRO | B | 104 | 18.780 | −59.687 | −23.204 | 1.00 | 10.19 C |
| 946 | ATOM | 791 | CB | PRO | B | 104 | 19.926 | −60.711 | −23.156 | 1.00 | 10.36 C |
| 947 | ATOM | 792 | CG | PRO | B | 104 | 20.263 | −60.922 | −24.563 | 1.00 | 9.98 C |
| 948 | ATOM | 793 | CD | PRO | B | 104 | 18.929 | −60.929 | −25.274 | 1.00 | 10.38 C |
| 949 | ATOM | 794 | C | PRO | B | 104 | 19.362 | −58.288 | −23.108 | 1.00 | 9.92 C |
| 950 | ATOM | 795 | O | PRO | B | 104 | 19.758 | −57.899 | −22.038 | 1.00 | 9.28 O |
| 951 | ATOM | 796 | N | THR | B | 105 | 19.474 | −57.544 | −24.205 | 1.00 | 9.58 N |
| 952 | ATOM | 797 | CA | THR | B | 105 | 20.072 | −56.210 | −24.132 | 1.00 | 10.80 C |
| 953 | ATOM | 798 | CB | THR | B | 105 | 20.020 | −55.512 | −25.517 | 1.00 | 10.60 C |
| 954 | ATOM | 799 | OG1 | THR | B | 105 | 20.878 | −56.203 | −26.442 | 1.00 | 11.24 O |
| 955 | ATOM | 800 | CG2 | THR | B | 105 | 20.487 | −54.059 | −25.419 | 1.00 | 11.45 C |
| 956 | ATOM | 801 | C | THR | B | 105 | 19.438 | −55.326 | −23.048 | 1.00 | 10.25 C |
| 957 | ATOM | 802 | O | THR | B | 105 | 20.120 | −54.677 | −22.309 | 1.00 | 10.44 O |
| 958 | ATOM | 803 | N | CYS | B | 106 | 18.114 | −55.309 | −22.968 | 1.00 | 10.48 N |
| 959 | ATOM | 804 | CA | CYS | B | 106 | 17.411 | −54.489 | −21.969 | 1.00 | 10.43 C |
| 960 | ATOM | 805 | CB | CYS | B | 106 | 15.905 | −54.724 | −22.076 | 1.00 | 10.55 C |
| 961 | ATOM | 806 | SG | CYS | B | 106 | 14.963 | −53.745 | −20.902 | 1.00 | 11.56 S |
| 962 | ATOM | 807 | C | CYS | B | 106 | 17.954 | −54.769 | −20.549 | 1.00 | 9.78 C |
| 963 | ATOM | 808 | O | CYS | B | 106 | 18.262 | −53.848 | −19.788 | 1.00 | 10.64 O |
| 964 | ATOM | 809 | N | THR | B | 107 | 18.075 | −56.040 | −20.191 | 1.00 | 10.32 N |
| 965 | ATOM | 810 | CA | THR | B | 107 | 18.643 | −56.418 | −18.892 | 1.00 | 10.56 C |
| 966 | ATOM | 811 | CB | THR | B | 107 | 18.538 | −57.947 | −18.661 | 1.00 | 11.03 C |
| 967 | ATOM | 812 | OG1 | THR | B | 107 | 17.155 | −58.345 | −18.797 | 1.00 | 10.55 O |
| 968 | ATOM | 813 | CG2 | THR | B | 107 | 19.028 | −58.312 | −17.282 | 1.00 | 11.41 C |
| 969 | ATOM | 814 | C | THR | B | 107 | 20.093 | −55.984 | −18.702 | 1.00 | 10.77 C |
| 970 | ATOM | 815 | O | THR | B | 107 | 20.486 | −55.573 | −17.600 | 1.00 | 10.58 O |
| 971 | ATOM | 816 | N | LEU | B | 108 | 20.898 | −56.149 | −19.748 | 1.00 | 11.35 N |
| 972 | ATOM | 817 | CA | LEU | B | 108 | 22.322 | −56.012 | −19.614 | 1.00 | 12.00 C |
| 973 | ATOM | 818 | CB | LEU | B | 108 | 23.040 | −56.923 | −20.602 | 1.00 | 12.13 C |
| 974 | ATOM | 819 | CG | LEU | B | 108 | 22.748 | −58.401 | −20.367 | 1.00 | 11.81 C |
| 975 | ATOM | 820 | CD1 | LEU | B | 108 | 23.311 | −59.175 | −21.524 | 1.00 | 12.14 C |
| 976 | ATOM | 821 | CD2 | LEU | B | 108 | 23.270 | −58.912 | −19.031 | 1.00 | 12.20 C |
| 977 | ATOM | 822 | C | LEU | B | 108 | 22.850 | −54.592 | −19.749 | 1.00 | 13.16 C |
| 978 | ATOM | 823 | O | LEU | B | 108 | 23.966 | −54.335 | −19.286 | 1.00 | 12.99 O |
| 979 | ATOM | 824 | N | VAL | B | 109 | 22.063 | −53.679 | −20.325 | 1.00 | 14.66 N |

APPENDIX I-continued

| | | | | | | | | | | |
|---|---|---|---|---|---|---|---|---|---|---|
| 980 | ATOM | 825 | CA | VAL | B | 109 | 22.520 | −52.291 | −20.558 | 1.00 | 15.19 C |
| 981 | ATOM | 826 | CB | VAL | B | 109 | 22.035 | −51.667 | −21.899 | 1.00 | 16.58 C |
| 982 | ATOM | 827 | CG1 | VAL | B | 109 | 22.489 | −52.532 | −23.041 | 1.00 | 19.68 C |
| 983 | ATOM | 828 | CG2 | VAL | B | 109 | 20.525 | −51.404 | −21.916 | 1.00 | 16.72 C |
| 984 | ATOM | 829 | C | VAL | B | 109 | 22.168 | −51.403 | −19.396 | 1.00 | 15.08 C |
| 985 | ATOM | 830 | O | VAL | B | 109 | 21.028 | −50.995 | −19.212 | 1.00 | 17.38 O |
| 986 | ATOM | 831 | N | THR | B | 110 | 23.185 | −51.084 | −18.608 | 1.00 | 14.35 N |
| 987 | ATOM | 832 | CA | THR | B | 110 | 23.004 | −50.308 | −17.398 | 1.00 | 14.83 C |
| 988 | ATOM | 833 | CB | THR | B | 110 | 23.859 | −50.907 | −16.259 | 1.00 | 15.57 C |
| 989 | ATOM | 834 | OG1 | THR | B | 110 | 25.219 | −50.966 | −16.679 | 1.00 | 16.26 O |
| 990 | ATOM | 835 | CG2 | THR | B | 110 | 23.398 | −52.307 | −15.936 | 1.00 | 16.95 C |
| 991 | ATOM | 836 | C | THR | B | 110 | 23.378 | −48.851 | −17.576 | 1.00 | 14.28 C |
| 992 | ATOM | 837 | O | THR | B | 110 | 23.092 | −48.047 | −16.696 | 1.00 | 15.03 O |
| 993 | ATOM | 838 | N | SER | B | 111 | 24.074 | −48.486 | −18.663 | 1.00 | 13.96 N |
| 994 | ATOM | 839 | CA | ASER | B | 111 | 24.471 | −47.097 | −18.866 | 0.50 | 13.40 C |
| 995 | ATOM | 840 | CA | BSER | B | 111 | 24.483 | −47.098 | −18.857 | 0.50 | 13.74 C |
| 996 | ATOM | 841 | CB | ASER | B | 111 | 25.506 | −46.996 | −19.975 | 0.50 | 13.29 C |
| 997 | ATOM | 842 | CB | BSER | B | 111 | 25.578 | −47.007 | −19.925 | 0.50 | 14.02 C |
| 998 | ATOM | 843 | OG | ASER | B | 111 | 25.767 | −45.642 | −20.264 | 0.50 | 12.70 O |
| 999 | ATOM | 844 | OG | BSER | B | 111 | 26.660 | −47.897 | −19.644 | 0.50 | 14.26 O |
| 1000 | ATOM | 845 | C | SER | B | 111 | 23.289 | −46.206 | −19.235 | 1.00 | 13.45 C |
| 1001 | ATOM | 846 | O | SER | B | 111 | 22.520 | −46.533 | −20.133 | 1.00 | 12.26 O |
| 1002 | ATOM | 847 | N | SER | B | 112 | 23.159 | −45.066 | −18.565 | 1.00 | 13.63 N |
| 1003 | ATOM | 848 | CA | SER | B | 112 | 22.113 | −44.082 | −18.893 | 1.00 | 13.03 C |
| 1004 | ATOM | 849 | CB | SER | B | 112 | 22.164 | −42.892 | −17.940 | 1.00 | 14.01 C |
| 1005 | ATOM | 850 | OG | SER | B | 112 | 23.414 | −42.221 | −18.003 | 1.00 | 14.35 O |
| 1006 | ATOM | 851 | C | SER | B | 112 | 22.190 | −43.578 | −20.343 | 1.00 | 12.91 C |
| 1007 | ATOM | 852 | O | SER | B | 112 | 21.167 | −43.230 | −20.929 | 1.00 | 13.03 O |
| 1008 | ATOM | 853 | N | GLY | B | 113 | 23.394 | −43.537 | −20.911 | 1.00 | 12.30 N |
| 1009 | ATOM | 854 | CA | GLY | B | 113 | 23.579 | −43.187 | −22.316 | 1.00 | 12.22 C |
| 1010 | ATOM | 855 | C | GLY | B | 113 | 22.809 | −43.978 | −23.342 | 1.00 | 12.52 C |
| 1011 | ATOM | 856 | O | GLY | B | 113 | 22.606 | −43.493 | −24.460 | 1.00 | 12.28 O |
| 1012 | ATOM | 857 | N | ALA | B | 114 | 22.413 | −45.215 | −22.997 | 1.00 | 12.06 N |
| 1013 | ATOM | 858 | CA | ALA | B | 114 | 21.680 | −46.087 | −23.923 | 1.00 | 12.44 C |
| 1014 | ATOM | 859 | CB | ALA | B | 114 | 21.686 | −47.510 | −23.420 | 1.00 | 12.39 C |
| 1015 | ATOM | 860 | C | ALA | B | 114 | 20.233 | −45.627 | −24.123 | 1.00 | 12.57 C |
| 1016 | ATOM | 861 | O | ALA | B | 114 | 19.634 | −45.915 | −25.163 | 1.00 | 13.19 O |
| 1017 | ATOM | 862 | N | PHE | B | 115 | 19.648 | −45.013 | −23.097 | 1.00 | 11.82 N |
| 1018 | ATOM | 863 | CA | PHE | B | 115 | 18.205 | −44.783 | −23.061 | 1.00 | 12.40 C |
| 1019 | ATOM | 864 | CB | PHE | B | 115 | 17.635 | −44.909 | −21.639 | 1.00 | 11.85 C |
| 1020 | ATOM | 865 | CG | PHE | B | 115 | 17.608 | −46.327 | −21.114 | 1.00 | 11.96 C |
| 1021 | ATOM | 866 | CD1 | PHE | B | 115 | 16.438 | −47.092 | −21.156 | 1.00 | 12.27 C |
| 1022 | ATOM | 867 | CE1 | PHE | B | 115 | 16.439 | −48.400 | −20.701 | 1.00 | 12.79 C |
| 1023 | ATOM | 868 | CZ | PHE | B | 115 | 17.608 | −48.974 | −20.225 | 1.00 | 12.79 C |
| 1024 | ATOM | 869 | CE2 | PHE | B | 115 | 18.790 | −48.238 | −20.236 | 1.00 | 12.69 C |
| 1025 | ATOM | 870 | CD2 | PHE | B | 115 | 18.784 | −46.925 | −20.672 | 1.00 | 12.18 C |
| 1026 | ATOM | 871 | C | PHE | B | 115 | 17.874 | −43.403 | −23.614 | 1.00 | 13.25 C |
| 1027 | ATOM | 872 | O | PHE | B | 115 | 18.415 | −42.388 | −23.169 | 1.00 | 13.33 O |
| 1028 | ATOM | 873 | N | GLN | B | 116 | 16.924 | −43.360 | −24.548 | 1.00 | 13.54 N |
| 1029 | ATOM | 874 | CA | GLN | B | 116 | 16.535 | −42.117 | −25.179 | 1.00 | 14.50 C |
| 1030 | ATOM | 875 | CB | GLN | B | 116 | 16.225 | −42.341 | −26.661 | 1.00 | 15.91 C |
| 1031 | ATOM | 876 | CG | GLN | B | 116 | 14.821 | −42.821 | −27.000 | 1.00 | 17.27 C |
| 1032 | ATOM | 877 | CD | GLN | B | 116 | 14.646 | −43.017 | −28.510 | 1.00 | 19.61 C |
| 1033 | ATOM | 878 | OE1 | GLN | B | 116 | 14.387 | −42.072 | −29.236 | 1.00 | 19.51 O |
| 1034 | ATOM | 879 | NE2 | GLN | B | 116 | 14.792 | −44.242 | −28.971 | 1.00 | 20.53 N |
| 1035 | ATOM | 880 | C | GLN | B | 116 | 15.410 | −41.354 | −24.491 | 1.00 | 14.33 C |
| 1036 | ATOM | 881 | O | GLN | B | 116 | 15.359 | −40.130 | −24.582 | 1.00 | 14.12 O |
| 1037 | ATOM | 882 | N | TYR | B | 117 | 14.543 | −42.050 | −23.764 | 1.00 | 14.08 N |
| 1038 | ATOM | 883 | CA | TYR | B | 117 | 13.429 | −41.418 | −23.100 | 1.00 | 13.80 C |
| 1039 | ATOM | 884 | CB | TYR | B | 117 | 12.098 | −42.095 | −23.486 | 1.00 | 13.80 C |
| 1040 | ATOM | 885 | CG | TYR | B | 117 | 11.845 | −42.144 | −24.966 | 1.00 | 14.36 C |
| 1041 | ATOM | 886 | CD1 | TYR | B | 117 | 11.669 | −40.977 | −25.684 | 1.00 | 14.82 C |
| 1042 | ATOM | 887 | CE1 | TYR | B | 117 | 11.435 | −41.000 | −27.041 | 1.00 | 15.07 C |
| 1043 | ATOM | 888 | CZ | TYR | B | 117 | 11.358 | −42.204 | −27.703 | 1.00 | 14.90 C |
| 1044 | ATOM | 889 | OH | TYR | B | 117 | 11.114 | −42.205 | −29.058 | 1.00 | 16.75 O |
| 1045 | ATOM | 890 | CE2 | TYR | B | 117 | 11.535 | −43.394 | −27.004 | 1.00 | 14.22 C |
| 1046 | ATOM | 891 | CD2 | TYR | B | 117 | 11.750 | −43.359 | −25.646 | 1.00 | 13.49 C |
| 1047 | ATOM | 892 | C | TYR | B | 117 | 13.585 | −41.357 | −21.576 | 1.00 | 13.47 C |
| 1048 | ATOM | 893 | O | TYR | B | 117 | 13.939 | −42.337 | −20.929 | 1.00 | 12.47 O |
| 1049 | ATOM | 894 | N | TRP | B | 118 | 13.298 | −40.190 | −21.032 | 1.00 | 13.56 N |
| 1050 | ATOM | 895 | CA | TRP | B | 118 | 13.507 | −39.894 | −19.588 | 1.00 | 13.60 C |
| 1051 | ATOM | 896 | CB | TRP | B | 118 | 14.811 | −39.089 | −19.415 | 1.00 | 14.07 C |
| 1052 | ATOM | 897 | CG | TRP | B | 118 | 15.964 | −39.875 | −19.726 | 1.00 | 13.89 C |
| 1053 | ATOM | 898 | CD1 | TRP | B | 118 | 16.532 | −40.094 | −20.963 | 1.00 | 14.60 C |
| 1054 | ATOM | 899 | NE1 | TRP | B | 118 | 17.577 | −40.962 | −20.844 | 1.00 | 14.67 N |
| 1055 | ATOM | 900 | CE2 | TRP | B | 118 | 17.688 | −41.342 | −19.532 | 1.00 | 13.93 C |
| 1056 | ATOM | 901 | CD2 | TRP | B | 118 | 16.678 | −40.693 | −18.814 | 1.00 | 13.39 C |
| 1057 | ATOM | 902 | CE3 | TRP | B | 118 | 16.576 | −40.919 | −17.454 | 1.00 | 13.73 C |
| 1058 | ATOM | 903 | CZ3 | TRP | B | 118 | 17.450 | −41.741 | −16.858 | 1.00 | 14.19 C |
| 1059 | ATOM | 904 | CH2 | TRP | B | 118 | 18.430 | −42.397 | −17.587 | 1.00 | 14.11 C |

APPENDIX I-continued

| | | | | | | | | | | |
|---|---|---|---|---|---|---|---|---|---|---|
| 1060 | ATOM | 905 | CZ2 | TRP | B | 118 | 18.562 | −42.219 | −18.927 | 1.00 | 13.86 C |
| 1061 | ATOM | 906 | C | TRP | B | 118 | 12.381 | −39.115 | −18.980 | 1.00 | 14.97 C |
| 1062 | ATOM | 907 | O | TRP | B | 118 | 11.860 | −38.166 | −19.592 | 1.00 | 16.19 O |
| 1063 | ATOM | 908 | N | GLY | B | 119 | 12.032 | −39.487 | −17.755 | 1.00 | 15.19 N |
| 1064 | ATOM | 909 | CA | GLY | B | 119 | 11.253 | −38.619 | −16.886 | 1.00 | 17.90 C |
| 1065 | ATOM | 910 | C | GLY | B | 119 | 12.066 | −37.448 | −16.367 | 1.00 | 19.29 C |
| 1066 | ATOM | 911 | O | GLY | B | 119 | 13.280 | −37.356 | −16.565 | 1.00 | 18.82 O |
| 1067 | ATOM | 912 | N | GLN | B | 120 | 11.357 | −36.540 | −15.703 | 1.00 | 21.11 N |
| 1068 | ATOM | 913 | CA | GLN | B | 120 | 11.915 | −35.316 | −15.185 | 1.00 | 21.66 C |
| 1069 | ATOM | 914 | CB | GLN | B | 120 | 10.774 | −34.269 | −15.108 | 1.00 | 25.70 C |
| 1070 | ATOM | 915 | CG | GLN | B | 120 | 9.755 | −34.460 | −13.962 | 1.00 | 29.90 C |
| 1071 | ATOM | 916 | CD | GLN | B | 120 | 8.727 | −35.601 | −14.124 | 1.00 | 34.12 C |
| 1072 | ATOM | 917 | OE1 | GLN | B | 120 | 8.501 | −36.154 | −15.212 | 1.00 | 34.07 O |
| 1073 | ATOM | 918 | NE2 | GLN | B | 120 | 8.081 | −35.944 | −13.007 | 1.00 | 39.14 N |
| 1074 | ATOM | 919 | C | GLN | B | 120 | 12.586 | −35.500 | −13.806 | 1.00 | 18.62 C |
| 1075 | ATOM | 920 | O | GLN | B | 120 | 13.267 | −34.601 | −13.290 | 1.00 | 18.21 O |
| 1076 | ATOM | 921 | N | GLY | B | 121 | 12.344 | −36.633 | −13.187 | 1.00 | 16.75 N |
| 1077 | ATOM | 922 | CA | GLY | B | 121 | 12.971 | −36.968 | −11.911 | 1.00 | 15.79 C |
| 1078 | ATOM | 923 | C | GLY | B | 121 | 12.105 | −36.624 | −10.711 | 1.00 | 15.32 C |
| 1079 | ATOM | 924 | O | GLY | B | 121 | 11.284 | −35.711 | −10.783 | 1.00 | 15.26 O |
| 1080 | ATOM | 925 | N | THR | B | 122 | 12.279 | −37.361 | −9.624 | 1.00 | 13.78 N |
| 1081 | ATOM | 926 | CA | THR | B | 122 | 11.559 | −37.085 | −8.381 | 1.00 | 13.40 C |
| 1082 | ATOM | 927 | CB | THR | B | 122 | 10.245 | −37.937 | −8.223 | 1.00 | 14.38 C |
| 1083 | ATOM | 928 | OG1 | THR | B | 122 | 9.521 | −37.481 | −7.083 | 1.00 | 14.86 O |
| 1084 | ATOM | 929 | CG2 | THR | B | 122 | 10.518 | −39.398 | −8.058 | 1.00 | 14.52 C |
| 1085 | ATOM | 930 | C | THR | B | 122 | 12.538 | −37.277 | −7.219 | 1.00 | 12.33 C |
| 1086 | ATOM | 931 | O | THR | B | 122 | 13.329 | −38.205 | −7.221 | 1.00 | 13.01 O |
| 1087 | ATOM | 932 | N | GLN | B | 123 | 12.498 | −36.395 | −6.237 | 1.00 | 11.20 N |
| 1088 | ATOM | 933 | CA | GLN | B | 123 | 13.457 | −36.436 | −5.141 | 1.00 | 10.96 C |
| 1089 | ATOM | 934 | CB | GLN | B | 123 | 13.549 | −35.061 | −4.473 | 1.00 | 11.18 C |
| 1090 | ATOM | 935 | CG | GLN | B | 123 | 14.552 | −34.997 | −3.323 | 1.00 | 11.71 C |
| 1091 | ATOM | 936 | CD | GLN | B | 123 | 16.007 | −35.136 | −3.773 | 1.00 | 12.28 C |
| 1092 | ATOM | 937 | OE1 | GLN | B | 123 | 16.427 | −34.565 | −4.769 | 1.00 | 13.10 O |
| 1093 | ATOM | 938 | NE2 | GLN | B | 123 | 16.785 | −35.881 | −3.008 | 1.00 | 13.39 N |
| 1094 | ATOM | 939 | C | GLN | B | 123 | 13.030 | −37.449 | −4.089 | 1.00 | 10.45 C |
| 1095 | ATOM | 940 | O | GLN | B | 123 | 11.890 | −37.427 | −3.640 | 1.00 | 10.03 O |
| 1096 | ATOM | 941 | N | VAL | B | 124 | 13.984 | −38.251 | −3.642 | 1.00 | 10.70 N |
| 1097 | ATOM | 942 | CA | VAL | B | 124 | 13.800 | −39.206 | −2.528 | 1.00 | 10.85 C |
| 1098 | ATOM | 943 | CB | VAL | B | 124 | 13.914 | −40.674 | −3.036 | 1.00 | 11.31 C |
| 1099 | ATOM | 944 | CG1 | VAL | B | 124 | 13.940 | −41.670 | −1.895 | 1.00 | 11.90 C |
| 1100 | ATOM | 945 | CG2 | VAL | B | 124 | 12.775 | −40.982 | −3.985 | 1.00 | 12.38 C |
| 1101 | ATOM | 946 | C | VAL | B | 124 | 14.887 | −38.890 | −1.503 | 1.00 | 10.60 C |
| 1102 | ATOM | 947 | O | VAL | B | 124 | 16.092 | −38.929 | −1.811 | 1.00 | 10.84 O |
| 1103 | ATOM | 948 | N | THR | B | 125 | 14.494 | −38.553 | −0.294 | 1.00 | 10.57 N |
| 1104 | ATOM | 949 | CA | THR | B | 125 | 15.462 | −38.248 | 0.731 | 1.00 | 11.11 C |
| 1105 | ATOM | 950 | CB | THR | B | 125 | 15.379 | −36.765 | 1.161 | 1.00 | 10.77 C |
| 1106 | ATOM | 951 | OG1 | THR | B | 125 | 15.681 | −35.928 | 0.032 | 1.00 | 10.61 O |
| 1107 | ATOM | 952 | CG2 | THR | B | 125 | 16.365 | −36.454 | 2.279 | 1.00 | 10.98 C |
| 1108 | ATOM | 953 | C | THR | B | 125 | 15.218 | −39.157 | 1.897 | 1.00 | 11.76 C |
| 1109 | ATOM | 954 | O | THR | B | 125 | 14.093 | −39.279 | 2.363 | 1.00 | 11.37 O |
| 1110 | ATOM | 955 | N | VAL | B | 126 | 16.292 | −39.765 | 2.396 | 1.00 | 13.01 N |
| 1111 | ATOM | 956 | CA | VAL | B | 126 | 16.205 | −40.602 | 3.580 | 1.00 | 14.04 C |
| 1112 | ATOM | 957 | CB | VAL | B | 126 | 16.645 | −42.052 | 3.296 | 1.00 | 14.17 C |
| 1113 | ATOM | 958 | CG1 | VAL | B | 126 | 16.378 | −42.922 | 4.531 | 1.00 | 14.44 C |
| 1114 | ATOM | 959 | CG2 | VAL | B | 126 | 15.930 | −42.630 | 2.080 | 1.00 | 14.04 C |
| 1115 | ATOM | 960 | C | VAL | B | 126 | 17.100 | −39.990 | 4.652 | 1.00 | 15.76 C |
| 1116 | ATOM | 961 | O | VAL | B | 126 | 18.316 | −39.916 | 4.478 | 1.00 | 15.97 O |
| 1117 | ATOM | 962 | N | SER | B | 127 | 16.495 | −39.518 | 5.731 | 1.00 | 18.00 N |
| 1118 | ATOM | 963 | CA | SER | B | 127 | 17.245 | −38.886 | 6.809 | 1.00 | 20.96 C |
| 1119 | ATOM | 964 | CB | SER | B | 127 | 17.413 | −37.393 | 6.531 | 1.00 | 22.59 C |
| 1120 | ATOM | 965 | OG | SER | B | 127 | 17.975 | −36.740 | 7.664 | 1.00 | 27.08 O |
| 1121 | ATOM | 966 | C | SER | B | 127 | 16.545 | −39.078 | 8.149 | 1.00 | 21.28 C |
| 1122 | ATOM | 967 | O | SER | B | 127 | 15.332 | −38.925 | 8.229 | 1.00 | 22.15 O |
| 1123 | ATOM | 968 | N | ALA | A | 18 | 32.394 | −38.055 | −22.849 | 1.00 | 28.08 N |
| 1124 | ATOM | 969 | CA | ALA | A | 18 | 31.602 | −39.292 | −22.650 | 1.00 | 27.15 C |
| 1125 | ATOM | 970 | CB | ALA | A | 18 | 30.163 | −38.945 | −22.272 | 1.00 | 28.68 C |
| 1126 | ATOM | 971 | C | ALA | A | 18 | 31.623 | −40.168 | −23.910 | 1.00 | 24.13 C |
| 1127 | ATOM | 972 | O | ALA | A | 18 | 31.998 | −39.726 | −24.996 | 1.00 | 24.63 O |
| 1128 | ATOM | 973 | N | PHE | A | 19 | 31.223 | −41.412 | −23.739 | 1.00 | 18.95 N |
| 1129 | ATOM | 974 | CA | PHE | A | 19 | 31.183 | −42.395 | −24.808 | 1.00 | 16.48 C |
| 1130 | ATOM | 975 | CB | PHE | A | 19 | 30.728 | −43.729 | −24.197 | 1.00 | 16.48 C |
| 1131 | ATOM | 976 | CG | PHE | A | 19 | 30.710 | −44.882 | −25.151 | 1.00 | 14.94 C |
| 1132 | ATOM | 977 | CD1 | PHE | A | 19 | 31.820 | −45.712 | −25.275 | 1.00 | 14.89 C |
| 1133 | ATOM | 978 | CE1 | PHE | A | 19 | 31.791 | −46.798 | −26.149 | 1.00 | 15.46 C |
| 1134 | ATOM | 979 | CZ | PHE | A | 19 | 30.654 | −47.055 | −26.909 | 1.00 | 14.58 C |
| 1135 | ATOM | 980 | CE2 | PHE | A | 19 | 29.547 | −46.225 | −26.803 | 1.00 | 14.93 C |
| 1136 | ATOM | 981 | CD2 | PHE | A | 19 | 29.574 | −45.150 | −25.923 | 1.00 | 14.80 C |
| 1137 | ATOM | 982 | C | PHE | A | 19 | 30.208 | −41.919 | −25.888 | 1.00 | 16.16 C |
| 1138 | ATOM | 983 | O | PHE | A | 19 | 29.042 | −41.643 | −25.592 | 1.00 | 15.23 O |
| 1139 | ATOM | 984 | N | THR | A | 20 | 30.691 | −41.780 | −27.123 | 1.00 | 15.04 N |

APPENDIX I-continued

| 1140 | ATOM | 985 | CA | THR | A | 20 | 29.871 | −41.220 | −28.199 | 1.00 | 14.98 | C |
|---|---|---|---|---|---|---|---|---|---|---|---|---|
| 1141 | ATOM | 986 | CB | THR | A | 20 | 30.300 | −39.777 | −28.574 | 1.00 | 18.36 | C |
| 1142 | ATOM | 987 | OG1 | THR | A | 20 | 30.290 | −38.953 | −27.418 | 1.00 | 18.93 | O |
| 1143 | ATOM | 988 | CG2 | THR | A | 20 | 29.330 | −39.154 | −29.592 | 1.00 | 17.99 | C |
| 1144 | ATOM | 989 | C | THR | A | 20 | 29.934 | −42.123 | −29.407 | 1.00 | 14.53 | C |
| 1145 | ATOM | 990 | O | THR | A | 20 | 31.002 | −42.577 | −29.810 | 1.00 | 14.49 | O |
| 1146 | ATOM | 991 | N | VAL | A | 21 | 28.762 | −42.406 | −29.960 | 1.00 | 13.06 | N |
| 1147 | ATOM | 992 | CA | VAL | A | 21 | 28.639 | −43.113 | −31.208 | 1.00 | 12.21 | C |
| 1148 | ATOM | 993 | CB | VAL | A | 21 | 27.458 | −44.101 | −31.173 | 1.00 | 12.44 | C |
| 1149 | ATOM | 994 | CG1 | VAL | A | 21 | 27.144 | −44.630 | −32.570 | 1.00 | 12.15 | C |
| 1150 | ATOM | 995 | CG2 | VAL | A | 21 | 27.741 | −45.240 | −30.221 | 1.00 | 12.47 | C |
| 1151 | ATOM | 996 | C | VAL | A | 21 | 28.440 | −42.060 | −32.300 | 1.00 | 12.07 | C |
| 1152 | ATOM | 997 | O | VAL | A | 21 | 27.711 | −41.081 | −32.105 | 1.00 | 11.53 | O |
| 1153 | ATOM | 998 | N | THR | A | 22 | 29.089 | −42.274 | −33.432 | 1.00 | 11.83 | N |
| 1154 | ATOM | 999 | CA | THR | A | 22 | 28.998 | −41.352 | −34.596 | 1.00 | 11.95 | C |
| 1155 | ATOM | 1000 | CB | THR | A | 22 | 30.319 | −40.605 | −34.812 | 1.00 | 12.69 | C |
| 1156 | ATOM | 1001 | OG1 | THR | A | 22 | 31.396 | −41.550 | −34.969 | 1.00 | 12.47 | O |
| 1157 | ATOM | 1002 | CG2 | THR | A | 22 | 30.625 | −39.662 | −33.638 | 1.00 | 12.52 | C |
| 1158 | ATOM | 1003 | C | THR | A | 22 | 28.647 | −42.116 | −35.849 | 1.00 | 11.88 | C |
| 1159 | ATOM | 1004 | O | THR | A | 22 | 28.738 | −43.352 | −35.887 | 1.00 | 11.53 | O |
| 1160 | ATOM | 1005 | N | VAL | A | 23 | 28.193 | −41.395 | −36.879 | 1.00 | 11.95 | N |
| 1161 | ATOM | 1006 | CA | VAL | A | 23 | 27.882 | −42.003 | −38.175 | 1.00 | 12.56 | C |
| 1162 | ATOM | 1007 | CB | VAL | A | 23 | 26.358 | −42.082 | −38.490 | 1.00 | 12.99 | C |
| 1163 | ATOM | 1008 | CG1 | VAL | A | 23 | 25.722 | −40.705 | −38.554 | 1.00 | 13.85 | C |
| 1164 | ATOM | 1009 | CG2 | VAL | A | 23 | 25.625 | −42.942 | −37.455 | 1.00 | 14.12 | C |
| 1165 | ATOM | 1010 | C | VAL | A | 23 | 28.622 | −41.254 | −39.294 | 1.00 | 11.30 | C |
| 1166 | ATOM | 1011 | O | VAL | A | 23 | 28.676 | −40.042 | −39.285 | 1.00 | 11.26 | O |
| 1167 | ATOM | 1012 | N | PRO | A | 24 | 29.231 | −41.981 | −40.248 | 1.00 | 11.77 | N |
| 1168 | ATOM | 1013 | CA | PRO | A | 24 | 29.814 | −41.257 | −41.404 | 1.00 | 11.46 | C |
| 1169 | ATOM | 1014 | CB | PRO | A | 24 | 30.635 | −42.337 | −42.151 | 1.00 | 11.89 | C |
| 1170 | ATOM | 1015 | CG | PRO | A | 24 | 30.180 | −43.650 | −41.597 | 1.00 | 12.14 | C |
| 1171 | ATOM | 1016 | CD | PRO | A | 24 | 29.575 | −43.415 | −40.234 | 1.00 | 11.65 | C |
| 1172 | ATOM | 1017 | C | PRO | A | 24 | 28.747 | −40.661 | −42.328 | 1.00 | 12.25 | C |
| 1173 | ATOM | 1018 | O | PRO | A | 24 | 29.001 | −39.657 | −43.020 | 1.00 | 11.85 | O |
| 1174 | ATOM | 1019 | N | LYS | A | 25 | 27.563 | −41.268 | −42.306 | 1.00 | 13.04 | N |
| 1175 | ATOM | 1020 | CA | LYS | A | 25 | 26.420 | −40.805 | −43.084 | 1.00 | 15.11 | C |
| 1176 | ATOM | 1021 | CB | LYS | A | 25 | 26.269 | −41.586 | −44.395 | 1.00 | 16.54 | C |
| 1177 | ATOM | 1022 | CG | LYS | A | 25 | 27.439 | −41.644 | −45.312 | 1.00 | 19.22 | C |
| 1178 | ATOM | 1023 | CD | LYS | A | 25 | 27.242 | −42.723 | −46.391 | 1.00 | 20.40 | C |
| 1179 | ATOM | 1024 | CE | LYS | A | 25 | 26.042 | −42.472 | −47.280 | 1.00 | 21.10 | C |
| 1180 | ATOM | 1025 | NZ | LYS | A | 25 | 26.195 | −43.182 | −48.590 | 1.00 | 21.30 | N |
| 1181 | ATOM | 1026 | C | LYS | A | 25 | 25.165 | −41.067 | −42.302 | 1.00 | 14.67 | C |
| 1182 | ATOM | 1027 | O | LYS | A | 25 | 24.971 | −42.167 | −41.806 | 1.00 | 14.84 | O |
| 1183 | ATOM | 1028 | N | ASP | A | 26 | 24.252 | −40.108 | −42.280 | 1.00 | 13.61 | N |
| 1184 | ATOM | 1029 | CA | ASP | A | 26 | 22.949 | −40.330 | −41.637 | 1.00 | 12.93 | C |
| 1185 | ATOM | 1030 | CB | ASP | A | 26 | 22.556 | −39.117 | −40.776 | 1.00 | 13.06 | C |
| 1186 | ATOM | 1031 | CG | ASP | A | 26 | 22.181 | −37.895 | −41.587 | 1.00 | 12.98 | C |
| 1187 | ATOM | 1032 | OD1 | ASP | A | 26 | 22.157 | −37.953 | −42.840 | 1.00 | 13.42 | O |
| 1188 | ATOM | 1033 | OD2 | ASP | A | 26 | 21.889 | −36.852 | −40.945 | 1.00 | 13.58 | O |
| 1189 | ATOM | 1034 | C | ASP | A | 26 | 21.819 | −40.728 | −42.605 | 1.00 | 13.29 | C |
| 1190 | ATOM | 1035 | O | ASP | A | 26 | 20.679 | −40.947 | −42.156 | 1.00 | 12.49 | O |
| 1191 | ATOM | 1036 | N | LEU | A | 27 | 22.144 | −40.836 | −43.899 | 1.00 | 13.21 | N |
| 1192 | ATOM | 1037 | CA | LEU | A | 27 | 21.183 | −41.135 | −44.961 | 1.00 | 14.05 | C |
| 1193 | ATOM | 1038 | CB | LEU | A | 27 | 20.605 | −39.846 | −45.563 | 1.00 | 16.07 | C |
| 1194 | ATOM | 1039 | CG | LEU | A | 27 | 19.685 | −40.087 | −46.783 | 1.00 | 16.24 | C |
| 1195 | ATOM | 1040 | CD1 | LEU | A | 27 | 18.341 | −40.646 | −46.339 | 1.00 | 16.91 | C |
| 1196 | ATOM | 1041 | CD2 | LEU | A | 27 | 19.509 | −38.816 | −47.585 | 1.00 | 17.60 | C |
| 1197 | ATOM | 1042 | C | LEU | A | 27 | 21.865 | −41.943 | −46.054 | 1.00 | 14.88 | C |
| 1198 | ATOM | 1043 | O | LEU | A | 27 | 22.925 | −41.558 | −46.553 | 1.00 | 15.28 | O |
| 1199 | ATOM | 1044 | N | TYR | A | 28 | 21.252 | −43.047 | −46.437 | 1.00 | 15.22 | N |
| 1200 | ATOM | 1045 | CA | TYR | A | 28 | 21.716 | −43.878 | −47.543 | 1.00 | 15.09 | C |
| 1201 | ATOM | 1046 | CB | TYR | A | 28 | 22.081 | −45.296 | −47.065 | 1.00 | 14.64 | C |
| 1202 | ATOM | 1047 | CG | TYR | A | 28 | 23.303 | −45.419 | −46.185 | 1.00 | 14.10 | C |
| 1203 | ATOM | 1048 | CD1 | TYR | A | 28 | 23.324 | −44.898 | −44.894 | 1.00 | 13.90 | C |
| 1204 | ATOM | 1049 | CE1 | TYR | A | 28 | 24.449 | −45.011 | −44.091 | 1.00 | 14.47 | C |
| 1205 | ATOM | 1050 | CZ | TYR | A | 28 | 25.558 | −45.680 | −44.570 | 1.00 | 14.76 | C |
| 1206 | ATOM | 1051 | OH | TYR | A | 28 | 26.680 | −45.837 | −43.780 | 1.00 | 16.77 | O |
| 1207 | ATOM | 1052 | CE2 | TYR | A | 28 | 25.554 | −46.205 | −45.845 | 1.00 | 15.17 | C |
| 1208 | ATOM | 1053 | CD2 | TYR | A | 28 | 24.438 | −46.067 | −46.642 | 1.00 | 13.96 | C |
| 1209 | ATOM | 1054 | C | TYR | A | 28 | 20.594 | −44.022 | −48.527 | 1.00 | 15.94 | C |
| 1210 | ATOM | 1055 | O | TYR | A | 28 | 19.452 | −44.307 | −48.147 | 1.00 | 15.83 | O |
| 1211 | ATOM | 1056 | N | VAL | A | 29 | 20.918 | −43.835 | −49.805 | 1.00 | 15.86 | N |
| 1212 | ATOM | 1057 | CA | VAL | A | 29 | 19.946 | −44.018 | −50.867 | 1.00 | 17.26 | C |
| 1213 | ATOM | 1058 | CB | VAL | A | 29 | 19.863 | −42.779 | −51.772 | 1.00 | 17.06 | C |
| 1214 | ATOM | 1059 | CG1 | VAL | A | 29 | 18.790 | −42.964 | −52.821 | 1.00 | 17.23 | C |
| 1215 | ATOM | 1060 | CG2 | VAL | A | 29 | 19.551 | −41.559 | −50.939 | 1.00 | 17.41 | C |
| 1216 | ATOM | 1061 | C | VAL | A | 29 | 20.405 | −45.207 | −51.681 | 1.00 | 19.08 | C |
| 1217 | ATOM | 1062 | O | VAL | A | 29 | 21.506 | −45.197 | −52.212 | 1.00 | 19.64 | O |
| 1218 | ATOM | 1063 | N | VAL | A | 30 | 19.564 | −46.231 | −51.773 | 1.00 | 20.01 | N |
| 1219 | ATOM | 1064 | CA | VAL | A | 30 | 20.007 | −47.525 | −52.246 | 1.00 | 21.79 | C |

APPENDIX I-continued

| 1220 | ATOM | 1065 | CB  | VAL | A | 30 | 20.079 | −48.507 | −51.049 | 1.00 | 22.63 | C |
| --- | --- | --- | --- | --- | --- | --- | --- | --- | --- | --- | --- | --- |
| 1221 | ATOM | 1066 | CG1 | VAL | A | 30 | 20.328 | −49.922 | −51.514 | 1.00 | 24.21 | C |
| 1222 | ATOM | 1067 | CG2 | VAL | A | 30 | 21.168 | −48.077 | −50.057 | 1.00 | 23.32 | C |
| 1223 | ATOM | 1068 | C   | VAL | A | 30 | 19.041 | −48.033 | −53.298 | 1.00 | 21.94 | C |
| 1224 | ATOM | 1069 | O   | VAL | A | 30 | 17.866 | −47.721 | −53.258 | 1.00 | 22.01 | O |
| 1225 | ATOM | 1070 | N   | GLU | A | 31 | 19.540 | −48.824 | −54.240 | 1.00 | 24.12 | N |
| 1226 | ATOM | 1071 | CA  | GLU | A | 31 | 18.683 | −49.393 | −55.275 | 1.00 | 24.90 | C |
| 1227 | ATOM | 1072 | CB  | GLU | A | 31 | 19.429 | −49.504 | −56.608 | 1.00 | 27.70 | C |
| 1228 | ATOM | 1073 | CG  | GLU | A | 31 | 19.221 | −48.291 | −57.515 | 1.00 | 31.38 | C |
| 1229 | ATOM | 1074 | CD  | GLU | A | 31 | 19.916 | −48.423 | −58.859 | 1.00 | 35.94 | C |
| 1230 | ATOM | 1075 | OE1 | GLU | A | 31 | 20.326 | −49.554 | −59.214 | 1.00 | 39.66 | O |
| 1231 | ATOM | 1076 | OE2 | GLU | A | 31 | 20.058 | −47.395 | −59.569 | 1.00 | 39.76 | O |
| 1232 | ATOM | 1077 | C   | GLU | A | 31 | 18.127 | −50.748 | −54.843 | 1.00 | 24.25 | C |
| 1233 | ATOM | 1078 | O   | GLU | A | 31 | 18.846 | −51.591 | −54.291 | 1.00 | 21.42 | O |
| 1234 | ATOM | 1079 | N   | TYR | A | 32 | 16.831 | −50.930 | −55.083 | 1.00 | 24.03 | N |
| 1235 | ATOM | 1080 | CA  | TYR | A | 32 | 16.168 | −52.227 | −54.943 | 1.00 | 25.39 | C |
| 1236 | ATOM | 1081 | CB  | TYR | A | 32 | 14.815 | −52.201 | −55.668 | 1.00 | 26.95 | C |
| 1237 | ATOM | 1082 | CG  | TYR | A | 32 | 14.009 | −53.468 | −55.507 | 1.00 | 28.88 | C |
| 1238 | ATOM | 1083 | CD1 | TYR | A | 32 | 13.255 | −53.687 | −54.364 | 1.00 | 29.52 | C |
| 1239 | ATOM | 1084 | CE1 | TYR | A | 32 | 12.513 | −54.845 | −54.202 | 1.00 | 30.82 | C |
| 1240 | ATOM | 1085 | CZ  | TYR | A | 32 | 12.523 | −55.803 | −55.188 | 1.00 | 31.17 | C |
| 1241 | ATOM | 1086 | OH  | TYR | A | 32 | 11.783 | −56.947 | −55.013 | 1.00 | 32.99 | O |
| 1242 | ATOM | 1087 | CE2 | TYR | A | 32 | 13.262 | −55.610 | −56.341 | 1.00 | 30.40 | C |
| 1243 | ATOM | 1088 | CD2 | TYR | A | 32 | 13.999 | −54.446 | −56.495 | 1.00 | 29.43 | C |
| 1244 | ATOM | 1089 | C   | TYR | A | 32 | 17.041 | −53.353 | −55.509 | 1.00 | 24.44 | C |
| 1245 | ATOM | 1090 | O   | TYR | A | 32 | 17.653 | −53.203 | −56.573 | 1.00 | 23.18 | O |
| 1246 | ATOM | 1091 | N   | GLY | A | 33 | 17.112 | −54.471 | −54.791 | 1.00 | 24.09 | N |
| 1247 | ATOM | 1092 | CA  | GLY | A | 33 | 17.922 | −55.621 | −55.221 | 1.00 | 25.13 | C |
| 1248 | ATOM | 1093 | C   | GLY | A | 33 | 19.425 | −55.551 | −54.961 | 1.00 | 25.76 | C |
| 1249 | ATOM | 1094 | O   | GLY | A | 33 | 20.113 | −56.576 | −55.023 | 1.00 | 26.89 | O |
| 1250 | ATOM | 1095 | N   | SER | A | 34 | 19.955 | −54.358 | −54.691 | 1.00 | 24.65 | N |
| 1251 | ATOM | 1096 | CA  | SER | A | 34 | 21.370 | −54.221 | −54.369 | 1.00 | 23.89 | C |
| 1252 | ATOM | 1097 | CB  | SER | A | 34 | 21.850 | −52.789 | −54.624 | 1.00 | 24.60 | C |
| 1253 | ATOM | 1098 | OG  | SER | A | 34 | 21.417 | −51.914 | −53.590 | 1.00 | 26.22 | O |
| 1254 | ATOM | 1099 | C   | SER | A | 34 | 21.640 | −54.637 | −52.915 | 1.00 | 23.06 | C |
| 1255 | ATOM | 1100 | O   | SER | A | 34 | 20.724 | −54.974 | −52.163 | 1.00 | 21.24 | O |
| 1256 | ATOM | 1101 | N   | ASN | A | 35 | 22.917 | −54.639 | −52.555 | 1.00 | 23.37 | N |
| 1257 | ATOM | 1102 | CA  | ASN | A | 35 | 23.359 | −54.889 | −51.199 | 1.00 | 23.75 | C |
| 1258 | ATOM | 1103 | CB  | ASN | A | 35 | 24.529 | −55.870 | −51.195 | 1.00 | 24.36 | C |
| 1259 | ATOM | 1104 | CG  | ASN | A | 35 | 24.131 | −57.260 | −51.661 | 1.00 | 25.45 | C |
| 1260 | ATOM | 1105 | OD1 | ASN | A | 35 | 22.957 | −57.597 | −51.744 | 1.00 | 25.86 | O |
| 1261 | ATOM | 1106 | ND2 | ASN | A | 35 | 25.122 | −58.072 | −51.975 | 1.00 | 27.59 | N |
| 1262 | ATOM | 1107 | C   | ASN | A | 35 | 23.784 | −53.569 | −50.576 | 1.00 | 22.93 | C |
| 1263 | ATOM | 1108 | O   | ASN | A | 35 | 24.317 | −52.686 | −51.257 | 1.00 | 22.77 | O |
| 1264 | ATOM | 1109 | N   | MET | A | 36 | 23.558 | −53.452 | −49.277 | 1.00 | 22.25 | N |
| 1265 | ATOM | 1110 | CA  | MET | A | 36 | 23.822 | −52.220 | −48.547 | 1.00 | 21.32 | C |
| 1266 | ATOM | 1111 | CB  | MET | A | 36 | 22.477 | −51.560 | −48.301 | 1.00 | 23.08 | C |
| 1267 | ATOM | 1112 | CG  | MET | A | 36 | 22.408 | −50.498 | −47.245 | 1.00 | 26.23 | C |
| 1268 | ATOM | 1113 | SD  | MET | A | 36 | 20.666 | −50.139 | −46.874 | 1.00 | 29.99 | S |
| 1269 | ATOM | 1114 | CE  | MET | A | 36 | 20.023 | −51.572 | −46.035 | 1.00 | 30.74 | C |
| 1270 | ATOM | 1115 | C   | MET | A | 36 | 24.500 | −52.535 | −47.219 | 1.00 | 18.56 | C |
| 1271 | ATOM | 1116 | O   | MET | A | 36 | 24.117 | −53.485 | −46.517 | 1.00 | 17.46 | O |
| 1272 | ATOM | 1117 | N   | THR | A | 37 | 25.489 | −51.722 | −46.867 | 1.00 | 16.08 | N |
| 1273 | ATOM | 1118 | CA  | THR | A | 37 | 26.111 | −51.801 | −45.547 | 1.00 | 15.49 | C |
| 1274 | ATOM | 1119 | CB  | THR | A | 37 | 27.568 | −52.310 | −45.639 | 1.00 | 15.24 | C |
| 1275 | ATOM | 1120 | OG1 | THR | A | 37 | 27.564 | −53.611 | −46.257 | 1.00 | 15.19 | O |
| 1276 | ATOM | 1121 | CG2 | THR | A | 37 | 28.217 | −52.380 | −44.272 | 1.00 | 16.19 | C |
| 1277 | ATOM | 1122 | C   | THR | A | 37 | 26.034 | −50.425 | −44.903 | 1.00 | 15.37 | C |
| 1278 | ATOM | 1123 | O   | THR | A | 37 | 26.505 | −49.432 | −45.483 | 1.00 | 15.31 | O |
| 1279 | ATOM | 1124 | N   | ILE | A | 38 | 25.403 | −50.356 | −43.735 | 1.00 | 14.84 | N |
| 1280 | ATOM | 1125 | CA  | ILE | A | 38 | 25.337 | −49.111 | −42.963 | 1.00 | 14.37 | C |
| 1281 | ATOM | 1126 | CB  | ILE | A | 38 | 23.887 | −48.682 | −42.627 | 1.00 | 13.98 | C |
| 1282 | ATOM | 1127 | CG1 | ILE | A | 38 | 23.164 | −49.693 | −41.736 | 1.00 | 13.93 | C |
| 1283 | ATOM | 1128 | CD1 | ILE | A | 38 | 21.793 | −49.194 | −41.288 | 1.00 | 13.33 | C |
| 1284 | ATOM | 1129 | CG2 | ILE | A | 38 | 23.093 | −48.466 | −43.897 | 1.00 | 14.37 | C |
| 1285 | ATOM | 1130 | C   | ILE | A | 38 | 26.195 | −49.228 | −41.708 | 1.00 | 14.88 | C |
| 1286 | ATOM | 1131 | O   | ILE | A | 38 | 26.373 | −50.333 | −41.157 | 1.00 | 15.99 | O |
| 1287 | ATOM | 1132 | N   | GLU | A | 39 | 26.736 | −48.091 | −41.267 | 1.00 | 14.36 | N |
| 1288 | ATOM | 1133 | CA  | GLU | A | 39 | 27.793 | −48.088 | −40.250 | 1.00 | 15.31 | C |
| 1289 | ATOM | 1134 | CB  | GLU | A | 39 | 29.104 | −47.809 | −40.987 | 1.00 | 16.56 | C |
| 1290 | ATOM | 1135 | CG  | GLU | A | 39 | 30.361 | −48.387 | −40.422 | 1.00 | 19.28 | C |
| 1291 | ATOM | 1136 | CD  | GLU | A | 39 | 31.505 | −48.129 | −41.381 | 1.00 | 20.06 | C |
| 1292 | ATOM | 1137 | OE1 | GLU | A | 39 | 31.967 | −49.100 | −42.034 | 1.00 | 21.68 | O |
| 1293 | ATOM | 1138 | OE2 | GLU | A | 39 | 31.835 | −46.942 | −41.555 | 1.00 | 18.05 | O |
| 1294 | ATOM | 1139 | C   | GLU | A | 39 | 27.592 | −47.061 | −39.125 | 1.00 | 13.81 | C |
| 1295 | ATOM | 1140 | O   | GLU | A | 39 | 27.205 | −45.908 | −39.354 | 1.00 | 15.22 | O |
| 1296 | ATOM | 1141 | N   | CYS | A | 40 | 27.866 | −47.493 | −37.898 | 1.00 | 13.46 | N |
| 1297 | ATOM | 1142 | CA  | CYS | A | 40 | 28.033 | −46.602 | −36.764 | 1.00 | 14.26 | C |
| 1298 | ATOM | 1143 | CB  | CYS | A | 40 | 27.050 | −46.948 | −35.653 | 1.00 | 14.88 | C |
| 1299 | ATOM | 1144 | SG  | CYS | A | 40 | 25.361 | −46.493 | −36.067 | 1.00 | 15.53 | S |

APPENDIX I-continued

| | | | | | | | | | | |
|---|---|---|---|---|---|---|---|---|---|---|
| 1300 | ATOM | 1145 | C | CYS | A | 40 | 29.451 | −46.838 | −36.284 | 1.00 | 14.89 C |
| 1301 | ATOM | 1146 | O | CYS | A | 40 | 29.985 | −47.961 | −36.395 | 1.00 | 15.65 O |
| 1302 | ATOM | 1147 | N | LYS | A | 41 | 30.084 | −45.771 | −35.792 | 1.00 | 14.06 N |
| 1303 | ATOM | 1148 | CA | LYS | A | 41 | 31.412 | −45.865 | −35.221 | 1.00 | 13.97 C |
| 1304 | ATOM | 1149 | CB | LYS | A | 41 | 32.332 | −44.876 | −35.939 | 1.00 | 13.97 C |
| 1305 | ATOM | 1150 | CG | LYS | A | 41 | 32.506 | −45.213 | −37.417 | 1.00 | 15.46 C |
| 1306 | ATOM | 1151 | CD | LYS | A | 41 | 33.407 | −44.209 | −38.109 | 1.00 | 16.79 C |
| 1307 | ATOM | 1152 | CE | LYS | A | 41 | 33.596 | −44.515 | −39.593 | 1.00 | 18.35 C |
| 1308 | ATOM | 1153 | NZ | LYS | A | 41 | 34.573 | −45.601 | −39.869 | 1.00 | 18.81 N |
| 1309 | ATOM | 1154 | C | LYS | A | 41 | 31.375 | −45.612 | −33.713 | 1.00 | 12.89 C |
| 1310 | ATOM | 1155 | O | LYS | A | 41 | 30.527 | −44.880 | −33.220 | 1.00 | 13.32 O |
| 1311 | ATOM | 1156 | N | PHE | A | 42 | 32.272 | −46.267 | −32.985 | 1.00 | 12.66 N |
| 1312 | ATOM | 1157 | CA | PHE | A | 42 | 32.381 | −46.145 | −31.539 | 1.00 | 12.98 C |
| 1313 | ATOM | 1158 | CB | PHE | A | 42 | 31.503 | −47.205 | −30.847 | 1.00 | 13.06 C |
| 1314 | ATOM | 1159 | CG | PHE | A | 42 | 31.906 | −48.626 | −31.121 | 1.00 | 12.92 C |
| 1315 | ATOM | 1160 | CD1 | PHE | A | 42 | 32.668 | −49.330 | −30.210 | 1.00 | 14.03 C |
| 1316 | ATOM | 1161 | CE1 | PHE | A | 42 | 33.031 | −50.635 | −30.459 | 1.00 | 13.16 C |
| 1317 | ATOM | 1162 | CZ | PHE | A | 42 | 32.617 | −51.270 | −31.607 | 1.00 | 13.36 C |
| 1318 | ATOM | 1163 | CE2 | PHE | A | 42 | 31.862 | −50.596 | −32.515 | 1.00 | 13.30 C |
| 1319 | ATOM | 1164 | CD2 | PHE | A | 42 | 31.497 | −49.281 | −32.267 | 1.00 | 13.28 C |
| 1320 | ATOM | 1165 | C | PHE | A | 42 | 33.847 | −46.282 | −31.088 | 1.00 | 13.64 C |
| 1321 | ATOM | 1166 | O | PHE | A | 42 | 34.685 | −46.774 | −31.846 | 1.00 | 12.43 O |
| 1322 | ATOM | 1167 | N | PRO | A | 43 | 34.153 | −45.846 | −29.872 | 1.00 | 15.24 N |
| 1323 | ATOM | 1168 | CA | PRO | A | 43 | 35.542 | −45.866 | −29.376 | 1.00 | 16.45 C |
| 1324 | ATOM | 1169 | CB | PRO | A | 43 | 35.418 | −45.265 | −27.977 | 1.00 | 17.11 C |
| 1325 | ATOM | 1170 | CG | PRO | A | 43 | 34.150 | −44.535 | −27.954 | 1.00 | 17.61 C |
| 1326 | ATOM | 1171 | CD | PRO | A | 43 | 33.290 | −44.970 | −29.066 | 1.00 | 16.21 C |
| 1327 | ATOM | 1172 | C | PRO | A | 43 | 36.162 | −47.273 | −29.321 | 1.00 | 17.44 C |
| 1328 | ATOM | 1173 | O | PRO | A | 43 | 35.486 | −48.233 | −28.931 | 1.00 | 20.94 O |
| 1329 | ATOM | 1174 | N | VAL | A | 44 | 37.403 | −47.418 | −29.789 | 1.00 | 16.76 N |
| 1330 | ATOM | 1175 | CA | VAL | A | 44 | 38.173 | −48.688 | −29.684 | 1.00 | 17.25 C |
| 1331 | ATOM | 1176 | CB | VAL | A | 44 | 39.072 | −48.977 | −30.940 | 1.00 | 17.89 C |
| 1332 | ATOM | 1177 | CG1 | VAL | A | 44 | 40.208 | −47.974 | −31.116 | 1.00 | 18.02 C |
| 1333 | ATOM | 1178 | CG2 | VAL | A | 44 | 38.242 | −49.061 | −32.202 | 1.00 | 20.15 C |
| 1334 | ATOM | 1179 | C | VAL | A | 44 | 39.099 | −48.708 | −28.479 | 1.00 | 16.60 C |
| 1335 | ATOM | 1180 | O | VAL | A | 44 | 39.582 | −47.661 | −28.040 | 1.00 | 14.65 O |
| 1336 | ATOM | 1181 | N | GLU | A | 45 | 39.309 | −49.909 | −27.947 | 1.00 | 17.90 N |
| 1337 | ATOM | 1182 | CA | GLU | A | 45 | 40.409 | −50.211 | −27.038 | 1.00 | 19.44 C |
| 1338 | ATOM | 1183 | CB | GLU | A | 45 | 39.942 | −51.182 | −25.934 | 1.00 | 21.63 C |
| 1339 | ATOM | 1184 | CG | GLU | A | 45 | 38.723 | −50.715 | −25.126 | 1.00 | 25.15 C |
| 1340 | ATOM | 1185 | CD | GLU | A | 45 | 38.248 | −51.745 | −24.094 | 1.00 | 29.48 C |
| 1341 | ATOM | 1186 | OE1 | GLU | A | 45 | 39.117 | −52.394 | −23.499 | 1.00 | 31.90 O |
| 1342 | ATOM | 1187 | OE2 | GLU | A | 45 | 37.011 | −51.926 | −23.879 | 1.00 | 34.83 O |
| 1343 | ATOM | 1188 | C | GLU | A | 45 | 41.503 | −50.849 | −27.906 | 1.00 | 19.58 C |
| 1344 | ATOM | 1189 | O | GLU | A | 45 | 41.271 | −51.155 | −29.070 | 1.00 | 18.02 O |
| 1345 | ATOM | 1190 | N | LYS | A | 46 | 42.677 | −51.097 | −27.336 | 1.00 | 19.83 N |
| 1346 | ATOM | 1191 | CA | LYS | A | 46 | 43.737 | −51.751 | −28.084 | 1.00 | 22.10 C |
| 1347 | ATOM | 1192 | CB | LYS | A | 46 | 45.049 | −51.650 | −27.310 | 1.00 | 23.41 C |
| 1348 | ATOM | 1193 | CG | LYS | A | 46 | 45.443 | −50.185 | −27.187 | 1.00 | 24.28 C |
| 1349 | ATOM | 1194 | CD | LYS | A | 46 | 46.633 | −49.914 | −26.285 | 1.00 | 27.04 C |
| 1350 | ATOM | 1195 | CE | LYS | A | 46 | 46.934 | −48.416 | −26.335 | 1.00 | 26.94 C |
| 1351 | ATOM | 1196 | NZ | LYS | A | 46 | 47.720 | −47.929 | −25.180 | 1.00 | 28.56 N |
| 1352 | ATOM | 1197 | C | LYS | A | 46 | 43.367 | −53.198 | −28.413 | 1.00 | 23.80 C |
| 1353 | ATOM | 1198 | O | LYS | A | 46 | 43.812 | −53.733 | −29.424 | 1.00 | 24.81 O |
| 1354 | ATOM | 1199 | N | GLN | A | 47 | 42.542 | −53.793 | −27.559 | 1.00 | 24.38 N |
| 1355 | ATOM | 1200 | CA | GLN | A | 47 | 42.044 | −55.155 | −27.717 | 1.00 | 28.46 C |
| 1356 | ATOM | 1201 | CB | GLN | A | 47 | 42.578 | −56.085 | −26.605 | 1.00 | 31.47 C |
| 1357 | ATOM | 1202 | CG | GLN | A | 47 | 44.079 | −56.072 | −26.398 | 1.00 | 37.12 C |
| 1358 | ATOM | 1203 | CD | GLN | A | 47 | 44.834 | −56.686 | −27.560 | 1.00 | 41.99 C |
| 1359 | ATOM | 1204 | OE1 | GLN | A | 47 | 44.501 | −57.778 | −28.022 | 1.00 | 47.20 O |
| 1360 | ATOM | 1205 | NE2 | GLN | A | 47 | 45.863 | −55.989 | −28.036 | 1.00 | 45.35 N |
| 1361 | ATOM | 1206 | C | GLN | A | 47 | 40.532 | −55.115 | −27.597 | 1.00 | 26.40 C |
| 1362 | ATOM | 1207 | O | GLN | A | 47 | 40.013 | −54.557 | −26.651 | 1.00 | 28.29 O |
| 1363 | ATOM | 1208 | N | LEU | A | 48 | 39.839 | −55.740 | −28.541 | 1.00 | 25.98 N |
| 1364 | ATOM | 1209 | CA | LEU | A | 48 | 38.396 | −55.871 | −28.486 | 1.00 | 25.73 C |
| 1365 | ATOM | 1210 | CB | LEU | A | 48 | 37.904 | −56.510 | −29.795 | 1.00 | 24.85 C |
| 1366 | ATOM | 1211 | CG | LEU | A | 48 | 36.392 | −56.642 | −29.972 | 1.00 | 25.30 C |
| 1367 | ATOM | 1212 | CD1 | LEU | A | 48 | 35.752 | −55.274 | −29.926 | 1.00 | 23.84 C |
| 1368 | ATOM | 1213 | CD2 | LEU | A | 48 | 36.044 | −57.369 | −31.270 | 1.00 | 24.72 C |
| 1369 | ATOM | 1214 | C | LEU | A | 48 | 37.991 | −56.747 | −27.270 | 1.00 | 24.04 C |
| 1370 | ATOM | 1215 | O | LEU | A | 48 | 38.291 | −57.937 | −27.261 | 1.00 | 25.79 O |
| 1371 | ATOM | 1216 | N | ASP | A | 49 | 37.377 | −56.147 | −26.247 | 1.00 | 21.27 N |
| 1372 | ATOM | 1217 | CA | ASP | A | 49 | 36.835 | −56.894 | −25.104 | 1.00 | 21.87 C |
| 1373 | ATOM | 1218 | CB | ASP | A | 49 | 36.899 | −56.061 | −23.825 | 1.00 | 24.32 C |
| 1374 | ATOM | 1219 | CG | ASP | A | 49 | 36.413 | −56.830 | −22.573 | 1.00 | 26.64 C |
| 1375 | ATOM | 1220 | OD1 | ASP | A | 49 | 36.458 | −56.242 | −21.470 | 1.00 | 31.65 O |
| 1376 | ATOM | 1221 | OD2 | ASP | A | 49 | 36.003 | −58.016 | −22.650 | 1.00 | 25.91 O |
| 1377 | ATOM | 1222 | C | ASP | A | 49 | 35.384 | −57.302 | −25.342 | 1.00 | 19.99 C |
| 1378 | ATOM | 1223 | O | ASP | A | 49 | 34.469 | −56.551 | −25.039 | 1.00 | 19.12 O |
| 1379 | ATOM | 1224 | N | LEU | A | 50 | 35.166 | −58.512 | −25.836 | 1.00 | 19.99 N |

APPENDIX I-continued

| | | | | | | | | | | |
|---|---|---|---|---|---|---|---|---|---|---|
| 1380 | ATOM | 1225 | CA | LEU | A | 50 | 33.796 | −58.946 | −26.135 | 1.00 | 20.24 C |
| 1381 | ATOM | 1226 | CB | LEU | A | 50 | 33.816 | −60.252 | −26.926 | 1.00 | 22.04 C |
| 1382 | ATOM | 1227 | CG | LEU | A | 50 | 34.507 | −60.098 | −28.288 | 1.00 | 22.42 C |
| 1383 | ATOM | 1228 | CD1 | LEU | A | 50 | 34.819 | −61.437 | −28.938 | 1.00 | 24.16 C |
| 1384 | ATOM | 1229 | CD2 | LEU | A | 50 | 33.700 | −59.222 | −29.225 | 1.00 | 23.78 C |
| 1385 | ATOM | 1230 | C | LEU | A | 50 | 32.886 | −59.041 | −24.905 | 1.00 | 20.65 C |
| 1386 | ATOM | 1231 | O | LEU | A | 50 | 31.676 | −58.839 | −25.015 | 1.00 | 20.99 O |
| 1387 | ATOM | 1232 | N | ALA | A | 51 | 33.446 | −59.312 | −23.726 | 1.00 | 19.63 N |
| 1388 | ATOM | 1233 | CA | ALA | A | 51 | 32.610 | −59.468 | −22.535 | 1.00 | 20.70 C |
| 1389 | ATOM | 1234 | CB | ALA | A | 51 | 33.428 | −59.967 | −21.344 | 1.00 | 21.61 C |
| 1390 | ATOM | 1235 | C | ALA | A | 51 | 31.873 | −58.183 | −22.187 | 1.00 | 20.89 C |
| 1391 | ATOM | 1236 | O | ALA | A | 51 | 30.744 | −58.228 | −21.689 | 1.00 | 21.96 O |
| 1392 | ATOM | 1237 | N | ALA | A | 52 | 32.463 | −57.045 | −22.559 | 1.00 | 20.43 N |
| 1393 | ATOM | 1238 | CA | ALA | A | 52 | 31.887 | −55.734 | −22.245 | 1.00 | 19.17 C |
| 1394 | ATOM | 1239 | CB | ALA | A | 52 | 32.988 | −54.761 | −21.914 | 1.00 | 20.15 C |
| 1395 | ATOM | 1240 | C | ALA | A | 52 | 31.019 | −55.140 | −23.350 | 1.00 | 18.09 C |
| 1396 | ATOM | 1241 | O | ALA | A | 52 | 30.189 | −54.278 | −23.054 | 1.00 | 20.70 O |
| 1397 | ATOM | 1242 | N | LEU | A | 53 | 31.174 | −55.625 | −24.576 | 1.00 | 14.83 N |
| 1398 | ATOM | 1243 | CA | LEU | A | 53 | 30.510 | −55.050 | −25.758 | 1.00 | 14.17 C |
| 1399 | ATOM | 1244 | CB | LEU | A | 53 | 31.335 | −55.374 | −27.009 | 1.00 | 13.67 C |
| 1400 | ATOM | 1245 | CG | LEU | A | 53 | 30.832 | −54.824 | −28.349 | 1.00 | 14.02 C |
| 1401 | ATOM | 1246 | CD1 | LEU | A | 53 | 30.866 | −53.303 | −28.362 | 1.00 | 14.23 C |
| 1402 | ATOM | 1247 | CD2 | LEU | A | 53 | 31.665 | −55.397 | −29.493 | 1.00 | 13.71 C |
| 1403 | ATOM | 1248 | C | LEU | A | 53 | 29.093 | −55.580 | −25.988 | 1.00 | 13.87 C |
| 1404 | ATOM | 1249 | O | LEU | A | 53 | 28.859 | −56.795 | −26.014 | 1.00 | 13.59 O |
| 1405 | ATOM | 1250 | N | ILE | A | 54 | 28.177 | −54.653 | −26.220 | 1.00 | 13.50 N |
| 1406 | ATOM | 1251 | CA | ILE | A | 54 | 26.876 | −54.957 | −26.764 | 1.00 | 13.82 C |
| 1407 | ATOM | 1252 | CB | ILE | A | 54 | 25.769 | −54.610 | −25.768 | 1.00 | 16.10 C |
| 1408 | ATOM | 1253 | CG1 | ILE | A | 54 | 25.846 | −55.473 | −24.519 | 1.00 | 18.30 C |
| 1409 | ATOM | 1254 | CD1 | ILE | A | 54 | 24.930 | −54.943 | −23.413 | 1.00 | 19.13 C |
| 1410 | ATOM | 1255 | CG2 | ILE | A | 54 | 24.388 | −54.755 | −26.416 | 1.00 | 17.11 C |
| 1411 | ATOM | 1256 | C | ILE | A | 54 | 26.633 | −54.103 | −28.000 | 1.00 | 12.68 C |
| 1412 | ATOM | 1257 | O | ILE | A | 54 | 26.825 | −52.894 | −27.947 | 1.00 | 13.48 O |
| 1413 | ATOM | 1258 | N | VAL | A | 55 | 26.199 | −54.738 | −29.086 | 1.00 | 11.80 N |
| 1414 | ATOM | 1259 | CA | VAL | A | 55 | 25.818 | −54.058 | −30.315 | 1.00 | 12.13 C |
| 1415 | ATOM | 1260 | CB | VAL | A | 55 | 26.719 | −54.474 | −31.486 | 1.00 | 12.90 C |
| 1416 | ATOM | 1261 | CG1 | VAL | A | 55 | 26.267 | −53.789 | −32.770 | 1.00 | 13.53 C |
| 1417 | ATOM | 1262 | CG2 | VAL | A | 55 | 28.164 | −54.086 | −31.188 | 1.00 | 13.38 C |
| 1418 | ATOM | 1263 | C | VAL | A | 55 | 24.373 | −54.374 | −30.630 | 1.00 | 11.31 C |
| 1419 | ATOM | 1264 | O | VAL | A | 55 | 24.024 | −55.547 | −30.721 | 1.00 | 11.24 O |
| 1420 | ATOM | 1265 | N | TYR | A | 56 | 23.555 | −53.331 | −30.811 | 1.00 | 10.81 N |
| 1421 | ATOM | 1266 | CA | TYR | A | 56 | 22.116 | −53.468 | −30.995 | 1.00 | 10.77 C |
| 1422 | ATOM | 1267 | CB | TYR | A | 56 | 21.361 | −52.923 | −29.765 | 1.00 | 10.17 C |
| 1423 | ATOM | 1268 | CG | TYR | A | 56 | 19.879 | −53.248 | −29.696 | 1.00 | 10.36 C |
| 1424 | ATOM | 1269 | CD1 | TYR | A | 56 | 19.426 | −54.342 | −28.953 | 1.00 | 9.94 C |
| 1425 | ATOM | 1270 | CE1 | TYR | A | 56 | 18.099 | −54.653 | −28.861 | 1.00 | 9.64 C |
| 1426 | ATOM | 1271 | CZ | TYR | A | 56 | 17.146 | −53.900 | −29.528 | 1.00 | 9.77 C |
| 1427 | ATOM | 1272 | OH | TYR | A | 56 | 15.834 | −54.285 | −29.447 | 1.00 | 9.73 O |
| 1428 | ATOM | 1273 | CE2 | TYR | A | 56 | 17.561 | −52.809 | −30.286 | 1.00 | 9.55 C |
| 1429 | ATOM | 1274 | CD2 | TYR | A | 56 | 18.922 | −52.487 | −30.354 | 1.00 | 10.21 C |
| 1430 | ATOM | 1275 | C | TYR | A | 56 | 21.723 | −52.695 | −32.246 | 1.00 | 11.03 C |
| 1431 | ATOM | 1276 | O | TYR | A | 56 | 21.989 | −51.521 | −32.334 | 1.00 | 11.89 O |
| 1432 | ATOM | 1277 | N | TRP | A | 57 | 21.157 | −53.377 | −33.224 | 1.00 | 10.85 N |
| 1433 | ATOM | 1278 | CA | TRP | A | 57 | 20.607 | −52.725 | −34.414 | 1.00 | 10.93 C |
| 1434 | ATOM | 1279 | CB | TRP | A | 57 | 21.236 | −53.269 | −35.704 | 1.00 | 11.23 C |
| 1435 | ATOM | 1280 | CG | TRP | A | 57 | 22.591 | −52.729 | −36.061 | 1.00 | 10.81 C |
| 1436 | ATOM | 1281 | CD1 | TRP | A | 57 | 23.789 | −53.334 | −35.889 | 1.00 | 11.58 C |
| 1437 | ATOM | 1282 | NE1 | TRP | A | 57 | 24.814 | −52.510 | −36.364 | 1.00 | 11.64 N |
| 1438 | ATOM | 1283 | CE2 | TRP | A | 57 | 24.249 | −51.386 | −36.900 | 1.00 | 11.01 C |
| 1439 | ATOM | 1284 | CD2 | TRP | A | 57 | 22.855 | −51.484 | −36.711 | 1.00 | 10.91 C |
| 1440 | ATOM | 1285 | CE3 | TRP | A | 57 | 22.028 | −50.451 | −37.208 | 1.00 | 10.79 C |
| 1441 | ATOM | 1286 | CZ3 | TRP | A | 57 | 22.626 | −49.331 | −37.786 | 1.00 | 11.40 C |
| 1442 | ATOM | 1287 | CH2 | TRP | A | 57 | 24.013 | −49.264 | −37.944 | 1.00 | 10.89 C |
| 1443 | ATOM | 1288 | CZ2 | TRP | A | 57 | 24.836 | −50.277 | −37.531 | 1.00 | 11.19 C |
| 1444 | ATOM | 1289 | C | TRP | A | 57 | 19.111 | −52.999 | −34.500 | 1.00 | 10.20 C |
| 1445 | ATOM | 1290 | O | TRP | A | 57 | 18.671 | −54.159 | −34.333 | 1.00 | 10.17 O |
| 1446 | ATOM | 1291 | N | GLU | A | 58 | 18.334 | −51.967 | −34.832 | 1.00 | 9.98 N |
| 1447 | ATOM | 1292 | CA | GLU | A | 58 | 16.912 | −52.113 | −35.054 | 1.00 | 10.05 C |
| 1448 | ATOM | 1293 | CB | GLU | A | 58 | 16.111 | −51.666 | −33.830 | 1.00 | 9.96 C |
| 1449 | ATOM | 1294 | CG | GLU | A | 58 | 16.413 | −50.239 | −33.412 | 1.00 | 10.42 C |
| 1450 | ATOM | 1295 | CD | GLU | A | 58 | 15.694 | −49.804 | −32.154 | 1.00 | 10.94 C |
| 1451 | ATOM | 1296 | OE1 | GLU | A | 58 | 15.871 | −48.620 | −31.772 | 1.00 | 12.26 O |
| 1452 | ATOM | 1297 | OE2 | GLU | A | 58 | 14.948 | −50.624 | −31.558 | 1.00 | 10.86 O |
| 1453 | ATOM | 1298 | C | GLU | A | 58 | 16.495 | −51.300 | −36.260 | 1.00 | 10.95 C |
| 1454 | ATOM | 1299 | O | GLU | A | 58 | 17.196 | −50.380 | −36.684 | 1.00 | 10.60 O |
| 1455 | ATOM | 1300 | N | MET | A | 59 | 15.341 | −51.645 | −36.825 | 1.00 | 11.60 N |
| 1456 | ATOM | 1301 | CA | MET | A | 59 | 14.701 | −50.761 | −37.777 | 1.00 | 14.34 C |
| 1457 | ATOM | 1302 | CB | MET | A | 59 | 14.534 | −51.448 | −39.130 | 1.00 | 17.20 C |
| 1458 | ATOM | 1303 | CG | MET | A | 59 | 14.150 | −50.510 | −40.253 | 1.00 | 21.16 C |
| 1459 | ATOM | 1304 | SD | MET | A | 59 | 12.395 | −50.205 | −40.333 | 1.00 | 28.85 S |

APPENDIX I-continued

| 1460 | ATOM | 1305 | CE | MET | A | 59 | 11.788 | −51.840 | −40.718 | 1.00 | 29.02 | C |
|---|---|---|---|---|---|---|---|---|---|---|---|---|
| 1461 | ATOM | 1306 | C | MET | A | 59 | 13.375 | −50.366 | −37.164 | 1.00 | 13.88 | C |
| 1462 | ATOM | 1307 | O | MET | A | 59 | 12.535 | −51.240 | −36.830 | 1.00 | 11.89 | O |
| 1463 | ATOM | 1308 | N | GLU | A | 60 | 13.194 | −49.056 | −37.006 | 1.00 | 14.09 | N |
| 1464 | ATOM | 1309 | CA | GLU | A | 60 | 12.153 | −48.499 | −36.124 | 1.00 | 15.52 | C |
| 1465 | ATOM | 1310 | CB | GLU | A | 60 | 10.743 | −48.651 | −36.714 | 1.00 | 17.72 | C |
| 1466 | ATOM | 1311 | CG | GLU | A | 60 | 10.644 | −48.228 | −38.190 | 1.00 | 22.20 | C |
| 1467 | ATOM | 1312 | CD | GLU | A | 60 | 10.774 | −46.742 | −38.460 | 1.00 | 26.96 | C |
| 1468 | ATOM | 1313 | OE1 | GLU | A | 60 | 10.672 | −45.976 | −37.482 | 1.00 | 32.79 | O |
| 1469 | ATOM | 1314 | OE2 | GLU | A | 60 | 10.948 | −46.334 | −39.676 | 1.00 | 30.76 | O |
| 1470 | ATOM | 1315 | C | GLU | A | 60 | 12.346 | −49.170 | −34.761 | 1.00 | 14.42 | C |
| 1471 | ATOM | 1316 | O | GLU | A | 60 | 13.380 | −48.905 | −34.121 | 1.00 | 14.01 | O |
| 1472 | ATOM | 1317 | N | ASP | A | 61 | 11.407 | −50.016 | −34.319 | 1.00 | 12.76 | N |
| 1473 | ATOM | 1318 | CA | ASP | A | 61 | 11.535 | −50.673 | −33.010 | 1.00 | 11.91 | C |
| 1474 | ATOM | 1319 | CB | ASP | A | 61 | 10.270 | −50.420 | −32.146 | 1.00 | 11.93 | C |
| 1475 | ATOM | 1320 | CG | ASP | A | 61 | 10.043 | −48.942 | −31.816 | 1.00 | 12.46 | C |
| 1476 | ATOM | 1321 | OD1 | ASP | A | 61 | 10.982 | −48.129 | −31.903 | 1.00 | 13.68 | O |
| 1477 | ATOM | 1322 | OD2 | ASP | A | 61 | 8.888 | −48.586 | −31.477 | 1.00 | 12.07 | O |
| 1478 | ATOM | 1323 | C | ASP | A | 61 | 11.775 | −52.169 | −33.169 | 1.00 | 11.81 | C |
| 1479 | ATOM | 1324 | O | ASP | A | 61 | 11.821 | −52.926 | −32.165 | 1.00 | 11.69 | O |
| 1480 | ATOM | 1325 | N | LYS | A | 62 | 11.932 | −52.632 | −34.412 | 1.00 | 10.74 | N |
| 1481 | ATOM | 1326 | CA | LYS | A | 62 | 12.087 | −54.066 | −34.659 | 1.00 | 11.47 | C |
| 1482 | ATOM | 1327 | CB | LYS | A | 62 | 11.499 | −54.498 | −36.002 | 1.00 | 11.85 | C |
| 1483 | ATOM | 1328 | CG | LYS | A | 62 | 11.759 | −55.986 | −36.329 | 1.00 | 12.62 | C |
| 1484 | ATOM | 1329 | CD | LYS | A | 62 | 11.260 | −56.985 | −35.290 | 0.50 | 13.20 | C |
| 1485 | ATOM | 1330 | CE | LYS | A | 62 | 11.796 | −58.404 | −35.538 | 0.50 | 13.78 | C |
| 1486 | ATOM | 1331 | NZ | LYS | A | 62 | 12.871 | −58.861 | −34.596 | 0.50 | 13.41 | N |
| 1487 | ATOM | 1332 | C | LYS | A | 62 | 13.553 | −54.454 | −34.611 | 1.00 | 10.29 | C |
| 1488 | ATOM | 1333 | O | LYS | A | 62 | 14.345 | −53.949 | −35.372 | 1.00 | 9.44 | O |
| 1489 | ATOM | 1334 | N | ASN | A | 63 | 13.904 | −55.370 | −33.723 | 1.00 | 10.40 | N |
| 1490 | ATOM | 1335 | CA | ASN | A | 63 | 15.298 | −55.736 | −33.568 | 1.00 | 10.58 | C |
| 1491 | ATOM | 1336 | CB | ASN | A | 63 | 15.550 | −56.550 | −32.317 | 1.00 | 11.00 | C |
| 1492 | ATOM | 1337 | CG | ASN | A | 63 | 16.994 | −56.942 | −32.197 | 1.00 | 11.11 | C |
| 1493 | ATOM | 1338 | OD1 | ASN | A | 63 | 17.342 | −58.077 | −32.445 | 1.00 | 12.57 | O |
| 1494 | ATOM | 1339 | ND2 | ASN | A | 63 | 17.856 | −55.985 | −31.898 | 1.00 | 10.95 | N |
| 1495 | ATOM | 1340 | C | ASN | A | 63 | 15.815 | −56.537 | −34.741 | 1.00 | 11.01 | C |
| 1496 | ATOM | 1341 | O | ASN | A | 63 | 15.115 | −57.419 | −35.233 | 1.00 | 10.67 | O |
| 1497 | ATOM | 1342 | N | ILE | A | 64 | 17.013 | −56.187 | −35.189 | 1.00 | 11.48 | N |
| 1498 | ATOM | 1343 | CA | ILE | A | 64 | 17.704 | −56.923 | −36.236 | 1.00 | 12.07 | C |
| 1499 | ATOM | 1344 | CB | ILE | A | 64 | 18.188 | −56.013 | −37.361 | 1.00 | 12.72 | C |
| 1500 | ATOM | 1345 | CG1 | ILE | A | 64 | 17.041 | −55.165 | −37.902 | 1.00 | 13.75 | C |
| 1501 | ATOM | 1346 | CD1 | ILE | A | 64 | 17.444 | −54.142 | −38.925 | 1.00 | 14.37 | C |
| 1502 | ATOM | 1347 | CG2 | ILE | A | 64 | 18.825 | −56.858 | −38.471 | 1.00 | 12.66 | C |
| 1503 | ATOM | 1348 | C | ILE | A | 64 | 18.882 | −57.673 | −35.660 | 1.00 | 12.60 | C |
| 1504 | ATOM | 1349 | O | ILE | A | 64 | 18.998 | −58.856 | −35.915 | 1.00 | 12.93 | O |
| 1505 | ATOM | 1350 | N | ILE | A | 65 | 19.735 | −56.991 | −34.886 | 1.00 | 12.95 | N |
| 1506 | ATOM | 1351 | CA | ILE | A | 65 | 20.955 | −57.579 | −34.324 | 1.00 | 13.47 | C |
| 1507 | ATOM | 1352 | CB | ILE | A | 65 | 22.243 | −56.898 | −34.913 | 1.00 | 14.25 | C |
| 1508 | ATOM | 1353 | CG1 | ILE | A | 65 | 22.360 | −57.087 | −36.431 | 1.00 | 15.77 | C |
| 1509 | ATOM | 1354 | CD1 | ILE | A | 65 | 22.459 | −58.517 | −36.897 | 1.00 | 15.27 | C |
| 1510 | ATOM | 1355 | CG2 | ILE | A | 65 | 23.510 | −57.366 | −34.211 | 1.00 | 14.61 | C |
| 1511 | ATOM | 1356 | C | ILE | A | 65 | 20.987 | −57.359 | −32.817 | 1.00 | 12.85 | C |
| 1512 | ATOM | 1357 | O | ILE | A | 65 | 20.706 | −56.261 | −32.339 | 1.00 | 12.76 | O |
| 1513 | ATOM | 1358 | N | GLN | A | 66 | 21.314 | −58.404 | −32.059 | 1.00 | 12.55 | N |
| 1514 | ATOM | 1359 | CA | GLN | A | 66 | 21.792 | −58.244 | −30.688 | 1.00 | 12.16 | C |
| 1515 | ATOM | 1360 | CB | GLN | A | 66 | 20.814 | −58.710 | −29.583 | 1.00 | 11.54 | C |
| 1516 | ATOM | 1361 | CG | GLN | A | 66 | 19.503 | −57.952 | −29.501 | 1.00 | 11.41 | C |
| 1517 | ATOM | 1362 | CD | GLN | A | 66 | 18.709 | −58.374 | −28.282 | 1.00 | 11.35 | C |
| 1518 | ATOM | 1363 | OE1 | GLN | A | 66 | 19.137 | −58.143 | −27.151 | 1.00 | 11.72 | O |
| 1519 | ATOM | 1364 | NE2 | GLN | A | 66 | 17.569 | −58.998 | −28.501 | 1.00 | 12.39 | N |
| 1520 | ATOM | 1365 | C | GLN | A | 66 | 23.040 | −59.106 | −30.574 | 1.00 | 12.06 | C |
| 1521 | ATOM | 1366 | O | GLN | A | 66 | 22.958 | −60.345 | −30.578 | 1.00 | 11.55 | O |
| 1522 | ATOM | 1367 | N | PHE | A | 67 | 24.172 | −58.433 | −30.496 | 1.00 | 12.19 | N |
| 1523 | ATOM | 1368 | CA | PHE | A | 67 | 25.477 | −59.062 | −30.332 | 1.00 | 13.05 | C |
| 1524 | ATOM | 1369 | CB | PHE | A | 67 | 26.419 | −58.562 | −31.401 | 1.00 | 14.35 | C |
| 1525 | ATOM | 1370 | CG | PHE | A | 67 | 27.707 | −59.306 | −31.465 | 1.00 | 14.31 | C |
| 1526 | ATOM | 1371 | CD1 | PHE | A | 67 | 27.764 | −60.591 | −32.040 | 1.00 | 15.19 | C |
| 1527 | ATOM | 1372 | CE1 | PHE | A | 67 | 28.971 | −61.285 | −32.105 | 1.00 | 15.77 | C |
| 1528 | ATOM | 1373 | CZ | PHE | A | 67 | 30.122 | −60.708 | −31.588 | 1.00 | 15.76 | C |
| 1529 | ATOM | 1374 | CE2 | PHE | A | 67 | 30.081 | −59.453 | −31.022 | 1.00 | 15.91 | C |
| 1530 | ATOM | 1375 | CD2 | PHE | A | 67 | 28.867 | −58.746 | −30.962 | 1.00 | 16.13 | C |
| 1531 | ATOM | 1376 | C | PHE | A | 67 | 25.995 | −58.768 | −28.941 | 1.00 | 14.08 | C |
| 1532 | ATOM | 1377 | O | PHE | A | 67 | 26.301 | −57.603 | −28.602 | 1.00 | 15.28 | O |
| 1533 | ATOM | 1378 | N | VAL | A | 68 | 25.977 | −59.828 | −28.122 | 1.00 | 14.30 | N |
| 1534 | ATOM | 1379 | CA | VAL | A | 68 | 26.113 | −59.751 | −26.680 | 1.00 | 15.49 | C |
| 1535 | ATOM | 1380 | CB | VAL | A | 68 | 24.726 | −60.014 | −26.036 | 1.00 | 16.91 | C |
| 1536 | ATOM | 1381 | CG1 | VAL | A | 68 | 24.850 | −60.211 | −24.532 | 1.00 | 17.52 | C |
| 1537 | ATOM | 1382 | CG2 | VAL | A | 68 | 23.787 | −58.882 | −26.377 | 1.00 | 18.28 | C |
| 1538 | ATOM | 1383 | C | VAL | A | 68 | 27.120 | −60.803 | −26.213 | 1.00 | 15.84 | C |
| 1539 | ATOM | 1384 | O | VAL | A | 68 | 27.060 | −61.932 | −26.634 | 1.00 | 14.36 | O |

APPENDIX I-continued

| 1540 | ATOM | 1385 | N | HIS | A | 69 | 28.064 | −60.459 | −25.347 | 1.00 | 19.24 | N |
|------|------|------|------|-----|---|----|--------|---------|---------|------|-------|---|
| 1541 | ATOM | 1386 | CA | HIS | A | 69 | 29.031 | −61.476 | −24.860 | 1.00 | 19.12 | C |
| 1542 | ATOM | 1387 | CB | HIS | A | 69 | 28.346 | −62.577 | −23.964 | 1.00 | 21.19 | C |
| 1543 | ATOM | 1388 | CG | HIS | A | 69 | 27.774 | −62.074 | −22.667 | 1.00 | 22.85 | C |
| 1544 | ATOM | 1389 | ND1 | HIS | A | 69 | 28.162 | −60.881 | −22.073 | 1.00 | 25.40 | N |
| 1545 | ATOM | 1390 | CE1 | HIS | A | 69 | 27.505 | −60.723 | −20.937 | 1.00 | 25.51 | C |
| 1546 | ATOM | 1391 | NE2 | HIS | A | 69 | 26.697 | −61.759 | −20.772 | 1.00 | 26.41 | N |
| 1547 | ATOM | 1392 | CD2 | HIS | A | 69 | 26.849 | −62.620 | −21.838 | 1.00 | 23.38 | C |
| 1548 | ATOM | 1393 | C | HIS | A | 69 | 29.750 | −62.174 | −26.059 | 1.00 | 17.86 | C |
| 1549 | ATOM | 1394 | O | HIS | A | 69 | 30.071 | −63.360 | −25.986 | 1.00 | 19.93 | O |
| 1550 | ATOM | 1395 | N | GLY | A | 70 | 29.950 | −61.480 | −27.173 | 1.00 | 15.60 | N |
| 1551 | ATOM | 1396 | CA | GLY | A | 70 | 30.621 | −62.098 | −28.325 | 1.00 | 15.98 | C |
| 1552 | ATOM | 1397 | C | GLY | A | 70 | 29.786 | −63.105 | −29.105 | 1.00 | 15.99 | C |
| 1553 | ATOM | 1398 | O | GLY | A | 70 | 30.320 | −63.863 | −29.925 | 1.00 | 15.54 | O |
| 1554 | ATOM | 1399 | N | GLU | A | 71 | 28.466 | −63.091 | −28.880 | 1.00 | 14.41 | N |
| 1555 | ATOM | 1400 | CA | GLU | A | 71 | 27.535 | −64.028 | −29.517 | 1.00 | 16.07 | C |
| 1556 | ATOM | 1401 | CB | GLU | A | 71 | 26.981 | −64.988 | −28.465 | 1.00 | 18.10 | C |
| 1557 | ATOM | 1402 | CG | GLU | A | 71 | 27.882 | −66.122 | −28.187 | 1.00 | 21.92 | C |
| 1558 | ATOM | 1403 | CD | GLU | A | 71 | 27.858 | −67.112 | −29.338 | 1.00 | 23.25 | C |
| 1559 | ATOM | 1404 | OE1 | GLU | A | 71 | 28.913 | −67.262 | −29.910 | 1.00 | 26.20 | O |
| 1560 | ATOM | 1405 | OE2 | GLU | A | 71 | 26.775 | −67.708 | −29.666 | 1.00 | 29.26 | O |
| 1561 | ATOM | 1406 | C | GLU | A | 71 | 26.352 | −63.297 | −30.104 | 1.00 | 14.43 | C |
| 1562 | ATOM | 1407 | O | GLU | A | 71 | 25.822 | −62.373 | −29.488 | 1.00 | 13.63 | O |
| 1563 | ATOM | 1408 | N | GLU | A | 72 | 25.934 | −63.682 | −31.290 | 1.00 | 13.89 | N |
| 1564 | ATOM | 1409 | CA | GLU | A | 72 | 24.680 | −63.173 | −31.819 | 1.00 | 14.39 | C |
| 1565 | ATOM | 1410 | CB | GLU | A | 72 | 24.613 | −63.386 | −33.330 | 1.00 | 15.77 | C |
| 1566 | ATOM | 1411 | CG | GLU | A | 72 | 23.411 | −62.756 | −33.990 | 1.00 | 16.41 | C |
| 1567 | ATOM | 1412 | CD | GLU | A | 72 | 23.356 | −61.239 | −33.820 | 1.00 | 17.93 | C |
| 1568 | ATOM | 1413 | OE1 | GLU | A | 72 | 24.402 | −60.553 | −33.730 | 1.00 | 16.51 | O |
| 1569 | ATOM | 1414 | OE2 | GLU | A | 72 | 22.214 | −60.745 | −33.740 | 1.00 | 17.68 | O |
| 1570 | ATOM | 1415 | C | GLU | A | 72 | 23.502 | −63.932 | −31.185 | 1.00 | 13.10 | C |
| 1571 | ATOM | 1416 | O | GLU | A | 72 | 23.515 | −65.143 | −31.143 | 1.00 | 13.28 | O |
| 1572 | ATOM | 1417 | N | ASP | A | 73 | 22.480 | −63.195 | −30.744 | 1.00 | 12.69 | N |
| 1573 | ATOM | 1418 | CA | ASP | A | 73 | 21.257 | −63.751 | −30.154 | 1.00 | 13.41 | C |
| 1574 | ATOM | 1419 | CB | ASP | A | 73 | 20.338 | −62.585 | −29.799 | 1.00 | 15.85 | C |
| 1575 | ATOM | 1420 | CG | ASP | A | 73 | 19.123 | −62.977 | −29.004 | 1.00 | 18.34 | C |
| 1576 | ATOM | 1421 | OD1 | ASP | A | 73 | 18.362 | −62.055 | −28.678 | 1.00 | 22.51 | O |
| 1577 | ATOM | 1422 | OD2 | ASP | A | 73 | 18.947 | −64.132 | −28.633 | 1.00 | 19.76 | O |
| 1578 | ATOM | 1423 | C | ASP | A | 73 | 20.587 | −64.584 | −31.228 | 1.00 | 12.89 | C |
| 1579 | ATOM | 1424 | O | ASP | A | 73 | 20.280 | −64.026 | −32.284 | 1.00 | 12.02 | O |
| 1580 | ATOM | 1425 | N | LEU | A | 74 | 20.349 | −65.864 | −30.990 | 1.00 | 12.04 | N |
| 1581 | ATOM | 1426 | CA | LEU | A | 74 | 19.774 | −66.716 | −32.031 | 1.00 | 12.55 | C |
| 1582 | ATOM | 1427 | CB | LEU | A | 74 | 19.936 | −68.191 | −31.714 | 1.00 | 13.19 | C |
| 1583 | ATOM | 1428 | CG | LEU | A | 74 | 19.428 | −69.167 | −32.770 | 1.00 | 13.40 | C |
| 1584 | ATOM | 1429 | CD1 | LEU | A | 74 | 20.131 | −68.986 | −34.098 | 1.00 | 14.31 | C |
| 1585 | ATOM | 1430 | CD2 | LEU | A | 74 | 19.661 | −70.560 | −32.249 | 1.00 | 13.82 | C |
| 1586 | ATOM | 1431 | C | LEU | A | 74 | 18.300 | −66.451 | −32.235 | 1.00 | 12.93 | C |
| 1587 | ATOM | 1432 | O | LEU | A | 74 | 17.502 | −66.741 | −31.345 | 1.00 | 14.21 | O |
| 1588 | ATOM | 1433 | N | LYS | A | 75 | 17.937 | −65.982 | −33.426 | 1.00 | 13.41 | N |
| 1589 | ATOM | 1434 | CA | LYS | A | 75 | 16.543 | −65.826 | −33.810 | 1.00 | 14.35 | C |
| 1590 | ATOM | 1435 | CB | LYS | A | 75 | 16.377 | −64.662 | −34.796 | 1.00 | 15.00 | C |
| 1591 | ATOM | 1436 | CG | LYS | A | 75 | 16.568 | −63.311 | −34.126 | 1.00 | 15.68 | C |
| 1592 | ATOM | 1437 | CD | LYS | A | 75 | 16.319 | −62.141 | −35.078 | 1.00 | 17.77 | C |
| 1593 | ATOM | 1438 | CE | LYS | A | 75 | 16.327 | −60.827 | −34.306 | 1.00 | 18.45 | C |
| 1594 | ATOM | 1439 | NZ | LYS | A | 75 | 17.610 | −60.669 | −33.551 | 1.00 | 19.74 | N |
| 1595 | ATOM | 1440 | C | LYS | A | 75 | 15.951 | −67.099 | −34.422 | 1.00 | 15.71 | C |
| 1596 | ATOM | 1441 | O | LYS | A | 75 | 16.603 | −67.824 | −35.185 | 1.00 | 15.27 | O |
| 1597 | ATOM | 1442 | N | VAL | A | 76 | 14.711 | −67.372 | −34.060 | 1.00 | 17.45 | N |
| 1598 | ATOM | 1443 | CA | VAL | A | 76 | 13.991 | −68.512 | −34.614 | 1.00 | 20.49 | C |
| 1599 | ATOM | 1444 | CB | VAL | A | 76 | 13.502 | −69.454 | −33.494 | 1.00 | 21.97 | C |
| 1600 | ATOM | 1445 | CG1 | VAL | A | 76 | 12.586 | −68.725 | −32.529 | 1.00 | 22.80 | C |
| 1601 | ATOM | 1446 | CG2 | VAL | A | 76 | 14.697 | −70.051 | −32.754 | 1.00 | 22.20 | C |
| 1602 | ATOM | 1447 | C | VAL | A | 76 | 12.803 | −68.082 | −35.478 | 1.00 | 23.97 | C |
| 1603 | ATOM | 1448 | O | VAL | A | 76 | 12.294 | −68.870 | −36.294 | 1.00 | 23.76 | O |
| 1604 | ATOM | 1449 | N | GLN | A | 77 | 12.330 | −66.857 | −35.269 | 1.00 | 27.13 | N |
| 1605 | ATOM | 1450 | CA | GLN | A | 77 | 11.166 | −66.364 | −35.997 | 1.00 | 31.32 | C |
| 1606 | ATOM | 1451 | CB | GLN | A | 77 | 10.522 | −65.192 | −35.264 | 1.00 | 32.80 | C |
| 1607 | ATOM | 1452 | CG | GLN | A | 77 | 9.826 | −65.619 | −33.989 | 1.00 | 35.62 | C |
| 1608 | ATOM | 1453 | CD | GLN | A | 77 | 9.434 | −64.454 | −33.103 | 1.00 | 37.66 | C |
| 1609 | ATOM | 1454 | OE1 | GLN | A | 77 | 10.269 | −63.907 | −32.381 | 1.00 | 39.52 | O |
| 1610 | ATOM | 1455 | NE2 | GLN | A | 77 | 8.160 | −64.078 | −33.141 | 1.00 | 38.95 | N |
| 1611 | ATOM | 1456 | C | GLN | A | 77 | 11.562 | −65.950 | −37.399 | 1.00 | 33.26 | C |
| 1612 | ATOM | 1457 | O | GLN | A | 77 | 12.438 | −65.101 | −37.579 | 1.00 | 32.62 | O |
| 1613 | ATOM | 1458 | N | HIS | A | 78 | 10.913 | −66.570 | −38.383 | 1.00 | 39.00 | N |
| 1614 | ATOM | 1459 | CA | HIS | A | 78 | 11.049 | −66.169 | −39.776 | 1.00 | 42.22 | C |
| 1615 | ATOM | 1460 | CB | HIS | A | 78 | 10.114 | −66.991 | −40.683 | 1.00 | 44.44 | C |
| 1616 | ATOM | 1461 | CG | HIS | A | 78 | 10.398 | −68.464 | −40.680 | 1.00 | 46.35 | C |
| 1617 | ATOM | 1462 | ND1 | HIS | A | 78 | 9.485 | −69.402 | −41.118 | 1.00 | 48.50 | N |
| 1618 | ATOM | 1463 | CE1 | HIS | A | 78 | 10.003 | −70.612 | −40.997 | 1.00 | 47.72 | C |
| 1619 | ATOM | 1464 | NE2 | HIS | A | 78 | 11.217 | −70.494 | −40.488 | 1.00 | 47.82 | N |

APPENDIX I-continued

| 1620 | ATOM | 1465 | CD2 | HIS | A | 78 | 11.487 | −69.161 | −40.280 | 1.00 | 46.53 | C |
|---|---|---|---|---|---|---|---|---|---|---|---|---|
| 1621 | ATOM | 1466 | C | HIS | A | 78 | 10.698 | −64.687 | −39.865 | 1.00 | 43.28 | C |
| 1622 | ATOM | 1467 | O | HIS | A | 78 | 9.611 | −64.285 | −39.457 | 1.00 | 44.43 | O |
| 1623 | ATOM | 1468 | N | SER | A | 79 | 11.627 | −63.870 | −40.346 | 1.00 | 43.42 | N |
| 1624 | ATOM | 1469 | CA | SER | A | 79 | 11.356 | −62.443 | −40.507 | 1.00 | 45.21 | C |
| 1625 | ATOM | 1470 | CB | SER | A | 79 | 11.836 | −61.648 | −39.280 | 1.00 | 45.04 | C |
| 1626 | ATOM | 1471 | OG | SER | A | 79 | 13.199 | −61.266 | −39.407 | 1.00 | 46.84 | O |
| 1627 | ATOM | 1472 | C | SER | A | 79 | 12.005 | −61.919 | −41.786 | 1.00 | 45.35 | C |
| 1628 | ATOM | 1473 | O | SER | A | 79 | 12.717 | −62.648 | −42.488 | 1.00 | 41.72 | O |
| 1629 | ATOM | 1474 | N | SER | A | 80 | 11.732 | −60.654 | −42.085 | 1.00 | 45.32 | N |
| 1630 | ATOM | 1475 | CA | SER | A | 80 | 12.291 | −59.992 | −43.258 | 1.00 | 44.64 | C |
| 1631 | ATOM | 1476 | CB | SER | A | 80 | 11.777 | −58.550 | −43.322 | 1.00 | 43.33 | C |
| 1632 | ATOM | 1477 | OG | SER | A | 80 | 12.370 | −57.839 | −44.386 | 1.00 | 44.76 | O |
| 1633 | ATOM | 1478 | C | SER | A | 80 | 13.824 | −60.006 | −43.213 | 1.00 | 43.69 | C |
| 1634 | ATOM | 1479 | O | SER | A | 80 | 14.492 | −60.287 | −44.206 | 1.00 | 44.35 | O |
| 1635 | ATOM | 1480 | N | TYR | A | 81 | 14.365 | −59.734 | −42.035 | 1.00 | 42.95 | N |
| 1636 | ATOM | 1481 | CA | TYR | A | 81 | 15.800 | −59.524 | −41.870 | 1.00 | 42.85 | C |
| 1637 | ATOM | 1482 | CB | TYR | A | 81 | 16.030 | −58.450 | −40.798 | 1.00 | 39.30 | C |
| 1638 | ATOM | 1483 | CG | TYR | A | 81 | 15.625 | −57.048 | −41.242 | 1.00 | 38.88 | C |
| 1639 | ATOM | 1484 | CD1 | TYR | A | 81 | 16.313 | −56.393 | −42.268 | 1.00 | 37.96 | C |
| 1640 | ATOM | 1485 | CE1 | TYR | A | 81 | 15.956 | −55.105 | −42.671 | 1.00 | 38.73 | C |
| 1641 | ATOM | 1486 | CZ | TYR | A | 81 | 14.904 | −54.458 | −42.039 | 1.00 | 38.68 | C |
| 1642 | ATOM | 1487 | OH | TYR | A | 81 | 14.544 | −53.185 | −42.432 | 1.00 | 39.56 | O |
| 1643 | ATOM | 1488 | CE2 | TYR | A | 81 | 14.208 | −55.091 | −41.017 | 1.00 | 36.31 | C |
| 1644 | ATOM | 1489 | CD2 | TYR | A | 81 | 14.569 | −56.375 | −40.627 | 1.00 | 36.50 | C |
| 1645 | ATOM | 1490 | C | TYR | A | 81 | 16.598 | −60.792 | −41.531 | 1.00 | 44.50 | C |
| 1646 | ATOM | 1491 | O | TYR | A | 81 | 17.799 | −60.859 | −41.814 | 1.00 | 44.52 | O |
| 1647 | ATOM | 1492 | N | ARG | A | 82 | 15.928 | −61.794 | −40.951 | 1.00 | 44.59 | N |
| 1648 | ATOM | 1493 | CA | ARG | A | 82 | 16.606 | −62.955 | −40.346 | 1.00 | 44.21 | C |
| 1649 | ATOM | 1494 | CB | ARG | A | 82 | 15.574 | −63.959 | −39.811 | 1.00 | 45.71 | C |
| 1650 | ATOM | 1495 | CG | ARG | A | 82 | 16.158 | −64.969 | −38.838 | 1.00 | 46.99 | C |
| 1651 | ATOM | 1496 | CD | ARG | A | 82 | 15.256 | −66.179 | −38.678 | 1.00 | 50.79 | C |
| 1652 | ATOM | 1497 | NE | ARG | A | 82 | 16.019 | −67.424 | −38.718 | 1.00 | 54.72 | N |
| 1653 | ATOM | 1498 | CZ | ARG | A | 82 | 15.493 | −68.639 | −38.593 | 1.00 | 58.04 | C |
| 1654 | ATOM | 1499 | NH1 | ARG | A | 82 | 16.287 | −69.702 | −38.648 | 1.00 | 59.38 | N |
| 1655 | ATOM | 1500 | NH2 | ARG | A | 82 | 14.186 | −68.803 | −38.407 | 1.00 | 60.03 | N |
| 1656 | ATOM | 1501 | C | ARG | A | 82 | 17.616 | −63.695 | −41.248 | 1.00 | 41.58 | C |
| 1657 | ATOM | 1502 | O | ARG | A | 82 | 18.589 | −64.257 | −40.735 | 1.00 | 43.56 | O |
| 1658 | ATOM | 1503 | N | GLN | A | 83 | 17.407 | −63.700 | −42.564 | 1.00 | 36.95 | N |
| 1659 | ATOM | 1504 | CA | GLN | A | 83 | 18.376 | −64.327 | −43.479 | 1.00 | 34.31 | C |
| 1660 | ATOM | 1505 | CB | GLN | A | 83 | 17.669 | −65.358 | −44.381 | 1.00 | 36.08 | C |
| 1661 | ATOM | 1506 | CG | GLN | A | 83 | 16.738 | −64.786 | −45.441 | 1.00 | 38.09 | C |
| 1662 | ATOM | 1507 | CD | GLN | A | 83 | 16.064 | −65.868 | −46.266 | 0.05 | 37.34 | C |
| 1663 | ATOM | 1508 | OE1 | GLN | A | 83 | 15.645 | −66.899 | −45.738 | 0.05 | 37.34 | O |
| 1664 | ATOM | 1509 | NE2 | GLN | A | 83 | 15.955 | −65.638 | −47.570 | 0.05 | 37.37 | N |
| 1665 | ATOM | 1510 | C | GLN | A | 83 | 19.239 | −63.333 | −44.307 | 1.00 | 31.24 | C |
| 1666 | ATOM | 1511 | O | GLN | A | 83 | 20.263 | −63.721 | −44.871 | 1.00 | 33.46 | O |
| 1667 | ATOM | 1512 | N | ARG | A | 84 | 18.854 | −62.061 | −44.363 | 1.00 | 25.33 | N |
| 1668 | ATOM | 1513 | CA | ARG | A | 84 | 19.527 | −61.090 | −45.228 | 1.00 | 22.64 | C |
| 1669 | ATOM | 1514 | CB | ARG | A | 84 | 18.491 | −60.262 | −45.976 | 1.00 | 21.94 | C |
| 1670 | ATOM | 1515 | CG | ARG | A | 84 | 17.544 | −61.081 | −46.835 | 1.00 | 22.05 | C |
| 1671 | ATOM | 1516 | CD | ARG | A | 84 | 16.666 | −60.175 | −47.693 | 1.00 | 21.48 | C |
| 1672 | ATOM | 1517 | NE | ARG | A | 84 | 15.765 | −59.399 | −46.836 | 1.00 | 21.81 | N |
| 1673 | ATOM | 1518 | CZ | ARG | A | 84 | 15.673 | −58.069 | −46.790 | 1.00 | 21.25 | C |
| 1674 | ATOM | 1519 | NH1 | ARG | A | 84 | 14.808 | −57.527 | −45.948 | 1.00 | 21.00 | N |
| 1675 | ATOM | 1520 | NH2 | ARG | A | 84 | 16.424 | −57.285 | −47.577 | 1.00 | 20.29 | N |
| 1676 | ATOM | 1521 | C | ARG | A | 84 | 20.440 | −60.127 | −44.464 | 1.00 | 21.15 | C |
| 1677 | ATOM | 1522 | O | ARG | A | 84 | 21.209 | −59.396 | −45.091 | 1.00 | 20.70 | O |
| 1678 | ATOM | 1523 | N | ALA | A | 85 | 20.333 | −60.131 | −43.135 | 1.00 | 20.43 | N |
| 1679 | ATOM | 1524 | CA | ALA | A | 85 | 21.017 | −59.129 | −42.288 | 1.00 | 19.84 | C |
| 1680 | ATOM | 1525 | CB | ALA | A | 85 | 20.041 | −58.465 | −41.347 | 1.00 | 20.36 | C |
| 1681 | ATOM | 1526 | C | ALA | A | 85 | 22.133 | −59.751 | −41.495 | 1.00 | 19.63 | C |
| 1682 | ATOM | 1527 | O | ALA | A | 85 | 21.965 | −60.804 | −40.872 | 1.00 | 19.65 | O |
| 1683 | ATOM | 1528 | N | ARG | A | 86 | 23.298 | −59.118 | −41.507 | 1.00 | 19.33 | N |
| 1684 | ATOM | 1529 | CA | ARG | A | 86 | 24.328 | −59.565 | −40.601 | 1.00 | 20.57 | C |
| 1685 | ATOM | 1530 | CB | ARG | A | 86 | 25.113 | −60.715 | −41.184 | 1.00 | 25.71 | C |
| 1686 | ATOM | 1531 | CG | ARG | A | 86 | 25.941 | −60.405 | −42.386 | 1.00 | 30.25 | C |
| 1687 | ATOM | 1532 | CD | ARG | A | 86 | 26.442 | −61.725 | −42.962 | 1.00 | 35.37 | C |
| 1688 | ATOM | 1533 | NE | ARG | A | 86 | 27.458 | −61.518 | −43.986 | 1.00 | 41.88 | N |
| 1689 | ATOM | 1534 | CZ | ARG | A | 86 | 28.760 | −61.324 | −43.758 | 1.00 | 44.93 | C |
| 1690 | ATOM | 1535 | NH1 | ARG | A | 86 | 29.588 | −61.148 | −44.789 | 1.00 | 47.61 | N |
| 1691 | ATOM | 1536 | NH2 | ARG | A | 86 | 29.242 | −61.298 | −42.516 | 1.00 | 48.03 | N |
| 1692 | ATOM | 1537 | C | ARG | A | 86 | 25.258 | −58.451 | −40.188 | 1.00 | 17.80 | C |
| 1693 | ATOM | 1538 | O | ARG | A | 86 | 25.468 | −57.485 | −40.934 | 1.00 | 17.43 | O |
| 1694 | ATOM | 1539 | N | LEU | A | 87 | 25.789 | −58.620 | −38.986 | 1.00 | 15.93 | N |
| 1695 | ATOM | 1540 | CA | LEU | A | 87 | 26.778 | −57.713 | −38.419 | 1.00 | 14.40 | C |
| 1696 | ATOM | 1541 | CB | LEU | A | 87 | 26.691 | −57.771 | −36.907 | 1.00 | 13.96 | C |
| 1697 | ATOM | 1542 | CG | LEU | A | 87 | 27.605 | −56.813 | −36.149 | 1.00 | 13.25 | C |
| 1698 | ATOM | 1543 | CD1 | LEU | A | 87 | 27.220 | −55.359 | −36.330 | 1.00 | 12.74 | C |
| 1699 | ATOM | 1544 | CD2 | LEU | A | 87 | 27.622 | −57.205 | −34.674 | 1.00 | 13.46 | C |

APPENDIX I-continued

| | | | | | | | | | | |
|---|---|---|---|---|---|---|---|---|---|---|
| 1700 | ATOM | 1545 | C | LEU | A | 87 | 28.150 | −58.196 | −38.880 | 1.00 | 13.98 C |
| 1701 | ATOM | 1546 | O | LEU | A | 87 | 28.441 | −59.400 | −38.788 | 1.00 | 12.32 O |
| 1702 | ATOM | 1547 | N | LEU | A | 88 | 28.963 | −57.277 | −39.413 | 1.00 | 13.32 N |
| 1703 | ATOM | 1548 | CA | LEU | A | 88 | 30.309 | −57.611 | −39.909 | 1.00 | 13.61 C |
| 1704 | ATOM | 1549 | CB | LEU | A | 88 | 30.779 | −56.631 | −40.966 | 1.00 | 13.73 C |
| 1705 | ATOM | 1550 | CG | LEU | A | 88 | 29.883 | −56.494 | −42.211 | 1.00 | 14.57 C |
| 1706 | ATOM | 1551 | CD1 | LEU | A | 88 | 30.547 | −55.658 | −43.282 | 1.00 | 14.09 C |
| 1707 | ATOM | 1552 | CD2 | LEU | A | 88 | 29.449 | −57.838 | −42.771 | 1.00 | 14.69 C |
| 1708 | ATOM | 1553 | C | LEU | A | 88 | 31.247 | −57.617 | −38.717 | 1.00 | 13.68 C |
| 1709 | ATOM | 1554 | O | LEU | A | 88 | 31.821 | −56.590 | −38.357 | 1.00 | 13.81 O |
| 1710 | ATOM | 1555 | N | LYS | A | 89 | 31.382 | −58.786 | −38.107 | 1.00 | 13.32 N |
| 1711 | ATOM | 1556 | CA | LYS | A | 89 | 32.082 | −58.898 | −36.844 | 1.00 | 14.62 C |
| 1712 | ATOM | 1557 | CB | LYS | A | 89 | 31.909 | −60.292 | −36.263 | 1.00 | 17.04 C |
| 1713 | ATOM | 1558 | CG | LYS | A | 89 | 30.450 | −60.582 | −35.966 | 1.00 | 19.23 C |
| 1714 | ATOM | 1559 | CD | LYS | A | 89 | 30.240 | −61.871 | −35.188 | 1.00 | 23.41 C |
| 1715 | ATOM | 1560 | CE | LYS | A | 89 | 30.791 | −63.113 | −35.858 | 1.00 | 26.35 C |
| 1716 | ATOM | 1561 | NZ | LYS | A | 89 | 30.014 | −63.511 | −37.061 | 1.00 | 29.04 N |
| 1717 | ATOM | 1562 | C | LYS | A | 89 | 33.555 | −58.525 | −36.887 | 1.00 | 13.38 C |
| 1718 | ATOM | 1563 | O | LYS | A | 89 | 34.079 | −58.042 | −35.908 | 1.00 | 14.08 O |
| 1719 | ATOM | 1564 | N | ASP | A | 90 | 34.213 | −58.736 | −38.010 | 1.00 | 13.75 N |
| 1720 | ATOM | 1565 | CA | ASP | A | 90 | 35.647 | −58.429 | −38.122 | 1.00 | 14.14 C |
| 1721 | ATOM | 1566 | CB | ASP | A | 90 | 36.247 | −59.037 | −39.390 | 1.00 | 16.12 C |
| 1722 | ATOM | 1567 | CG | ASP | A | 90 | 36.280 | −60.553 | −39.383 | 1.00 | 19.19 C |
| 1723 | ATOM | 1568 | OD1 | ASP | A | 90 | 36.565 | −61.097 | −40.476 | 1.00 | 22.12 O |
| 1724 | ATOM | 1569 | OD2 | ASP | A | 90 | 36.051 | −61.213 | −38.332 | 1.00 | 20.29 O |
| 1725 | ATOM | 1570 | C | ASP | A | 90 | 35.896 | −56.902 | −38.141 | 1.00 | 12.94 C |
| 1726 | ATOM | 1571 | O | ASP | A | 90 | 37.032 | −56.466 | −38.059 | 1.00 | 12.64 O |
| 1727 | ATOM | 1572 | N | GLN | A | 91 | 34.849 | −56.097 | −38.252 | 1.00 | 12.11 N |
| 1728 | ATOM | 1573 | CA | GLN | A | 91 | 35.022 | −54.645 | −38.212 | 1.00 | 11.53 C |
| 1729 | ATOM | 1574 | CB | GLN | A | 91 | 34.000 | −53.975 | −39.113 | 1.00 | 12.09 C |
| 1730 | ATOM | 1575 | CG | GLN | A | 91 | 34.294 | −54.184 | −40.587 | 1.00 | 12.45 C |
| 1731 | ATOM | 1576 | CD | GLN | A | 91 | 35.503 | −53.423 | −41.057 | 1.00 | 12.17 C |
| 1732 | ATOM | 1577 | OE1 | GLN | A | 91 | 35.573 | −52.209 | −40.900 | 1.00 | 13.17 O |
| 1733 | ATOM | 1578 | NE2 | GLN | A | 91 | 36.455 | −54.129 | −41.646 | 1.00 | 12.61 N |
| 1734 | ATOM | 1579 | C | GLN | A | 91 | 34.906 | −54.078 | −36.775 | 1.00 | 11.06 C |
| 1735 | ATOM | 1580 | O | GLN | A | 91 | 35.279 | −52.931 | −36.540 | 1.00 | 10.71 O |
| 1736 | ATOM | 1581 | N | LEU | A | 92 | 34.419 | −54.871 | −35.824 | 1.00 | 11.00 N |
| 1737 | ATOM | 1582 | CA | LEU | A | 92 | 34.185 | −54.368 | −34.463 | 1.00 | 10.78 C |
| 1738 | ATOM | 1583 | CB | LEU | A | 92 | 33.492 | −55.410 | −33.582 | 1.00 | 11.27 C |
| 1739 | ATOM | 1584 | CG | LEU | A | 92 | 32.085 | −55.822 | −34.016 | 1.00 | 11.16 C |
| 1740 | ATOM | 1585 | CD1 | LEU | A | 92 | 31.569 | −57.075 | −33.299 | 1.00 | 11.89 C |
| 1741 | ATOM | 1586 | CD2 | LEU | A | 92 | 31.153 | −54.647 | −33.780 | 1.00 | 11.63 C |
| 1742 | ATOM | 1587 | C | LEU | A | 92 | 35.452 | −53.870 | −33.795 | 1.00 | 11.47 C |
| 1743 | ATOM | 1588 | O | LEU | A | 92 | 35.428 | −52.797 | −33.156 | 1.00 | 11.44 O |
| 1744 | ATOM | 1589 | N | SER | A | 93 | 36.557 | −54.582 | −33.971 | 1.00 | 11.35 N |
| 1745 | ATOM | 1590 | CA | SER | A | 93 | 37.831 | −54.169 | −33.328 | 1.00 | 11.41 C |
| 1746 | ATOM | 1591 | CB | SER | A | 93 | 38.857 | −55.293 | −33.363 | 1.00 | 12.34 C |
| 1747 | ATOM | 1592 | OG | SER | A | 93 | 39.503 | −55.319 | −34.633 | 1.00 | 13.90 O |
| 1748 | ATOM | 1593 | C | SER | A | 93 | 38.418 | −52.871 | −33.915 | 1.00 | 11.05 C |
| 1749 | ATOM | 1594 | O | SER | A | 93 | 39.324 | −52.271 | −33.320 | 1.00 | 10.90 O |
| 1750 | ATOM | 1595 | N | LEU | A | 94 | 37.912 | −52.459 | −35.077 | 1.00 | 10.30 N |
| 1751 | ATOM | 1596 | CA | LEU | A | 94 | 38.259 | −51.186 | −35.697 | 1.00 | 10.83 C |
| 1752 | ATOM | 1597 | CB | LEU | A | 94 | 38.315 | −51.328 | −37.226 | 1.00 | 11.44 C |
| 1753 | ATOM | 1598 | CG | LEU | A | 94 | 39.527 | −52.058 | −37.815 | 1.00 | 12.52 C |
| 1754 | ATOM | 1599 | CD1 | LEU | A | 94 | 39.661 | −53.525 | −37.470 | 1.00 | 13.04 C |
| 1755 | ATOM | 1600 | CD2 | LEU | A | 94 | 39.428 | −51.921 | −39.319 | 1.00 | 13.05 C |
| 1756 | ATOM | 1601 | C | LEU | A | 94 | 37.267 | −50.091 | −35.307 | 1.00 | 10.87 C |
| 1757 | ATOM | 1602 | O | LEU | A | 94 | 37.367 | −48.963 | −35.773 | 1.00 | 10.06 O |
| 1758 | ATOM | 1603 | N | GLY | A | 95 | 36.320 | −50.407 | −34.428 | 1.00 | 10.55 N |
| 1759 | ATOM | 1604 | CA | GLY | A | 95 | 35.378 | −49.394 | −33.963 | 1.00 | 10.83 C |
| 1760 | ATOM | 1605 | C | GLY | A | 95 | 34.226 | −49.172 | −34.909 | 1.00 | 10.97 C |
| 1761 | ATOM | 1606 | O | GLY | A | 95 | 33.575 | −48.116 | −34.842 | 1.00 | 11.44 O |
| 1762 | ATOM | 1607 | N | ASN | A | 96 | 33.956 | −50.152 | −35.774 | 1.00 | 11.01 N |
| 1763 | ATOM | 1608 | CA | ASN | A | 96 | 32.849 | −50.067 | −36.733 | 1.00 | 11.79 C |
| 1764 | ATOM | 1609 | CB | ASN | A | 96 | 33.320 | −50.342 | −38.174 | 1.00 | 13.92 C |
| 1765 | ATOM | 1610 | CG | ASN | A | 96 | 34.183 | −49.261 | −38.750 | 1.00 | 16.01 C |
| 1766 | ATOM | 1611 | OD1 | ASN | A | 96 | 33.908 | −48.074 | −38.605 | 1.00 | 17.60 O |
| 1767 | ATOM | 1612 | ND2 | ASN | A | 96 | 35.215 | −49.669 | −39.502 | 1.00 | 17.27 N |
| 1768 | ATOM | 1613 | C | ASN | A | 96 | 31.791 | −51.111 | −36.422 | 1.00 | 11.29 C |
| 1769 | ATOM | 1614 | O | ASN | A | 96 | 32.093 | −52.304 | −36.400 | 1.00 | 10.16 O |
| 1770 | ATOM | 1615 | N | ALA | A | 97 | 30.575 | −50.653 | −36.146 | 1.00 | 10.94 N |
| 1771 | ATOM | 1616 | CA | ALA | A | 97 | 29.372 | −51.486 | −36.112 | 1.00 | 11.06 C |
| 1772 | ATOM | 1617 | CB | ALA | A | 97 | 28.434 | −50.999 | −35.026 | 1.00 | 11.75 C |
| 1773 | ATOM | 1618 | C | ALA | A | 97 | 28.734 | −51.405 | −37.502 | 1.00 | 11.92 C |
| 1774 | ATOM | 1619 | O | ALA | A | 97 | 28.110 | −50.403 | −37.833 | 1.00 | 11.97 O |
| 1775 | ATOM | 1620 | N | ALA | A | 98 | 28.917 | −52.449 | −38.308 | 1.00 | 11.60 N |
| 1776 | ATOM | 1621 | CA | ALA | A | 98 | 28.532 | −52.439 | −39.709 | 1.00 | 11.75 C |
| 1777 | ATOM | 1622 | CB | ALA | A | 98 | 29.738 | −52.715 | −40.602 | 1.00 | 11.77 C |
| 1778 | ATOM | 1623 | C | ALA | A | 98 | 27.477 | −53.494 | −39.939 | 1.00 | 12.05 C |
| 1779 | ATOM | 1624 | O | ALA | A | 98 | 27.738 | −54.675 | −39.731 | 1.00 | 11.78 O |

APPENDIX I-continued

| | | | | | | | | | | |
|---|---|---|---|---|---|---|---|---|---|---|
| 1780 | ATOM | 1625 | N | LEU | A | 99 | 26.302 | −53.038 | −40.359 | 1.00 | 12.88 N |
| 1781 | ATOM | 1626 | CA | LEU | A | 99 | 25.162 | −53.917 | −40.680 | 1.00 | 13.01 C |
| 1782 | ATOM | 1627 | CB | LEU | A | 99 | 23.887 | −53.334 | −40.054 | 1.00 | 13.04 C |
| 1783 | ATOM | 1628 | CG | LEU | A | 99 | 22.569 | −54.057 | −40.357 | 1.00 | 13.40 C |
| 1784 | ATOM | 1629 | CD1 | LEU | A | 99 | 22.589 | −55.436 | −39.763 | 1.00 | 13.07 C |
| 1785 | ATOM | 1630 | CD2 | LEU | A | 99 | 21.393 | −53.244 | −39.885 | 1.00 | 13.72 C |
| 1786 | ATOM | 1631 | C | LEU | A | 99 | 24.997 | −54.035 | −42.173 | 1.00 | 13.92 C |
| 1787 | ATOM | 1632 | O | LEU | A | 99 | 24.713 | −53.051 | −42.868 | 1.00 | 13.87 O |
| 1788 | ATOM | 1633 | N | GLN | A | 100 | 25.162 | −55.249 | −42.662 | 1.00 | 14.55 N |
| 1789 | ATOM | 1634 | CA | GLN | A | 100 | 25.056 | −55.562 | −44.071 | 1.00 | 17.03 C |
| 1790 | ATOM | 1635 | CB | GLN | A | 100 | 26.163 | −56.519 | −44.469 | 1.00 | 18.67 C |
| 1791 | ATOM | 1636 | CG | GLN | A | 100 | 26.203 | −56.951 | −45.930 | 1.00 | 20.84 C |
| 1792 | ATOM | 1637 | CD | GLN | A | 100 | 27.241 | −58.043 | −46.122 | 1.00 | 22.30 C |
| 1793 | ATOM | 1638 | OE1 | GLN | A | 100 | 27.045 | −59.200 | −45.723 | 1.00 | 26.10 O |
| 1794 | ATOM | 1639 | NE2 | GLN | A | 100 | 28.370 | −57.670 | −46.651 | 1.00 | 23.57 N |
| 1795 | ATOM | 1640 | C | GLN | A | 100 | 23.718 | −56.219 | −44.308 | 1.00 | 17.45 C |
| 1796 | ATOM | 1641 | O | GLN | A | 100 | 23.393 | −57.227 | −43.662 | 1.00 | 17.85 O |
| 1797 | ATOM | 1642 | N | ILE | A | 101 | 22.955 | −55.642 | −45.235 | 1.00 | 17.86 N |
| 1798 | ATOM | 1643 | CA | ILE | A | 101 | 21.683 | −56.199 | −45.637 | 1.00 | 19.20 C |
| 1799 | ATOM | 1644 | CB | ILE | A | 101 | 20.512 | −55.228 | −45.339 | 1.00 | 20.63 C |
| 1800 | ATOM | 1645 | CG1 | ILE | A | 101 | 20.361 | −55.021 | −43.824 | 1.00 | 22.07 C |
| 1801 | ATOM | 1646 | CD1 | ILE | A | 101 | 19.500 | −53.832 | −43.458 | 1.00 | 23.91 C |
| 1802 | ATOM | 1647 | CG2 | ILE | A | 101 | 19.216 | −55.748 | −45.961 | 1.00 | 21.47 C |
| 1803 | ATOM | 1648 | C | ILE | A | 101 | 21.792 | −56.507 | −47.125 | 1.00 | 19.03 C |
| 1804 | ATOM | 1649 | O | ILE | A | 101 | 22.112 | −55.631 | −47.937 | 1.00 | 17.59 O |
| 1805 | ATOM | 1650 | N | THR | A | 102 | 21.546 | −57.764 | −47.478 | 1.00 | 19.53 N |
| 1806 | ATOM | 1651 | CA | THR | A | 102 | 21.610 | −58.185 | −48.867 | 1.00 | 20.30 C |
| 1807 | ATOM | 1652 | CB | THR | A | 102 | 22.182 | −59.599 | −48.995 | 1.00 | 20.65 C |
| 1808 | ATOM | 1653 | OG1 | THR | A | 102 | 21.364 | −60.494 | −48.243 | 1.00 | 21.02 O |
| 1809 | ATOM | 1654 | CG2 | THR | A | 102 | 23.598 | −59.653 | −48.469 | 1.00 | 21.07 C |
| 1810 | ATOM | 1655 | C | THR | A | 102 | 20.228 | −58.172 | −49.504 | 1.00 | 21.47 C |
| 1811 | ATOM | 1656 | O | THR | A | 102 | 19.205 | −58.259 | −48.807 | 1.00 | 21.57 O |
| 1812 | ATOM | 1657 | N | ASP | A | 103 | 20.213 | −58.070 | −50.828 | 1.00 | 21.98 N |
| 1813 | ATOM | 1658 | CA | ASP | A | 103 | 18.973 | −58.107 | −51.614 | 1.00 | 22.70 C |
| 1814 | ATOM | 1659 | CB | ASP | A | 103 | 18.381 | −59.514 | −51.628 | 1.00 | 23.96 C |
| 1815 | ATOM | 1660 | CG | ASP | A | 103 | 17.348 | −59.697 | −52.729 | 1.00 | 25.31 C |
| 1816 | ATOM | 1661 | OD1 | ASP | A | 103 | 17.311 | −58.867 | −53.663 | 1.00 | 24.07 O |
| 1817 | ATOM | 1662 | OD2 | ASP | A | 103 | 16.573 | −60.671 | −52.660 | 1.00 | 28.50 O |
| 1818 | ATOM | 1663 | C | ASP | A | 103 | 17.931 | −57.122 | −51.084 | 1.00 | 22.25 C |
| 1819 | ATOM | 1664 | O | ASP | A | 103 | 16.835 | −57.507 | −50.698 | 1.00 | 21.20 O |
| 1820 | ATOM | 1665 | N | VAL | A | 104 | 18.295 | −55.845 | −51.094 | 1.00 | 22.31 N |
| 1821 | ATOM | 1666 | CA | VAL | A | 104 | 17.490 | −54.791 | −50.487 | 1.00 | 21.73 C |
| 1822 | ATOM | 1667 | CB | VAL | A | 104 | 18.234 | −53.428 | −50.592 | 1.00 | 22.17 C |
| 1823 | ATOM | 1668 | CG1 | VAL | A | 104 | 17.301 | −52.255 | −50.323 | 1.00 | 22.28 C |
| 1824 | ATOM | 1669 | CG2 | VAL | A | 104 | 19.407 | −53.393 | −49.611 | 1.00 | 22.49 C |
| 1825 | ATOM | 1670 | C | VAL | A | 104 | 16.065 | −54.734 | −51.082 | 1.00 | 22.70 C |
| 1826 | ATOM | 1671 | O | VAL | A | 104 | 15.868 | −54.808 | −52.300 | 1.00 | 22.31 O |
| 1827 | ATOM | 1672 | N | LYS | A | 105 | 15.077 | −54.640 | −50.200 | 1.00 | 22.87 N |
| 1828 | ATOM | 1673 | CA | LYS | A | 105 | 13.666 | −54.581 | −50.595 | 1.00 | 24.43 C |
| 1829 | ATOM | 1674 | CB | LYS | A | 105 | 12.889 | −55.719 | −49.924 | 1.00 | 26.37 C |
| 1830 | ATOM | 1675 | CG | LYS | A | 105 | 13.074 | −57.059 | −50.618 | 1.00 | 28.82 C |
| 1831 | ATOM | 1676 | CD | LYS | A | 105 | 13.360 | −58.186 | −49.629 | 1.00 | 30.68 C |
| 1832 | ATOM | 1677 | CE | LYS | A | 105 | 13.427 | −59.542 | −50.319 | 1.00 | 32.99 C |
| 1833 | ATOM | 1678 | NZ | LYS | A | 105 | 14.310 | −59.554 | −51.529 | 1.00 | 34.88 N |
| 1834 | ATOM | 1679 | C | LYS | A | 105 | 13.060 | −53.225 | −50.240 | 1.00 | 21.95 C |
| 1835 | ATOM | 1680 | O | LYS | A | 105 | 13.611 | −52.477 | −49.415 | 1.00 | 19.62 O |
| 1836 | ATOM | 1681 | N | LEU | A | 106 | 11.907 | −52.919 | −50.842 | 1.00 | 21.87 N |
| 1837 | ATOM | 1682 | CA | LEU | A | 106 | 11.237 | −51.644 | −50.583 | 1.00 | 21.05 C |
| 1838 | ATOM | 1683 | CB | LEU | A | 106 | 9.950 | −51.509 | −51.402 | 1.00 | 22.48 C |
| 1839 | ATOM | 1684 | CG | LEU | A | 106 | 10.149 | −51.501 | −52.920 | 1.00 | 23.51 C |
| 1840 | ATOM | 1685 | CD1 | LEU | A | 106 | 8.830 | −51.269 | −53.621 | 1.00 | 23.74 C |
| 1841 | ATOM | 1686 | CD2 | LEU | A | 106 | 11.169 | −50.446 | −53.343 | 1.00 | 23.79 C |
| 1842 | ATOM | 1687 | C | LEU | A | 106 | 10.943 | −51.476 | −49.097 | 1.00 | 20.89 C |
| 1843 | ATOM | 1688 | O | LEU | A | 106 | 11.032 | −50.368 | −48.570 | 1.00 | 19.71 O |
| 1844 | ATOM | 1689 | N | GLN | A | 107 | 10.661 | −52.591 | −48.427 | 1.00 | 20.04 N |
| 1845 | ATOM | 1690 | CA | GLN | A | 107 | 10.297 | −52.587 | −47.016 | 1.00 | 21.90 C |
| 1846 | ATOM | 1691 | CB | GLN | A | 107 | 9.678 | −53.930 | −46.616 | 1.00 | 23.22 C |
| 1847 | ATOM | 1692 | CG | GLN | A | 107 | 8.310 | −54.152 | −47.226 | 1.00 | 25.25 C |
| 1848 | ATOM | 1693 | CD | GLN | A | 107 | 8.346 | −54.547 | −48.695 | 1.00 | 26.03 C |
| 1849 | ATOM | 1694 | OE1 | GLN | A | 107 | 9.402 | −54.903 | −49.246 | 1.00 | 25.96 O |
| 1850 | ATOM | 1695 | NE2 | GLN | A | 107 | 7.171 | −54.508 | −49.338 | 1.00 | 26.33 N |
| 1851 | ATOM | 1696 | C | GLN | A | 107 | 11.485 | −52.298 | −46.115 | 1.00 | 20.18 C |
| 1852 | ATOM | 1697 | O | GLN | A | 107 | 11.302 | −52.031 | −44.939 | 1.00 | 20.34 O |
| 1853 | ATOM | 1698 | N | ASP | A | 108 | 12.695 | −52.392 | −46.668 | 1.00 | 18.77 N |
| 1854 | ATOM | 1699 | CA | ASP | A | 108 | 13.918 | −52.008 | −45.959 | 1.00 | 17.84 C |
| 1855 | ATOM | 1700 | CB | ASP | A | 108 | 15.145 | −52.621 | −46.642 | 1.00 | 18.18 C |
| 1856 | ATOM | 1701 | CG | ASP | A | 108 | 15.122 | −54.143 | −46.654 | 1.00 | 19.77 C |
| 1857 | ATOM | 1702 | OD1 | ASP | A | 108 | 14.557 | −54.755 | −45.724 | 1.00 | 19.95 O |
| 1858 | ATOM | 1703 | OD2 | ASP | A | 108 | 15.681 | −54.752 | −47.599 | 1.00 | 21.43 O |
| 1859 | ATOM | 1704 | C | ASP | A | 108 | 14.118 | −50.484 | −45.807 | 1.00 | 17.49 C |

APPENDIX I-continued

| | | | | | | | | | | |
|---|---|---|---|---|---|---|---|---|---|---|
| 1860 | ATOM | 1705 | O | ASP | A | 108 | 15.023 | −50.052 | −45.082 | 1.00 17.65 O |
| 1861 | ATOM | 1706 | N | ALA | A | 109 | 13.316 | −49.674 | −46.497 | 1.00 17.31 N |
| 1862 | ATOM | 1707 | CA | ALA | A | 109 | 13.378 | −48.220 | −46.347 | 1.00 17.11 C |
| 1863 | ATOM | 1708 | CB | ALA | A | 109 | 12.618 | −47.530 | −47.469 | 1.00 17.25 C |
| 1864 | ATOM | 1709 | C | ALA | A | 109 | 12.834 | −47.797 | −44.984 | 1.00 17.59 C |
| 1865 | ATOM | 1710 | O | ALA | A | 109 | 11.819 | −48.309 | −44.522 | 1.00 17.55 O |
| 1866 | ATOM | 1711 | N | GLY | A | 110 | 13.536 | −46.897 | −44.308 | 1.00 16.52 N |
| 1867 | ATOM | 1712 | CA | GLY | A | 110 | 13.050 | −46.377 | −43.036 | 1.00 15.39 C |
| 1868 | ATOM | 1713 | C | GLY | A | 110 | 14.198 | −45.979 | −42.145 | 1.00 14.51 C |
| 1869 | ATOM | 1714 | O | GLY | A | 110 | 15.344 | −45.839 | −42.623 | 1.00 13.19 O |
| 1870 | ATOM | 1715 | N | VAL | A | 111 | 13.894 | −45.815 | −40.857 | 1.00 12.74 N |
| 1871 | ATOM | 1716 | CA | VAL | A | 111 | 14.902 | −45.352 | −39.913 | 1.00 13.61 C |
| 1872 | ATOM | 1717 | CB | VAL | A | 111 | 14.294 | −44.333 | −38.950 | 1.00 14.16 C |
| 1873 | ATOM | 1718 | CG1 | VAL | A | 111 | 15.320 | −43.915 | −37.940 | 1.00 14.31 C |
| 1874 | ATOM | 1719 | CG2 | VAL | A | 111 | 13.753 | −43.137 | −39.738 | 1.00 14.99 C |
| 1875 | ATOM | 1720 | C | VAL | A | 111 | 15.488 | −46.522 | −39.143 | 1.00 13.49 C |
| 1876 | ATOM | 1721 | O | VAL | A | 111 | 14.744 | −47.287 | −38.521 | 1.00 14.77 O |
| 1877 | ATOM | 1722 | N | TYR | A | 112 | 16.817 | −46.652 | −39.202 | 1.00 12.42 N |
| 1878 | ATOM | 1723 | CA | TYR | A | 112 | 17.584 | −47.636 | −38.478 | 1.00 11.99 C |
| 1879 | ATOM | 1724 | CB | TYR | A | 112 | 18.662 | −48.258 | −39.391 | 1.00 12.11 C |
| 1880 | ATOM | 1725 | CG | TYR | A | 112 | 18.080 | −49.144 | −40.460 | 1.00 12.01 C |
| 1881 | ATOM | 1726 | CD1 | TYR | A | 112 | 17.443 | −48.595 | −41.563 | 1.00 12.26 C |
| 1882 | ATOM | 1727 | CE1 | TYR | A | 112 | 16.890 | −49.403 | −42.553 | 1.00 12.88 C |
| 1883 | ATOM | 1728 | CZ | TYR | A | 112 | 17.013 | −50.773 | −42.459 | 1.00 13.27 C |
| 1884 | ATOM | 1729 | OH | TYR | A | 112 | 16.441 | −51.587 | −43.436 | 1.00 14.30 O |
| 1885 | ATOM | 1730 | CE2 | TYR | A | 112 | 17.652 | −51.342 | −41.377 | 1.00 13.03 C |
| 1886 | ATOM | 1731 | CD2 | TYR | A | 112 | 18.180 | −50.527 | −40.386 | 1.00 12.67 C |
| 1887 | ATOM | 1732 | C | TYR | A | 112 | 18.236 | −46.956 | −37.270 | 1.00 12.10 C |
| 1888 | ATOM | 1733 | O | TYR | A | 112 | 18.531 | −45.750 | −37.306 | 1.00 12.45 O |
| 1889 | ATOM | 1734 | N | ARG | A | 113 | 18.452 | −47.711 | −36.195 | 1.00 11.66 N |
| 1890 | ATOM | 1735 | CA | ARG | A | 113 | 19.192 | −47.191 | −35.076 | 1.00 12.11 C |
| 1891 | ATOM | 1736 | CB | ARG | A | 113 | 18.231 | −46.741 | −33.959 | 1.00 13.50 C |
| 1892 | ATOM | 1737 | CG | ARG | A | 113 | 18.952 | −46.101 | −32.765 | 1.00 15.74 C |
| 1893 | ATOM | 1738 | CD | ARG | A | 113 | 18.059 | −45.401 | −31.732 | 1.00 18.48 C |
| 1894 | ATOM | 1739 | NE | ARG | A | 113 | 17.331 | −46.385 | −30.993 | 1.00 21.69 N |
| 1895 | ATOM | 1740 | CZ | ARG | A | 113 | 17.235 | −46.514 | −29.663 | 1.00 18.89 C |
| 1896 | ATOM | 1741 | NH1 | ARG | A | 113 | 17.780 | −45.669 | −28.761 | 1.00 20.26 N |
| 1897 | ATOM | 1742 | NH2 | ARG | A | 113 | 16.505 | −47.486 | −29.269 | 1.00 18.96 N |
| 1898 | ATOM | 1743 | C | ARG | A | 113 | 20.195 | −48.215 | −34.568 | 1.00 12.03 C |
| 1899 | ATOM | 1744 | O | ARG | A | 113 | 19.872 | −49.399 | −34.463 | 1.00 11.09 O |
| 1900 | ATOM | 1745 | N | CYS | A | 114 | 21.410 | −47.740 | −34.265 | 1.00 11.75 N |
| 1901 | ATOM | 1746 | CA | CYS | A | 114 | 22.430 | −48.545 | −33.625 | 1.00 12.20 C |
| 1902 | ATOM | 1747 | CB | CYS | A | 114 | 23.755 | −48.443 | −34.358 | 1.00 13.56 C |
| 1903 | ATOM | 1748 | SG | CYS | A | 114 | 24.383 | −46.726 | −34.325 | 1.00 15.30 S |
| 1904 | ATOM | 1749 | C | CYS | A | 114 | 22.586 | −48.026 | −32.202 | 1.00 12.53 C |
| 1905 | ATOM | 1750 | O | CYS | A | 114 | 22.631 | −46.809 | −31.990 | 1.00 13.70 O |
| 1906 | ATOM | 1751 | N | MET | A | 115 | 22.631 | −48.939 | −31.239 | 1.00 12.13 N |
| 1907 | ATOM | 1752 | CA | MET | A | 115 | 23.044 | −48.626 | −29.873 | 1.00 12.61 C |
| 1908 | ATOM | 1753 | CB | MET | A | 115 | 21.892 | −48.812 | −28.898 | 1.00 12.87 C |
| 1909 | ATOM | 1754 | CG | MET | A | 115 | 22.172 | −48.415 | −27.462 | 1.00 12.80 C |
| 1910 | ATOM | 1755 | SD | MET | A | 115 | 23.274 | −49.510 | −26.514 | 1.00 12.96 S |
| 1911 | ATOM | 1756 | CE | MET | A | 115 | 22.205 | −50.896 | −26.239 | 1.00 13.86 C |
| 1912 | ATOM | 1757 | C | MET | A | 115 | 24.250 | −49.516 | −29.552 | 1.00 12.30 C |
| 1913 | ATOM | 1758 | O | MET | A | 115 | 24.226 | −50.720 | −29.774 | 1.00 11.08 O |
| 1914 | ATOM | 1759 | N | ILE | A | 116 | 25.338 | −48.879 | −29.135 | 1.00 12.37 N |
| 1915 | ATOM | 1760 | CA | ILE | A | 116 | 26.527 | −49.585 | −28.739 | 1.00 13.11 C |
| 1916 | ATOM | 1761 | CB | ILE | A | 116 | 27.735 | −49.259 | −29.642 | 1.00 14.54 C |
| 1917 | ATOM | 1762 | CG1 | ILE | A | 116 | 27.414 | −49.587 | −31.122 | 1.00 17.59 C |
| 1918 | ATOM | 1763 | CD1 | ILE | A | 116 | 27.388 | −48.397 | −32.012 | 1.00 19.85 C |
| 1919 | ATOM | 1764 | CG2 | ILE | A | 116 | 28.960 | −50.059 | −29.241 | 1.00 14.61 C |
| 1920 | ATOM | 1765 | C | ILE | A | 116 | 26.815 | −49.250 | −27.287 | 1.00 12.49 C |
| 1921 | ATOM | 1766 | O | ILE | A | 116 | 26.762 | −48.087 | −26.880 | 1.00 11.42 O |
| 1922 | ATOM | 1767 | N | SER | A | 117 | 27.114 | −50.295 | −26.529 | 1.00 13.49 N |
| 1923 | ATOM | 1768 | CA | SER | A | 117 | 27.554 | −50.197 | −25.143 | 1.00 13.57 C |
| 1924 | ATOM | 1769 | CB | SER | A | 117 | 26.519 | −50.813 | −24.193 | 1.00 14.93 C |
| 1925 | ATOM | 1770 | OG | SER | A | 117 | 27.026 | −50.871 | −22.871 | 1.00 14.54 O |
| 1926 | ATOM | 1771 | C | SER | A | 117 | 28.912 | −50.887 | −25.002 | 1.00 14.56 C |
| 1927 | ATOM | 1772 | O | SER | A | 117 | 29.087 | −52.043 | −25.391 | 1.00 13.16 O |
| 1928 | ATOM | 1773 | N | TYR | A | 118 | 29.888 | −50.156 | −24.453 | 1.00 16.63 N |
| 1929 | ATOM | 1774 | CA | TYR | A | 118 | 31.288 | −50.616 | −24.422 | 1.00 18.82 C |
| 1930 | ATOM | 1775 | CB | TYR | A | 118 | 31.934 | −50.488 | −25.822 | 1.00 19.77 C |
| 1931 | ATOM | 1776 | CG | TYR | A | 118 | 33.235 | −51.255 | −26.092 | 1.00 20.65 C |
| 1932 | ATOM | 1777 | CD1 | TYR | A | 118 | 33.418 | −52.563 | −25.651 | 1.00 21.15 C |
| 1933 | ATOM | 1778 | CE1 | TYR | A | 118 | 34.589 | −53.254 | −25.937 | 1.00 22.00 C |
| 1934 | ATOM | 1779 | CZ | TYR | A | 118 | 35.603 | −52.648 | −26.690 | 1.00 23.86 C |
| 1935 | ATOM | 1780 | OH | TYR | A | 118 | 36.777 | −53.341 | −26.978 | 1.00 24.63 O |
| 1936 | ATOM | 1781 | CE2 | TYR | A | 118 | 35.441 | −51.346 | −27.138 | 1.00 22.46 C |
| 1937 | ATOM | 1782 | CD2 | TYR | A | 118 | 34.256 | −50.672 | −26.862 | 1.00 21.86 C |
| 1938 | ATOM | 1783 | C | TYR | A | 118 | 31.919 | −49.720 | −23.380 | 1.00 21.22 C |
| 1939 | ATOM | 1784 | O | TYR | A | 118 | 32.698 | −48.826 | −23.703 | 1.00 23.28 O |

APPENDIX I-continued

| 1940 | ATOM | 1785 | N | GLY | A | 119 | 31.508 | −49.967 | −22.142 | 1.00 | 21.83 | N |
|---|---|---|---|---|---|---|---|---|---|---|---|---|
| 1941 | ATOM | 1786 | CA | GLY | A | 119 | 31.750 | −49.108 | −20.979 | 1.00 | 24.68 | C |
| 1942 | ATOM | 1787 | C | GLY | A | 119 | 30.519 | −48.211 | −20.811 | 1.00 | 24.52 | C |
| 1943 | ATOM | 1788 | O | GLY | A | 119 | 29.524 | −48.546 | −20.129 | 1.00 | 32.28 | O |
| 1944 | ATOM | 1789 | N | GLY | A | 120 | 30.580 | −47.084 | −21.477 | 1.00 | 21.51 | N |
| 1945 | ATOM | 1790 | CA | GLY | A | 120 | 29.457 | −46.172 | −21.608 | 1.00 | 17.79 | C |
| 1946 | ATOM | 1791 | C | GLY | A | 120 | 28.610 | −46.675 | −22.762 | 1.00 | 15.28 | C |
| 1947 | ATOM | 1792 | O | GLY | A | 120 | 28.847 | −47.765 | −23.301 | 1.00 | 14.96 | O |
| 1948 | ATOM | 1793 | N | ALA | A | 121 | 27.574 | −45.912 | −23.098 | 1.00 | 13.41 | N |
| 1949 | ATOM | 1794 | CA | ALA | A | 121 | 26.702 | −46.287 | −24.199 | 1.00 | 12.18 | C |
| 1950 | ATOM | 1795 | CB | ALA | A | 121 | 25.578 | −47.171 | −23.718 | 1.00 | 12.15 | C |
| 1951 | ATOM | 1796 | C | ALA | A | 121 | 26.125 | −45.037 | −24.901 | 1.00 | 11.67 | C |
| 1952 | ATOM | 1797 | O | ALA | A | 121 | 26.016 | −43.942 | −24.294 | 1.00 | 10.77 | O |
| 1953 | ATOM | 1798 | N | ASP | A | 122 | 25.800 | −45.216 | −26.177 | 1.00 | 11.93 | N |
| 1954 | ATOM | 1799 | CA | ASP | A | 122 | 25.194 | −44.154 | −26.982 | 1.00 | 12.05 | C |
| 1955 | ATOM | 1800 | CB | ASP | A | 122 | 26.262 | −43.133 | −27.376 | 1.00 | 12.43 | C |
| 1956 | ATOM | 1801 | CG | ASP | A | 122 | 25.716 | −41.842 | −27.975 | 1.00 | 12.80 | C |
| 1957 | ATOM | 1802 | OD1 | ASP | A | 122 | 26.493 | −41.217 | −28.732 | 1.00 | 13.47 | O |
| 1958 | ATOM | 1803 | OD2 | ASP | A | 122 | 24.561 | −41.422 | −27.705 | 1.00 | 13.90 | O |
| 1959 | ATOM | 1804 | C | ASP | A | 122 | 24.537 | −44.792 | −28.202 | 1.00 | 12.57 | C |
| 1960 | ATOM | 1805 | O | ASP | A | 122 | 24.623 | −46.007 | −28.409 | 1.00 | 12.75 | O |
| 1961 | ATOM | 1806 | N | TYR | A | 123 | 23.852 | −43.975 | −28.988 | 1.00 | 12.44 | N |
| 1962 | ATOM | 1807 | CA | TYR | A | 123 | 23.133 | −44.481 | −30.150 | 1.00 | 13.08 | C |
| 1963 | ATOM | 1808 | CB | TYR | A | 123 | 21.706 | −44.924 | −29.730 | 1.00 | 13.51 | C |
| 1964 | ATOM | 1809 | CG | TYR | A | 123 | 20.915 | −43.833 | −29.042 | 1.00 | 15.31 | C |
| 1965 | ATOM | 1810 | CD1 | TYR | A | 123 | 20.857 | −43.731 | −27.647 | 1.00 | 15.77 | C |
| 1966 | ATOM | 1811 | CE1 | TYR | A | 123 | 20.162 | −42.701 | −27.037 | 1.00 | 17.57 | C |
| 1967 | ATOM | 1812 | CZ | TYR | A | 123 | 19.518 | −41.780 | −27.805 | 1.00 | 17.56 | C |
| 1968 | ATOM | 1813 | OH | TYR | A | 123 | 18.816 | −40.752 | −27.224 | 1.00 | 19.78 | O |
| 1969 | ATOM | 1814 | CE2 | TYR | A | 123 | 19.542 | −41.861 | −29.185 | 1.00 | 16.95 | C |
| 1970 | ATOM | 1815 | CD2 | TYR | A | 123 | 20.241 | −42.880 | −29.791 | 1.00 | 16.19 | C |
| 1971 | ATOM | 1816 | C | TYR | A | 123 | 23.069 | −43.400 | −31.197 | 1.00 | 12.85 | C |
| 1972 | ATOM | 1817 | O | TYR | A | 123 | 23.187 | −42.207 | −30.893 | 1.00 | 12.16 | O |
| 1973 | ATOM | 1818 | N | LYS | A | 124 | 22.847 | −43.835 | −32.439 | 1.00 | 12.54 | N |
| 1974 | ATOM | 1819 | CA | LYS | A | 124 | 22.566 | −42.931 | −33.557 | 1.00 | 12.16 | C |
| 1975 | ATOM | 1820 | CB | LYS | A | 124 | 23.840 | −42.604 | −34.362 | 1.00 | 12.63 | C |
| 1976 | ATOM | 1821 | CG | LYS | A | 124 | 24.889 | −41.749 | −33.669 | 1.00 | 12.79 | C |
| 1977 | ATOM | 1822 | CD | LYS | A | 124 | 24.309 | −40.349 | −33.427 | 1.00 | 13.24 | C |
| 1978 | ATOM | 1823 | CE | LYS | A | 124 | 25.224 | −39.413 | −32.680 | 1.00 | 13.52 | C |
| 1979 | ATOM | 1824 | NZ | LYS | A | 124 | 25.491 | −39.912 | −31.298 | 1.00 | 13.53 | N |
| 1980 | ATOM | 1825 | C | LYS | A | 124 | 21.557 | −43.555 | −34.503 | 1.00 | 13.21 | C |
| 1981 | ATOM | 1826 | O | LYS | A | 124 | 21.449 | −44.779 | −34.610 | 1.00 | 12.50 | O |
| 1982 | ATOM | 1827 | N | ARG | A | 125 | 20.863 | −42.686 | −35.233 | 1.00 | 13.36 | N |
| 1983 | ATOM | 1828 | CA | ARG | A | 125 | 19.914 | −43.093 | −36.259 | 1.00 | 14.01 | C |
| 1984 | ATOM | 1829 | CB | ARG | A | 125 | 18.611 | −42.326 | −36.092 | 1.00 | 15.18 | C |
| 1985 | ATOM | 1830 | CG | ARG | A | 125 | 17.845 | −42.632 | −34.811 | 1.00 | 17.57 | C |
| 1986 | ATOM | 1831 | CD | ARG | A | 125 | 16.597 | −41.783 | −34.641 | 1.00 | 19.32 | C |
| 1987 | ATOM | 1832 | NE | ARG | A | 125 | 16.156 | −41.891 | −33.252 | 1.00 | 25.95 | N |
| 1988 | ATOM | 1833 | CZ | ARG | A | 125 | 16.585 | −41.141 | −32.241 | 1.00 | 27.16 | C |
| 1989 | ATOM | 1834 | NH1 | ARG | A | 125 | 17.462 | −40.146 | −32.417 | 1.00 | 29.63 | N |
| 1990 | ATOM | 1835 | NH2 | ARG | A | 125 | 16.092 | −41.368 | −31.031 | 1.00 | 31.58 | N |
| 1991 | ATOM | 1836 | C | ARG | A | 125 | 20.429 | −42.841 | −37.679 | 1.00 | 14.15 | C |
| 1992 | ATOM | 1837 | O | ARG | A | 125 | 21.085 | −41.836 | −37.932 | 1.00 | 13.00 | O |
| 1993 | ATOM | 1838 | N | ILE | A | 126 | 20.044 | −43.728 | −38.588 | 1.00 | 13.53 | N |
| 1994 | ATOM | 1839 | CA | ILE | A | 126 | 20.409 | −43.672 | −39.997 | 1.00 | 13.03 | C |
| 1995 | ATOM | 1840 | CB | ILE | A | 126 | 21.457 | −44.751 | −40.334 | 1.00 | 13.03 | C |
| 1996 | ATOM | 1841 | CG1 | ILE | A | 126 | 22.771 | −44.499 | −39.573 | 1.00 | 12.94 | C |
| 1997 | ATOM | 1842 | CD1 | ILE | A | 126 | 23.712 | −45.675 | −39.652 | 1.00 | 13.12 | C |
| 1998 | ATOM | 1843 | CG2 | ILE | A | 126 | 21.685 | −44.832 | −41.838 | 1.00 | 13.15 | C |
| 1999 | ATOM | 1844 | C | ILE | A | 126 | 19.143 | −43.955 | −40.807 | 1.00 | 12.83 | C |
| 2000 | ATOM | 1845 | O | ILE | A | 126 | 18.427 | −44.926 | −40.533 | 1.00 | 12.94 | O |
| 2001 | ATOM | 1846 | N | THR | A | 127 | 18.849 | −43.089 | −41.767 | 1.00 | 12.85 | N |
| 2002 | ATOM | 1847 | CA | THR | A | 127 | 17.715 | −43.298 | −42.652 | 1.00 | 13.06 | C |
| 2003 | ATOM | 1848 | CB | THR | A | 127 | 17.064 | −41.944 | −43.016 | 1.00 | 13.83 | C |
| 2004 | ATOM | 1849 | OG1 | THR | A | 127 | 16.547 | −41.320 | −41.834 | 1.00 | 13.37 | O |
| 2005 | ATOM | 1850 | CG2 | THR | A | 127 | 15.916 | −42.127 | −44.019 | 1.00 | 14.47 | C |
| 2006 | ATOM | 1851 | C | THR | A | 127 | 18.167 | −43.983 | −43.931 | 1.00 | 13.53 | C |
| 2007 | ATOM | 1852 | O | THR | A | 127 | 19.217 | −43.625 | −44.517 | 1.00 | 12.83 | O |
| 2008 | ATOM | 1853 | N | VAL | A | 128 | 17.360 | −44.934 | −44.415 | 1.00 | 13.32 | N |
| 2009 | ATOM | 1854 | CA | VAL | A | 128 | 17.623 | −45.589 | −45.696 | 1.00 | 14.05 | C |
| 2010 | ATOM | 1855 | CB | VAL | A | 128 | 17.833 | −47.114 | −45.523 | 1.00 | 13.76 | C |
| 2011 | ATOM | 1856 | CG1 | VAL | A | 128 | 17.926 | −47.817 | −46.872 | 1.00 | 14.60 | C |
| 2012 | ATOM | 1857 | CG2 | VAL | A | 128 | 19.070 | −47.383 | −44.680 | 1.00 | 14.43 | C |
| 2013 | ATOM | 1858 | C | VAL | A | 128 | 16.445 | −45.327 | −46.621 | 1.00 | 14.32 | C |
| 2014 | ATOM | 1859 | O | VAL | A | 128 | 15.298 | −45.534 | −46.228 | 1.00 | 14.69 | O |
| 2015 | ATOM | 1860 | N | LYS | A | 129 | 16.735 | −44.850 | −47.827 | 1.00 | 15.36 | N |
| 2016 | ATOM | 1861 | CA | LYS | A | 129 | 15.722 | −44.742 | −48.894 | 1.00 | 17.48 | C |
| 2017 | ATOM | 1862 | CB | LYS | A | 129 | 15.728 | −43.352 | −49.529 | 1.00 | 19.55 | C |
| 2018 | ATOM | 1863 | CG | LYS | A | 129 | 15.455 | −42.245 | −48.530 | 1.00 | 21.72 | C |
| 2019 | ATOM | 1864 | CD | LYS | A | 129 | 15.177 | −40.894 | −49.193 | 1.00 | 25.38 | C |

APPENDIX I-continued

| | | | | | | | | | | |
|---|---|---|---|---|---|---|---|---|---|---|
| 2020 | ATOM | 1865 | CE | LYS | A | 129 | 14.742 | −39.839 | −48.169 | 1.00 | 26.92 C |
| 2021 | ATOM | 1866 | NZ | LYS | A | 129 | 13.834 | −40.380 | −47.088 | 1.00 | 28.71 N |
| 2022 | ATOM | 1867 | C | LYS | A | 129 | 16.058 | −45.769 | −49.948 | 1.00 | 17.29 C |
| 2023 | ATOM | 1868 | O | LYS | A | 129 | 17.224 | −45.961 | −50.260 | 1.00 | 16.75 O |
| 2024 | ATOM | 1869 | N | VAL | A | 130 | 15.028 | −46.421 | −50.485 | 1.00 | 17.25 N |
| 2025 | ATOM | 1870 | CA | VAL | A | 130 | 15.193 | −47.445 | −51.492 | 1.00 | 18.24 C |
| 2026 | ATOM | 1871 | CB | VAL | A | 130 | 14.616 | −48.810 | −51.035 | 1.00 | 17.69 C |
| 2027 | ATOM | 1872 | CG1 | VAL | A | 130 | 14.786 | −49.847 | −52.132 | 1.00 | 17.98 C |
| 2028 | ATOM | 1873 | CG2 | VAL | A | 130 | 15.314 | −49.271 | −49.764 | 1.00 | 17.76 C |
| 2029 | ATOM | 1874 | C | VAL | A | 130 | 14.478 | −47.005 | −52.759 | 1.00 | 19.71 C |
| 2030 | ATOM | 1875 | O | VAL | A | 130 | 13.335 | −46.605 | −52.715 | 1.00 | 20.19 O |
| 2031 | ATOM | 1876 | N | ASN | A | 131 | 15.185 | −47.059 | −53.874 | 1.00 | 22.04 N |
| 2032 | ATOM | 1877 | CA | ASN | A | 131 | 14.603 | −46.761 | −55.190 | 1.00 | 24.23 C |
| 2033 | ATOM | 1878 | CB | ASN | A | 131 | 15.558 | −45.873 | −55.965 | 1.00 | 24.48 C |
| 2034 | ATOM | 1879 | CG | ASN | A | 131 | 15.665 | −44.487 | −55.359 | 1.00 | 25.82 C |
| 2035 | ATOM | 1880 | OD1 | ASN | A | 131 | 14.720 | −44.000 | −54.735 | 1.00 | 27.38 O |
| 2036 | ATOM | 1881 | ND2 | ASN | A | 131 | 16.803 | −43.847 | −55.539 | 1.00 | 26.19 N |
| 2037 | ATOM | 1882 | C | ASN | A | 131 | 14.327 | −48.042 | −55.949 | 1.00 | 26.56 C |
| 2038 | ATOM | 1883 | O | ASN | A | 131 | 15.007 | −49.035 | −55.722 | 1.00 | 26.66 O |
| 2039 | ATOM | 1884 | N | ALA | A | 132 | 13.305 | −48.018 | −56.813 | 1.00 | 28.59 N |
| 2040 | ATOM | 1885 | CA | ALA | A | 132 | 12.965 | −49.130 | −57.721 | 1.00 | 29.74 C |
| 2041 | ATOM | 1886 | CB | ALA | A | 132 | 11.652 | −49.790 | −57.316 | 1.00 | 29.90 C |
| 2042 | ATOM | 1887 | C | ALA | A | 132 | 12.863 | −48.617 | −59.150 | 1.00 | 29.48 C |
| 2043 | ATOM | 1888 | O | ALA | A | 132 | 13.878 | −48.366 | −59.792 | 1.00 | 31.04 O |
| 2044 | HETATM | 1889 | O | HOH | C | 1 | 37.188 | −45.275 | −39.513 | 1.00 | 26.27 O |
| 2045 | HETATM | 1890 | O | HOH | C | 2 | 35.043 | −46.132 | −42.489 | 1.00 | 23.40 O |
| 2046 | HETATM | 1891 | O | HOH | C | 3 | 24.038 | −43.123 | −50.394 | 1.00 | 23.72 O |
| 2047 | HETATM | 1892 | O | HOH | C | 4 | 24.139 | −41.577 | −8.135 | 1.00 | 25.62 O |
| 2048 | HETATM | 1893 | O | HOH | C | 5 | 36.489 | −57.402 | −34.644 | 1.00 | 21.94 O |
| 2049 | HETATM | 1894 | O | HOH | C | 6 | 33.105 | −59.496 | −40.650 | 1.00 | 23.99 O |
| 2050 | HETATM | 1895 | O | HOH | C | 7 | 32.426 | −42.152 | −32.126 | 1.00 | 27.03 O |
| 2051 | HETATM | 1896 | O | HOH | C | 8 | 3.363 | −58.326 | −20.205 | 1.00 | 25.32 O |
| 2052 | HETATM | 1897 | O | HOH | C | 10 | 6.142 | −48.920 | −21.236 | 1.00 | 25.95 O |
| 2053 | HETATM | 1898 | O | HOH | C | 11 | −4.537 | −50.482 | −15.782 | 1.00 | 25.66 O |
| 2054 | HETATM | 1899 | O | HOH | C | 12 | 40.334 | −53.095 | −30.922 | 1.00 | 27.77 O |
| 2055 | HETATM | 1900 | O | HOH | C | 13 | 17.046 | −59.332 | −10.069 | 1.00 | 26.11 O |
| 2056 | HETATM | 1901 | O | HOH | C | 14 | 23.405 | −41.114 | −25.302 | 1.00 | 26.12 O |
| 2057 | HETATM | 1902 | O | HOH | C | 15 | 4.627 | −50.112 | −19.101 | 1.00 | 22.53 O |
| 2058 | HETATM | 1903 | O | HOH | C | 16 | 12.491 | −46.465 | −28.584 | 1.00 | 22.97 O |
| 2059 | HETATM | 1904 | O | HOH | C | 17 | 34.344 | −57.368 | −42.654 | 1.00 | 29.07 O |
| 2060 | HETATM | 1905 | O | HOH | C | 19 | 19.641 | −35.621 | −10.719 | 1.00 | 29.56 O |
| 2061 | HETATM | 1906 | O | HOH | C | 21 | 6.417 | −52.372 | −7.734 | 1.00 | 28.26 O |
| 2062 | HETATM | 1907 | O | HOH | C | 22 | 11.430 | −44.670 | −30.348 | 1.00 | 22.95 O |
| 2063 | HETATM | 1908 | O | HOH | C | 23 | 21.370 | −37.022 | −38.362 | 1.00 | 25.74 O |
| 2064 | HETATM | 1909 | O | HOH | C | 24 | 30.589 | −54.440 | −37.158 | 1.00 | 17.18 O |
| 2065 | HETATM | 1910 | O | HOH | C | 26 | 25.783 | −50.440 | −20.482 | 1.00 | 18.26 O |
| 2066 | HETATM | 1911 | O | HOH | C | 27 | 14.572 | −44.402 | −32.161 | 1.00 | 17.47 O |
| 2067 | HETATM | 1912 | O | HOH | C | 28 | 12.389 | −61.032 | −21.231 | 1.00 | 15.25 O |
| 2068 | HETATM | 1913 | O | HOH | C | 30 | 26.627 | −44.259 | −41.415 | 1.00 | 19.76 O |
| 2069 | HETATM | 1914 | O | HOH | C | 31 | 14.453 | −53.188 | −31.308 | 1.00 | 14.67 O |
| 2070 | HETATM | 1915 | O | HOH | C | 32 | 6.581 | −54.988 | −28.481 | 1.00 | 15.20 O |
| 2071 | HETATM | 1916 | O | HOH | C | 34 | 16.601 | −61.143 | −18.655 | 1.00 | 18.33 O |
| 2072 | HETATM | 1917 | O | HOH | C | 35 | 13.213 | −65.051 | −32.498 | 1.00 | 19.97 O |
| 2073 | HETATM | 1918 | O | HOH | C | 37 | 20.569 | −39.673 | −34.207 | 1.00 | 17.66 O |
| 2074 | HETATM | 1919 | O | HOH | C | 38 | 12.902 | −59.761 | −25.696 | 1.00 | 19.30 O |
| 2075 | HETATM | 1920 | O | HOH | C | 39 | 4.976 | −51.110 | −23.664 | 1.00 | 21.24 O |
| 2076 | HETATM | 1921 | O | HOH | C | 40 | 25.110 | −61.309 | −37.580 | 1.00 | 23.32 O |
| 2077 | HETATM | 1922 | O | HOH | C | 41 | 31.102 | −61.518 | −39.509 | 1.00 | 28.33 O |
| 2078 | HETATM | 1923 | O | HOH | C | 42 | 13.537 | −47.104 | −31.318 | 1.00 | 24.38 O |
| 2079 | HETATM | 1924 | O | HOH | C | 43 | 11.955 | −56.649 | −31.970 | 1.00 | 18.30 O |
| 2080 | HETATM | 1925 | O | HOH | C | 44 | 8.902 | −51.189 | −35.285 | 1.00 | 23.42 O |
| 2081 | HETATM | 1926 | O | HOH | C | 45 | 3.547 | −50.732 | −30.197 | 1.00 | 26.22 O |
| 2082 | HETATM | 1927 | O | HOH | C | 46 | 24.103 | −47.875 | −14.146 | 1.00 | 23.60 O |
| 2083 | HETATM | 1928 | O | HOH | C | 47 | 12.692 | −37.944 | −23.026 | 1.00 | 26.51 O |
| 2084 | HETATM | 1929 | O | HOH | C | 48 | 30.009 | −58.748 | −27.529 | 1.00 | 29.75 O |
| 2085 | HETATM | 1930 | O | HOH | C | 49 | 33.292 | −40.729 | −36.495 | 1.00 | 21.73 O |
| 2086 | HETATM | 1931 | O | HOH | C | 50 | 30.867 | −37.812 | −42.975 | 1.00 | 21.72 O |
| 2087 | HETATM | 1932 | O | HOH | C | 51 | 22.912 | −45.909 | 4.337 | 1.00 | 32.59 O |
| 2088 | HETATM | 1933 | O | HOH | C | 52 | 24.128 | −59.784 | −45.063 | 1.00 | 30.82 O |
| 2089 | HETATM | 1934 | O | HOH | C | 53 | 20.895 | −36.365 | −44.556 | 1.00 | 25.76 O |
| 2090 | HETATM | 1935 | O | HOH | C | 54 | 36.124 | −51.393 | −30.950 | 1.00 | 32.31 O |
| 2091 | HETATM | 1936 | O | HOH | C | 55 | 38.157 | −52.486 | −29.304 | 1.00 | 23.58 O |
| 2092 | HETATM | 1937 | O | HOH | C | 56 | 27.544 | −65.480 | −33.031 | 1.00 | 25.59 O |
| 2093 | HETATM | 1938 | O | HOH | C | 57 | 23.650 | −60.114 | −12.092 | 1.00 | 30.65 O |
| 2094 | HETATM | 1939 | O | HOH | C | 58 | 36.621 | −45.288 | −32.882 | 1.00 | 25.25 O |
| 2095 | HETATM | 1940 | O | HOH | C | 59 | 20.110 | −61.890 | −33.877 | 1.00 | 28.24 O |
| 2096 | HETATM | 1941 | O | HOH | C | 60 | 5.043 | −42.258 | −1.805 | 1.00 | 29.26 O |
| 2097 | HETATM | 1942 | O | HOH | C | 61 | 19.890 | −65.384 | −35.609 | 1.00 | 26.84 O |
| 2098 | HETATM | 1943 | O | HOH | C | 62 | 14.946 | −59.805 | −30.085 | 1.00 | 25.34 O |
| 2099 | HETATM | 1944 | O | HOH | C | 63 | 32.261 | −41.042 | −38.960 | 1.00 | 32.92 O |

APPENDIX I-continued

| | | | | | | | | | | |
|---|---|---|---|---|---|---|---|---|---|---|
| 2100 | HETATM | 1945 | O | HOH | C | 64 | 33.591 | −40.996 | −27.369 | 1.00 | 28.61 O |
| 2101 | HETATM | 1946 | O | HOH | C | 65 | 26.786 | −48.816 | −16.493 | 1.00 | 30.52 O |
| 2102 | HETATM | 1947 | O | HOH | C | 66 | 24.885 | −44.670 | −16.175 | 1.00 | 25.55 O |
| 2103 | HETATM | 1948 | O | HOH | C | 67 | 5.200 | −37.213 | −3.900 | 1.00 | 23.49 O |
| 2104 | HETATM | 1949 | O | HOH | C | 68 | 35.994 | −47.110 | −37.312 | 1.00 | 27.56 O |
| 2105 | HETATM | 1950 | O | HOH | C | 69 | 10.974 | −56.523 | −9.191 | 1.00 | 25.89 O |
| 2106 | HETATM | 1951 | O | HOH | C | 70 | 36.681 | −53.952 | −45.239 | 1.00 | 24.89 O |
| 2107 | HETATM | 1952 | O | HOH | C | 71 | 21.318 | −42.962 | −3.829 | 1.00 | 28.30 O |
| 2108 | HETATM | 1953 | O | HOH | C | 72 | 14.966 | −59.821 | −16.578 | 1.00 | 25.63 O |
| 2109 | HETATM | 1954 | O | HOH | C | 73 | 4.162 | −56.203 | −13.190 | 1.00 | 32.94 O |
| 2110 | HETATM | 1955 | O | HOH | C | 74 | 11.621 | −61.664 | −13.746 | 1.00 | 28.10 O |
| 2111 | HETATM | 1956 | O | HOH | C | 76 | 39.116 | −57.250 | −36.443 | 1.00 | 28.70 O |
| 2112 | HETATM | 1957 | O | HOH | C | 77 | 9.948 | −50.192 | 4.847 | 1.00 | 33.01 O |
| 2113 | HETATM | 1958 | O | HOH | C | 78 | 8.566 | −53.649 | −33.320 | 1.00 | 14.56 O |
| 2114 | HETATM | 1959 | O | HOH | C | 79 | 32.765 | −37.971 | −36.210 | 1.00 | 22.93 O |
| 2115 | HETATM | 1960 | O | HOH | C | 81 | 25.373 | −55.468 | −17.364 | 1.00 | 29.85 O |
| 2116 | HETATM | 1961 | O | HOH | C | 82 | 30.457 | −42.342 | −20.837 | 1.00 | 39.12 O |
| 2117 | HETATM | 1962 | O | HOH | C | 83 | 15.008 | −46.840 | −35.215 | 1.00 | 30.91 O |
| 2118 | HETATM | 1963 | O | HOH | C | 86 | 36.801 | −52.770 | −47.629 | 1.00 | 26.00 O |
| 2119 | HETATM | 1964 | O | HOH | C | 87 | 31.488 | −36.598 | −40.467 | 1.00 | 27.74 O |
| 2120 | HETATM | 1965 | O | HOH | C | 89 | 28.371 | −58.174 | −23.747 | 1.00 | 26.49 O |
| 2121 | HETATM | 1966 | O | HOH | C | 90 | 4.742 | −53.305 | −5.630 | 1.00 | 38.65 O |
| 2122 | HETATM | 1967 | O | HOH | C | 91 | 9.527 | −42.476 | 7.815 | 1.00 | 32.33 O |
| 2123 | HETATM | 1968 | O | HOH | C | 92 | 12.226 | −32.701 | −11.441 | 1.00 | 33.55 O |
| 2124 | HETATM | 1969 | O | HOH | C | 93 | 4.700 | −36.587 | −7.102 | 1.00 | 35.46 O |
| 2125 | HETATM | 1970 | O | HOH | C | 94 | 24.469 | −52.674 | −7.233 | 1.00 | 29.01 O |
| 2126 | HETATM | 1971 | O | HOH | C | 95 | 27.154 | −41.518 | −23.710 | 1.00 | 32.26 O |
| 2127 | HETATM | 1972 | O | HOH | C | 96 | 12.511 | −61.826 | −23.898 | 1.00 | 26.55 O |
| 2128 | HETATM | 1973 | O | HOH | C | 97 | 2.740 | −42.317 | −5.104 | 1.00 | 39.12 O |
| 2129 | HETATM | 1974 | O | HOH | C | 98 | 13.201 | −30.635 | −13.114 | 1.00 | 27.04 O |
| 2130 | HETATM | 1975 | O | HOH | C | 99 | 9.219 | −56.229 | −33.019 | 1.00 | 31.25 O |
| 2131 | HETATM | 1976 | O | HOH | C | 100 | 22.953 | −39.684 | −29.075 | 1.00 | 34.70 O |
| 2132 | HETATM | 1977 | O | HOH | C | 101 | 16.238 | −36.572 | −17.213 | 1.00 | 45.18 O |
| 2133 | HETATM | 1978 | O | HOH | C | 102 | 13.011 | −43.819 | −45.817 | 1.00 | 30.05 O |
| 2134 | HETATM | 1979 | O | HOH | C | 103 | 30.242 | −37.572 | −37.174 | 1.00 | 36.14 O |
| 2135 | HETATM | 1980 | O | HOH | C | 104 | 3.159 | −40.030 | −20.096 | 1.00 | 34.06 O |
| 2136 | HETATM | 1981 | O | HOH | C | 105 | 13.171 | −63.127 | −19.750 | 1.00 | 23.69 O |
| 2137 | HETATM | 1982 | O | HOH | C | 106 | 23.513 | −50.662 | −12.086 | 1.00 | 37.44 O |
| 2138 | HETATM | 1983 | O | HOH | C | 107 | 9.056 | −57.668 | −26.633 | 1.00 | 30.29 O |
| 2139 | HETATM | 1984 | O | HOH | C | 108 | 18.154 | −34.523 | 0.054 | 1.00 | 29.96 O |
| 2140 | HETATM | 1985 | O | HOH | C | 109 | 21.619 | −48.243 | −1.720 | 1.00 | 32.32 O |
| 2141 | HETATM | 1986 | O | HOH | C | 110 | 9.391 | −37.785 | −21.032 | 1.00 | 27.36 O |
| 2142 | HETATM | 1987 | O | HOH | C | 111 | 26.832 | −54.159 | −49.008 | 1.00 | 35.12 O |
| 2143 | HETATM | 1988 | O | HOH | C | 112 | 10.535 | −45.824 | −33.264 | 1.00 | 39.29 O |
| 2144 | HETATM | 1989 | O | HOH | C | 113 | 4.064 | −57.390 | −15.759 | 1.00 | 30.25 O |
| 2145 | HETATM | 1990 | O | HOH | C | 114 | −4.236 | −46.128 | −18.412 | 1.00 | 40.09 O |
| 2146 | HETATM | 1991 | O | HOH | C | 115 | 17.114 | −61.679 | −30.956 | 1.00 | 36.01 O |
| 2147 | HETATM | 1992 | O | HOH | C | 116 | 13.952 | −37.971 | −26.054 | 1.00 | 34.17 O |
| 2148 | HETATM | 1993 | O | HOH | C | 117 | 22.398 | −49.062 | −54.419 | 1.00 | 37.00 O |
| 2149 | HETATM | 1994 | O | HOH | C | 118 | 9.992 | −52.191 | −38.312 | 1.00 | 34.78 O |
| 2150 | HETATM | 1995 | O | HOH | C | 119 | 37.049 | −60.456 | −25.057 | 1.00 | 38.41 O |
| 2151 | HETATM | 1996 | O | HOH | C | 120 | 17.550 | −40.983 | −39.503 | 1.00 | 32.32 O |
| 2152 | HETATM | 1997 | O | HOH | C | 121 | 3.547 | −55.239 | −23.394 | 1.00 | 27.96 O |
| 2153 | HETATM | 1998 | O | HOH | C | 122 | 25.808 | −37.512 | −29.438 | 1.00 | 35.29 O |
| 2154 | HETATM | 1999 | O | HOH | C | 123 | 0.234 | −44.484 | −9.232 | 1.00 | 41.65 O |
| 2155 | HETATM | 2000 | O | HOH | C | 124 | 12.296 | −45.387 | −49.897 | 1.00 | 33.71 O |
| 2156 | HETATM | 2001 | O | HOH | C | 125 | 2.401 | −53.000 | −8.538 | 1.00 | 40.92 O |
| 2157 | HETATM | 2002 | O | HOH | C | 126 | 29.881 | −54.866 | −46.845 | 1.00 | 36.75 O |
| 2158 | HETATM | 2003 | O | HOH | C | 127 | 7.054 | −57.092 | −11.445 | 1.00 | 34.64 O |
| 2159 | HETATM | 2004 | O | HOH | C | 128 | 32.443 | −55.531 | −46.350 | 1.00 | 30.67 O |
| 2160 | HETATM | 2005 | O | HOH | C | 129 | 34.161 | −55.075 | −44.344 | 1.00 | 26.86 O |
| 2161 | HETATM | 2006 | O | HOH | C | 130 | 6.459 | −62.252 | −16.352 | 1.00 | 27.95 O |
| 2162 | HETATM | 2007 | O | HOH | C | 131 | 27.963 | −53.499 | −22.670 | 1.00 | 36.75 O |
| 2163 | HETATM | 2008 | O | HOH | C | 132 | 27.316 | −64.019 | −35.495 | 1.00 | 32.63 O |
| 2164 | HETATM | 2009 | O | HOH | C | 133 | −0.197 | −44.690 | −21.887 | 1.00 | 35.38 O |
| 2165 | HETATM | 2010 | O | HOH | C | 135 | 4.483 | −53.619 | −27.504 | 1.00 | 33.65 O |
| 2166 | HETATM | 2011 | O | HOH | C | 136 | 13.820 | −61.135 | −27.849 | 1.00 | 31.22 O |
| 2167 | HETATM | 2012 | O | HOH | C | 137 | 0.094 | −44.328 | −25.157 | 1.00 | 35.33 O |
| 2168 | HETATM | 2013 | O | HOH | C | 138 | 14.157 | −40.143 | −41.816 | 1.00 | 35.12 O |
| 2169 | HETATM | 2014 | O | HOH | C | 139 | 12.462 | −45.417 | −57.965 | 1.00 | 45.23 O |
| 2170 | HETATM | 2015 | O | HOH | C | 140 | 0.088 | −48.546 | −22.309 | 1.00 | 40.36 O |
| 2171 | HETATM | 2016 | O | HOH | C | 141 | 20.825 | −40.817 | −22.386 | 1.00 | 29.92 O |
| 2172 | HETATM | 2017 | O | HOH | C | 142 | 0.232 | −42.990 | −18.830 | 1.00 | 35.48 O |
| 2173 | HETATM | 2018 | O | HOH | C | 143 | 7.776 | −44.216 | −31.365 | 1.00 | 42.13 O |
| 2174 | HETATM | 2019 | O | HOH | C | 144 | 10.173 | −37.899 | −23.522 | 1.00 | 43.13 O |
| 2175 | HETATM | 2020 | O | HOH | C | 145 | 27.913 | −48.735 | −47.681 | 1.00 | 31.07 O |
| 2176 | HETATM | 2021 | O | HOH | C | 146 | 22.318 | −39.796 | −36.682 | 1.00 | 29.90 O |
| 2177 | HETATM | 2022 | O | HOH | C | 147 | 15.955 | −33.312 | −13.044 | 1.00 | 39.44 O |
| 2178 | HETATM | 2023 | O | HOH | C | 148 | 22.719 | −40.558 | −1.363 | 1.00 | 38.00 O |
| 2179 | HETATM | 2024 | O | HOH | C | 149 | 0.579 | −40.377 | −19.825 | 1.00 | 39.83 O |

APPENDIX I-continued

| | | | | | | | | | | |
|---|---|---|---|---|---|---|---|---|---|---|
| 2180 | HETATM | 2025 O | HOH | C | 151 | 17.096 | −70.551 | −35.722 | 1.00 | 37.16 O |
| 2181 | HETATM | 2026 O | HOH | C | 152 | 7.320 | −61.746 | −32.342 | 1.00 | 47.66 O |
| 2182 | HETATM | 2027 O | HOH | C | 153 | 19.651 | −39.577 | −38.429 | 1.00 | 33.53 O |
| 2183 | HETATM | 2028 O | HOH | C | 154 | 6.474 | −58.365 | −14.123 | 1.00 | 32.60 O |
| 2184 | HETATM | 2029 O | HOH | C | 155 | 18.348 | −38.632 | −35.639 | 1.00 | 42.22 O |
| 2185 | HETATM | 2030 O | HOH | C | 156 | 11.929 | −71.559 | −36.715 | 1.00 | 38.43 O |
| 2186 | HETATM | 2031 O | HOH | C | 157 | 22.843 | −49.119 | −8.696 | 1.00 | 44.43 O |
| 2187 | HETATM | 2032 O | HOH | C | 158 | −3.074 | −50.433 | −22.982 | 1.00 | 32.63 O |
| 2188 | HETATM | 2033 O | HOH | C | 159 | 49.707 | −49.496 | −25.578 | 1.00 | 43.76 O |
| 2189 | HETATM | 2034 O | HOH | C | 166 | 19.391 | −54.307 | −0.825 | 1.00 | 40.03 O |
| 2190 | HETATM | 2035 O | HOH | C | 168 | 7.809 | −44.766 | 5.694 | 1.00 | 37.87 O |
| 2191 | HETATM | 2036 O | HOH | C | 170 | 0.301 | −46.377 | −6.359 | 1.00 | 35.05 O |
| 2192 | HETATM | 2037 O | HOH | C | 171 | 38.892 | −45.123 | −27.414 | 1.00 | 29.19 O |
| 2193 | HETATM | 2038 O | HOH | C | 172 | 13.526 | −66.322 | −42.158 | 1.00 | 40.46 O |
| 2194 | HETATM | 2039 O | HOH | C | 173 | 9.999 | −54.912 | −52.120 | 1.00 | 41.44 O |
| 2195 | HETATM | 2040 O | HOH | C | 174 | −0.051 | −42.166 | −8.364 | 1.00 | 35.26 O |
| 2196 | HETATM | 2041 O | HOH | C | 175 | 29.834 | −41.270 | −10.110 | 1.00 | 45.67 O |
| 2197 | HETATM | 2042 O | HOH | C | 176 | 23.360 | −43.360 | −6.029 | 1.00 | 36.04 O |
| 2198 | HETATM | 2043 O | HOH | C | 177 | 36.074 | −47.721 | −25.561 | 1.00 | 37.27 O |
| 2199 | HETATM | 2044 O | HOH | C | 180 | 27.496 | −38.455 | −35.813 | 1.00 | 12.13 O |
| 2200 | HETATM | 2045 O | HOH | C | 181 | 26.703 | −43.726 | −20.624 | 1.00 | 26.42 O |
| 2201 | HETATM | 2046 O | HOH | C | 182 | 48.441 | −45.478 | −24.997 | 1.00 | 35.65 O |
| 2202 | HETATM | 2047 O | HOH | C | 183 | −1.423 | −46.138 | −10.881 | 1.00 | 40.09 O |
| 2203 | HETATM | 2048 O4 | SO4 | D | 1 | 18.846 | −38.312 | −28.292 | 0.65 | 44.33 O |
| 2204 | HETATM | 2049 S | SO4 | D | 1 | 17.663 | −38.195 | −29.167 | 0.65 | 41.61 S |
| 2205 | HETATM | 2050 O1 | SO4 | D | 1 | 18.115 | −38.161 | −30.579 | 0.65 | 38.73 O |
| 2206 | HETATM | 2051 O2 | SO4 | D | 1 | 16.961 | −36.931 | −28.870 | 0.65 | 41.36 O |
| 2207 | HETATM | 2052 O3 | SO4 | D | 1 | 16.766 | −39.319 | −28.897 | 0.65 | 36.23 O |
| 2208 | HETATM | 2053 NA | NA | G | 1 | −4.618 | −51.923 | −13.118 | 1.00 | 52.27 NA |
| 2209 | HETATM | 2054 NA | NA | I | 1 | 41.625 | −57.214 | −31.414 | 1.00 | 35.45 NA |
| 2210 | HETATM | 2055 CL | CL | E | 1 | 24.028 | −55.339 | −9.940 | 1.00 | 42.19 CL |
| 2211 | HETATM | 2056 CL | CL | L | 1 | 20.019 | −52.512 | −12.655 | 1.00 | 32.69 CL |
| 2212 | HETATM | 2057 CL | CL | H | 1 | −3.177 | −53.552 | −12.089 | 1.00 | 60.33 CL |

---

The invention claimed is:

1. An isolated polypeptide comprising an amino acid sequence set forth in SEQ ID NO: 4, which is capable of specifically binding to human PD-L1 and blocking the interaction of PD-L1 and PD1,
wherein the polypeptide does not comprise the amino acid sequence of SEQ ID NO: 2 and/or SEQ ID NO: 3, and
wherein the polypeptide comprises the amino acid sequence of any one of SEQ ID NOs: 10, 12, 16-18, 20, and/or 23.

2. A method of producing a polypeptide that binds to PD-L1 and an additional target, comprising replacing the CDR1 and/or the CDR2 of the antibody of SEQ ID NO: 1 with CDR(s) of an antibody that recognizes the additional target and/or a polypeptide that binds to the additional target, thereby producing a polypeptide that binds to PD-L1 and the additional target.

3. A method of producing a polypeptide that binds to PD-L1 and an additional target, comprising grafting the CDR3 of the antibody of SEQ ID NO: 1 onto an antibody recognizing the additional target, thereby producing a polypeptide that binds to PD-L1 and the additional target.

4. A method of producing a PD-L1 binding non-immunoglobulin, comprising grafting the CDR3 of the antibody of SEQ ID NO: 1 onto a non-immunoglobulin having a CDR loop-like structure, thereby allowing the non-immunoglobulin to bind to PD-L1.

5. The method of claim 2, wherein the additional target is selected from tumor antigens and immunological checkpoint-associated antigens.

6. The method of claim 5, wherein the tumor antigen is selected from VEGFR, ERBB family proteins, and CMET.

7. The method of claim 5, wherein the immunological checkpoint-associated antigen is CTLA4.

8. The method of claim 3, wherein the additional target is selected from tumor antigens and immunological checkpoint-associated antigens.

9. The method of claim 8, wherein the tumor antigen is selected from VEGFR, ERBB family proteins, and CMET.

10. The method of claim 8, wherein the immunological checkpoint-associated antigen is CTLA4.

11. The method of claim 4, wherein the non-immunoglobulin having a CDR loop-like structure is a CTLA4 protein, or a fibronectin type III domain.

* * * * *